(12) United States Patent
Weuster-Botz et al.

(10) Patent No.: US 10,954,494 B2
(45) Date of Patent: *Mar. 23, 2021

(54) 7BETA-HYDROXYSTEROID DEHYDROGENASE MUTANTS AND PROCESS FOR THE PREPARATION OF URSODEOXYCHOLIC ACID

(71) Applicant: PharmaZell GmbH, Raubling (DE)

(72) Inventors: Dirk Weuster-Botz, Munich (DE); Michael Braun, Bad Mergentheim-Edelfingen (DE); Arno Aigner, Tuntenhausen (DE); Boqiao Sun, Munich (DE); Christina Kantzow, Munich (DE); Sven Bresch, Munich (DE); Daniel Bakonyi, Cologne (DE); Werner Hummel, Titz (DE)

(73) Assignee: Pharmazell GmbH, Raubling (DE)

( * ) Notice: Subject to any disclaimer, the term of this patent is extended or adjusted under 35 U.S.C. 154(b) by 781 days.

This patent is subject to a terminal disclaimer.

(21) Appl. No.: 15/093,570

(22) Filed: Apr. 7, 2016

(65) Prior Publication Data

US 2017/0015978 A1    Jan. 19, 2017

Related U.S. Application Data

(63) Continuation of application No. 13/993,235, filed as application No. PCT/EP2011/073141 on Dec. 16, 2011, now abandoned.

(30) Foreign Application Priority Data

Dec. 16, 2010 (EP) ..................................... 10015726

(51) Int. Cl.
   C12N 9/04    (2006.01)
   C12N 9/02    (2006.01)
   C12P 33/00   (2006.01)
   C12P 33/02   (2006.01)

(52) U.S. Cl.
   CPC ......... *C12N 9/0006* (2013.01); *C12N 9/0008* (2013.01); *C12P 33/00* (2013.01); *C12P 33/02* (2013.01); *C12Y 101/01201* (2013.01)

(58) Field of Classification Search
   CPC .. C12N 9/0006; C12N 9/0042; C12N 9/0071; C12N 9/0095; C12N 9/0008
   See application file for complete search history.

(56) References Cited

U.S. PATENT DOCUMENTS

| | | |
|---|---|---|
| 9,096,825 B2 | 8/2015 | Schmid et al. |
| 2011/0091921 A1 | 4/2011 | Aigner |
| 2013/0040341 A1 | 2/2013 | Liu |

FOREIGN PATENT DOCUMENTS

| | | |
|---|---|---|
| EP | 1114869 A1 | 1/2001 |
| EP | 2327790 A1 | 6/2001 |
| JP | 2001136993 A | 5/2001 |
| WO | 2000015831 A1 | 3/2000 |
| WO | 2009/118176 | 10/2009 |
| WO | 2010098505 A1 | 9/2010 |
| WO | 2011/064404 | 6/2011 |
| WO | PCT/ISA/210 A1 | 6/2012 |
| WO | PCT/IPEA/409 | 3/2013 |

OTHER PUBLICATIONS

Office Action dated Oct. 30, 2015 issued in Japanese Patent Application No. 2013-543826.
Monti, et al., One-Pot Multienzymatic Synthesis of 12-Ketoursodeoxycholic Acid: Subtle Cofactor Specificities Rule the Reaction Equilibria of Five Biocatalysts Working in a Row, Advanced Synthesis & Catalysis, 2009, 351(9): 1303-1311.
Zhu, et al., Enzymatic enatioselective reduction of—ketoesters by a thermostable 7-hydroxysteroid dehydrogenase from Bacteroides fragilis, Tetrahedron, 2006. 62(18), 4535-4539.
MacDonald, et al., Bile induction of 7 alpha- and 7 beta-hydroxysteroid dehydrogenases in Clostridium absonum, Biochim Biophys Acta, 1981, 665(2), 262-9.
Hirano, et al., Characterization of NADP-dependent 7 beta-hydroxysteroid dehydrogenases from Peptostreptococcus productus and Eubacterium aerofaciens, Appl Environ Microbiol, 1982, 43(5), 1057-63.
Pawlowski, et al., Cloning and Sequencing of the cDNA for Rat Liver 3a-Hydroxysteroid/Dihydrodiol Dehydrogenase, the Journal of Biological Chemistry 1991, 266(14), 8820-8825.
Database Uniprot [Online]: "Subname: Full=Short-chain dehydrogenases of various substrate specificities". EBI Accession No. Uniprot:D4M4P2, XP002671823, the whole document.
Carrea Giacomo et al: "Enzymatic synthesis of 12-ketoursodeoxycholic acid from dehydrocholic acid in a 2 membrane reactor". Biotechnology Letiers, Kew, Surrey, GB, vol. 14, No. 12, Dec. 1, 1992, pp. 1131-1135.
Macdonald I A et al.: "Epimerization versus dehydroxylation of the 7alpha-hydroxyl-group of primary bile acids: Competitive studies with Clostridium absonum and 7alpha-dehydroxylating bacteria (*Eubacterium* SP.)"Journal of Steroid Biochemistry, Pergamon Press PLC, GB vol. 17 No. 3, Sep. 1, 1982, pp. 257-293.

*Primary Examiner* — Maryam Monshipouri
(74) *Attorney, Agent, or Firm* — Saul Ewing Arnstein & Lehr LLP; Brian R. Landry; Justin W. Crotty

(57) ABSTRACT

The invention relates to novel 7ß-hydroxysteroid dehydrogenase mutants, to the sequences which encode these enzyme mutants, to processes for the preparation of the enzyme mutants and to their use in enzymatic reactions of cholic acid compounds, in particular in the preparation of ursodeoxycholic acid (UDCS). The invention also relates to novel processes for the synthesis of UDCS using the enzyme mutants; and to the preparation of UDCS using recombinant, multiply-modified microorganisms.

2 Claims, 22 Drawing Sheets
Specification includes a Sequence Listing.

Accession: ZP_01773061 (SEQ ID NO: 2)

```
  1 mnlrekygew glilgategv gkafcekiaa ggmnvvmvgr reeklnvlag eiretygvet
 61 kvvradfsqp gaaetvfaat egldmgfmsy vaclhsfgki qdtpwekhea minvnvvtfl
121 kcfhhymrif aaqdrgavin vssmtgisss pwngqygagk afilkmteav acecegtgvd
181 vevitlgttl tpsllsnlpg gpqgeavmki altpeecvde afeklgkels viagqrnkds
241 vhdwkanhte deyirymgsf yrd
```

Fig. 1A

Accession No.: NZ_AAVN02000010, Region: 52005. 52796 (SEQ ID NO: 1)

```
  1 atgaacctga gggagaagta cggtgagtgg ggcctgatcc tgggcgcgac cgagggcgtc
 61 ggcaaggcgt tctgcgagaa gatcgccgcc ggcggcatga acgtcgtcat ggtcggccgt
121 cgcgaggaga agctgaacgt gctcgcaggc gagatccgcg agacctacgg cgtggagacc
181 aaggtcgtgc gcgccgactt tagccagccc ggcgctgccg agaccgtctt cgccgcgacc
241 gagggcctgg acatgggctt catgagctac gtggcctgcc tgcacagctt cggtaagatc
301 caggacaccc cctgggagaa gcacgaggcc atgatcaacg tcaacgtcgt gaccttcctc
361 aagtgcttcc accactacat gcggatcttt gccgcccagg accgcggcgc cgtgatcaac
421 gtctcgtcga tgaccggcat cagctccagc cctggaacg gccagtacgg cgcgggcaag
481 gccttcatcc tcaagatgac cgaggccgtg gcctgcgagt gcgagggcac cggcgtcgac
541 gtcgaggtca tcaccctcgg caccacccta accccagcc tgctgtccaa cctccccggc
601 ggcccgcagg gcgaggccgt catgaagatc gccctcaccc ccgaggagtg cgttgacgag
661 gcctttgaga agctgggtaa ggagctctcc gtcatcgccg ccagcgcaa caaggactcc
721 gtccacgact ggaaggcaaa ccacaccgag gacgagtaca tccgctacat ggggtcgttc
781 taccgcgact ag
```

Fig. 1B

3α-HSDH (SEQ ID NO: 6)

Source: *Comamonas testosteroni* ATCC 11996

```
  1 msiivisgca tgigaatrkv leaaghqivg idirdaevia dlstaegrkq aiadvlakcs
 61 kgmdglvlca glgpqtkvlg nvvsvnyfga telmdaflpa lkkghqpaav vissvasahl
121 afdknplala leageeakar aivehageqg gnlayagskn altvavrkra aawgeagvrl
181 ntiapgatet pllqaglqdp rygesiakfv ppmgrraeps emasviaflm spaasyvhga
241 qividggida vmrptqf
```

Fig. 1C

Nucleic acid sequence coding for 3α-HSDH (SEQ ID NO: 5)

Source: *Comamonas testosteroni* ATCC 11996

Accession: AF092031, Region: 158..931

```
  1 atgtccatca tcgtgataag cggctgcgcc accggcattg gtgcggctac gcgcaaggtc
 61 ctggaggcgg ccggtcacca gatcgtaggc atcgatatac gcgatgcgga agtgattgcc
121 gatctctcga cggccgaagg tcgaaagcag gcgattgccg atgtactggc gaagtgcagc
181 aagggcatgg acggcctggt gctgtgcgcc ggcctgggac cgcagaccaa ggtgcttggc
241 aatgtggttt cggtcaatta ttttggcgcg accgagctga tggatgcctt tttgccagcg
301 ctgaaaaaag gccatcagcc cgcagccgtc gtcatctcgt ccgtggcttc cgcgcatctg
361 gcttttgaca gaaacccact ggcgctggca ctggaagccg gcgaggaagc caaggcccgc
421 gccattgtcg aacatgcggg agagcagggc ggaaatctgg cctatgcggg cagcaagaat
481 gctttgacgg tggctgtgcg caaacgcgcc gccgcctggg gcgaggctgg cgtgcgcctg
541 aacaccatcg cccccggtgc aaccgagact cccttgctgc aggcgggcct gcaggacccg
601 cgctatggcg aatccattgc caagttcgtt cctcccatgg gccgccgtgc cgagccgtcc
661 gagatggcgt cggtcatcgc ctttttgatg agcccggccg caagctatgt gcatggcgcg
721 cagatcgtca ttgatggcgg cattgatgcg gtgatgcgcc cgacacagtt ctga
```

Fig. 1D

3α-HSDH (SEQ ID NO: 8)

Source: Rattus norvegicus (Norway rat)
Genbank ACCESSION    M61937

MDSISLRVALNDGNFIPVLGFGTTVPEKVAKDEVIKATKIAIDN
GFRHFDSAYLYEVEEEVGQAIRSKIEDGTVKREDIFYTSKLWSTFHRPELVRTCLEKT
LKSTQLDYVDLYIIHFPMALQPGDIFFPRDEHGKLLFETVDICDTWEAMEKCKDAGLA
KSIGVSNFNCRQLERILNKPGLKYKPVCNQVECHLYLNQSKMLDYCKSKDIILVSYCT
LGSSRDKTWVDQKSPVLLDDPVLCAIAKKYKQTPALVALRYQLQRGVVPLIRSFNAKR
IKELTQVFEFQLASEDMKALDGLNRNFRYNNAKYFDDHPNHPFTDE

Fig. 1E (SEQ ID NO: 7)

```
atggattcca tatctctgcg tgtagcacta aatgatggta acttcattcc tgtactgggg
tttggaacca ctgtgcctga gaaggttgct aaggatgaag ttatcaaggc tactaaaata
gctatagata atggattccg ccattttgac tctgcttatt tgtacgaagt agaagaggaa
gtgggccaag ccattagaag caagattgaa gacggcactg tgaagagaga agatatattc
tatacttcaa agctttggag cactttccat agaccagagc tggtccgaac ttgcttggaa
aagacactga aaagcactca actggactat gtggatcttt atattattca tttcccaatg
gctttgcagc ctggagatat attttttccca cgagatgagc atggaaaact attgtttgaa
acagtggata tctgtgacac atggggaggcc atggaaaagt gtaaggatgc aggattggcc
aagtctattg gggtgtccaa ctttaactgc aggcagctgg agaggattct gaataagcca
gggctcaaat acaagcctgt gtgcaaccag gtggaatgtc acctttatct caaccagagc
aaaatgctgg actattgtaa gtcaaaagac atcattctgg tttcctactg cacgctggga
agttcacgag acaaaacatg ggtggatcag aaaagtccag ttctcctaga tgatccagtt
ctttgtgcca tagcaaagaa gtacaagcaa accccagccc tagttgccct tcgctaccag
ctgcagcgtg gggttgtgcc cctgatcagg agtttcaacg cgaagcggat caaagagcta
acacaggttt ttgaattcca gttggcttca gaggacatga agccctgga tggcttgaac
agaaatttca gatacaacaa tgcaaaatat tttgatgacc atcccaatca tccatttact
gatgaatag
```

Fig. 1F

FDH-Sequence, D221G mutant (SEQ ID NO: 14)

```
atggcaaaggtcctgtgcgttctttacgatgatccggtcgacggctacccgaagacctatgcccgcgacgatcttccgaa
gatcgaccactatccgggcggccagatcttgccgacgccgaaggccatcgacttcacgcccgggcagttgctcggctccg
tctccggcgagctcggcctgcgcgaatatctcgaatccaacggccacaccctggtcgtgacctccgacaaggacggcccc
gactcggtgttcgagcgcgagctggtcgatgcggatgtcgtcatctcccagcccttctggccggcctatctgacgcccga
gcgcatcgccaaggccaagaacctgaagctcgcgctcaccgccggcatcggttccgaccacgtcgatcttcagtcggcta
tcgaccgcaacgtcaccgtggcggaagtcacctactgcaactcgatcagcgtcgccgagcatgtggtgatgatgatcctg
tcgctggtgcgcaactatctgccctcgcacgaatgggcgcggaagggcggctggaacatcgccgactgcgtctcccacgc
ctacgacctcgaggcgatgcatgtcggcaccgtggccgccgccgcatcggtctcgcggtgctgcgccgtctggcgccgt
tcgacgtgcacctgcactacaccggccgtcaccgcctgccggaatcggtcgagaaggagctcaacctcacctggcacgcg
acccgcgaggacatgtatccggtttgcgacgtggtgacgctgaactgcccgctgcaccccgaaaccgagcacatgatcaa
tgacgagacgctgaagctgttcaagcgtggcgcctacatcgtcaacaccgcccgcggcaagctgtgcgaccgcgatgccg
tggcacgtgcgctcgaatccggccggctggccggctatgccggcgacgtgtggttcccgcagccggcgccgaaggaccac
ccctggcggacgatgccctataacggcatgaccccgcacatctccggcaccacgctgaccgcgcaggcgcgttatgcggc
gggcacccgcgagatcctggagtgcttcttcgagggccgtccgatccgcgacgaatacctcatcgtgcagggcggcgctc
ttgccggcaccggcgcgcattcctactcgaagggcaatgccaccggcggttcggaagaggccgccaagttcaagaaggcg
gtctga
```

Fig. 1G

Amino acid sequence of the D221G mutant (SEQ ID NO: 15)

MAKVLCVLYDDPVDGYPKTYARDDLPKIDHYPGGQILPTPKAIDFTPGQLLGSVSGELGLREYLESNGHTLVVTSDKDGPDSVFER
ELVDADVVISQPFWPAYLTPERIAKAKNLKLALTAGIGSDHVDLQSAIDRNVTVAEVTYCNSISVAEHVVMMILSLVRNYLPSHEW
ARKGGWNIADCVSHAYDLEAMHVGTVAAGRIGLAVLRRLAPFDVHLHYTGRHRLPESVEKELNLTWHATREDMYPVCDVVTLNCPL
HPETEHMINDETLKLFKRGAYIVNTARGKLCDRDAVARALESGRLAGYAGDVWFPQPAPKDHPWRTMPYNGMTPHISGTTLTAQAR
YAAGTREILECFFEGRPIRDEYLIVQGGALAGTGAHSYSKGNATGGSEEAAKFKKAV*

Fig. 1H

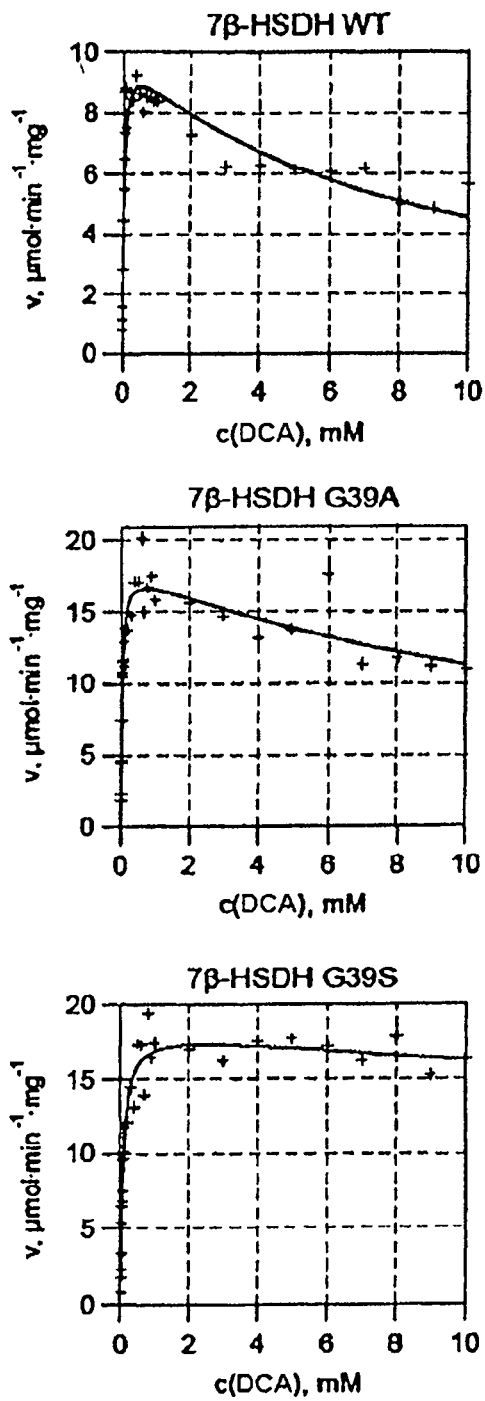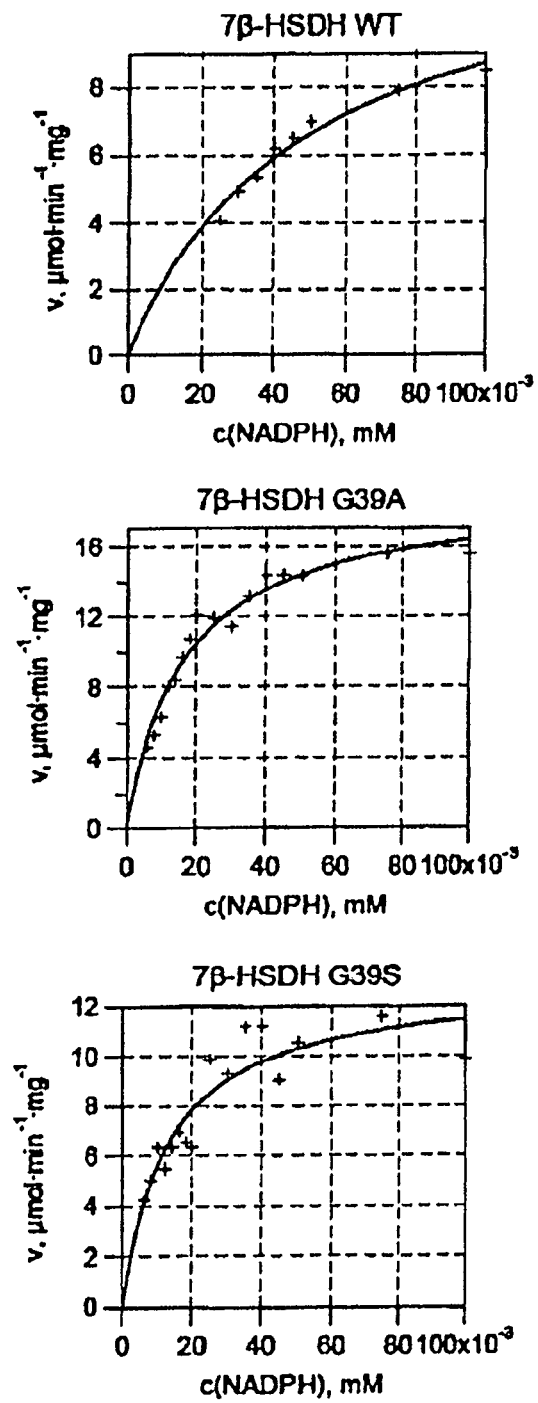
Fig. 6A
Fig. 6B

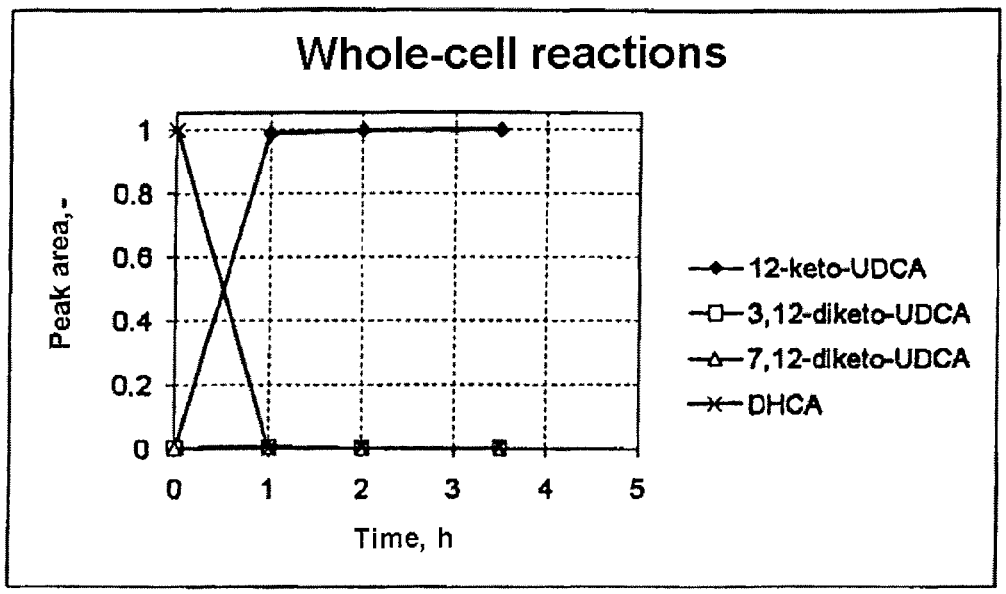

Fig. 9

| | | | | |
|---|---|---|---|---|
| 7beta-HSDH wild-type | MNLREKYGEW | GLILGATEGV | GKAFCEKIAA | GGMNVVMVGR | REEKLNVLAG |
| 7beta-HSDH G39D | MNLREKYGEW | GLILGATEGV | GKAFCEKIAA | GGMNVVMV■R | REEKLNVLAG |
| 7beta-HSDH G39D R40L | MNLREKYGEW | GLILGATEGV | GKAFCEKIAA | GGMNVVMV■ | REEKLNVLAG |
| 7beta-HSDH G39D R40I | MNLREKYGEW | GLILGATEGV | GKAFCEKIAA | GGMNVVMV■ | REEKLNVLAG |
| 7beta-HSDH G39D R40V | MNLREKYGEW | GLILGATEGV | GKAFCEKIAA | GGMNVVMV■ | REEKLNVLAG |
| 7beta-HSDH wild-type | EIRETYGVET | KVVRADFSQP | GAAETVFAAT | EGLDMGFMSY | VACLHSFGKI |
| 7beta-HSDH G39D | EIRETYGVET | KVVRADFSQP | GAAETVFAAT | EGLDMGFMSY | VACLHSFGKI |
| 7beta-HSDH G39D R40L | EIRETYGVET | KVVRADFSQP | GAAETVFAAT | EGLDMGFMSY | VACLHSFGKI |
| 7beta-HSDH G39D R40I | EIRETYGVET | KVVRADFSQP | GAAETVFAAT | EGLDMGFMSY | VACLHSFGKI |
| 7beta-HSDH G39D R40V | EIRETYGVET | KVVRADFSQP | GAAETVFAAT | EGLDMGFMSY | VACLHSFGKI |
| 7beta-HSDH wild-type | QDTPWEKHEA | MINVNVVTFL | KCFHHYMRIF | AAQDRGAVIN | VSSMTGISSS |
| 7beta-HSDH G39D | QDTPWEKHEA | MINVNVVTFL | KCFHHYMRIF | AAQDRGAVIN | VSSMTGISSS |
| 7beta-HSDH G39D R40L | QDTPWEKHEA | MINVNVVTFL | KCFHHYMRIF | AAQDRGAVIN | VSSMTGISSS |
| 7beta-HSDH G39D R40I | QDTPWEKHEA | MINVNVVTFL | KCFHHYMRIF | AAQDRGAVIN | VSSMTGISSS |
| 7beta-HSDH G39D R40V | QDTPWEKHEA | MINVNVVTFL | KCFHHYMRIF | AAQDRGAVIN | VSSMTGISSS |
| 7beta-HSDH wild-type | PWNGQYGAGK | AFILKMTEAV | ACECEGTGVD | VEVITLGTTL | TPSLLSNLPG |
| 7beta-HSDH G39D | PWNGQYGAGK | AFILKMTEAV | ACECEGTGVD | VEVITLGTTL | TPSLLSNLPG |
| 7beta-HSDH G39D R40L | PWNGQYGAGK | AFILKMTEAV | ACECEGTGVD | VEVITLGTTL | TPSLLSNLPG |
| 7beta-HSDH G39D R40I | PWNGQYGAGK | AFILKMTEAV | ACECEGTGVD | VEVITLGTTL | TPSLLSNLPG |
| 7beta-HSDH G39D R40V | PWNGQYGAGK | AFILKMTEAV | ACECEGTGVD | VEVITLGTTL | TPSLLSNLPG |
| 7beta-HSDH wild-type | GPQGEAVMKI | ALTPEECVDE | AFEKLGKELS | VIAGQRNKDS | VHDWKANHTE |
| 7beta-HSDH G39D | GPQGEAVMKI | ALTPEECVDE | AFEKLGKELS | VIAGQRNKDS | VHDWKANHTE |
| 7beta-HSDH G39D R40L | GPQGEAVMKI | ALTPEECVDE | AFEKLGKELS | VIAGQRNKDS | VHDWKANHTE |
| 7beta-HSDH G39D R40I | GPQGEAVMKI | ALTPEECVDE | AFEKLGKELS | VIAGQRNKDS | VHDWKANHTE |
| 7beta-HSDH G39D R40V | GPQGEAVMKI | ALTPEECVDE | AFEKLGKELS | VIAGQRNKDS | VHDWKANHTE |
| 7beta-HSDH wild-type | DEYIRYMGSF | YRD | | | |
| 7beta-HSDH G39D | DEYIRYMGSF | YRD | | | |
| 7beta-HSDH G39D R40L | DEYIRYMGSF | YRD | | | |
| 7beta-HSDH G39D R40I | DEYIRYMGSF | YRD | | | |
| 7beta-HSDH G39D R40V | DEYIRYMGSF | YRD | | | |

Fig. 10

7BETA-HYDROXYSTEROID DEHYDROGENASE MUTANTS AND PROCESS FOR THE PREPARATION OF URSODEOXYCHOLIC ACID

This application is a continuation of U.S. Ser. No. 13/993,235, which is the U.S. national phase pursuant to under 35 U.S.C. § 371 of PCT international application No. PCT/EP2011/073141, filed Dec. 16, 2011, which claims priority to EP patent application No. 10015726, filed Dec. 16, 2012. The entire contents of each of the aforementioned patent applications are incorporated herein by this reference.

The invention relates to novel 7β-hydroxysteroid dehydrogenase mutants, to the sequences that code for these enzyme mutants, to processes for the preparation of the enzyme mutants and use thereof in enzymatic reactions of cholic acid compounds, and especially in the preparation of ursodeoxycholic acid (UDCA); the invention also relates to novel processes for the synthesis of UDCA using the enzyme mutants; and to the preparation of UDCA using recombinant, multiply-modified microorganisms.

SEQUENCE LISTING

The instant application contains a Sequence Listing which has been submitted electronically in ASCII format and is hereby incorporated by reference in its entirety. Said ASCII copy, created on Aug. 11, 2016, is named 054410_00062 (CON)_SL.txt and is 218,431 bytes in size.

BACKGROUND OF THE INVENTION

The active substances ursodeoxycholic acid (UDCA) and the related diastereomer chenodeoxycholic acid (CDCA), among others, have been used for many years for the drug treatment of gallstone disease. The two compounds differ only in the configuration of the hydroxyl group on carbon atom 7 (UDCA: β-configuration, CDCA: α-configuration). Various processes are described in the prior art for the preparation of UDCA, which are carried out purely chemically or consist of a combination of chemical and enzymatic process steps. The starting point is in each case cholic acid (CA) or CDCA prepared from cholic acid.

Thus, the classical chemical method for UDCA preparation can be represented schematically as follows:

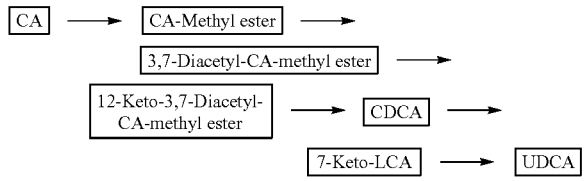

A serious disadvantage is, among other things, the following: as the chemical oxidation is not selective, the carboxyl group and the 3α and 7α-hydroxyl group must be protected by esterification.

An alternative chemical/enzymatic process based on the use of the enzyme 12α-hydroxysteroid dehydrogenase (12α-HSDH) can be represented as follows and is for example described in PCT/EP2009/002190 of the present applicant.

The 12α-HSDH oxidizes CA selectively to 12-keto-CDCA. The two protection steps required according to the classical chemical method are then omitted.

Furthermore, Monti, D., et al., (*One-Pot Multienzymatic Synthesis of 12-Ketoursodeoxycholic Acid: Subtle Cofactor Specificities Rule the Reaction Equilibria of Five Biocatalysts Working in a Row*. Advanced Synthesis & Catalysis, 2009) describe an alternative enzymatic-chemical process, which can be represented schematically as follows:

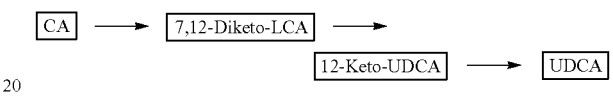

The CA is first oxidized from 7α-HSDH from *Bacteroides fragilis* ATCC 25285 (Zhu, D., et al., Enzymatic enantioselective reduction of -ketoesters by a thermostable 7-hydroxysteroid dehydrogenase from *Bacteroides fragilis*. Tetrahedron, 2006. 62(18): p. 4535-4539) and 12α-HSDH to 7,12-diketo-LCA. These two enzymes are each NADH-dependent. After reduction by 7β-HSDH (NADPH-dependent) from *Clostridium absonum* ATCC 27555 (DSM 599) (MacDonald, I. A. and P. D. Roach, *Bile induction of 7 alpha- and 7 beta-hydroxysteroid dehydrogenases in Clostridium absonum*. Biochim Biophys Acta, 1981. 665(2): p. 262-9), 12-keto-UDCA is formed. The end product is obtained by Wolff-Kishner reduction. This method has the drawback that owing to the position of the equilibrium of the catalyzed reaction, a complete reaction is not possible, and that for the first step of the reaction it is necessary to use two different enzymes, which makes the process more expensive. For cofactor regeneration, lactate dehydrogenase (LDH; for regeneration of $NAD^+$) and glucose dehydrogenase (GlcDH or GDH, for regeneration of NADPH) are used. A disadvantage with the cofactor regeneration used there is that the resultant co-product can only be removed from the reaction mixture with great difficulty, so that the reaction equilibrium cannot be influenced positively, which results in incomplete reaction of the educt.

A 7β-HSDH from the strain *Collinsella aerofaciens* ATCC 25986 (DSM 3979; formerly *Eubacterium aerofaciens*) was described in the year 1982 by Hirano and Masuda (Hirano, S. and N. Masuda, *Characterization of NADP-dependent 7 beta-hydroxysteroid dehydrogenases from Peptostreptococcus productus and Eubacterium aerofaciens*. Appl Environ Microbiol, 1982. 43(5): p. 1057-63). Sequence information for this enzyme was not disclosed. The molecular weight determined by gel filtration was 45 000 Da (cf. Hirano, page 1059, left column). Furthermore, for the enzyme there, the reduction of the 7-oxo group to the 7β-hydroxyl group was not observed (cf. Hirano, page 1061, Discussion 1st paragraph). A person skilled in the art can therefore see that the enzyme described by Hirano et al. is not suitable for catalysis of the reduction of dehydrocholic acid (DHCA) in position 7 to 3,12-diketo-7β-CA.

The applicant's earlier international patent application PCT/EP2010/068576 describes a novel 7β-HSDH from *Collinsella aerofaciens* ATCC 25986, which among other things has a molecular weight (in SDS-gel electrophoresis) of about 28-32 kDa, a molecular weight (in gel filtration, in nondenaturing conditions, such as in particular without SDS) from about 53 to 60 kDa, and the capacity for stereoselective reduction of the 7-carbonyl group of 7-keto-LCA to a 7β-hydroxyl group.

In addition, in PCT/EP2010/068576, a process is provided for the preparation of UDCA, which can be represented schematically as follows:

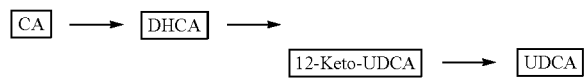

In this case the oxidation of CA takes place simply, by a classical chemical route. DHCA is reduced by the pair of enzymes 7β-HSDH and 3α-HSDH individually in succession or in one pot to 12-keto-UDCA. Combined with Wolff-Kishner reduction, UDCA can therefore be synthesized from CA in just three steps. 7β-HSDH is dependent on the cofactor NADPH, whereas 3α-HSDH requires the cofactor NADH. The availability of pairs of enzymes with dependence on the same cofactor or extended dependence (e.g. on the cofactors NADH and NADPH) would be advantageous, because this could simplify cofactor regeneration.

The problem to be solved by the invention is to provide further improved 7β-HSDHs. In particular, enzyme mutants should be provided, which can be used even more advantageously for enzymatic or microbial preparation of UDCA via the stereospecific reduction of DHCA in 7-position to 3,12-diketo-7β-CA, and in particular have reduced substrate inhibition and/or have altered cofactor usage (increased, altered specificity or extended dependence).

Another problem is to provide novel enzymatic and microbial synthesis routes, which in particular are also characterized by simplified cofactor regeneration in the reductive preparation of UDCA via DHCA.

SUMMARY OF THE INVENTION

The above problems were solved, surprisingly, by the production and characterization of mutants of a novel regio- and stereospecific 7β-HSDH from aerobic bacteria of the genus *Collinsella*, especially of the strain *Collinsella aerofaciens* and use thereof in the reaction of cholic acid compounds, especially in the preparation of UDCA.

Furthermore, the above problem was solved by providing a biocatalytic (microbial or enzymatic) process, comprising the enzymatic conversion of DHCA via two partial reductive steps catalyzed by 7β-HSDH or 3α-HSDH, which can take place simultaneously or with a time delay in any order, to 12-keto-UDCA and cofactor regeneration using dehydrogenases, such as in particular formate dehydrogenase (FDH) enzymes or glucose dehydrogenase (GDH) enzymes, which regenerate the spent cofactor from the two partial reductive steps.

DESCRIPTION OF THE FIGURES

FIG. 1A shows the amino acid sequence of 7β-HSDH from *Collinsella aerofaciens* and FIG. 1B shows the coding nucleic acid sequence for the amino acid sequence of FIG. 1A; FIG. 1C shows the amino acid sequence of 3α-HSDH from *Comanomonas testosteroni* and FIG. 1D shows the coding nucleic acid sequence for the amino acid sequence of FIG. 1C; FIG. 1E shows the amino acid sequence of 3α-HSDH from *Rattus norvegicus* and FIG. 1F shows the coding nucleic acid sequence for the amino acid sequence of FIG. 1E; FIG. 1G shows the coding nucleic acid sequence of the FDH mutant D221G and FIG. 1H shows the amino acid sequence for the nucleic acid sequence of FIG. 1G.

FIG. 6A and FIG. 6B show an activity comparison for 7β-HSDH wild type and the 7β-HSDH mutants G39A and G39S; specifically, Fig. A is a plot of the specific enzyme activity versus different substrate concentrations used at constant cofactor concentration of 100 μM; and Fig. B is a plot of enzyme activity versus different cofactor concentrations used at constant substrate concentration of 0.3 mM.

FIG. 9 shows the course of whole-cell biotransformation of DHCA. The proportionate peak areas (according to HPLC analysis) of 12-keto-UDCA, 3,12-diketo-UDCA, 7,12-diketo-UDCA and DHCA are shown as a function of time.

FIG. 10 shows a sequence comparison between the 7β-HSDH wild type and selected mutants. The sequences designated as "7beta-HSDH wild type", "7beta-HSDH G39D", "7beta-HSDH G39D R40L", "7beta-HSDH G39D R40I" and "7beta-HSDH G39D R40V" correspond to SEQ ID NO:2, SEQ ID NO:37, SEQ ID NO:38 and SEQ ID NO:39.

SPECIAL EMBODIMENTS OF THE INVENTION

Figure 2:
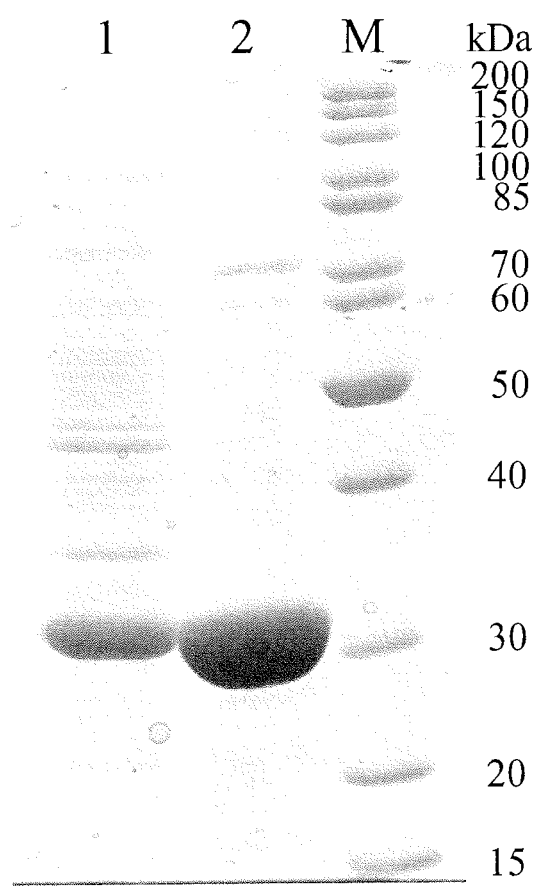
FIG. 2 shows the SDS-gel of a purified 7β-HSDH prepared according to the invention, with, on lane 1: cell raw extract; lane 2: purified protein; lane M: Page Rouler™, molecular weight marker (Fermentas, Germany).

The invention relates in particular to the following special embodiments:

1. A 7β-hydroxysteroid dehydrogenase (7β-HSDH) mutant, which catalyzes at least the stereospecific enzymatic reduction of a 7-ketosteroid to the corresponding 7-hydroxysteroid, wherein the mutant has a decreased substrate inhibition (especially for the 7-ketosteroid substrate) compared to the unmutated enzyme, such as in particular an enzyme comprising SEQ ID NO:2 and/or at least the sequence motif VMVGRRE according to position 36 to 42 thereof; and/or an altered cofactor usage (e.g. increased, altered specificity with respect to a cofactor (especially NADH or NADPH) or an extended dependence, i.e. usage of an additional cofactor not used previously).

2. Mutant according to embodiment 1, which does not display any substrate inhibition or which has a K$_i$ value for the 7-ketosteroid substrate, especially for dehydrocholic acid (DHCA), in the range from >10 mM, e.g. at 11 to 200 mM, 12 to 150 mM, 15 to 100 mM.

3. Mutant according to one of the preceding embodiments, wherein the specific activity (U/mg) in the presence of the cofactor NADPH, compared to the unmutated enzyme, is raised or lowered by at least 1, 5 or 10%, but especially at least 1-fold, especially 2- to 10-fold; or essentially is absent and is replaced by the usage of NADH, or has an extended usage of NADPH and HADH.

4. A 7β-hydroxysteroid dehydrogenase (7β-HSDH) mutant, which catalyzes at least the stereospecific enzymatic reduction of a 7-ketosteroid to the corresponding 7-hydroxysteroid, optionally according to one of the preceding embodiments, wherein the mutant has at least one mutation in the amino acid sequence according to SEQ ID NO:2 or an amino acid sequence derived therefrom with at least 60% sequence identity, e.g. at least 65, 70, 75, 80, 85, or 90, e.g. at least 91, 92, 93, 94, 95, 96, 97, 98, 99 or 99.5% to this sequence.

5. A 7β-hydroxysteroid dehydrogenase (7β-HSDH) mutant, which catalyzes at least the stereospecific enzymatic reduction of a 7-ketosteroid to the corresponding 7-hydroxysteroid, optionally according to one of the preceding embodiments, wherein the mutant has at least one mutation in the sequence motif VMVGRRE according to position 36 to 42 of SEQ ID NO:2 or in the corresponding sequence motif of an amino acid sequence derived therefrom with at least 60% sequence identity, e.g. at least 65, 70, 75, 80, 85, or 90, e.g. at least 91, 92, 93, 94, 95, 96, 97, 98, 99 or 99.5% to this sequence.

6. Mutant according to embodiment 4 or 5, selected from
a) the single mutants G39X$_1$ and R40X$_2$,
b) the double mutants (G39X$_1$, R40X$_2$), (R40X$_2$, R41X$_3$) and (G39X$_1$, R41X$_3$) or
c) the triple mutant (G39X$_1$, R40X$_2$, R41X$_3$),
(in each case relative to SEQ ID NO:2)
wherein X$_1$, X$_2$ and X$_3$ in each case independently of one another stand for any amino acid, especially any, especially natural, amino acid, different from G or R, that decreases substrate inhibition and/or modifies cofactor usage or cofactor dependence;
or
d) the corresponding single, double or triple mutants of an amino acid sequence derived from SEQ ID NO:2 with at least 60% sequence identity, e.g. at least 65, 70, 75, 80, 85, or 90, e.g. at least 91, 92, 93, 94, 95, 96, 97, 98, 99 or 99.5% to this sequence.

Examples of suitable single mutants comprise: G39A, G39S, G39D, G39V, G39T, G39P, G39N, G39E, G39Q, G39H, G39R, G39K and G39W, and R40D, R40E, R40I, R40V, R40L, R40G, R40A.

Examples of suitable double mutants comprise:

double combinations of the above G39$X_1$ and R40$X_2$ mutants, wherein $X_1$ stands in particular for D or E and/or $X_2$ can be any amino acid, especially proteinogenic amino acid, such as in particular an amino acid with aliphatic side chain, for example (G39D,R40I), (G39D,R40L), (G39D,R40V); and the analogous double mutants with G39E instead of G39D; and double combinations of the above G39$X_1$ mutants or R40$X_2$ mutants with R41$X_3$ mutants, in which $X_3$ is any amino acid, especially an, especially natural, amino acid, that decreases substrate inhibition and/or that modifies cofactor usage or cofactor dependence, different from R, for example of the type (G39$X_1$,R41$X_3$) or (R40$X_2$,R41$X_3$), e.g. with $X_1$=D or E; $X_2$=I, L or V; $X_3$=N, I, L or V) for example (R40D,R41I); (R40D,R41L); (R40D,R41V); (R40I,R41I); (R40V,R41I), (R40L,R41I).

Examples of suitable triple mutants comprise any triple combinations of the above single mutants G39$X_1$, R40$X_2$ and R41$X_3$; wherein $X_1$, $X_2$ and $X_3$ are as defined above; but especially wherein $X_1$ stands for D, or E and/or $X_2$ and $X_3$ stand independently of one another for any amino acid, especially a proteinogenic amino acid, such as in particular triple mutants of the type (G39$X_1$=D or E; R40$X_2$=1, L or V; R41$X_3$=N, I, L or V), for example (G39D,R40I,R41N).

Optionally the mutants of embodiments 1 to 6 can have, additionally or alternatively, especially additionally, at least one further substitution, for example 1, 2, 3 or 4 substitutions in the positions K44, R53, K61 and R64. In this case these residues can be replaced, independently of one another, with any amino acid, especially a proteinogenic amino acid, especially a substitution such that the resultant mutant has a decreased substrate inhibition (especially for the 7-ketosteroid substrate); and/or has an altered cofactor usage or cofactor dependence (e.g. increased, altered specificity with respect to a cofactor or an extended dependence, i.e. usage of an additional cofactor not used previously) as defined herein.

7. Nucleic acid sequence coding for a 7β-HSDH mutant according to one of the preceding embodiments.

8. Expression cassette, comprising a nucleic acid sequence according to embodiment 7 under the genetic control of at least one regulatory nucleic acid sequence, and optionally coding sequences for at least one (for example 1, 2 or 3) further enzyme, selected from hydroxysteroid dehydrogenases, especially 3α-HSDH, and dehydrogenases suitable for cofactor regeneration, for example FDH, GDH, ADH, G-6-PDH, PDH. In particular the enzymes contained in an expression cassette can use different, but preferably the same pairs of cofactors, for example the pair of cofactors NAD$^+$/NADH or NADP$^+$/NADPH.

9. Vector comprising at least one expression cassette according to embodiment 8.

10. Recombinant microorganism, bearing at least one nucleic acid sequence according to embodiment 7 or at least one expression cassette according to embodiment 8 or bearing at least one vector according to embodiment 9 and additionally, optionally, bearing the coding sequence for a 3α-hydroxysteroid dehydrogenase (3α-HSDH).

11. Process for the enzymatic or microbial synthesis of 7β-hydroxysteroids, wherein the corresponding 7-ketosteroid is reacted in the presence of a 7β-HSDH mutant according to the definition in one of the embodiments 1 to 6 or in the presence of a recombinant microorganism expressing this mutant according to embodiment 10, and at least one resultant reduction product is optionally isolated from the reaction mixture.

12. The process according to embodiment 11, wherein the ketosteroid to be reduced is selected from
 a) dehydrocholic acid (DHCA),
 b) 7-keto-lithocholic acid (7-keto-LCA),
 c) 7,12-diketo-lithocholic acid (7,12-diketo-LCA) and
 d) derivatives thereof, such as in particular a salt, amide or alkyl ester of the acid.

13. The process according to one of the embodiments 11 and 12, wherein the reduction takes place in the presence of (and with the consumption of) NADPH and/or NADH.

14. A process for enzymatic or microbial oxidation of 7β-hydroxysteroids, wherein the hydroxysteroid is reacted in the presence of a 7β-HSDH mutant according to the definition in one of the embodiments 1 to 6 or in the presence of a microorganism expressing this mutant according to embodiment 10, and a resultant oxidation product is optionally isolated from the reaction mixture.

15. The process according to embodiment 14, wherein the 7β-hydroxysteroid is 3,12-diketo-7β-CA or a derivative thereof, such as in particular a salt, amide or alkyl ester.

16. The process according to one of the embodiments 14 and 15, wherein the oxidation takes place in the presence of (and with the consumption of) NADP$^+$ and/or NAD$^+$.

17. The process according to one of the embodiments 13 and 16, wherein the spent redox equivalents are regenerated chemically, electrochemically or enzymatically, especially in situ.

18. The process according to embodiment 17, wherein spent NADPH is regenerated by coupling with an NADPH-regenerating enzyme, wherein this is selected in particular from NADPH dehydrogenases, alcohol dehydrogenases (ADH), and NADPH regenerating formate dehydrogenases (FDH), and glucose dehydrogenase (GDH)-, glucose-6-phosphate dehydrogenase (G-6-PDH), or phosphite dehydrogenases (PtDH), wherein the NADPH-regenerating enzyme is optionally expressed by a recombinant microorganism; or wherein spent NADH is regenerated by coupling with an NADH-regenerating enzyme, wherein this is selected in particular from NADH dehydrogenases, NADH regenerating formate dehydrogenases (FDH), NADH regenerating alcohol dehydrogenases (ADH), NADH regenerating glucose-6-phosphate dehydrogenases (G6PDH), NADH regenerating phosphite dehydrogenases (PtDH) and NADH regenerating glucose dehydrogenases (GDH), wherein the NADH-regenerating enzyme is optionally expressed in a recombinant microorganism.

Expression of the cofactor-regenerating enzyme in a recombinant microorganism is preferred.

19. The process according to embodiment 18, wherein the NADPH-regenerating enzyme is selected from natural or recombinant, isolated or enriched
 a) alcohol dehydrogenases (EC 1.1.1.2) and
 b) functional equivalents derived therefrom.

20. The process according to embodiment 18, wherein the NADPH-regenerating enzyme is selected from mutants of an NAD$^+$-dependent formate dehydrogenase (FDH), which in particular catalyzes at least the enzymatic oxidation of formic acid to $CO_2$, wherein the mutant accepts, compared to the unmutated enzyme, exclusively or additionally, especially additionally, $NADP^+$ as cofactor; or wherein the NADH-regenerating enzyme is selected from an $NAD^+$-dependent FDH or an $NAD^+$-dependent GDH, such as in particular an FDH from *Mycobacterium vaccae* N10, according to SEQ ID NO:36 and a GDH from *Bacillus subtilis* according to SEQ ID NO:48 (which regenerates NADPH and/or NADH) or a modified form thereof in each case functionally equivalent (with respect to cofactor regeneration) to the two stated enzymes.

21. The process according to embodiment 20, wherein the FDH mutant reduces $NADP^+$ with a specific activity to NADPH, which corresponds to about 0.1 to 1000%, such as 1 to 100%, 5 to 80% or 10 to 50%, of the specific activity of the unmutated (wild-type) enzyme for the reduction of $NAD^+$ to NADH.

22. The process according to one of the embodiments 20 and 21, wherein the $NADP^+$-accepting FDH mutant has at least one mutation in the amino acid sequence of an FDH from *Mycobacterium vaccae* N10 according to SEQ ID NO:36 or an amino acid sequence derived therefrom with at least 60% sequence identity, e.g. at least 65, 70, 75, 80, 85, or 90, e.g. at least 91, 92, 93, 94, 95, 96, 97, 98, 99 or 99.5% to this sequence.

23. The process according to one of the embodiments 20 to 22, wherein the $NADP^+$-accepting mutant has at least one mutation in the sequence motif TDRHRL according to position 221 to 226 of SEQ ID NO:36 or in the corresponding sequence motif of an amino acid sequence derived therefrom with at least 60% sequence identity, e.g. at least 65, 70, 75, 80, 85, or 90, e.g. at least 91, 92, 93, 94, 95, 96, 97, 98, 99 or 99.5% to this sequence.

Non-limiting examples of possibly suitable FDH mutants comprise mutations in the positions D222 and/or R223 of SEQ ID NO:36. As examples we may mention D222X with X=G, A, K or N; and R223X with X=H or Y, and combinations of mutations in position 222 and 223.

24. The process according to one of the embodiments 20 to 23, wherein the $NADP^+$-accepting mutant is selected from the single mutant D222G according to SEQ ID NO:36 (herein also more often designated as "D221G" mutant (with counting, starting from Ala in position 2 of SEQ ID NO:36 as first amino acid) or the corresponding single mutants of an amino acid sequence derived therefrom with at least 60% sequence identity, e.g. at least 65, 70, 75, 80, 85, or 90, e.g. at least 91, 92, 93, 94, 95, 96, 97, 98, 99 or 99.5% to this sequence. As concrete examples, we may mention FDH mutants according to SEQ ID NO: 15, 19 and 35.

Further suitable FDH enzymes are accessible starting from the wild-type enzymes that can be isolated e.g. from *Candida boidinii* or *Pseudomonas* sp, and insertion of at least one functional mutation corresponding to the above mutations for altering the cofactor specificity. Moreover, there have been numerous studies in the prior art for improving various FDH properties, such as chemical or thermal stability or catalytic activity. These are summarized e.g. in Tishkov et al., Biomolecular Engineering 23 (2006), 89-110. Thus, single or multiple point mutations described there can be combined, for example for increasing enzyme stability, with the mutations described according to the invention for modified cofactor usage.

25. A nucleic acid sequence, selected from nucleic acid sequences a) simultaneously coding for an FDH mutant according to one of the embodiments 22 to 24 and a 7β-HSDH mutant according to one of the embodiments 1 to 6 and optionally a 3α-HSDH; or b) simultaneously coding for an FDH mutant according to one of the embodiments 22 to 24 and an unmutated 7β-HSDH and optionally a 3α-HSDH; or c) coding for a fusion protein comprising an FDH mutant according to one of the embodiments 22 to 24 and a 7β-HSDH mutant according to one of the embodiments 1 to 6 and optionally a 3α-HSDH; or d) coding for a fusion protein comprising an FDH mutant according to one of the embodiments 22 to 24 and an unmutated 7β-HSDH and optionally a 3α-HSDH, e) simultaneously coding for FDH wild type and a 7β-HSDH mutant according to one of the embodiments 1 to 6 and optionally a 3α-HSDH; or f) coding for a fusion protein, comprising the FDH wild type, a 7β-HSDH mutant according to one of the embodiments 1 to 6 and optionally a 3α-HSDH; g) simultaneously coding for a GDH, a 7β-HSDH wild type and optionally a 3α-HSDH; h) coding for a fusion protein, comprising a GDH, a 7β-HSDH wild type and optionally a 3α-HSDH; i) simultaneously coding for a GDH, a 7β-HSDH mutant according to one of the embodiments 1 to 6 and optionally a 3α-HSDH; and k) coding for a fusion protein, comprising a GDH, a 7β-HSDH mutant according to one of the embodiments 1 to 6 and optionally a 3α-HSDH;

wherein the coding sequences can be contained, independently of one another, singly or multiply in the construct, for example in 2, 3, 4, 5, or 6 to 10 copies. Through selection of the appropriate copy number, optionally occurring activity differences in the individual expression products can be compensated.

26. Expression cassette, comprising a nucleic acid sequence according to embodiment 25 under the genetic control of at least one regulatory nucleic acid sequence, wherein the coding sequences, independently of one another, can be contained singly or multiply in the construct, for example in 2, 3, 4, 5, or 6 to 10 copies. Through selection of the appropriate copy number, optionally occurring activity differences in the individual expression products can be compensated.

27. A vector comprising at least one expression cassette according to embodiment 26, wherein the coding sequences, independently of one another, can be contained singly or multiply in the vector construct, for example in 2, 3, 4, 5, or 6 to 10 copies. Through selection of the appropriate copy number, optionally occurring activity differences in the individual expression products can be compensated.

28. A recombinant microorganism bearing at least one nucleic acid sequence according to embodiment 25 or at least one expression cassette according to embodiment 27 or bearing at least one vector according to embodiment 28.

29. A recombinant microorganism that is capable of simultaneous expression of 7β-HSDH (wild type), an $NADP^+$-accepting FDH mutant and/or the corresponding FDH wild type and optionally of 3α-HSDH; or which is capable of simultaneous expression of 7β-HSDH (wild type), a GDH described herein and optionally a 3α-HSDH described herein.

30. A recombinant microorganism that is capable of simultaneous expression of a 7β-HSDH mutant, an $NADP^+$-accepting FDH mutant and/or the corresponding FDH wild type and optionally of 3α-HSDH; or which is capable of simultaneous expression of a 7β-HSDH mutant, a GDH described herein and optionally a 3α-HSDH described herein.

31. The recombinant microorganism according to embodiment 30, wherein the 7β-HSDH mutant is a mutant according to one of the embodiments 1 to 6.

32. The recombinant microorganism according to embodiment 29 or 30, wherein the FDH mutant is a mutant according to the definition in one of the embodiments 20 to 24; and wherein the FDH wild type is an FDH from *Mycobacterium vaccae* N10 according to SEQ ID NO:36 or an FDH derived therefrom with at least 60% sequence identity, e.g. at least 65, 70, 75, 80, 85, or 90, e.g. at least 91, 92, 93, 94, 95, 96, 97, 98, 99 or 99.5% to this sequence.

33. The recombinant microorganism according to embodiment 29 or 30, wherein the 3α-HSDH is an enzyme comprising an amino acid sequence according to SEQ ID NO: 6 or 8 or 22 or an amino acid sequence derived therefrom with at least 60% sequence identity, e.g. at least 65, 70, 75, 80, 85, or 90, e.g. at least 91, 92, 93, 94, 95, 96, 97, 98, 99 or 99.5% to this sequence.

34. The recombinant microorganism according to one of the embodiments 29 to 33, bearing the coding sequences for 7β-HSDH, FDH and 3α-HSDH on one or more (different) expression constructs. The invention therefore relates to recombinant microorganisms, which are modified (for example transformed) with a single-plasmid system, bearing the coding sequences for 7β-HSDH or mutants thereof, FDH or mutants thereof and 3α-HSDH or mutants thereof in one or more copies, for example in 2, 3, 4, 5, or 6 to 10 copies. The invention therefore also relates to recombinant microorganisms, which are modified (for example transformed) with a single-plasmid system, bearing the coding sequences for 7β-HSDH or mutants thereof, GDH or mutants thereof and 3α-HSDH or mutants thereof in one or more copies, for example in 2, 3, 4, 5 or 6 to 10 copies. The enzymes (7β-HSDH, FDH and 3α-HSDH or mutants thereof) can, however, also be contained on 2 or 3 separate, mutually compatible plasmids in one or more copies. Suitable basis vectors for preparing single-plasmid systems and multicopy plasmids are known by a person skilled in the art. As examples we may mention, for single-plasmid system, e.g. pET21a and for multicopy plasmids e.g. the duet vectors marketed by the company Novagen, such as pACYCDuet-1, pETDuet-1, pCDFDuet-1, pRSFDuet-1 and pCOLADuet-1. Vectors of this kind, their compatibility with other vectors and microbial host strains are given e.g. in the "User Protocol TB340 Rev. E0305" of the company Novagen.

The optimal combination of enzymes for the generation of plasmid systems can be undertaken by a person skilled in the art without undue effort, taking into account the teaching of the present invention. Thus, a person skilled in the art can, for example, depending on the cofactor specificity of the 7β-HSDH enzyme used in each case, select the most suitable enzyme for cofactor regeneration, selected from the aforementioned dehydrogenases, especially FDH, GDH and the respective mutants thereof.

Furthermore, there is the possibility of distributing the enzymes selected for the reaction on two or more plasmids and, with the resultant plasmids, producing two or more different recombinant microorganisms, which are then used together for the biocatalytic reaction according to the invention. The particular enzyme combination used for preparing the plasmid can in particular also be applied specifying comparable cofactor usage. For example, a first microorganism can be modified with a plasmid, which bears the coding sequence for an NADPH-dependent 7β-HSDH mutant and an FDH mutant regenerating this cofactor according to the present invention, or which bears the coding sequence for an NADPH-dependent 7β-HSDH mutant and NADPH-regenerating GDH, or the coding sequence for an NADH-dependent 7β-HSDH and an NADH-regenerating FDH and/or GDH. A second microorganism can, in contrast, be modified with a plasmid that bears the coding sequence for an NADH-dependent 3α-HSDH and the coding sequence for an NADH-regenerating FDH wild type and/or for an NADH-regenerating GDH. Both microorganisms can then be used simultaneously for the biocatalytic reaction according to the invention.

The use of two separate biocatalysts (recombinant microorganisms) can offer two essential advantages over the use of only one biocatalyst, in which all synthesis enzymes are expressed:

a) The two biocatalysts can be genetically modified and optimized separately from one another. In particular it is possible to use different cofactor regeneration enzymes, which are either optimized for NADH regeneration or for NADPH regeneration.

b) For the biocatalysis, the biocatalysts can be used in different proportions. This permits intervention in the individual reaction rates of the multienzyme process during biocatalysis, even after all biocatalysts have already been prepared.

Surprisingly, it was also possible to show, in the context of the present invention, that the additional membrane transport steps of the substances that are to react, made necessary by the use of two biocatalysts, have little or no effect on the reaction rates, so that these presumed negative aspects are outweighed by the advantages of the two-cell system.

35. A process for the preparation of ursodeoxycholic acid (UDCA) of formula (1)

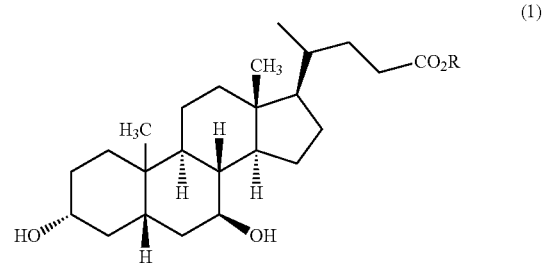

in which

R stands for alkyl, $NR^1R^2$, H, an alkali metal ion or $N(R^3)_4^+$, in which the residues $R^3$ may be identical or different and stand for H or alkyl, wherein a) optionally a cholic acid (CA) of formula (2)

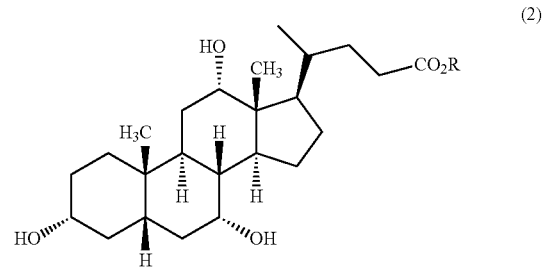

in which R has the meanings given above, is oxidized chemically to the dehydrocholic acid (DHCA) of formula (3)

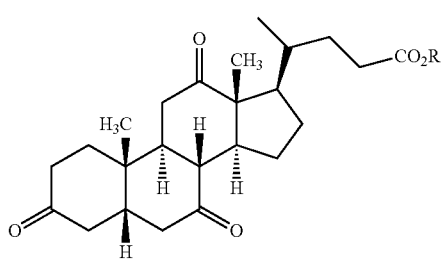

(3)

in which R has the meanings given above;

b) DHCA is reduced in the presence of at least one 7β-HSDH mutant (present as isolated enzyme or expressed by a corresponding recombinant microorganism) according to the definition in one of the embodiments 1 to 6 and in the presence of at least one 3α-hydroxysteroid dehydrogenase (3α-HSDH) (present as isolated enzyme or expressed by a corresponding recombinant microorganism) to the corresponding 12-keto-ursodeoxycholic acid (12-keto UDCA) of formula (5)

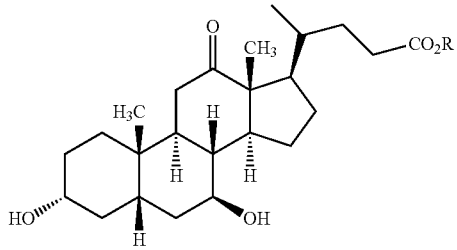

(5)

in which R has the meanings given above, (in the presence of and with consumption of NADH and/or NADPH) and then d) 12-keto-UDCA of formula (5) is reduced chemically to UDCA; and e) the reaction product is optionally further purified.

Process step b) can be configured differently. Either both enzymes (7β-HSDH mutant and 3α-HSDH) can be present simultaneously (e.g. one-pot reaction with both isolated enzymes or one or more corresponding recombinant microorganisms are present, which express both enzymes), or the partial reactions can take place in any order (first the 7β-HSDH-mutant-catalyzed reduction and then the 3α-HSDH-catalyzed reduction; or first the 3α-HSDH-catalyzed reduction and then the 7β-HSDH mutant-catalyzed reduction).

A process variant for the preparation of UDCA of formula (1) could therefore be for example as follows:

a) optionally a cholic acid (CA) of formula (2) is oxidized chemically;

b) DHCA is reduced in the presence of at least one 7β-HSDH mutant (present as isolated enzyme or expressed by a corresponding recombinant microorganism) according to the definition in one of the embodiments 1 to 6 to the 3,12-diketo-7β-cholanic acid (3,12-diketo-7β-CA) of formula (4)

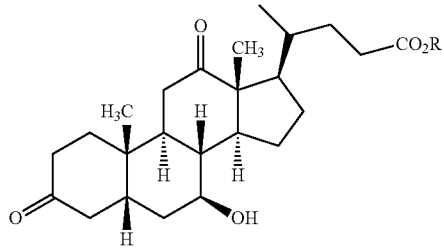

(4)

(in the presence of and with consumption of NADPH and/or NADH), c) 3,12-diketo-7β-CA is reduced in the presence of at least one 3α-hydroxysteroid dehydrogenase (3α-HSDH) (present as isolated enzyme or expressed by a corresponding recombinant microorganism) to the corresponding 12-keto-ursodeoxycholic acid (12-keto UDCA) of formula (5)

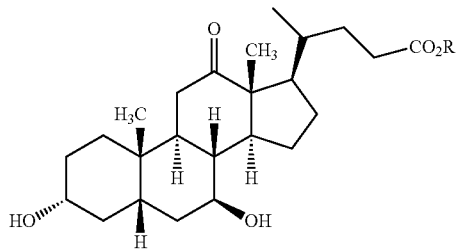

(5)

in which R has the meanings given above, (in the presence of and with consumption of NADH and/or NADPH, depending on the 3α-HSDH used) and then d) 12-keto-UDCA of formula (5) is reduced chemically to UDCA; and e) the reaction product is optionally further purified.

36. The process according to embodiment 35, wherein steps b) and c) are carried out in the presence of one or more recombinant microorganisms described herein, such as at least one microorganism according to embodiment 10.

37. The process according to embodiment 35 or 36, wherein steps b) and/or c) are coupled to identical or different cofactor regeneration systems (present as isolated enzyme or expressed by a corresponding recombinant microorganism).

38. The process according to embodiment 37, wherein step b) is coupled to a cofactor regeneration system, in which NADPH is regenerated by an NADP$^+$-accepting FDH mutant according to the definition in one of the embodiments 20 to 24 with consumption of formic acid or a salt thereof; or is coupled to a cofactor regeneration system, in which NADPH is regenerated by an ADH with consumption of isopropanol; or is coupled to a cofactor regeneration system in which NADPH is regenerated by a GDH with consumption of glucose; or is coupled to a cofactor regeneration system in which spent NADH is regenerated by an NADH regenerating GDH, ADH or FDH.

39. The process according to embodiment 37 or 38, wherein step c) is coupled to a cofactor regeneration step, in which NADPH is regenerated by an NADP$^+$-accepting FDH mutant according to the definition in one of the embodiments 20 to 24 with consumption of formic acid or a salt thereof; or wherein step c) is coupled to a cofactor regeneration step in which NADH is regenerated by an NADH-regenerating FDH mutant according to the definition in one of the embodiments 20 to 24 or by the unmutated FDH with consumption of formic acid or a salt thereof or by an NADH-regenerating GDH with consumption of glucose.

40. A process for microbial preparation of ursodeoxycholic acid (UDCA) of formula (1)

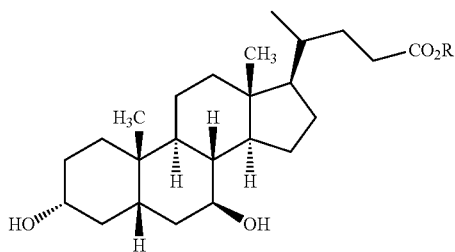

(1)

in which

R stands for alkyl, $NR^1R^2$, H, an alkali metal ion or $N(R^3)_4^+$, in which the residues $R^3$ may be identical or different and stand for H or alkyl, wherein a) optionally a cholic acid (CA) of formula (2)

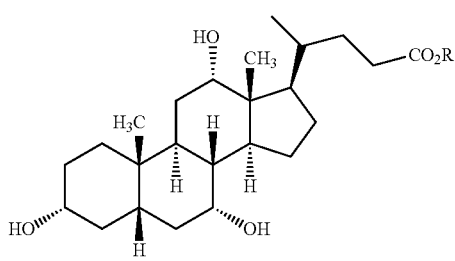

(2)

in which R has the meanings given above, is oxidized chemically to the dehydrocholic acid (DHCA) of formula (3)

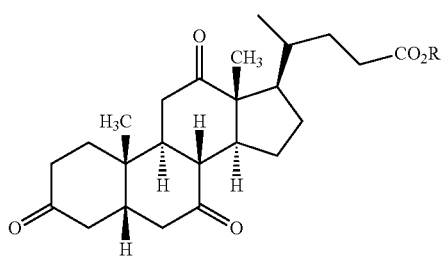

(3)

in which R has the meanings given above;

b) DHCA is reduced in the presence of at least one 7β-HSDH and in the presence of at least one 3α-HSDH to the corresponding 12-keto-ursodeoxycholic acid (12-keto UDCA) of formula (5)

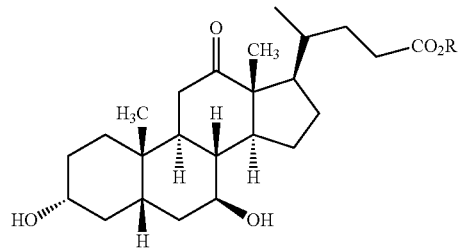

(5)

in which R has the meanings given above, (in the presence of and with consumption of NADH and/or NADPH) and then c) 12-keto-UDCA of formula (5) is reduced chemically to UDCA; and d) the reaction product is optionally further purified;

wherein the reactions of step b) take place microbially, i.e. in the presence of whole cells of one or more different recombinant microorganisms according to one of the embodiments 28 or 29 to 34, wherein the microorganism or microorganisms carry the enzymes necessary for the reaction and cofactor regeneration in a manner described in more detail herein, or else using at least one nucleic acid sequence according to embodiment 25.

For example, DHCA can be reduced in the presence of at least one 7β-HSDH or mutant thereof to 3,12-diketo-7β-cholanic acid (3,12-diketo-7β-CA) of formula (4)

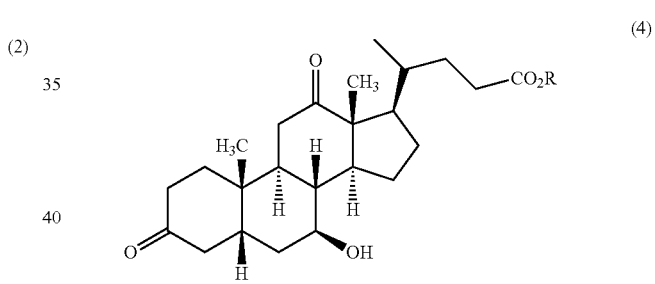

(4)

(in the presence of and with consumption of NADPH), and 3,12-diketo-7β-CA can be reduced in the presence of at least one 3α-hydroxysteroid dehydrogenase (3α-HSDH) or mutant thereof to the corresponding 12-keto-ursodeoxycholic acid (12-keto UDCA) of formula (5)

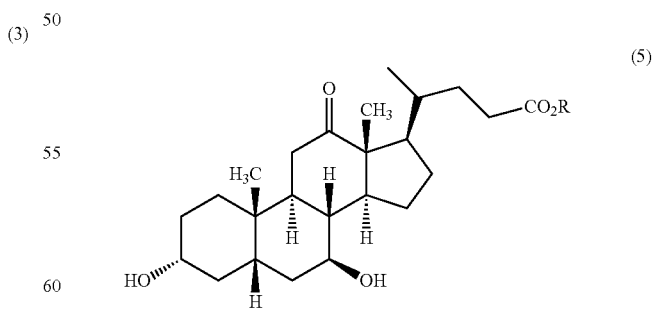

(5)

in which R has the meanings given above, (in the presence of and with consumption of NADH and/or NADPH).

Furthermore, however, a reaction sequence is also conceivable, comprising the reduction of DHCA first with 3α-HSDH and the subsequent reduction of the resultant reaction product with 7β-HSDH, as well as both reaction sequences taking place simultaneously, on the basis of the simultaneous presence of both HSDHs.

41. The process according to embodiment 40, wherein one or more, in particular one, recombinant microorganism according to one of the embodiments 29 to 34 is used, which for example simultaneously expresses at least one 7β-HSDH mutant according to one of the embodiments 1 to 6, at least one NADP$^+$-accepting FDH mutant according to one of the embodiments 20 to 24 and at least one 3α-HSDH, such as in particular according to SEQ ID NO: 6, 8 or 22 or mutants thereof in a sequence identity of at least about 60%; or which simultaneously expresses at least one 7β-HSDH mutant according to one of the embodiments 1 to 6, at least one GDH and at least one 3α-HSDH, such as in particular according to SEQ ID NO: 6, 8 or 22 or mutants thereof in a sequence identity of at least about 60%.

42. A bioreactor for carrying out a process according to one of the embodiments 35 to 41, in particular containing at least one of the enzymes (7β-HSDH, FDH, and/or 3α-HSDH or mutants thereof; or 7β-HSDH, GDH and/or 3α-HSDH or mutants thereof) or a recombinant microorganism recombinantly expressing at least one of these enzymes, especially in immobilized form.

The present invention is not limited to the concrete embodiments described herein. Rather, a person skilled in the art will be enabled, through the teaching of the present invention, to provide further configurations of the invention without undue effort. He can, for example, also purposefully generate further enzyme mutants and screen and optimize these for the desired property profile (improved cofactor dependence and/or stability, reduced substrate inhibition); or isolate further suitable wild-type enzymes (7β- and 3α-HSDHs, FDHs, GDHs ADHs etc.) and use them according to the invention. Furthermore, for example depending on the property profile (especially cofactor dependence) of the HSDHs used, such as in particular 7β-HSDH and 3α-HSDH or mutants thereof, he can select suitable dehydrogenases usable for cofactor regeneration (GDH, FHD, ADH etc.) and mutants thereof, and distribute the selected enzymes to one or more expression constructs or vectors and therefore if necessary produce one or more recombinant microorganisms, which then make an optimized whole-cell-based method of production possible.

Further Configurations of the Invention

1. General Definitions and Abbreviations Used

Unless stated otherwise, the term "7β-HSDH" denotes a dehydrogenase enzyme, which catalyzes at least the stereospecific and/or regiospecific reduction of DHCA or 7,12-diketo-3α-CA (7,12-diketo-LCA) to 3,12-diketo-7β-CA or 12-keto-UDCA in particular with stoichiometric consumption of NADPH, and optionally the corresponding reverse reaction. The enzyme can be a native or recombinantly produced enzyme. The enzyme can basically be mixed with cellular, for example protein impurities, but preferably is in pure form. Suitable methods of detection are described for example in the experimental section given below or are known from the literature (e.g. *Characterization of NADP-dependent 7 beta-hydroxysteroid dehydrogenases from Peptostreptococcus productus and Eubacterium aerofaciens.* S Hirano and N Masuda. Appl Environ Microbiol. 1982). Enzymes with this activity are classified under the EC number 1.1.1.201.

Unless stated otherwise, the term "3α-HSDH" denotes a dehydrogenase enzyme that catalyzes at least the stereospecific and/or regiospecific reduction of 3,12-diketo-7β-CA or DHCA to 12-keto-UDCA or 7,12-diketo-3α-CA (7,12-diketo-LCA), in particular with stoichiometric consumption of NADH and/or NADPH, and optionally the corresponding reverse reaction. Suitable methods of detection are described for example in the experimental section given below or are known from the literature. Suitable enzymes are obtainable e.g. from *Comanomonas testosteroni* (e.g. ATCC11996). An NADPH-dependent 3α-HSDH is known for example from rodents and can also be used. (Cloning and sequencing of the cDNA for rat liver 3 alpha-hydroxysteroid/dihydrodiol dehydrogenase, J E Pawlowski, M Huizinga and T M Penning, May 15, 1991, The Journal of Biological Chemistry, 266, 8820-8825). Enzymes with this activity are classified under EC number 1.1.1.50.

Unless stated otherwise, the term "GDH" denotes a dehydrogenase enzyme that catalyzes at least the oxidation of β-D-glucose to D-glucono-1,5-lactone with stoichiometric consumption of NAD$^+$ and/or NADP$^+$ and optionally the corresponding reverse reaction. Suitable enzymes are obtainable e.g. from *Bacillus subtilis* or *Bacillus megaterium*. Enzymes with this activity are classified under EC number 1.1.1.47. Unless stated otherwise, the term "FDH" denotes a dehydrogenase enzyme that catalyzes at least the oxidation of formic acid (or corresponding formate salts) to carbon dioxide with stoichiometric consumption of NAD$^+$ and/or NADP$^+$, and optionally the corresponding reverse reaction. Suitable methods of detection are for example described in the experimental section given below or are known from the literature. Suitable enzymes are obtainable e.g. from *Candida boidinii, Pseudomonas* sp, or *Mycobacterium vaccae*. Enzymes with this activity are classified under EC number 1.2.1.2.

A "pure form" or a "pure" or "substantially pure" enzyme is to be understood according to the invention as an enzyme with a degree of purity above 80, preferably above 90, especially above 95, and quite particularly above 99 wt %, relative to the total protein content, determined by means of usual methods of detecting proteins, for example the biuret method or protein detection according to Lowry et al. (cf. description in R. K. Scopes, Protein Purification, Springer Verlag, New York, Heidelberg, Berlin (1982)).

A "redox equivalent" means a low-molecular organic compound usable as electron donor or electron acceptor, for example nicotinamide derivatives such as NAD$^+$ and NADH$^+$ or their reduced forms NADH and NADPH respectively. "Redox equivalent" and "cofactor" are used as synonyms in the context of the present invention. Thus, a "cofactor" in the sense of the invention can also be described as "redox-capable cofactor", i.e. as a cofactor that can be present in a reduced and an oxidized form.

A "spent" cofactor is to be understood as the reduced or oxidized form of the cofactor, which in the course of a specified reduction or oxidation reaction of a substrate is transformed into the corresponding oxidized or reduced form. By regeneration, the oxidized or reduced cofactor form that is formed in the reaction is converted back to the reduced or oxidized starting form, so that it is available again for the reaction of the substrate.

An "altered cofactor usage" is to be understood in the context of the present invention as a qualitative or quantitative change compared to a reference. In particular, an altered cofactor usage can be observed by undertaking amino acid sequence mutations. This change can then be determined compared to the unmutated starting enzyme. Moreover, the activity with respect to a particular cofactor can be increased or reduced by undertaking a mutation or can be prevented completely. An altered cofactor usage also comprises, however, changes such that instead of a specificity for an individual cofactor, now at least one further second cofactor, different from the first cofactor, is usable (i.e. there is an extended cofactor usage). Conversely, however, a capacity for usage of two different cofactors that was originally present can be altered so that specificity is only increased for one of these cofactors or only reduced for one of these cofactors or is completely eliminated. For example, an enzyme that is dependent on the cofactor NAD (NADH) can now, owing to a change of the cofactor usage, be dependent both on NAD (NADH) and the cofactor NADP (NADPH) or the original dependence on NAD (NADH) can be completely transformed to a dependence on NADP (NADPH) and vice versa.

The terms "NAD$^+$/NADH dependence" or "NADP$^+$/NADPH dependence", unless stated otherwise, are to be interpreted widely according to the invention. These terms comprise both "specific" dependences, i.e. exclusively dependence on NAD$^+$/NADH or NADP$^+$/NADPH, as well as the dependence of the enzymes used according to the invention on both cofactors, i.e. dependence on NAD$^+$/NADH and NADP$^+$/NADPH.

This applies correspondingly to the terms "NAD$^+$/NADH-accepting" or "NADP$^+$/NADPH-accepting".

The terms "NAD$^+$/NADH-regenerating" or "NADP$^+$/NADPH-regenerating", unless stated otherwise, are to be interpreted widely according to the invention. These terms comprise both "specific" i.e. exclusive capacity for regenerating spent cofactor NAD$^+$/NADH or NADP$^+$/NADPH, and the capacity for regenerating both cofactors, i.e. NAD$^+$/NADH and NADP$^+$/NADPH.

"Proteinogenic" amino acids comprise in particular (single-letter code): G, A, V, L, I, F, P, M, W, S, T, C, Y, N, Q, D, E, K, R and H.

"Immobilization" means, according to the invention, the covalent or noncovalent binding of a biocatalyst used according to the invention, for example a 7β-HSDH on a solid, i.e. essentially insoluble in the surrounding liquid medium, carrier material. According to the invention, whole cells, such as the recombinant microorganisms used according to the invention, can correspondingly also be immobilized by means of such carriers.

A "substrate inhibition reduced in comparison with the unmutated enzyme" means that the substrate inhibition observed with the unmutated enzyme for a particular substrate is no longer observed, i.e. essentially is no longer measurable, or only occurs at higher substrate concentration, i.e. the $K_i$ value is increased.

"Cholic acid compound" means compounds according to the invention with the carbon skeleton structure, especially the steroid structure of cholic acid and the presence of keto and/or hydroxy or acyloxy groups in ring position 7 and optionally ring positions 3 and/or 12.

A compound of a special type, for example a "cholic acid compound" or an "ursodeoxycholic acid compound" in particular also means derivatives of the underlying starting compound (for example cholic acid or ursodeoxycholic acid).

Said derivatives comprise "salts", for example alkali metal salts such as lithium, sodium and potassium salts of the compounds; and ammonium salts, wherein an ammonium salt comprises the NH$_4^+$ salt or those ammonium salts in which at least one hydrogen atom can be replaced with a C$_1$-C$_6$-alkyl residue. Typical alkyl residues are, in particular, C$_1$-C$_4$-alkyl residues, such as methyl, ethyl, n- or i-propyl-, n-, sec- or tert-butyl, and n-pentyl and n-hexyl and the singly or multiply branched analogs thereof.

"Alkyl esters" of compounds according to the invention are, in particular, lower alkyl esters, for example C$_1$-C$_6$-alkyl esters. As nonlimiting examples, we may mention methyl, ethyl, n- or i-propyl, n-, sec- or tert-butyl esters, or longer-chain esters, for example n-pentyl and n-hexyl esters and the singly or multiply branched analogs thereof.

"Amides" are, in particular, reaction products of acids according to the invention with ammonia or primary or secondary monoamines. Such amines are for example mono- or di-C$_1$-C$_6$-alkyl monoamines, wherein the alkyl residues can optionally be further substituted independently of one another, for example with carboxyl, hydroxyl, halogen (such as F, C, Br, I), nitro and sulfonate groups.

"Acyl groups" according to the invention are, in particular, nonaromatic groups with 2 to 4 carbon atoms, for example acetyl, propionyl and butyryl, and aromatic groups with an optionally substituted mononuclear aromatic ring, wherein suitable substituents are selected for example from hydroxyl, halogen (such as F, C, Br, I), nitro and C$_1$-C$_6$-alkyl groups, for example benzoyl or toluoyl.

The hydroxysteroid compounds used or prepared according to the invention, for example cholic acid, ursodeoxycholic acid, 12-keto-chenodeoxycholic acid, chenodeoxycholic acid and 7-keto-lithocholic acid, can be used in stereoisomerically pure form or in a mixture with other stereoisomers in the process according to the invention or obtained therefrom. Preferably, however, the compounds used or prepared are used or isolated in substantially stereoisomerically pure form.

The following table gives the structural formulas, chemical names and the abbreviations used for important chemical compounds:

| Formula | Abbreviation | Chemical name |
|---|---|---|
| 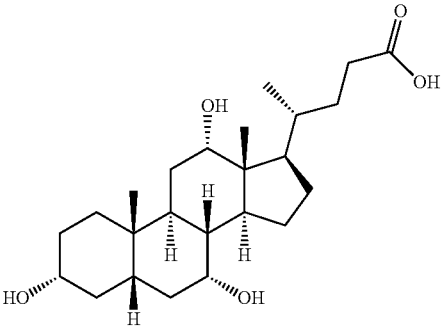 Cholic acid | CA | Cholic acid |

-continued
| Formula | Abbreviation | Chemical name |
|---|---|---|
| 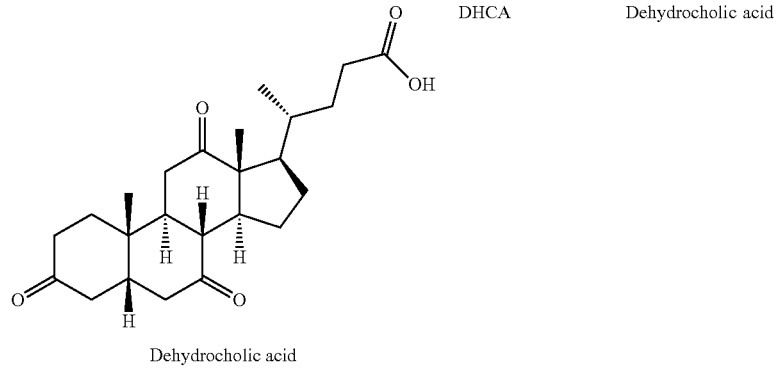 Dehydrocholic acid | DHCA | Dehydrocholic acid |
| 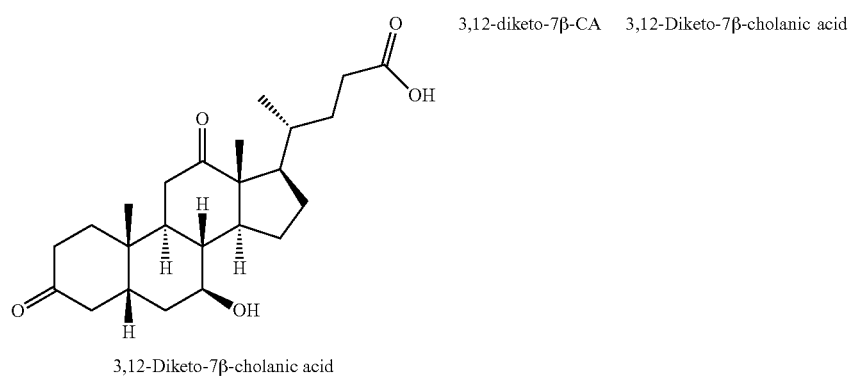 3,12-Diketo-7β-cholanic acid | 3,12-diketo-7β-CA | 3,12-Diketo-7β-cholanic acid |
| 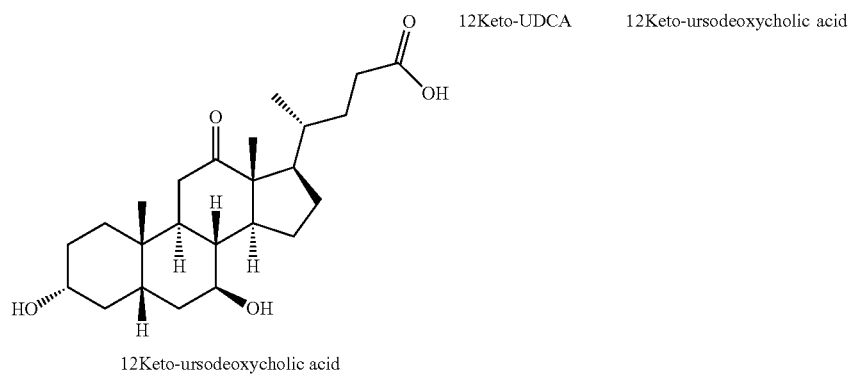 12Keto-ursodeoxycholic acid | 12Keto-UDCA | 12Keto-ursodeoxycholic acid |
| 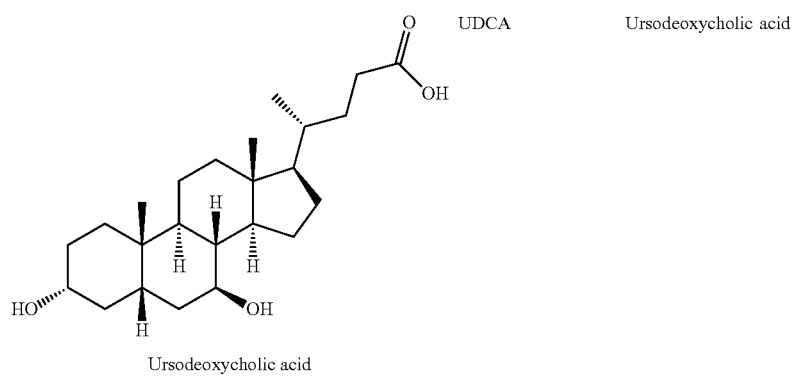 Ursodeoxycholic acid | UDCA | Ursodeoxycholic acid |

-continued

| Formula | Abbreviation | Chemical name |
|---|---|---|
| Cholic acid methyl ester | CA methyl ester | Cholic acid methyl ester |
| 3,7-Diacetyl-cholic acid methyl ester | 3,7-diacetyl-CA-methyl ester | 3,7-Diacetyl-cholic acid methyl ester* |
| 12-Keto-3,7-diacetyl cholanic acid methyl ester | 12-keto-3,7-diacetyl-CA methyl ester | 12-Keto-3,7-diacetyl cholanic acid methyl ester* |
| Chenodeoxycholic acid | CDCA | Chenodeoxycholic acid |

-continued

| Formula | Abbreviation | Chemical name |
|---|---|---|
| 7-Keto-lithocholic acid (structure) | 7-Keto-LCA | 7-Keto-lithocholic acid |
| 7,12-Diketo-lithocholic acid (structure) | 7,12-Diketo-LCA | 7,12-Diketo-lithocholic acid |
| 12-Keto-chenodeoxycholic acid (structure) | 12-Keto-CDCA | 12-Keto-chenodeoxycholic acid |

2. Proteins

The present invention is not limited to the concretely disclosed proteins or enzymes with 7β-HSDH, FDH, GDH or 3α-HSDH activity or mutants thereof, but rather also extends to functional equivalents thereof.

"Functional equivalents" or analogs of the concretely disclosed enzymes are, in the context of the present invention, polypeptides that are different from them, but still possess the desired biological activity, for example 7β HSDH activity.

For example, "functional equivalents" are to be understood as enzymes that have, in the test used for 7β-HSDH, FDH, GDH or 3α-HSDH activity, an activity that is higher or lower by at least 1%, e.g. at least 10% or 20%, e.g. at least 50% or 75% or 90% than that of a starting enzyme, comprising an amino acid sequence defined herein.

Functional equivalents are in addition preferably stable in the pH range from 4 to 11 and advantageously possess an optimal pH in a pH range from 6 to 10, such as in particular 8.5 to 9.5, and an optimal temperature in the range from 15° C. to 80° C. or 20° C. to 70° C., for example about 45 to 60° C. or about 50 to 55° C.

The 7β-HSDH activity can be detected using various known tests. Without being restricted to this, we may mention a test using a reference substrate, e.g. CA or DHCA, under standardized conditions, as defined in the experimental section.

Tests for determining the FDH, GDH or 3α-HSDH activity are also known per se.

"Functional equivalents" according to the invention also means, in particular, "mutants", which have in at least one sequence position of the aforementioned amino acid sequences an amino acid other than that concretely stated, but nevertheless possess one of the aforementioned biological activities. "Functional equivalents" therefore comprise the mutants obtainable by one or more, for example 1, 2, 3, 4, 5, 6, 7, 8, 9, 10, 11, 12, 13, 14 or 15, amino acid additions, substitutions, deletions and/or inversions, wherein the stated changes can occur in any sequence position, provided they lead to a mutant with the property profile according to the invention. Functional equivalence in particular also obtains when the patterns of reactivity between mutant and unaltered polypeptide coincide qualitatively, i.e. for example the same substrates are converted at different rates. Examples of suitable amino acid substitutions are presented in the following table:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| Ile | Leu; Val |
| Leu | Ile; Val |
| Lys | Arg; Gln; Glu |
| Met | Leu; Ile |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described and "functional derivatives" and "salts" of the polypeptides.

"Precursors" are natural or synthetic precursors of the polypeptides with or without the desired biological activity.

The expression "salts" means both salts of carboxyl groups and acid addition salts of amino groups of the protein molecules according to the invention. Salts of carboxyl groups can be prepared in a manner known per se and comprise inorganic salts, for example sodium, calcium, ammonium, iron and zinc salts, and salts with organic bases, for example amines, such as triethanolamine, arginine, lysine, piperidine and the like. Acid addition salts, for example salts with mineral acids, such as hydrochloric acid or sulfuric acid and salts with organic acids, such as acetic acid and oxalic acid, are also an object of the invention.

"Functional derivatives" of polypeptides according to the invention can also be prepared on functional amino acid side groups or on their N- or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, prepared by reaction with acyl groups; or O-acyl derivatives of free hydroxyl groups, prepared by reaction with acyl groups.

"Functional equivalents" naturally also comprise polypeptides that are obtainable from other organisms, and naturally occurring variants. For example, by sequence comparison, homologous sequence regions can be found and equivalent enzymes can be determined based on the concrete instructions of the invention.

"Functional equivalents" also comprise fragments, preferably individual domains or sequence motifs, of the polypeptides according to the invention, which for example have the desired biological function.

"Functional equivalents" are in addition fusion proteins that have one of the aforementioned polypeptide sequences or functional equivalents derived therefrom and at least one further, functionally different therefrom, heterologous sequence in functional N- or C-terminal linkage (i.e. without mutual substantial functional impairment of the fusion protein parts). Nonlimiting examples of said heterologous sequences are e.g. signal peptides, histidine anchors or enzymes.

"Functional equivalents" that are also included according to the invention are homologs of the concretely disclosed proteins. These possess at least 60%, preferably at least 75%, especially at least 85%, for example 90, 91, 92, 93, 94, 95, 96, 97, 98 or 99%, homology (or identity) to one of the concretely disclosed amino acid sequences, calculated according to the algorithm of Pearson and Lipman, Proc. Natl. Acad. Sci. (USA) 85(8), 1988, 2444-2448. A percentage homology or identity of a homologous polypeptide according to the invention means, in particular, percentage identity of the amino acid residues relative to the total length of one of the amino acid sequences concretely described herein.

The percentage identity values can also be determined on the basis of BLAST alignments, the blastp (protein-protein BLAST) algorithm, or using the Clustal settings given below.

In the case of a possible protein glycosylation, "functional equivalents" according to the invention comprise proteins of the type designated above in deglycosylated or glycosylated form and modified forms obtainable by altering the glycosylation pattern.

Homologs of the proteins or polypeptides according to the invention can be produced by mutagenesis, e.g. by point mutation, lengthening or shortening of the protein.

Homologs of the proteins according to the invention can be identified by screening combinatorial libraries of mutants, for example shortened mutants. For example, a variegated database of protein variants can be produced by combinatorial mutagenesis at the nucleic acid level, for example by enzymatic ligation of a mixture of synthetic oligonucleotides. There are a great many methods that can be used for preparing libraries of potential homologs from a degenerated oligonucleotide sequence. The chemical synthesis of a degenerated gene sequence can be carried out in an automatic DNA synthesizer, and the synthetic gene can then be ligated into a suitable expression vector. The use of a degenerated set of genes makes it possible to provide all sequences in one mixture, which encode the desired set of potential protein sequences. Methods of synthesis of degenerated oligonucleotides are known by a person skilled in the art (e.g. Narang, S. A. (1983) Tetrahedron 39: 3; Itakura et al. (1984) Annu. Rev. Biochem. 53: 323; Itakura et al., (1984) Science 198: 1056; Ike et al. (1983) Nucleic Acids Res. 11: 477).

Several techniques are known in the prior art for screening gene products of combinatorial libraries, that have been produced by point mutations or shortening, and for screening cDNA libraries for gene products with a selected property. These techniques can be adapted to the rapid screening of gene banks that have been produced by combinatorial mutagenesis of homologs according to the invention. The techniques used most often for screening large gene banks, which are based on a high-throughput analysis, comprise cloning the gene bank into replicatable expression vectors, transforming suitable cells with the resultant vector bank and expressing the combinatorial genes under conditions in which detection of the desired activity facilitates the isolation of the vector that encodes the gene whose product was detected. Recursive ensemble mutagenesis (REM), a technique that increases the frequency of functional mutants in the banks, can be used in combination with the screening tests, in order to identify homologs (Arkin and Yourvan (1992) PNAS 89: 7811-7815; Delgrave et al. (1993) Protein Engineering 6(3): 327-331).

The invention further comprises the use of the 7β-HSDH wild type from *Collinsella aerofaciens* ATCC 25986, as described in the applicant's earlier international patent application PCT/EP2010/068576, which is expressly referred to hereby.

This 7β-HSDH obtainable from *Collinsella aerofaciens* DSM 3979 is in particular characterized by at least one other of the following properties, for example 2, 3, 4, 5, 6 or 7 or all such properties:

a) molecular weight (SDS-gel electrophoresis): about 28-32 kDa, especially about 29 to 31 kDa or about 30 kDa;

b) molecular weight (gel filtration, in nondenaturing conditions, such as in particular without SDS): about 53 to 60 kDa, especially about 55 to 57 kDa, such as 56.1 kDa. This proves the dimeric nature of the 7β-HSDH from *Collinsella aerofaciens* DSM 3979;

c) stereoselective reduction of the 7-carbonyl group of 7-keto-LCA to a 7β-hydroxyl group;

d) optimal pH for the oxidation of UDCA in the range from pH 8.5 to 10.5, especially 9 to 10;

e) optimal pH for the reduction of DHCA and 7-keto-LCA in the range from pH 3.5 to 6.5, especially at pH 4 to 6;

f) at least one kinetic parameter from the following table for at least one of the substrates/cofactors mentioned there; in the range of 20%, especially 10%, 5%, 3%, 2% or ±1% around the value stated concretely in each case in the following table.

| | $K_M$ (µM) | $V_{max}$ (U/mg protein)[b] | $k_{cat}$ (1 µmol/ (µmol × min)) |
|---|---|---|---|
| NADP+ | 5.32 | 30.58 | 944.95 |
| NADPH | 4.50 | 33.44 | 1033.44 |
| UDCA | 6.23 | 38.17 | 1179.39 |
| 7-Keto-LCA | 5.20 | 30.77 | 950.77 |
| DHCA | 9.23 | 28.33 | 875.35 |
| NAD+ | —[a] | — | Traces |
| NADH | — | — | Traces |

[a] could not be determined, owing to the very low activity
[b] 1 U = 1 µmol/min g) phylogenetic sequence similarity of the prokaryotic 7β-HSDH from *Collinsella aerofaciens* DSM 3979, related to the animal 11β-HSDH subgroup, comprising *Cavia porcellus*, *Homo sapiens* and *Mus musculus*.

For example, this 7β-HSDH shows the following properties or combinations of properties: a); b); a) and b); a) and/or b) and c); a) and/or b) and c) and d); a) and/or b) and c) and d) and e); a) and/or b) and c) and d) and e) and f).

A 7β-HSDH of this kind or a functional equivalent derived therefrom is moreover characterized by
a) the stereospecific reduction of a 7-ketosteroid to the corresponding 7β-hydroxysteroid, and/or
b) the regiospecific hydroxylation of a ketosteroid comprising a keto group in 7-position and at least one further keto group on the steroid skeleton to the corresponding 7β-hydroxysteroid, such as in particular catalyzed by dehydrocholic acid (DHCA) in 7-position to the corresponding 3,12-diketo-7β-cholanic acid, and e.g. is NADPH-dependent.

Said 7β-HSDH has in particular an amino acid sequence according to SEQ ID NO:2 (accession No.: ZP_01773061) or a sequence derived therefrom with a degree of identity of at least 60%, e.g. at least 65, 70, 75, 80, 85, or 90, e.g. at least 91, 92, 93, 94, 95, 96, 97, 98, 99 or 99.5% to this sequence; optionally additionally characterized by one of the following properties or combinations of properties: a); b); a) and b); a) and/or b) and c); a) and/or b) and c) and d); a) and/or b) and c) and d) and e); a) and/or b) and c) and d) and e) and f) according to the above definition.

3. Nucleic Acids and Constructs 3. 1 Nucleic Acids

The invention also relates to nucleic acid sequences that code for an enzyme with 7β-HSDH, FDH, GDH and/or 3α-HSDH activity and the mutants thereof.

The present invention also relates to nucleic acids with a specified degree of identity to the concrete sequences described herein.

"Identity" between two nucleic acids means the identity of the nucleotides over the total nucleic acid length in each case, especially the identity that is calculated by comparison by means of the Vector NTI Suite 7.1 software of the company Informax (USA) employing the Clustal method (Higgins D G, Sharp P M. Fast and sensitive multiple sequence alignments on a microcomputer. Comput Appl Biosci. 1989 April; 5(2): 151-1) setting the following parameters:

| Multiple alignment parameters: | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighting | 0 |
| Pairwise alignment parameters: | |
| FAST algorithm | on |
| K-tuple size | 1 |
| Gap penalty | 3 |
| Window size | 5 |
| Number of best diagonals | 5 |

As an alternative, the identity can also be determined according to Chenna, Ramu, Sugawara, Hideaki, Koike, Tadashi, Lopez, Rodrigo, Gibson, Toby J, Higgins, Desmond G, Thompson, Julie D. Multiple sequence alignment with the Clustal series of programs. (2003) Nucleic Acids Res 31 (13): 3497-500, according to internet address: http://www.ebi.ac.uk/Tools/clustlw/index.html# and with the following parameters:

| DNA gap open penalty | 15.0 |
|---|---|
| DNA gap extension penalty | 6.66 |
| DNA matrix | Identity |
| Protein gap open penalty | 10.0 |
| Protein gap extension penalty | 0.2 |
| Protein matrix | Gonnet |
| Protein/DNA ENDGAP | −1 |
| Protein/DNA GAPDIST | 4 |

All nucleic acid sequences mentioned herein (single- and double-stranded DNA and RNA sequences, for example cDNA and mRNA) can be produced in a manner known per se by chemical synthesis from the nucleotide building blocks, for example by fragment condensation of individual overlapping, complementary nucleic acid building blocks of the double helix. The chemical synthesis of oligonucleotides can be carried out for example in a known manner by the phosphoroamidite method (Voet, Voet, 2nd edition, Wiley Press New York, pages 896-897). The adding on of synthetic oligonucleotides and filling of gaps using the Klenow fragment of DNA polymerase and ligation reactions and general cloning techniques are described in Sambrook et al. (1989), Molecular Cloning: A Laboratory Manual, Cold Spring Harbor Laboratory Press.

The invention also relates to nucleic acid sequences (single- and double-stranded DNA and RNA sequences, for example cDNA and mRNA) coding for one of the above polypeptides and functional equivalents thereof, which are accessible for example using artificial nucleotide analogs.

The invention relates both to isolated nucleic acid molecules, which code for polypeptides or proteins according to the invention or biologically active segments thereof, and to nucleic acid fragments that can be used e.g. as hybridization probes or primers for identification or amplification of coding nucleic acids according to the invention.

The nucleic acid molecules according to the invention can moreover contain untranslated sequences from the 3'- and/or 5'-end of the coding gene region.

The invention further comprises the nucleic acid molecules complementary to the concretely described nucleotide sequences, or a segment thereof.

The nucleotide sequences according to the invention make it possible to produce probes and primers that can be used for identification and/or cloning of homologous sequences in other cell types and organisms. These probes or primers usually comprise a nucleotide sequence region, which hybridizes under "stringent" conditions (see below) to at least about 12, preferably at least about 25, for example about 40, 50 or 75 successive nucleotides of a sense strand of a nucleic acid sequence according to the invention or a corresponding antisense strand.

An "isolated" nucleic acid molecule is separated from other nucleic acid molecules that are present in the natural source of the nucleic acid and can moreover be essentially free from other cellular material or culture medium, when it is produced by recombinant techniques, or free from chemical precursors or other chemicals, when it is synthesized chemically.

A nucleic acid molecule according to the invention can be isolated using standard techniques of molecular biology and the sequence information provided according to the invention. For example, cDNA can be isolated from a suitable cDNA library, using one of the concretely disclosed complete sequences or a segment thereof as hybridization probe and standard hybridization techniques (as described for example in Sambrook, J., Fritsch, E. F. and Maniatis, T. Molecular Cloning: A Laboratory Manual. 2nd ed., Cold Spring Harbor Laboratory, Cold Spring Harbor Laboratory Press, Cold Spring Harbor, N.Y., 1989). Moreover, a nucleic acid molecule, comprising one of the disclosed sequences or a segment thereof, can be isolated by polymerase chain reaction, using the oligonucleotide primers that are prepared on the basis of this sequence. The nucleic acid thus amplified can be cloned into a suitable vector and can be characterized by DNA sequence analysis. The oligonucleotides according to the invention can also be produced by standard synthesis techniques, e.g. with an automatic DNA synthesizer.

Nucleic acid sequences according to the invention or derivatives thereof, homologs or parts of these sequences can be isolated for example with usual hybridization methods or PCR technology from other bacteria, e.g. via genomic or cDNA libraries. These DNA sequences hybridize under standard conditions to the sequences according to the invention.

"Hybridize" means the capacity of a polynucleotide or oligonucleotide for binding to an almost complementary sequence under standard conditions, whereas under these conditions nonspecific bindings do not occur between non-complementary partners. For this, the sequences can be complementary to 90-100%. The property of complementary sequences of being able to bind specifically to one another is utilized for example in Northern or Southern blotting or in primer binding in PCR or RT-PCR.

Advantageously, short oligonucleotides of the conserved regions are used for hybridization. It is also possible, however, to use longer fragments of the nucleic acids according to the invention or the complete sequences for hybridization. These standard conditions vary depending on the nucleic acid used (oligonucleotide, longer fragment or complete sequence) or depending on which type of nucleic acid, DNA or RNA, is used for the hybridization. Thus, for example, the melting points for DNA:DNA hybrids are approx. 10° C. lower than those of DNA:RNA hybrids of the same length.

Standard conditions mean for example, depending on the nucleic acid, temperatures between 42 and 58° C. in an aqueous buffer solution with a concentration between 0.1 and 5×SSC (1×SSC=0.15 M NaCl, 15 mM sodium citrate, pH 7.2) or additionally in the presence of 50% formamide such as for example 42° C. in 5×SSC, 50% formamide. Advantageously the hybridization conditions for DNA:DNA hybrids are 0.1×SSC and temperatures between about 20° C. and 45° C., preferably between about 30° C. and 45° C. For DNA:RNA hybrids the hybridization conditions are advantageously 0.1×SSC and temperatures between about 30° C. and 55° C., preferably between about 45° C. and 55° C. These temperatures stated for the hybridization are for example calculated melting point values for a nucleic acid with a length of approx. 100 nucleotides and a G+C content of 50% in the absence of formamide. The experimental conditions for DNA hybridization are described in relevant genetics textbooks, for example Sambrook et al., "Molecular Cloning", Cold Spring Harbor Laboratory, 1989, and can be calculated from formulas known by a person skilled in the art for example depending on the length of the nucleic acids, the type of hybrids or the G+C content. A person skilled in the art can find further information on hybridization from the following textbooks: Ausubel et al. (eds), 1985, Current Protocols in Molecular Biology, John Wiley & Sons, New York; Hames and Higgins (eds), 1985, Nucleic Acids Hybridization: A Practical Approach, IRL Press at Oxford University Press, Oxford; Brown (ed), 1991, Essential Molecular Biology: A Practical Approach, IRL Press at Oxford University Press, Oxford.

"Hybridization" can in particular take place under stringent conditions. These hybridization conditions are described for example in Sambrook, J., Fritsch, E. F., Maniatis, T., in: Molecular Cloning (A Laboratory Manual), 2nd edition, Cold Spring Harbor Laboratory Press, 1989, pages 9.31-9.57 or in Current Protocols in Molecular Biology, John Wiley & Sons, N.Y. (1989), 6.3.1-6.3.6.

"Stringent" hybridization conditions are understood in particular as: incubation at 42° C. overnight in a solution consisting of 50% formamide, 5×SSC (750 mM NaCl, 75 mM trisodium citrate), 50 mM sodium phosphate (pH7.6), 5×Denhardt solution, 10% dextran sulfate and 20 g/ml denatured, sheared salmon sperm DNA, followed by a filter washing step with 0.1×SSC at 65° C.

The invention also relates to derivatives of the concretely disclosed or derivable nucleic acid sequences.

Thus, further nucleic acid sequences according to the invention can be derived e.g. from SEQ ID NO:1, 5, 7, 14, 19, 34 or 47 and differ from them by addition, substitution, insertion or deletion of individual or several nucleotides, but furthermore code for polypeptides with the desired property profile.

The invention also covers those nucleic acid sequences that comprise so-called silent mutations or are altered corresponding to the codon usage of a special original or host organism, compared to a concretely stated sequence, as well as naturally occurring variants, for example splice variants or allele variants, thereof.

The invention also relates to sequences obtainable by conservative nucleotide substitutions (i.e. the amino acid in question is replaced with an amino acid of the same charge, size, polarity and/or solubility).

The invention also relates to the molecules derived by sequence polymorphisms from the concretely disclosed nucleic acids. These genetic polymorphisms can exist between individuals within a population owing to natural variation. These natural variations usually bring about a variance from 1 to 5% in the nucleotide sequence of a gene.

Derivatives of the nucleic acid sequence according to the invention with the sequence SEQ ID NO:1, 5, 7, 14, 19, 34 or 47 mean for example allele variants that have at least 60% homology at the derived amino acid level, preferably at least 80% homology, quite especially preferably at least 90% homology over the total sequence region (regarding homology at the amino acid level, reference may be made to the above information for the polypeptides). The homologies can advantageously be higher on partial regions of the sequences.

Furthermore, derivatives are also to be understood as homologs of the nucleic acid sequences according to the invention, especially of SEQ ID NO:1, 5, 7, 14, 19, 34 or 47, for example fungal or bacterial homologs, shortened sequences, single-stranded DNA or RNA of the coding and noncoding DNA sequence. For example, homologs to SEQ ID NO:1, 5, 7, 14, 19, 34 or 47 possess, at DNA level, a homology of at least 40%, preferably of at least 60%, especially preferably of at least 70%, quite especially preferably of at least 80% over the whole DNA region given in SEQ ID NO:1, 5, 7, 14, 19, 34 or 47.

In addition, derivatives are to be understood for example as fusions with promoters. The promoters that precede the stated nucleotide sequences can be altered by at least one nucleotide exchange, at least one insertion, inversion and/or deletion, but without the functionality or effectiveness of the promoters being impaired. Moreover, the effectiveness of the promoters can be increased by altering their sequence or they can be exchanged completely with more effective promoters even of organisms of a different species.

Furthermore, methods for producing functional mutants are known by a person skilled in the art.

Depending on the technology used, a person skilled in the art can insert completely random or even more targeted mutations in genes or also noncoding nucleic acid regions (which are for example important for the regulation of expression) and then prepare gene banks. The methods of molecular biology required for this are known by a person skilled in the art and for example are described in Sambrook and Russell, Molecular Cloning. 3rd edition, Cold Spring Harbor Laboratory Press 2001.

Methods for modifying genes and therefore for modifying the protein that these encode have long been familiar to a person skilled in the art, such as for example
- site-directed mutagenesis, giving targeted exchange of individual or several nucleotides of a gene (Trower M K (Publ.) 1996; In vitro mutagenesis protocols. Humana Press, New Jersey),
- saturation mutagenesis, in which a codon for any amino acid can be exchanged or added at any site of a gene (Kegler-Ebo D M, Docktor C M, DiMaio D (1994) Nucleic Acids Res 22: 1593; Barettino D, Feigenbutz M, Valcarel R, Stunnenberg H G (1994) Nucleic Acids Res 22: 541; Barik S (1995) Mol Biotechnol 3: 1),
- the error-prone polymerase chain reaction (error-prone PCR), in which nucleotide sequences are mutated by incorrectly functioning DNA polymerases (Eckert K A, Kunkel T A (1990) Nucleic Acids Res 18: 3739);
- the passaging of genes in mutator strains, in which, for example owing to defective DNA-repair mechanisms, there is an increased mutation rate of nucleotide sequences (Greener A, Callahan M, Jerpseth B (1996) An efficient random mutagenesis technique using an E. coli mutator strain. In: Trower M K (Publ.) In vitro mutagenesis protocols. Humana Press, New Jersey), or
- DNA shuffling, in which a pool of closely related genes is formed and digested and the fragments are used as template for a polymerase chain reaction, in which through repeated strand separation and bringing together again, finally mosaic genes of full length are produced (Stemmer W P C (1994) Nature 370: 389; Stemmer W P C (1994) Proc Natl Acad Sci USA 91: 10747).

Using so-called directed evolution (described inter alia in Reetz M T and Jaeger K-E (1999), Topics Curr Chem 200: 31; Zhao H, Moore J C, Volkov A A, Arnold F H (1999), Methods for optimizing industrial enzymes by directed evolution, In: Demain A L, Davies J E (Publ.) Manual of industrial microbiology and biotechnology. American Society for Microbiology), a person skilled in the art can produce functional mutants in a targeted manner and on a large scale. In a first step, firstly gene banks of the respective proteins are produced, for example using the methods given above. The gene banks are expressed in a suitable manner, for example by bacteria or by phage-display systems.

The relevant genes of host organisms that express functional mutants with properties that largely correspond to the desired properties can be submitted to another round of mutation. The steps of mutation and of selection or screening can be repeated iteratively until the functional mutants present have the desired properties to a sufficient degree. With this iterative procedure, a limited number of mutations, for example 1 to 5 mutations, can be performed in steps and assessed and selected for their influence on the relevant enzyme property. The selected mutant can then be submitted to another mutation step in the same way. As a result, the number of individual mutants to be investigated can be reduced significantly.

The results according to the invention provide important information regarding structure and sequence of the enzymes in question, which is necessary for targeted generation of further enzymes with desired modified properties. In particular, so-called "hot spots" can be defined, i.e. sequence segments that are potentially suitable for modifying an enzyme property by introducing targeted mutations.

3.2 Constructs

The invention further relates to expression constructs containing, under the genetic control of regulatory nucleic acid sequences, a nucleic acid sequence coding for at least one polypeptide according to the invention; and vectors, comprising at least one of these expression constructs.

"Expression unit" means, according to the invention, a nucleic acid with expression activity, which comprises a promoter, as defined herein, and, after functional linking with a nucleic acid to be expressed or a gene, regulates the expression, i.e. the transcription and the translation of this nucleic acid or of this gene. Therefore the term "regulatory nucleic acid sequence" is also used in this context. In addition to the promoter, other regulatory elements, for example enhancers, can be present.

"Expression cassette" or "expression construct" means, according to the invention, an expression unit that is functionally linked to the nucleic acid to be expressed or the gene to be expressed. In contrast to an expression unit, an expression cassette therefore comprises not only nucleic acid sequences that regulate transcription and translation, but also the nucleic acid sequences that should be expressed as protein as a result of the transcription and translation.

The terms "expression" or "overexpression" describe, in the context of the invention, the production or increase in the intracellular activity of one or more enzymes in a microorganism, which are encoded by the corresponding DNA. For this, for example a gene can be inserted in an organism, a gene that is present can be replaced with another gene, the copy number of the gene or genes can be increased, a strong promoter can be used or a gene can be used that codes for a corresponding enzyme with a high activity, and these measures can optionally be combined.

Preferably said constructs according to the invention comprise a promoter 5'-upstream of the respective coding sequence and 3-downstream a terminator sequence and optionally further usual regulatory elements, in each case operatively linked with the coding sequence.

"Promoter", a "nucleic acid with promoter activity" or a "promoter sequence" mean, according to the invention, a nucleic acid, which in functional linkage with a nucleic acid to be transcribed, regulates the transcription of said nucleic acid.

"Functional" or "operational" linkage means in this context for example the sequential arrangement of one of the nucleic acids with promoter activity and a nucleic acid sequence to be transcribed and optionally further regulatory elements, for example nucleic acid sequences that ensure the transcription of nucleic acids, and for example a terminator, in such a way that each of the regulatory elements can fulfill its function in the transcription of the nucleic acid sequence. This does not necessarily require a direct linkage in the chemical sense. Genetic control sequences, for example enhancer sequences, can exert their function on the target sequence even from more remote positions or even from other DNA molecules. Arrangements are preferred in which the nucleic acid sequence to be transcribed is positioned behind the promoter sequence (i.e. at the 3'-end), so that the two sequences are linked together covalently.

The distance between the promoter sequence and the nucleic acid sequence that is to undergo transgene expression can be less than 200 base pairs, or less than 100 base pairs or less than 50 base pairs.

In addition to promoters and terminators, examples of other regulatory elements that may be mentioned are targeting sequences, enhancers, polyadenylation signals, selectable markers, amplification signals, replication origins and the like. Suitable regulatory sequences are described for example in Goeddel, Gene Expression Technology: Methods in Enzymology 185, Academic Press, San Diego, Calif. (1990).

Nucleic acid constructs according to the invention comprise, in particular, sequence SEQ ID NO:1, 5, 7, 14, 19, 34 or 47 or derivatives and homologs thereof, and the nucleic acid sequences that can be derived therefrom, which can advantageously be linked operationally or functionally with one or more regulatory signals for controlling, e.g. increasing, gene expression.

In addition to these regulatory sequences, the natural regulation of these sequences can still be present before the actual structural genes and optionally can have been genetically modified, so that the natural regulation is switched off and expression of the genes is increased. However, the nucleic acid construct can also be of simpler construction, i.e. no additional regulatory signals have been inserted before the coding sequence and the natural promoter with its regulation has not been removed. Instead, the natural regulatory sequence is mutated so that regulation no longer occurs and gene expression is increased.

A preferred nucleic acid construct advantageously also contains one or more of the aforementioned "enhancer" sequences, functionally linked to the promoter, which make increased expression of the nucleic acid sequence possible. Additional advantageous sequences can also be inserted at the 3-end of the DNA sequences, such as further regulatory elements or terminators. The construct can contain one or more copies of the nucleic acids according to the invention. The construct can also contain further markers, such as antibiotic resistances or auxotrophic complementation genes, optionally for selection of the construct.

Examples of suitable regulatory sequences are contained in promoters such as cos, tac, trp, tet, trp-tet, lpp, lac, lpp-lac, lacI$^{q-}$, T7, T5, T3, gal, trc, ara, rhaP (rhaP$_{BAD}$)SP6, lambda-P$_R$ or in the lambda-P$_L$ promoter, which advantageously find application in Gram-negative bacteria. Further advantageous regulatory sequences are contained for example in the Gram-positive promoters amy and SPO2, in the yeast or fungus promoters ADC1, MFalpha, AC, P-60, CYC1, GAPDH, TEF, rp28, ADH. Artificial promoters can also be used for regulation.

For expression in a host organism, the nucleic acid construct is advantageously inserted into a vector, for example a plasmid or a phage, which makes optimal expression of the genes in the host possible. Apart from plasmids and phages, vectors are also to be understood as all other vectors known by a person skilled in the art, e.g. viruses, such as SV40, CMV, baculovirus and adenovirus, transposons, IS elements, phasmids, cosmids, and linear or circular DNA. These vectors can be replicated autonomously in the host organism or can be replicated chromosomally. These vectors represent another configuration of the invention.

Suitable plasmids are for example pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, Agt1 or pBdC in *E. coli*, pIJ101, pIJ364, pIJ702 or pIJ361 in *Streptomyces*, pUB110, pC194 or pBD214 in *Bacillus*, pSA77 or pAJ667 in *Corynebacterium*, pALS1, pIL2 or pBB116 in fungi, 2alphaM, pAG-1, YEp6, YEp13 or pEMBLYe23 in yeasts or pLGV23, pGHlac$^+$, pBIN19, pAK2004 or pDH51 in plants. The aforementioned plasmids represent a small selection of the possible plasmids. Further plasmids are well known by a person skilled in the art and can for example be found in the book Cloning Vectors (eds. Pouwels P. H. et al. Elsevier, Amsterdam-New York-Oxford, 1985, ISBN 0 444 904018).

In another configuration of the vector, the vector containing the nucleic acid construct according to the invention or the nucleic acid according to the invention can also advantageously be inserted in the form of a linear DNA into the microorganisms and can be integrated by heterologous or homologous recombination into the genome of the host organism. This linear DNA can consist of a linearized vector such as a plasmid or only of the nucleic acid construct or the nucleic acid according to the invention.

For optimal expression of heterologous genes in organisms, it is advantageous to modify the nucleic acid sequences according to the specific "codon usage" used in the organism. The "codon usage" can easily be determined on the basis of computer evaluations of other known genes of the organism in question.

An expression cassette according to the invention is prepared by fusion of a suitable promoter with a suitable coding nucleotide sequence and a terminator or polyadenylation signal. For this, usual recombination and cloning techniques are used, such as are described for example in T. Maniatis, E. F. Fritsch and J. Sambrook, Molecular Cloning: A Laboratory Manual, Cold Spring Harbor Laboratory, Cold Spring Harbor, N.Y. (1989) and in T. J. Sihavy, M. L. Berman and L. W. Enquist, Experiments with Gene Fusions, Cold Spring Harbor Laboratory, Cold Spring Harbor, N.Y. (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector, which makes optimal expression of the genes in the host possible. Vectors are well known by a person skilled in the art and can be found for example in "Cloning Vectors" (Pouwels P. H. et al., Publ., Elsevier, Amsterdam-New York-Oxford, 1985).

4. Microorganisms

Depending on context, the term "microorganism" means the starting (wild-type) microorganism or a genetically modified, recombinant microorganism, or both.

Using the vectors according to the invention, recombinant microorganisms can be produced, which for example have been transformed with at least one vector according to the invention and can be used for producing the polypeptides according to the invention. Advantageously, the recombinant constructs according to the invention described above are introduced into a suitable host system and expressed. Preferably, common cloning and transfection methods known by a person skilled in the art are used, for example coprecipitation, protoplast fusion, electroporation, retroviral transfection and the like, to bring about expression of the stated nucleic acids in the respective expression system. Suitable systems are described for example in Current Protocols in Molecular Biology, F. Ausubel et al., Publ., Wiley Interscience, New York 1997, or Sambrook et al. Molecular Cloning: A Laboratory Manual. 2nd ed., Cold Spring Harbor Laboratory, Cold Spring Harbor Laboratory Press, Cold Spring Harbor, N.Y., 1989. A review of bacterial expression systems for the heterologous expression of proteins is also provided for example by Terpe, K. Appl. Microbiol. Biotechnol. (2006) 72: 211-222.

In principle, all prokaryotic or eukaryotic organisms may come into consideration as recombinant host organisms for the nucleic acid according to the invention or the nucleic acid construct. Advantageously, microorganisms such as bacteria, fungi or yeasts are used as host organisms. Advantageously, Gram-positive or Gram-negative bacteria are used, preferably bacteria of the families Enterobacteriaceae, Pseudomonadaceae, Rhizobiaceae, Streptomycetaceae or Nocardiaceae, especially preferably bacteria of the genera *Escherichia, Pseudomonas, Streptomyces, Nocardia, Burkholderia, Salmonella, Agrobacterium, Clostridium* or *Rhodococcus*. The genus and species *Escherichia coli* is quite especially preferred. Further advantageous bacteria can be found, moreover, in the group of alpha-proteobacteria, beta-proteobacteria or gamma-proteobacteria.

The host organism or the host organisms according to the invention preferably contain at least one of the nucleic acid sequences, nucleic acid constructs or vectors described in this invention, which code for an enzyme with 7β-HSDH activity according to the above definition.

The organisms used in the process according to the invention are grown or cultured in a manner known by a person skilled in the art, depending on the host organism. Microorganisms are as a rule grown in a liquid medium, which contains a carbon source generally in the form of sugars, a nitrogen source generally in the form of organic nitrogen sources such as yeast extract or salts such as ammonium sulfate, trace elements such as iron, manganese, magnesium salts and optionally vitamins, at temperatures between 0° C. and 100° C., preferably between 10° C. and 60° C. with oxygen aeration. The pH of the liquid nutrient medium can be maintained at a fixed value, i.e. during growing it may or may not be regulated. Culture can be batchwise, semi-batchwise or continuous. Nutrients can be supplied at the start of fermentation or can be replenished semi-continuously or continuously.

5. Preparation of UDCA

Step 1: Chemical Reaction from CA to DHCA

The hydroxy groups of CA are oxidized with chromic acid or chromates in acidic solution (e.g. $H_2SO_4$) to carbonyl groups in a manner known per se by the classical chemical route. DHCA is formed.

Step 2: Enzymatic or Microbial Conversion of DHCA to 12-Keto-UDCA

In aqueous solution, DHCA is reduced by 3α-HSDH and 7β-HSDH or mutants thereof specifically to 12-keto-UDCA in the presence of NADPH or NADH. The cofactor NADPH or NADH can be regenerated by an ADH or FDH or GDH or mutants thereof from isopropanol or sodium formate or glucose. The reaction goes under mild conditions. For example, the reaction can be carried out at pH=6 to 9, especially about pH=8 and at about 10 to 30, 15 to 25 or about 23° C.

In the case of a microbial reaction step, recombinant microorganisms that express the necessary enzyme activity/activities can be cultured in the presence of the substrate to be converted (DHCA) anaerobically or aerobically in suitable liquid media. Suitable cultivation conditions are known per se by a person skilled in the art. They comprise reactions in the pH range of for example 5 to 10 or 6 to 9, at temperatures in the range from 10 to 60 or 15 to 45 or 25 to 40 or 37° C. Suitable media comprise for example the LB and TB media described below. The reaction can take place for example batchwise or continuously or in other usual process variants (as described above). The reaction time can for example range from minutes to several hours or days, and can be e.g. 1 h to 48 h. Optionally, if enzyme activity is not expressed continuously, this can be induced by adding a suitable inductor, after reaching a target cell density, e.g. of about $OD_{600}$=0.5 to 1.0.

Further possible suitable modifications of the microbial production process with respect to fermentation mode, additions to the medium, enzyme immobilization and isolation of the valuable substances can also be found in the following section concerning "Production of the enzymes or mutants".

Step 3: Chemical Conversion of 12-Keto-UDCA to UDCA

The 12-carbonyl group of 12-keto-UDCA is removed by means of Wolff-Kishner reduction in a manner known per se, with formation of UDCA from 12-keto-UDCA. In the reaction, first the carbonyl group is reacted with hydrazine to hydrazone. Then the hydrazone is heated in the presence of a base (e.g. KOH) to 200° C., with cleavage of nitrogen and formation of UDCA.

6. Recombinant Production of the Enzymes and Mutants

The invention further relates to processes for recombinant production of polypeptides according to the invention or functional, biologically active fragments thereof, wherein a polypeptide-producing microorganism is cultured, optionally expression of the polypeptides is induced and the latter are isolated from the culture. The polypeptides can also be produced on an industrial scale in this way, if this is desirable.

The microorganisms produced according to the invention can be cultured continuously or discontinuously in the batch method (batch culture) or in the fed batch or repeated fed batch method. A summary of known cultivation methods can be found in Chmiel's textbook (Bioprozeßtechnik 1. Einführung in die Bioverfahrenstechnik [Bioprocess technology 1. Introduction to bioprocess engineering] (Gustav Fischer Verlag, Stuttgart, 1991)) or in the textbook by Storhas (Bioreaktoren und periphere Einrichtungen [Bioreactors and peripheral equipment]) (Vieweg Verlag, Brunswick/Wiesbaden, 1994)).

The culture medium to be used must suitably fulfill the requirements of the respective strains. Descriptions of culture media for various microorganisms are given in the manual "Manual of Methods for General Bacteriology" of the American Society for Bacteriology (Washington D.C., USA, 1981).

These media usable according to the invention usually comprise one or more carbon sources, nitrogen sources, inorganic salts, vitamins and/or trace elements.

Preferred carbon sources are sugars, such as mono-, di- or polysaccharides. Very good carbon sources are for example glucose, fructose, mannose, galactose, ribose, sorbose, ribulose, lactose, maltose, sucrose, raffinose, starch or cellulose. Sugars can also be added to the media via complex compounds, such as molasses, or other by-products of sugar refining. It may also be advantageous to add mixtures of various carbon sources. Other possible carbon sources are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Nitrogen sources are usually organic or inorganic nitrogen compounds or materials that contain these compounds. Examples of nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as corn-steep liquor, soybean flour, soybean protein, yeast extract, meat extract and others. The nitrogen sources can be used individually or as a mixture.

Inorganic salt compounds that can be contained in the media comprise the chloride, phosphorus or sulfate salts of calcium, magnesium, sodium, cobalt, molybdenum, potassium, manganese, zinc, copper and iron.

The sulfur source used can be inorganic sulfur compounds such as sulfates, sulfites, dithionites, tetrathionates, thiosulfates, sulfides but also organic sulfur compounds, such as mercaptans and thiols.

The phosphorus source used can be phosphoric acid, potassium dihydrogen phosphate or dipotassium hydrogen phosphate or the corresponding sodium-containing salts.

Chelating agents can be added to the medium in order to keep the metal ions in solution. Especially suitable chelating agents comprise dihydroxyphenols, such as catechol or protocatechuate, or organic acids, such as citric acid.

The fermentation media used according to the invention usually also contain other growth factors, such as vitamins or growth promoters, which include for example biotin, riboflavin, thiamine, folic acid, nicotinic acid, panthothenate and pyridoxine. Growth factors and salts are often derived from complex components of the media, such as yeast extract, molasses, corn-steep liquor and the like. Moreover, suitable precursors can be added to the culture medium. The exact composition of compounds in the medium is strongly dependent on the particular experiment and is decided individually for each specific case. Information on media optimization can be found in the textbook "Applied Microbiol. Physiology, A Practical Approach" (Publ. P. M. Rhodes, P. F. Stanbury, IRL Press (1997) p. 53-73, ISBN 0 19 963577 3). Growth media can also be obtained from commercial suppliers, such as Standard 1 (Merck) or BHI (brain heart infusion, DIFCO) and the like.

All components of the media are sterilized, either with heat (20 min at 1.5 bar and 121° C.) or by sterile filtration. The components can either be sterilized together or separately if necessary. All components of the media can be present at the start of culture or can optionally be added continuously or batchwise.

The culture temperature is normally between 15° C. and 45° C., preferably at 25° C. to 40° C. and can be kept constant or varied during the experiment. The pH of the medium should be in the range from 5 to 8.5, preferably around 7.0. The culture pH can be controlled during culture by adding basic compounds such as sodium hydroxide, potassium hydroxide, ammonia or ammonia water or acid compounds such as phosphoric acid or sulfuric acid. To control foaming it is possible to use antifoaming agents, such as fatty acid polyglycol esters. For maintaining the stability of plasmids, suitable selectively acting substances, such as antibiotics, can be added to the medium. To maintain aerobic conditions, oxygen or oxygen-containing gas mixtures, such as ambient air, are fed into the culture. The culture temperature is normally at 20° C. to 45° C. Culture is continued until a maximum of the desired product has formed. This target is normally reached within 10 hours to 160 hours.

The fermentation broth is then processed further. Depending on the requirements, the biomass is removed from the fermentation broth completely or partially by separation techniques, such as centrifugation, filtration, decanting or a combination of these methods or can be left in it completely.

If the polypeptides are not secreted into the culture medium, the cells can also be disrupted and the product can be obtained from the lysate by known methods of protein isolation. The cells can optionally be disrupted with high-frequency ultrasound, by high pressure, for example in a French press, by osmolysis, by the action of detergents, lytic enzymes or organic solvents, using homogenizers or by a combination of several of the methods listed.

The polypeptides can be purified by known chromatographic methods, such as molecular sieve chromatography (gel filtration), such as Q-sepharose chromatography, ion exchange chromatography and hydrophobic chromatography, and with other usual methods such as ultrafiltration, crystallization, salting-out, dialysis and native gel electrophoresis. Suitable methods are described for example in Cooper, F. G., Biochemische Arbeitsmethoden [Methods of Biochemical Processing], Verlag Walter de Gruyter, Berlin, N.Y. or in Scopes, R., Protein Purification, Springer Verlag, New York, Heidelberg, Berlin.

For isolating the recombinant protein, it may be advantageous to use vector systems or oligonucleotides that lengthen the cDNA with defined nucleotide sequences and therefore code for modified polypeptides or fusion proteins, which for example serve for easier purification. Suitable modifications of this kind are for example so-called "tags" functioning as anchors, for example the modification known as hexa-histidine anchors, or epitopes that can be recognized as antigens by antibodies (described for example in Harlow, E. and Lane, D., 1988, Antibodies: A Laboratory Manual. Cold Spring Harbor (N.Y.) Press). These anchors can serve for attaching the proteins to a solid carrier, for example a polymer matrix, which can for example be packed in a chromatography column, or can be used on a microtiter plate or on some other support.

At the same time, these anchors can also be used for recognizing the proteins. For recognition of the proteins, in addition usual markers, such as fluorescent dyes, enzyme markers, which form a detectable reaction product after reaction with a substrate, or radioactive markers, can be used, alone or in combination with the anchors for derivatization of the proteins.

7. Enzyme Immobilization

In the method described herein, the enzymes according to the invention can be used free or immobilized. An immobilized enzyme is to be understood as an enzyme that is fixed to an inert support. Suitable support materials and the enzymes immobilized thereon are known from EP-A-1149849, EP-A-1 069 183 and DE-OS 100193773 and from the literature references cited therein. Regarding this, full reference is made to the disclosure of these documents. Suitable support materials include for example clays, clay minerals, such as kaolinite, diatomaceous earth, perlite, silicon dioxide, aluminum oxide, sodium carbonate, calcium carbonate, cellulose powder, anion exchanger materials, synthetic polymers, such as polystyrene, acrylic resins, phenol-formaldehyde resins, polyurethanes and polyolefins, such as polyethylene and polypropylene. For preparing the supported enzymes, the support materials are usually used in a finely-divided, particulate form, with porous forms being preferred. The particle size of the support material is usually not more than 5 mm, especially not more than 2 mm (particle-size distribution curve). Similarly, when using dehydrogenase as whole-cell catalyst, a free or immobilized form can be selected. Support materials are for example Ca-alginate, and carrageenan. Enzymes as well as cells can also be crosslinked directly with glutaraldehyde (crosslinking to CLEAs). Corresponding and further methods of immobilization are described for example in J. Lalonde and A. Margolin "Immobilization of Enzymes" and in K. Drauz and H. Waldmann, Enzyme Catalysis in Organic Synthesis 2002, Vol. III, 991-1032, Wiley-VCH, Weinheim.

Experimental Section

Unless stated otherwise, the cloning steps carried out in the context of the present invention, for example restriction cleavage, agarose gel electrophoresis, purification of DNA fragments, transfer of nucleic acids onto nitrocellulose and nylon membranes, linkage of DNA fragments, transformation of microorganisms, culturing of microorganisms, multiplication of phages and sequence analysis of recombinant DNA are carried out as described in Sambrook et al. (1989) op. cit.

A. General Information

Materials:

The genomic DNA of *Collinsella aerofaciens* DSM 3979 (ATCC 25986, former designation *Eubacterium aerofaciens*) was obtained from the German Collection of Microorganisms and Cell Cultures (DSMZ). UDCA and 7-keto-LCA are starting compounds that are known per se and are described in the literature. All other chemicals were obtained from Sigma-Aldrich and Fluka (Germany). All restriction endonucleases, T4 DNA ligase, Taq DNA polymerase, Phusion DNA polymerase and isopropyl-$\beta$-D-1-thiogalactopyranoside (IPTG) were obtained from Fermentas (Germany).

Media:

LB medium, containing tryptone 10 g, yeast extract 5 g, NaCl 10 g per liter of medium TB medium, containing tryptone 12 g, yeast extract 24 g, 4 mL glycerol, 10% TB buffer (11.55 g $KH_2PO_4$, 62.7 g $K_2HPO_4$, $H_2O$ to 500 mL) per liter of medium Minimal medium, modified according to Wilms et al., BIOTECHNOLOGY AND BIOENGINEERING, 2001 VOL. 73, No. 2, 95-103

Expression Vectors and Vector Constructs

Figure 3A:
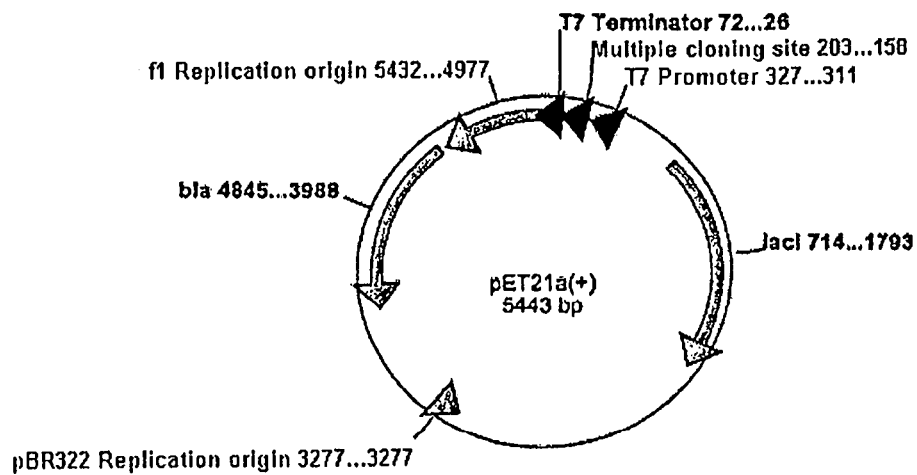
FIG. 3A, FIG. 3B, FIG. 3C and FIG. 3D shows the construction schemes of (A) pET21a(+), pET22b(+), pCOLA (Mod) and pET28a(+), respectively.
Figure 3B:
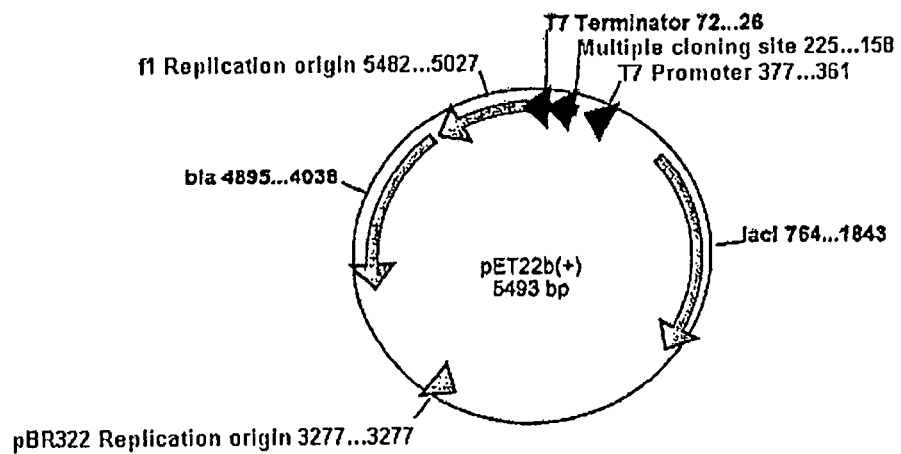
Figure 3C:
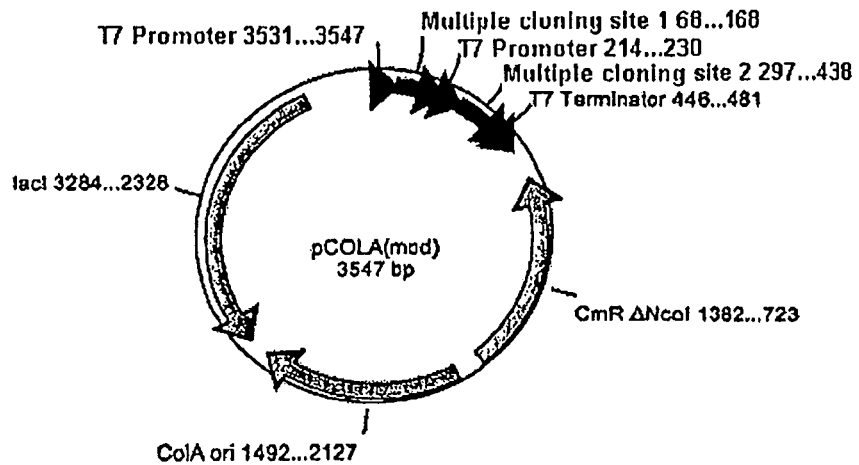
Figure 3D:
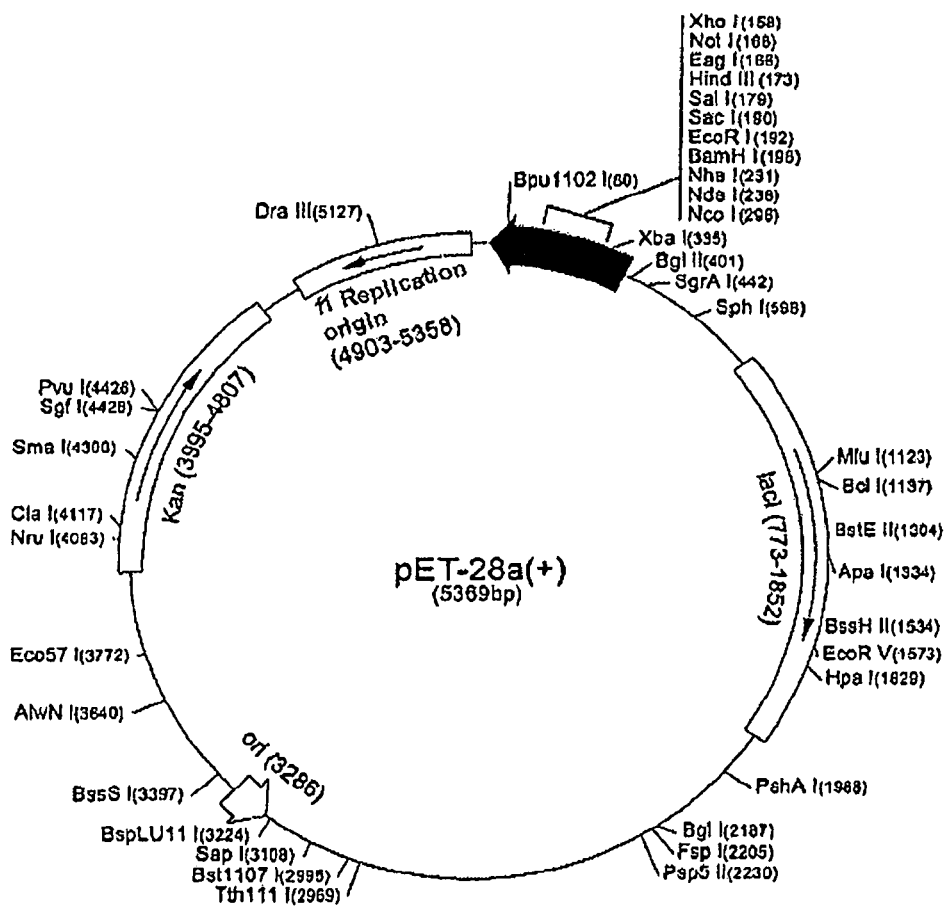

For the expression of recombinant proteins, the following expression vectors that are known per were used:

pET21a(+), (cf. FIG. 3a)
pET22b(+) (cf. FIG. 3b)
pET28a(+) (cf. FIG. 3d) and
pCOLADuet-1
(in each case Novagen, Madison, Wis., USA).

The vectors pET21a(+) and pET22b(+) each possess a multiple cloning site (MCS), in each case under the control of a T7-promoter with downstream lac-operator and the subsequent ribosomal binding site (rbs). In the C-terminal region of the expression domain there is in each case a T7-terminator. Both plasmids have a ColE1-replicon (pBR322-replicon), an ampicillin resistance gene (b/a), an f1-origin and a gene coding for the lac-inhibitor (lacI).

In addition, the pET21a(+)-plasmid has a T7-Tag in the N-terminal region of the MCS and an optional His-Tag C-terminally of the MCS. The pET22b(+)-plasmid has, in the N-terminal region of the MCS, a pelB signal sequence and a His-Tag C-terminally of the MCS.

The pCOLADuet-1 vector has two MCSs, each of which is under the control of a T7-promoter with downstream lac-operator and subsequent ribosomal binding site (rbs). C-terminally of the two MCSs there is a T7-terminator. Moreover, this vector has a gene that codes for the lac-inhibitor and a COLA-replicon (ColA-replicon).

A modified variant of the commercially available pCOLADuet-1 vector was used in the present work. In this modified plasmid variant (designated pCOLA(mod); cf. FIG. 3c)) the kanamycin resistance gene of the original vector was replaced with a chloramphenicol resistance gene. In addition, an NcoI restriction site was removed from the chloramphenicol resistance gene by site-directed point mutagenesis. In the N-terminal region of the first MCS there is a His-Tag, whereas C-terminally of the second MCS there is an S-Tag.

The ColE1-replicons of the pET-plasmids and the COLA-replicon of the pCOLA-plasmid are mutually compatible. This permits simultaneous stable insertion of a pET-plasmid and of a pCOLA-plasmid in *Escherichia coli*. In this way, combinations of various genes can be cloned into *Escheri-* chia coli, without their being located on the same operon. Owing to the different copy numbers of pET-vectors (~40) and pCOLA-vectors (20-40), it is moreover possible to influence the expression level of cotransformed genes.

Figure 4A:
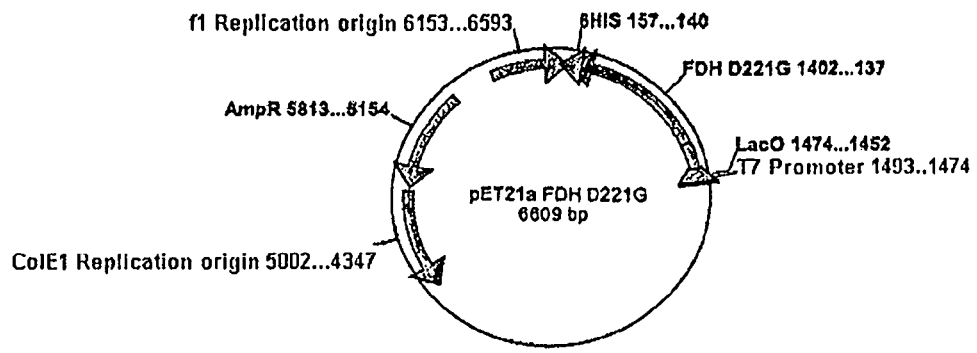
FIG. 4A and FIG. 4B show the construction schemes of pET21a(+) FDH D221G and pET21a(+) FDH 7β-HSDH, respectively.
Figure 4B:
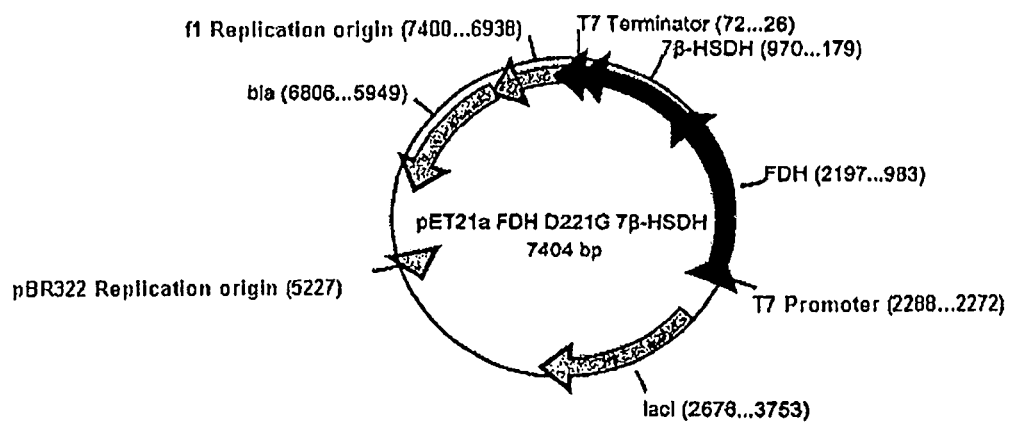
Figure 5:
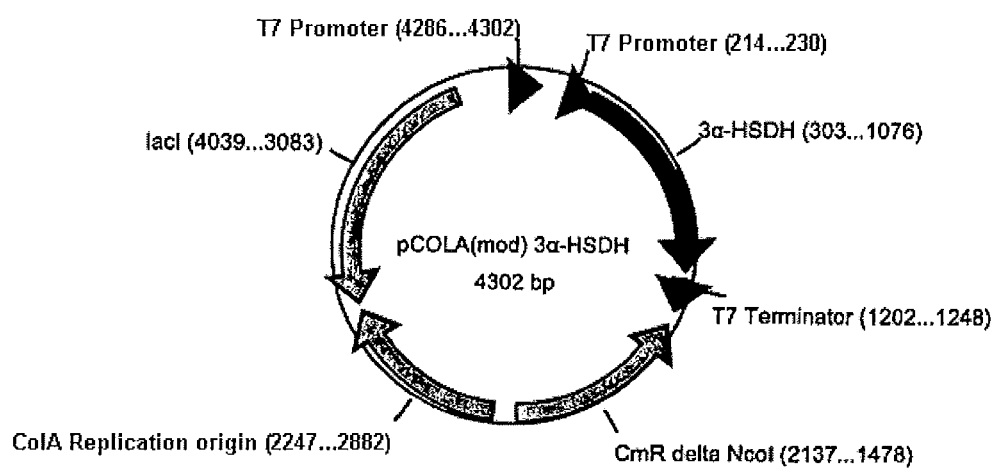
FIG. 5 shows the construction scheme of pCOLA(mod) 3α-HSDH.
Figure 8:
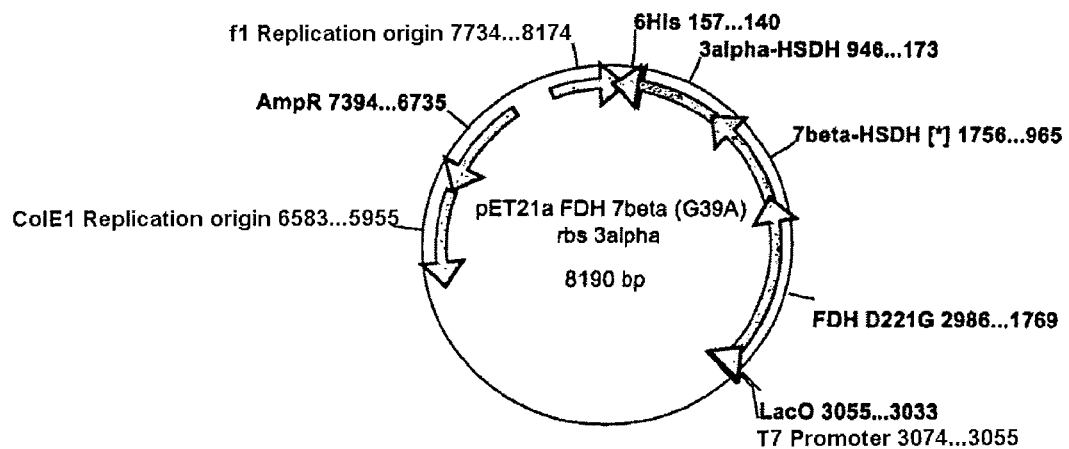
FIG. 8 shows the construction scheme of the triple vector pET21a(+) FDH 7beta (G39A) that bears the coding sequences for FDH D221G, 7β-HSDH G39A and 3α-HSDH.

The following vector constructs were used pET22b(+) 7β-HSDH: a pET22b(+) vector into which the 7β-HSDH from *Collinsella aerofaciens* ATCC 25986 had been cloned via the Nde I and Hind III cleavage sites in the usual way.

pET22b(+) 3α-HSDH: a pET22b(+) vector into which the 3α-HSDH from *Comamonas testosteroni* had been cloned via the Nde I and EcoR I cleavage sites in the usual way (Oppermann et al., J Biochem, 1996, 241(3): 744-749).

pET21a(+) FDH D221G (cf. FIG. 4a): a pET21a(+) vector into which the formate dehydrogenase from *Mycobacterium vaccae* N10 had been cloned via the Nde I and EcoR I cleavage sites. With site-directed mutagenesis, the aspartate residue (D) at position 221 (without taking into account methionine in position 1) or position 222 (counting from methionine in position 1; cf. SEQ ID NO: 15, 19, 35) of formate dehydrogenase was replaced with a glycine residue (cf. production example 4, below). Formate dehydrogenase carries, at position 1202 of the nucleotide sequence, a single base deletion, which leads to exchange of the last amino acid valine for an alanine. Simultaneously, this base deletion leads to switching-off of the stop codon and to activation of the His-Tag that was originally outside of the reading frame (cf. SEQ ID NO: 34 and 35).

pET21a(+) 7β-HSDH: a pET21a(+) vector, into which the 7β-HSDH from *Collinsella aerofaciens* ATCC 25986 had been cloned via the Nde I and Xho I cleavage sites in the usual way pET21a(+) FDH D221G 7β-HSDH (cf. FIG. 4b)

pET21a(+) FDH 7β-HSDH(G39A) 3α-HSDH (cf. FIG. 8)

pCOLA(mod) 3α-HSDH (cf. FIG. 5)

Microorganisms

| Strain | Genotype |
|---|---|
| *Escherichia coli* DH5α | F⁻ endA1 glnV44 thi-1 recA1 relA1 gyrA96 deoR nupG Φ80dlacZΔM15 Δ(lacZYA-argF)U169, hsdR17($r_K^- m_K^+$),λ⁻ |
| *Escherichia coli* BL21(DE3) | F⁻ ompT gal dcm lon hsdS$_B$($r_B^- m_B^-$) λ(DE3 [lacI lacUV5-T7 gene 1 ind1 sam7 nin5]) |
| *Escherichia coli* BL21 (DE3) hdhA⁻ KanR⁺ (7α-HSDH knock-out strain) (cf. production example 5) | F⁻ ompT gal dcm lon hsdS$_B$($r_B^- m_B^-$) λ(DE3 [lacI lacUV5-T7 gene 1 ind1 sam7 nin5]) hdhA⁻ KanR⁺ |

The *Escherichia coli* strain DH5α (Novagen, Madison, Wis., USA) was multiplied at 37° C. in LB medium containing suitable antibiotics.

The *Escherichia coli* strain BL21(DE3) (Novagen, Madison, Wis., USA) was multiplied at 37° C. in LB medium containing suitable antibiotics and after induction at $OD_{600}$=0.8 with 0.5 mM IPTG was held at 25° C. and 140 rpm.

Methods

1. Standard Conditions for Determination of 7β-HSDH Activity

The reaction mixture contains a total volume of 1 ml:
880 µl 50 mM potassium phosphate buffer, pH 8.0
10 µl 10 mM UDCA (dissolved in water, pH 8)
10 µl enzyme solution (in buffer as above, in the range from 1 to 10 U/ml)
100 µl 1 mM NADP⁺ (in buffer as above)

The increase in extinction at 340 nm is measured and the activity is calculated as enzyme unit (U, i.e. µmol/min) using the molar extinction coefficient of 6.22 mM⁻¹×cm⁻¹.

Standard Conditions for Determination of 7β-HSDH Activity According to Production Example 7

The reaction mixture contains a total volume of 1 ml
870 µl 50 mM potassium phosphate (KPi) buffer, pH 8.0
100 µl 100 mM DHCA (dissolved in 50 mM KPi, pH 8)
10 µl enzyme solution (in buffer as above, in the range from 2 to 6 U/ml)
20 µl 12.5 mM NADPH (dissolved in ddH₂O)

The increase in extinction at 340 nm is measured and the activity is calculated as enzyme unit (U, i.e. µmol/min) using the molar extinction coefficient of 6.22 mM⁻¹×cm⁻¹.

2. Determination of Protein by BCA Assay

The samples were mixed with BCA reagent (from Interchim) and incubated at 37° C. for 45 min. The protein content was determined at 562 nm against a calibration curve (BSA) in the concentration range of the assay used.

3. Thin-Layer Chromatography 5 to 10 µg of sample was applied to a TLC Film Silica Gel 60 (Merck). Authentic substances were applied as reference. One end of the TLC film was dipped in solvent until the top of the mobile phase was reached. The TLC film was dried and was developed with phosphomolybdic acid.

4. Molecular Biology Procedures:

Molecular biology operations are carried out, unless stated otherwise, on the basis of established methods, e.g. described in:

Sambrook, J., Fritsch, E. F. and Maniatis, T. Molecular Cloning: A Laboratory Manual. 2nd ed., Cold Spring Harbor Laboratory, Cold Spring Harbor Laboratory Press, Cold Spring Harbor, N.Y., 1989; Ausubel et al. (eds.), Current Protocols in Molecular Biology, John Wiley & Sons, N Y (1993); Kriegler, Gene Transfer and Expression, A Laboratory Manual, Stockton Press, NY (1990).

B. EXAMPLES

Production Example 1: Identification of 7β-HSDH Activity

The genomic DNA sequence of *Collinsella aerofaciens* ATCC 25986 was published in the year 2007 by "Washington University Genome Sequencing Center" for the "human gut microbiome project" at GenBank. HSDHs belong to the "short-chain dehydrogenases". As the biochemical function of the "short-chain dehydrogenases" from *Collinsella aerofaciens* ATCC 25986 had not been annotated in GenBank, 9 candidates were cloned into vector pET22b+, and then expressed in *E. coli* BL21(DE3).

For this, 7β-HSDH coding sequences were PCR-amplified. The PCR products were obtained using the genomic DNA of *Collinsella aerofaciens* ATCC 25986 (DSM 3979) as template and the primers 5'-gggaattcCATATGAACCTGAGGGAGAAGTA-3' (SEQ ID NO:3) and 5'-cccAAGCTTCTAGTCGCGGTAGAACGA-3' (SEQ ID NO:4). The NdeI and HindIII cleavage sites in the primer sequences are underlined. The PCR product was purified using the PCR-Purification-Kit (Qiagen) and then cut with the enzymes NdeI and HindIII. The corresponding vector was also cut with NdeI and HindIII. The products were applied to agarose gel, separated, cut out and purified. The cut PCR product and the cut vector were ligated by means of T4-ligase. The ligant was transformed into *E. coli* DH5a. The resultant vector (contains the gene of 7β-HSDH) was confirmed by sequencing and transformed into *E. coli* BL21 (DE3) and induced with IPTG and expressed.

Expression was carried out in 50 ml LB medium. For preparation of a preculture, a colony on LB-agar plate in 5 ml LB medium (contains corresponding antibiotics) was picked and incubated overnight at 37° C. and 160 rpm. The 50 ml LB medium (contains corresponding antibiotics) was inoculated with 500 µl of preculture. The culture was incubated at 37° C. and 160 rpm. Up to OD600 approx. 0.8, expression was induced by adding 0.5 mM IPTG. After 6 h or overnight, the cells were centrifuged off. The pellets were resuspended in 6 ml potassium phosphate buffer (50 mM, pH 8, contains 0.1 mM PMSF) and disrupted with ultrasound. The cell debris was removed by centrifugation.

For identification of 7β-HSDH activity, the activity was investigated by a photometric method. In a 1 ml cuvette, enzyme and 0.1 mM of test substance (UDCA) were mixed in potassium phosphate buffer (50 mM, pH8). After adding NADPH(NADH) or NADP$^+$(NAD$^+$), the degradation or formation of NAD(P)H was measured. One enzyme out of the 9 candidates shows activity (60 U/ml) against UDCA in the presence of NADP$^+$, but no activity against CA. The NADPH-dependent 7β-HSDH activity of this enzyme was identified.

In the photometric investigation, 7β-HSDH showed activity of 60 U/ml against UDCA, activity of 35 U/ml against 7-keto-LCA and activity of 119 U/ml against DHCA in the presence of NADP$^+$ or NADPH. The activity against CA is not detectable.

The gene that codes for 7β-HSDH was subcloned into pET28a+ with His-Tag, to permit rapid purification. This 7β-HSDH with His-Tag was actively expressed in *E. coli* BL21(DE3) as described above. Purification was carried out with a Talon column. The column was first equilibrated with potassium phosphate buffer (50 mM, pH 8, with 300 mM NaCl). After loading of the cell lysate, the column was washed with potassium phosphate buffer (50 mM, pH 8, with 300 mM NaCl). The 7β-HSDH was eluted with potassium phosphate buffer (50 mM, pH 8, with 300 mM NaCl and 200 mM imidazole). The imidazole in the eluate was removed by dialysis. The yield in purification was 76% with purity of approx. 90%.

Production Example 2: Preparative-Scale Cloning, Expression and Purification of 7β-HSDH from *Collinsella aerofaciens* ATCC 25986 and Further Characterization of the Enzyme 2.1 Cloning and Production of an Expression Construct The gene coding for 7β-HSDH was once again amplified from the genomic DNA by PCR and using primers, as described above for production example 1:

The PCR product was once again purified as described above and digested with the restriction endonucleases NdeI and HindIII. The digested PCR product was purified again and cloned into the pET-28a(+) vector using the T4-ligase, to produce an expression vector. The resultant expression construct was then transformed into *E. coli* DH5α cells. The protein to be expected should have 20 amino acid residues comprising a signal peptide and an N-terminal 6×His-Tag and a thrombin cleavage site. The sequence of the inserted DNA was verified by sequencing.

2.2 Overexpression and Purification of 7β-HSDH

*E. coli* BL21(DE3) was transformed with the expression construct. For this, the *E. coli* BL21(DE3) strain containing the expression construct was multiplied in LB medium (2×400 ml in 2-liter shaking bottles) containing 30 µg/ml kanamycin. The cells were harvested by centrifugation (10.000×g, 15 min, 4° C.). The pellet was resuspended in 20 ml phosphate buffer (50 mM, pH 8, containing 0.1 mM PMSF). The cells were disrupted by ultrasound treatment for 1 minute with constant cooling (40 W power, 40% working interval and 1 min pause) using Sonifier 250 ultrasonic equipment (Branson, Germany). Lysis was repeated three times. The cell extract was centrifuged (22.000×g, 20 min, 4° C.). The supernatant was loaded on a Talon column (Clontech, USA), equilibrated with loading buffer (50 mM potassium phosphate, 300 mM NaCl, pH 8). The procedure was carried out at 24° C. Unbound material was washed away by washing the column with loading buffer (3 column volumes). Weakly binding protein was removed by washing with washing buffer (20 mM imidazole in the loading buffer; 3 column volumes). The His-Tag-7β-HSDH protein was eluted with elution buffer (200 mM imidazole in the loading buffer). The eluate was dialyzed overnight in a dialysis tube with a molecular exclusion limit of 5 kDa (Sigma, USA) in 2 liters of potassium phosphate buffer (50 mM, pH 8) at 4° C. Finally the sample was transferred to a new tube and stored at −20° C. for further analysis. The protein concentration was determined using a BCA Test Kit (Thermo, USA) according to the manufacturer's instructions. In addition the sample was analyzed by 12.5% SDS-PAGE and staining with Coomassie Brilliant Blue. The purity of the protein was determined densitometrically using Scion Image Beta 4.0.2 (Scion, USA).

2.3 Gel Filtration

Gel filtration was carried out on a Pharmacia AKTA protein purification system, in order to determine the molecular weight of 7β-HSDH. The purified enzyme was applied on a Sephadex G-200 column, which had been equilibrated beforehand with 50 mM Tris-HCl (pH 8), containing 200 mM sodium chloride. The protein was eluted with the same buffer at a flow rate of 1 ml/min. The molecular weight of 7β-HSDH was determined by comparing its elution volume with that of protein standards (serum albumin (66 kDa), α-amylase from *Aspergillus oryzae* (52 kDa), pig pancreas trypsin (24 kDa) and hen's egg lysozyme (14.4 kDa)).

2.4 Enzyme Assay and Kinetic Analysis

The reaction mixture for the enzyme assay contained, in a total volume of 1 ml, 50 µmol potassium phosphate (pH 8), 0.1 µmol NAD(P)H or NAD(P)$^+$, substrates and protein. The reaction mixture was contained in cuvettes with a light path length of 1 cm. The 7β-HSDH activity was determined by recording the variation in NAD(P)H concentration against the extinction at 340 nm using a spectrophotometer (Ultraspec 3000, Pharmacia Biotech, Great Britain). The enzyme activities were determined as enzyme units (U, i.e. µmol/min) using the molar extinction coefficient of 6.22 mM$^{-1}$-cm$^{-1}$ at 25° C. Several different measurements were performed with the variables substrate, coenzyme, concentration, pH, buffer and incubation temperature. The kinetic constants were determined using standard methods.

2.5 Biotransformation of 7-Keto-Lithocholic Acid by 7β-HSDH

The transformation of 7-keto-LCA by 7β-HSDH was carried out in order to verify the biochemical function of 7β-HSDH. 0.4 g 7-keto-LCA was suspended in 10 ml potassium phosphate buffer (50 mM, pH 8) and the pH was adjusted to pH 8 by adding 2 M sodium hydroxide. 0.2 ml isopropanol, 100 U 7β-HSDH and 80 U alcohol dehydrogenase (ADH-TE) from *Thermoanaerobacter ethanoicus* (kindly donated by Dr. K. Momoi, ITB University, Stuttgart) and 1 µmol NADP$^+$ were added. The same buffer was added, to give a total reaction volume of 20 ml. The reaction mixture was incubated at 24° C. and stirred for 24 hours. During this, NADPH was regenerated with ADH via oxidation of 2-propanol. The product was acidified with 1 ml of 2 M hydrochloric acid and was extracted 5× with 5 ml ethyl acetate. The organic solution was then distilled.

2.6 Determination of Chromatographic Product

An HPLC analysis was carried out on a column of the Purospher® STAR RP-18 type (Hitbar® RT 125-4 Pre-Packed Column, Purospher® STAR RP-18 endcapped, Merck, Germany), provided with a precolumn of the LiChroCART® STAR RP18 type (endcapped, Merck, Germany) on an HPLC system LC20AD (Shimadzu, Japan) at a flow rate of 1 ml/min. The mobile phase consisted of two eluents. Eluent A contained acetonitrile and eluent B contained distilled water (pH 2.6, adjusted with orthophosphoric acid, 85%). The following gradient was used: A 35% (8 min)-35%-43% (1% $min^{-1}$)-43%-70% (1% $min^{-1}$)-70% (5 min)-70%-35% (17.5% $min^{-1}$)-35% (5 min); eluent A 65% (8 min)-65%-57% (1% $min^{-1}$)-57%-30% (1% $min^{-1}$)-30% (5 min)-30%-65% (17.5% $min^{-1}$)-65% (5 min). 20 µl samples (1 mg/ml) were analyzed. Authentic UDCA, 7-keto-LCA and CDCA were used at the same concentration as standards. Recording was carried out by UV detection at 200 nm.

2.7 Sequence Alignment and Phylogenetic Analysis

Multiple sequence alignments were produced using the Clustal X-Software (Thompson et al., 1997, Nucleic Acid Research 25: 4876-82) and modified using the Jalview software (Clamp et al., 2004, Bioinformatics 20: 426-7). The phylogenetic tree was produced using the program TreeView 1.6.6 (Roderic 2001, http://taxonomy.zoology.gla.ac.kuk/rod/rod.html).

2.8 Test Results:

2.8.1 Identification of 7β-HSDH Activity in a Preparative Biotransformation

To confirm the function of the enzyme, a biotransformation of 7-keto-LCA was carried out at the 10-ml scale, wherein the isolated enzyme was used in combination with ADH for regeneration of NADPH using 2-propanol, as already described. The HPLC analysis showed that UDCA was the only reaction product produced by the enzyme (90% conversion). CDCA (retention time 19.4 min) was not detected in the reaction mixture. The result shows that the enzyme is an NADPH-dependent 7β-HSDH and is capable of selective reduction of the 7-carbonyl group of 7-keto-LCA to a 7β-hydroxyl group.

Retention time UDCA: 15.5 min

Retention time 7-keto-LCA: 18.3 min 2.8.2. Purification and Gel Filtration

After cloning the 7β-HSDH gene from *Collinsella aerofaciens* DSM 3979 into the expression vector pET28a(+) and subsequent overexpression, a fusion protein provided with a His-Tag on the N-terminus was obtained with a 7β-HSDH yield of 332.5 mg (5828 U) per liter of culture. The 7β-HSDH provided with the His-Tag was purified in one step by immobilized metal ion affinity chromatography (purity>90%, yield 76%, cf. FIG. 2). The main bands of lanes 1 and 2 represent the expected expression product at 30 kDa, which corresponds to the predicted molecular weight derived from the amino acid sequence of the gene. However, a molecular weight of 56.1 kDa is found for 7β-HSDH by gel filtration. This proves the dimeric nature of the 7β-HSDH from *Collinsella aerofaciens* DSM 3979.

2.8.3. Sequence Alignments

The amino acid sequence of the 7β-HSDH used according to the invention was compared with known HSDH sequences (alignment not shown). The observed sequence similarity indicates that the enzyme according to the invention belongs to the family of short-chain dehydrogenases (SDR). It is known that SDRs have very low homology and sequence identity (Jornvall, H., B. Persson, M. Krook, S. Atrian, R. Gonzalez-Duarte, J. Jeffery, and D. Ghosh. 1995. Short-chain dehydrogenases/reductases (SDR). Biochemistry 34: 6003-13 and Persson, B., M. Krook, and H. Jornvall. 1991. Characteristics of short-chain alcohol dehydrogenases and related enzymes. Eur J Biochem 200: 537-43). However, the sequence alignment clearly shows the conserved domains in the SDR primary structure. The N-terminal motif Gly-X-X-X-Gly-X-Gly (corresponding to Gly-41, Gly-45 and Gly-47, numbering corresponding to the alignment) corresponds to the characteristic dinucleotide binding motif of the SDR superfamily. Furthermore, three strongly conserved residues Ser-177, Tri-190 and Lys-194 are observed, which correspond to the catalytic triad of the SDR enzymes.

2.8.4. Phylogenetic Analysis

7α-HSDHs from *Clostridium sordellii, Brucella melitensis* and *Escherichia coli* belong to the same subgroup. The two 3α-HSDHs show a more pronounced similarity than other HSDHs. Interestingly, the prokaryotic 7β-HSDH is related to the animal 11β-HSDH subgroup, comprising *Cavia porcellus, Homo sapiens* and *Mus musculus*.

2.8.5. Kinetic Constants

Kinetic equilibrium analyses were carried out, in order to determine the absolute values for $V_{max}$ and $K_M$ for UDCA, 7-keto-LCA, DHCA, $NADP^+$ and NADPH by Lineweaver-Burk plots. The following table presents all kinetic data for the substrates and coenzymes tested, which were obtained from substrate saturation curves and reciprocal plots. The $V_{max}$, $K_M$ and $k_{cat}$ values for all substrates and coenzymes are in the same region, whereas the $K_M$ value for DHCA was significantly higher than with the other substrates, possibly caused by the low solubility in water. The enzyme is NADPH-dependent and kinetic constants could not be determined for $NAD^+$ and NADH owing to the very low activity. Summary of kinetic constants for 7β-HSDH from *Collinsella aerofaciens* DSM 3979.

|  | $K_M$ (µM) | $V_{max}$ (U/mg protein)[b] | $k_{cat}$ (1 µmol/ (µmol × min)) |
| --- | --- | --- | --- |
| $NADP^+$ | 5.32 | 30.58 | 944.95 |
| NADPH | 4.50 | 33.44 | 1033.44 |
| UDCA | 6.23 | 38.17 | 1179.39 |
| 7-Keto-LCA | 5.20 | 30.77 | 950.77 |
| DHCA | 9.23 | 28.33 | 875.35 |
| $NAD^+$ | —[a] | — | Traces |
| NADH | — | — | Traces |

[a] could not be determined owing to the very low activity
[b] 1 U = 1 µmol/min 2.8.6. Optimal pH In addition, the 7β-HSDH activity was determined with purified enzyme for various substrates as a function of the pH. For the oxidation of UDCA with 7β-HSDH, an optimal activity was observed in the range from pH 9 to 10 with gradual decline on the acidic side. In contrast, for the reduction of DHCA and 7-keto-LCA by 7β-HSDH, there was an optimal activity in the range from pH 4 to 6 with a sharp decline on the acidic side and a gradual decline on the alkaline side. Different buffers only have a slight influence on the activity of 7β-HSDH at identical pH.

2.8.7. Thermal Stability

The NADP-dependent 7β-HSDH used according to the invention shows the following stability behavior: after 400 min the activity at 30° C. was about 30% lower than at 23° C. At 30° C., the enzyme was completely inactivated after 1500 min, whereas at 23° C. and 1500 min the residual activity was 20%. No significant activity loss was observed during storage at −20° C. in potassium phosphate buffer (50 mM, pH 8) over a period of some months after repeated freezing and thawing.

Production Example 3: Production of 7β-HSDH Mutants and Characterization Thereof Position 39 of the amino acid sequence (comprising start methionine) (cf. SEQ ID NO:2) was mutated.
3.1 Primers The mutagenesis primers stated below were used for the site-directed mutagenesis of 7β-HSDH. The primers were selected based on the 7β-HSDH gene sequence, so that they bring about the desired amino acid exchange. It was borne in mind that the base to be mutated is localized centrally in the primer, and that the melting points of the primer pairs are in the same region.

The primer pair 7beta_mut_G39A_fwd and 7beta_mut_G39A_rev was used for preparing the G39A mutant. The primer pair 7beta_mut_G39S_fwd and 7beta_mut_G39S_rev was used for preparing the G39S mutant.

```
Glycine→Alanine
Forward:
7beta_mut_G39A_fwd:
                                      SEQ ID NO: 9)
CGTCGTCATGGTCGCCCGTCGCGAGG.

Reverse:
7beta_mut_G39A_rev:
                                      SEQ ID NO: 10)
CCTCGCGACGGGCGACCATGACGACG.

Glycine→Serine
Forward:
7beta_mut_G39S_fwd:
                                      SEQ ID NO: 11)
CGTCGTCATGGTCAGCCGTCGCGAGG.

Reverse:
7beta_mut_G39S_rev:
                                      SEQ ID NO: 12)
CCTCGCGACGGCTGACCATGACGACG.
```

3.2 PCR Program

In the reaction, first a 2-min initial denaturation step was carried out at 98° C. Then 25 cycles of denaturation (30 s at 98° C.), primer hybridization (2.5 min at 58° C.) and elongation (6 min at 72° C.) were carried out. As the last step, a final elongation of 15 min was carried out at 72° C. before the polymerase chain reaction was stopped by cooling to 4° C.

3.3 PCR assay

| | |
|---|---|
| HF buffer (5x) | 4 µl |
| dNTP-mix (10 mM) | 0.4 µl |
| Forward primer (10 µM) | 2 µl |
| Reverse primer (10 µM) | 2 µl |
| Template | 1 µl |
| Phusion polymerase (2 U µL$^{-1}$) | 0.2 µl |
| DMSO | 1 µl |
| ddH$_2$O | 9.4 µl |
| | 20 µl |

A pET22b vector with 7β-HSDH was used as template.

3.4 Procedure

To allow targeted exchange of amino acids in protein sequences, the DNA sequence of the corresponding gene is submitted to site-directed mutation. For this, mutually complementary primers are used, which bear the desired mutation in their sequence. N6-adenine-methylated, double-stranded plasmid DNA, which bears the gene to be mutated, serves as template. N6-adenine-methylated plasmid DNA is isolated from dam$^+$ E. coli strain such as for example E. coli DH5.

The polymerase chain reaction is carried out as described above. The primers are lengthened complementarily to the template, so that plasmids with the desired mutation are formed, which have a strand break. Unlike other PCR reactions, in this case the increase in DNA yield is only linear, as newly formed DNA molecules cannot serve as template for the PCR reaction.

On completion of the PCR reaction, the parental, N6-adenine-methylated DNA is digested by the restriction enzyme DpnI. This enzyme has the particular feature that it restricts nonspecifically N6-adenine-methylated DNA, but not the newly formed, nonmethylated DNA. Restriction was carried out by adding 1 µL DpnI to the PCR reaction mixture and incubating for 1 h at 37° C.

10 µl of this preparation was used for the transformation of 200 µl of chemically-competent DH5α cells. After plasmid isolation, successful mutation was confirmed by sequencing.

3.5 Characterization

For each of the mutants and for the wild-type enzyme, kinetic measurements were carried out in the microtiter plate photometer, recording the conversion rates of the enzymes both with constant substrate concentrations with variation of cofactor concentrations and vice versa. To determine the specific enzyme activity, the enzyme concentrations in the cell lysate were determined by densitometry.

To determine the dependence of the substrate conversion rate on the substrate concentration, a cofactor concentration of 100 µM NADPH relative to the reaction volume was used, while the substrate concentration was varied over a range from 7 µM to 10 mM dehydrocholic acid with 31 different concentrations (in each case relative to the reaction mixture).

To determine the dependence of the substrate conversion rate on the cofactor concentration, a substrate concentration of 0.3 mM dehydrocholic acid relative to the reaction volume was used, whereas the cofactor concentration was varied over a range from 25 µM to 100 µM NADPH with 8 different concentrations of the wild-type protein or over a range from 6 µM to 100 µM NADPH with 16 different concentrations for both mutants (in each case relative to the reaction mixture). In these measurement series, the reaction rate was determined by linear regression over the first 4 measurements (0 s-18 s).

The data obtained were evaluated with IGOR Pro. From the plots of substrate or cofactor concentration against the specific enzyme activity, the typical curve of Michaelis-Menten kinetics can be seen for the measurement series at constant substrate concentration and variation of cofactor concentration. From the plots of the measurement series with constant cofactor concentration and variation of substrate concentration, however, typical curves of Michaelis-Menten kinetics with substrate inhibition can be seen (cf. FIG. 6). For this reason, the classical Michaelis-Menten model was used for evaluating the measurement series at constant substrate concentration and variation of cosubstrate concentration, and the Michaelis-Menten model with substrate inhibition was used for the measurement series with constant cosubstrate concentration and variation of substrate concentration.

$v_{max}$, $K_m$ and $K_i$ were determined by nonlinear regression.

$$v = v_{max} \cdot \frac{c_S}{K_m + \left(1 + \frac{c_S}{K_i}\right)c_S}$$

v specific enzyme activity, U mg$^{-1}$=µmol min$^{-1}$ mg$^{-1}$
$v_{max}$ maximum specific enzyme activity, U mg$^{-1}$=µmol min$^{-1}$ mg$^{-1}$
$c_s$ substrate or cofactor concentration, mol L$^{-1}$
$K_m$ semisaturation concentration, mol L$^{-1}$
$K_i$ inhibition constant, mol L$^{-1}$
The parameters found are shown in the table.

TABLE

Parameters found for the three different 7β-HSDH variants

| | $K_{m, DCS}$, µM | $K_{i, DCS}$, mM | $K_{m, NADPH}$, µM | $v_{max}$, U/mg |
|---|---|---|---|---|
| 7β-HSDH WT | 31 ± 5 | 8.6 ± 1.5 | 46 ± 7 | 14.6 ± 1.0 |
| 7β-HSDH G39A | 33 ± 6 | 17 ± 4 | 16.4 ± 1.9 | 21.0 ± 1.1 |
| 7β-HSDH G39S | 75 ± 9 | 80 ± 50 | 13.1 ± 2.9 | 20.7 ± 1.0 |

On examining the measured data, it is clear that 7β-HSDH displays substrate inhibition via dehydrocholic acid, which is strongest for the wild-type protein and weakest with the G39S mutant. Especially in the case of this last-mentioned protein, it may be asked whether substrate inhibition occurs at all, as indicated by the high $K_i$ and its large error. The semisaturation concentrations for dehydrocholic acid are in the two-digit micromolar range. Whereas these do not differ significantly for the wild-type protein and the G39A mutant, at 31±5 µM and 33±6 µM respectively, for the G39S mutant this value, at 75±9 µM, is roughly double the value for the other two enzymes. In the case of the semisaturation concentrations for NADPH, lower values are found for the mutant enzymes than for the wild-type enzyme (46±7 µM in the wild-type versus 16.4±1.9 µM for the G39A mutant and 13.1±2.9 µM for the G39S mutant).

For both mutants, the values for $v_{max}$ are roughly 1.5 times the value of the wild-type protein (21.0±1.1 U/mg for the G39A mutant and 20.1±1.0 U/mg for the G38S mutant versus 14.6±1.0 U/mg for the wild-type protein). In contrast to the classical Michaelis-Menten model, however, for the Michaelis-Menten model with substrate inhibition the $v_{max}$ values are not to be regarded as maximum attainable specific enzyme activities, since with increasing substrate concentration the specific enzyme activities do not approach $v_{max}$ asymptotically, but decrease again. The maximum attainable enzyme activities, i.e. the specific enzyme activities at the maxima of the kinetic curves, are ~13 U/mg for the wild-type protein and ~19 U/mg (G39A) and ~20 U/mg (G39S) for the mutant proteins. The enzyme activities that can be reached at the substrate concentrations used for whole-cell biotransformation are more interesting than the maximum attainable enzyme activities. As an example, these are to be compared for the substrate concentration of 10 mM dehydrocholic acid, and are ~6.7 U/mg for the wild-type protein, ~13 U/mg for the G39A mutant and ~18 U/mg for the G39S mutant. At 10 mM substrate concentration, the G39A mutant would accordingly be twice as active as the wild-type protein, and the G39S mutant would even have about 3 times its activity. These differences should be even more pronounced at higher substrate concentrations, as the wild-type protein displays stronger substrate inhibition than the G39A mutant, and the G39A mutant is in its turn more strongly substrate-inhibited than the G39S mutant.

Production Example 4: Production and Characterization of the FDH D221G Mutant 4.1 Cloning pET21a(+) FDH
4.1.1 PCR Amplification of *Mycobacterium vaccae* Formate Dehydrogenase The template used for the amplification is genomic DNA of *Mycobacterium vaccae*, which was obtained from the German Collection of Microorganisms and Cell Cultures (Deutsche Sammlung von Mikroorganismen und Zellkulturen GmbH, DMSZ), Brunswick. The primers for the amplification were fdh_for
(SEQ ID NO: 23)
(5'-CGAT<u>CATATG</u>GCAAAGGTCCTGTGCGTTC-3')
and fdh_rev
(SEQ ID NO: 24)
(5'-GCTA<u>GAATTC</u>TCAGCCGCCTTCTTGAACT-3'), obtained from Eurofins MWG GmbH, Ebersberg. The recognition sites for the restriction enzymes are underlined. The rev-primer contains the EcoRI cleavage site and the for-primer contains the NdeI cleavage site.

The PCR assays and PCR programs are shown in the following table.

TABLE

PCR assay for the amplification of formate dehydrogenase from *Mycobacterium vaccae*

| Component | Volume [µl] |
|---|---|
| 10x Taq buffer (with Mg$^{2+}$) | 5 |
| dNTPs (10 mM) | 1 |
| Fdh_for (100 µM) | 0.5 |
| Fdh_rev (100 µM) | 0.5 |
| Template DNA (≥100 ng/µL) | 1 |
| Taq DNA polymerase (5 U/mL) | 0.5 |
| Distilled water | 41.5 |

TABLE

PCR program for the amplification of formate dehydrogenase from *Mycobacterium vaccae*

| Segment | Cycle number | Denaturation | Annealing | Elongation |
|---|---|---|---|---|
| 1 | 1 | 94° C., 2 min | | |
| 2 | 5 | 94° C., 30 s | 55.6° C., 30 s | 72° C., 75 s |
| 3 | 25 | 94° C., 30 s | 58.6° C., 30 s | 72° C., 75 s |
| 4 | 1 | | | 72° C., 75 s |

4.1.2 Restriction Digestion of pET21a(+) and FDH PCR Product

5 µl 10× NEBuffer EcoRI, 2.5 µl NdeI (20 U/mL) and 2.5 µl EcoRI (20 U/mL) (in each case New England Biolabs, Frankfurt) were added to 1-5 µg of DNA (pET21a(+) or FDH PCR product) dissolved in water, and made up to 50 µl total volume with distilled water. The preparations were in each case incubated for 1 h at 37° C. Then the cut DNA fragments were applied to 1% agarose gel (1% (w/v) agarose, 0.05% (v/v) ethidium bromide) and the DNA fragments were separated electrophoretically for 55 minutes at 120 V. Then the bands of the correct size (1.2 kb for the FDH-gene, 5.4 kb for the pET21a(+)-plasmid) were cut out of the agarose gel with a scalpel and were isolated using the QIAquick Gel Extraction Kit (QIAGEN, Hilden) according to the manufacturer's protocol 4.1.3 Ligation of Cut pET21a(+) and FDH 1 µl T4 ligase (3 U/µL) and 1 µl 10× ligase buffer (in each case New England Biolabs, Frankfurt) were added to 100 ng of cut vector DNA and 111 ng of cut FDH DNA and made up to a total volume of 10 µl with distilled water. The ligation preparation was incubated overnight at 4° C.

4.1.4 Transformation of the Ligation Preparation into Chemically Competent E. coli DH5a At the end of the ligation step, the 10 µL ligation preparation is added to 200 µl of chemically competent E. coli DH5α prepared according to the standard protocol. Next there is a 30-min incubation step on ice, followed by heat shock at 42° C. (90 seconds). Then 600 µl of sterile LB medium is added to the transformation preparation and the cells are incubated at 200 rpm and 37° C. in a shaking incubator for 45 minutes. In the next step, the preparation is centrifuged at 3000 rpm for 60 seconds in a benchtop centrifuge, 700 µl of the supernatant is discarded, the cells are resuspended in the remaining supernatant and plated out on an LB-agar plate with 100 mg/l ampicillin. The agar plate is then incubated overnight at 37° C.

4.2. Production of pET21a(+) FDH D221G

The production of an FDH mutant, which can regenerate not only NADH, but also NADHP, will be explained in more detail with the mutant D221G.

Aspartate (D) 221 is an amino acid with a negatively-charged large side chain, which is located directly next to the arginine (R) residue, by which $NADP^+$ is to be bound. This can lead to repulsion of the phosphate group in the $NADP^+$, which is also negatively charged. The aspartate is therefore replaced with the small uncharged amino acid residue glycine (G).

4.2.1 Primers Used mt1:
(SEQ ID NO: 30)
5'-C CTG CAC TAC ACC GGC CGT CAC CGC CTG C-3'

NI_fdh_R:
(SEQ ID NO: 31)
5'-GCTCGAATTCTCAGACCGCCTTC-3'

4.2.2 Procedure

First a set of two complementary megaprimers was produced using the mt-primer and the primer NI_fdh_R.

Plasmid pET21a(+)FDH was used as template. The PCR program used is shown in the following table:

TABLE

Megaprimer PCR program

| Segment | Cycle number | Denaturation | Annealing | Elongation |
|---|---|---|---|---|
| 1 | 1 | 94° C., 2 min | | |
| 2 | 30 | 94° C., 30 s | 60° C., 30 s | 72° C., 40 s |
| 3 | 1 | 72° C., 5 min | | |

By combining primer mt1 with the primer NI_fdh_R, the length of the megaprimer becomes 650 bp. With this PCR product of the first PCR, gel electrophoresis and isolation of the desired band from the gel are carried out. A second PCR is carried out as whole plasmid PCR with the megaprimers as primers and the plasmid DNA (pETfdh) as template. The reaction mixture and the temperature scheme for the whole plasmid PCR are shown in the following tables. The 2× EZClone enzyme mix, the EZClone solution 1, the 1.1 kb marker and the DpnI were obtained from the GeneMorph II EZClone Domain Mutagenesis Kit (Stratagene).

TABLE

Preparation for a MEGA WHOP PCR (total volume 50 µL)

| Component | |
|---|---|
| Megaprimer | 250 ng (~2.5 µL from a standard-PCR) |
| Template (pETfdh) | 50 ng |
| 2x EZClone enzyme mix | 25 µL |
| EZClone solution 1 | 3 µL |
| distilled water | to 50 µL |

The first step in the PCR program (68° C., 5 min) is for removing the bases appended nonspecifically by the Taq-polymerase by the 3'→5' exonuclease activity of the polymerase used in the MEGA WHOP PCR.

TABLE

MEGA WHOP PCR program

| Segment | Cycle number | Denaturation | Annealing | Elongation |
|---|---|---|---|---|
| 1 | 1 | | | 68° C., 5 min |
| 2 | 1 | 95° C., 1 min | | |
| 3 | 25 | 95° C., 50 s | 60° C., 50 s | 68° C., 13 min |

The PCR product is a double-stranded plasmid with single-strand breaks, which are only closed in E. coli. 10 U DpnI were added to the 50 µL PCR product and the preparation was incubated at 37° C. for two hours. DpnI only degrades methylated DNA, i.e. the template DNA used, but not the megaprimer or the synthesized plasmid. The template plasmid must be produced with a $dam^+$ strain (such as DH10B or JM109), to obtain methylated starting DNA.

4.3 Expression and Isolation of the Mutant D221G

First an LB preculture was inoculated from frozen stored material or with a colony from an agar plate and the preculture was incubated overnight. Incubation was carried out at 37° C. and 250 rpm. The OD of the preculture was determined and the culture was inoculated to an OD of 0.1. On reaching an OD of 0.5-1 (after about 2.5 h), it was induced with IPTG (final concentration 1 mM). The cells were harvested three hours after induction.

The cells were disrupted mechanically with glass beads. For this, 0.5 mL of glass beads were added to 0.5 mL of cell sample in a 1.5-mL reaction vessel and the reaction vessel was shaken for 3 min at maximum frequency (30 $s^{-1}$) in a Retsch vibratory mill. After cell maceration, the glass beads were centrifuged off (2 min, 13000 rpm). Before and after maceration, the culture was put on ice, to minimize protein denaturation through heating of the sample in the vibratory mill. This maceration protocol is optimized for the use of samples frozen at −20° C.

4.4 Characterization of the Mutant D221G
Summary of kinetic constants of FDH at pH 6, 7 and 8.

| Enzyme | pH | Substrate | Cofactor | Specific activity (U × mg$^{-1}$) | $K_M$ (mM) sub-strate | $K_M$ (mM) co-factor |
|---|---|---|---|---|---|---|
| FDH | 6 | Sodium formate | NAD$^+$ | 4.6 | 46.86 | 0.83 |
|  | 6 | Sodium formate | NADP$^+$ | 1 |  | 0.3 |
|  | 7 | Sodium formate | NAD$^+$ | 5.1 | 45.56 | 0.61 |
|  | 7 | Sodium formate | NADP$^+$ | 1.2 |  | 0.51 |
|  | 8 | Sodium formate | NAD$^+$ | 4.7 | 59.26 | 0.52 |
|  | 8 | Sodium formate | NADP$^+$ | 1 |  | 1.01 |

The data prove that the mutant produced can utilize both NAD$^+$ and NADP$^+$ as cofactor.

Production Example 5: Production of an E. coli 7α-HSDH Knockout Mutant (E. coli BL21 (DE3) hdhA$^-$ KanR$^+$)

The target is deletion of the disturbing 7α-HSDH activity in the expression strain E. coli BL21 (DE3).

With the method described below, an antibiotic resistance gene is inserted in the target gene of 7α-HSDH, so that the target gene is switched off.

5.1 Sequence Information for 7α-HSDH from E. coli BL21 (DE3)
Amino acid sequence: (SEQ ID NO:26)
Nucleotide sequence (SEQ ID NO:25)
Accession: NC_012971 REGION: 1642470 . . . 1643237
5.2 Primers Used
The following primers were prepared for switching off the 7α-HSDH from E. coli BL21(DE3):
Primer for the Retargeting of the LI.LtrB Intron:

```
467|468a-IBS
                                       (SEQ ID NO: 27)
AAAAAAGCTTATAATTATCCTTATAGGACGTCATGGTGCGCCCAGATAG
GGTG

467|468a-EBS1d
                                       (SEQ ID NO: 28)
CAGATTGTACAAATGTGGTGATAACAGATAAGTCGTCATGTTTAACTTA
CCTTTCTTTGT

467|468a-EBS2
                                       (SEQ ID NO: 29)
TGAACGCAAGTTTCTAATTTCGGTTTCCTATCGATAGAGGAAAGTGTCT

Insertion
Location
467|468a
GCAGCTTTAGATGATGCATAGGAAGTCATG-intron-TTTATATTTTT
ATTT
```

5.3 Preparation of the Knockout Mutant
The knockout mutant was prepared using the kit TargeTron™ Gene Knockout System from Sigma Aldrich according to the manufacturer's instructions. The QIAquick PCR Purification Kit from Qiagen was used for purifying the PCR product according to step B.6. of the TargeTron™ Gene Knockout System.

Ligation of the HindIII/BsrGI-digested intron PCR product into the linearized pACD4K-C vector was carried out as follows: the reaction was carried out overnight at 16° C. 20 µl Preparation:

| 2 µl | pACD4K-C linear vector (40 ng) |
| 6 µl | HindIII/BsrGI-digested intron PCR product |
| 2 µl | ATP (10 mM) |
| 2 µl | ligase buffer (10 x) (Fermentas) |
| 2 µl | T4-ligase (Fermentas) |
| 6 µl | H$_2$O |

5 µl of ligation reaction solution was added to 200 µl of chemically-competent cells of E. coli BL21 (DE3) and incubated on ice for 20 min. Further transformation was carried out as described by the manufacturer.

The transformation preparations were plated out on LB-agar plates, containing 33 µg/mL kanamycin. Kanamycin-resistant cells were picked and these were in each case inoculated over several nights in 5 ml LB overnight cultures (in each case with 5 µl of a kanamycin solution (33 mg/ml)). Finally a 200 ml LB culture (with 200 µl kanamycin solution (33 mg/mL)) was inoculated with an overnight culture and was incubated for 5 h at 37° C. and 180 rpm in a shaking incubator. Then the temperature was raised to 42° C. for 1 hour. This culture was used for inoculating a 5 mL LB overnight culture (in each case with 5 µl of a kanamycin solution (33 mg/mL)). After incubation overnight at 37° C. and 180 rpm, the culture was streaked on an LB-agar plate with 33 µg/mL kanamycin. After overnight incubation at 37° C., colonies were picked and streaked on LB-agar plate with 33 µg/mL kanamycin and 34 µg/mL chloramphenicol.

After overnight incubation at 37° C., chloramphenicol-sensitive mutants were found. This is necessary in order to confirm the loss of the plasmid that is carried by the inducible knockout system and is no longer required after successful knockout.

5.4. Detection of the Knockout

The 7α-HSDH gene was amplified by colony PCR with the primers

```
7alpha-ko-check_fwd
                                       SEQ ID NO: 32
(5'-TTAATTGAGCTCCTGTACCCCACCACC-3')
and 7alpha-ko-check_rev
                                       SEQ ID NO: 33
(5'-GTGTTTAATTCTGACAACCTGAGACTCGAC-3').
```

The resultant fragment had a length of approx. 2.5-3 kb and was sequenced with the primer 7alpha-ko-check_fwd. The sequencing showed that the DNA sequence of 7α-HSDH is interrupted by an insert from the pACD4K vector, resulting in knockout of 7α-HSDH (sequencing data not shown).

Reaction Example 1: Enzymatic Conversion of 7-Keto-LCA by 7β-HSDH

For verification of the biochemical function of 7β-HSDH, conversion of 7-keto-LCA by 7β-HSDH was carried out. The 20 ml reaction mixture contains 50 mM 7-keto-LCA (approx. 0.4 g), 5 U/ml 7β-HSDH and 0.05 mM NADP$^+$. 4 U/ml ADH and 1% isopropanol were used for regeneration of NADPH (see Scheme 1). The reaction was carried out in a fume cupboard at pH8 and 24° C. with stirring. As acetone evaporates more quickly than isopropanol, the reaction is shifted toward formation of UDCA. Further 1% isopropanol was added after 24 h, 48 h and 72 h. The product was analyzed by TLC (silica gel 60, Merck, solvent petroleum ether and ethyl acetate 1:10, vol:vol). In TLC, the product was compared with authentic references 7-keto-LCA, UDCA and CDCA. The TLC analysis shows that UDCA was formed from 7-keto-LCA by the 7β-HSDH. The enantiomer CDCA is not detectable in TLC.

Scheme 1: Schematic representation of reduction of 7-keto-LCA by 7β-HSDH. The ADH regenerates the cofactor NADPH.

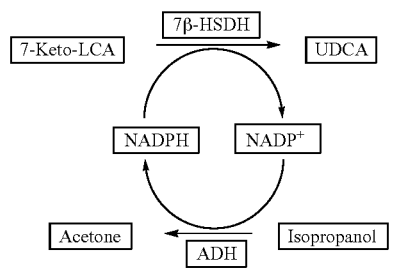

Reaction Example 2: Enzymatic Production of 3,12-Diketo-7β-CA from DHCA by 7β-HSDH To verify the usability of 7β-HSDH for preparing 12-keto-UDCA from DHCA, conversion of DHCA by 7β-HSDH was carried out. The 50 ml of reaction mixture contain 50 mM DHCA (1 g), 5 U/ml 7β-HSDH and 0.05 mM NADP$^+$. 4 U/ml ADH and 1% isopropanol were used for regeneration of NADPH (see Scheme 2). The reaction was carried out in a fume cupboard at pH8 and 24° C. with stirring. As acetone evaporates more quickly than isopropanol, the reaction is shifted toward formation of 3,12-diketo-7β-CA. In order to achieve complete conversion, further 1% isopropanol was added after 24 h, 48 h and 72 h. The intermediate 3,12-diketo-7β-CA was analyzed by TLC. The educt DHCA was no longer detectable in TLC (silica gel 60, Merck; solvent chloroform:methanol:acetic acid 10:1:0.08 vol:vol:vol).

Scheme 2: Schematic representation of reduction of DHCA by 7β-HSDH. The ADH regenerates the cofactor NADPH.

Scheme 2: Schematic representation of reduction of DHCA by 7β-HSDH. The ADH regenerates the cofactor NADPH.

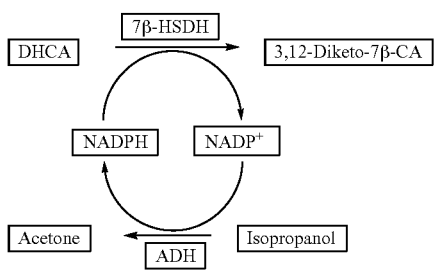

Reaction Example 3: Enzymatic Conversion of 3,12-Diketo-7β-CA to 12-Keto-UDCA The intermediate 3,12-diketo-7β-CA (produced according to reaction example 2) was transformed further by 3α-HSDH (SEQ ID NO:5 and 6) from *Comamonas testosteroni* (Mobus, E. and E. Maser, *Molecular Cloning, overexpression, and characterization of steroid-inducible 3alpha-hydroxysteroid dehydrogenase/carbonyl reductase from Comamonas testosteroni. A novel member of the short-chain dehydrogenase/reductase superfamily*. J Biol Chem, 1998. 273(47): p. 30888-96) to 12-keto-UDCA. This 3α-HSDH requires cofactor NADH, which was regenerated by the FDH (see FIG. 3). 4 U/ml 3α-HSDH, 1 U/ml FDH (NADH-dependent, Codexis), 200 mM sodium formate and 0.05 mM NAD$^+$ were added to the reaction mixture. After 40 h the product was acidified with 2 M HCl to pH2 and extracted with 6×10 ml ethyl acetate. After evaporation, 1.07 g of product was obtained. The product 12-keto-UDCA was analyzed and confirmed by TLC and NMR. 3alpha-HSDH was prepared as for the preparation of 7β-HSDH, but with the plasmid pET22b+, and was used without further purification.

Scheme 3: Schematic representation of reduction of 3,12-diketo-7β-CA by 3α-HSDH. The FDH regenerates the cofactor NADPH.

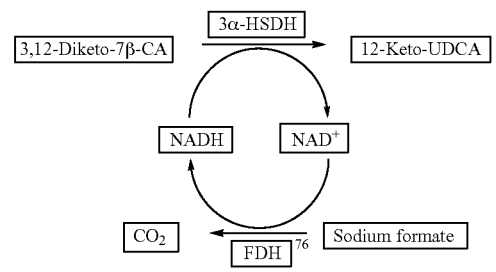

Reaction Example 4: Chemical Reaction of CA to DHCA

1320 L of glacial acetic acid is put in a 2000 L stirred vessel and 110 kg (260 mol) of cholic acid (CA) is dissolved therein. 422 L of sodium hypochloride solution (2.3 molar) is added to this solution at 20 to 40° C. and the reaction solution is then stirred for at least a further 1 hour for completion of the reaction. Dehydrocholic acid (DHCA) is isolated by centrifugation at a yield of 100 kg (90%).

Reaction Example 5: Chemical Reaction of 12-Keto-UDCA to UDCA 105 g (0.258 mol) of 12-keto-UDCA is dissolved in 384 ml triethylene glycol, 52.2 g (1.304 mol) sodium hydroxide and 75.95 ml (1.563 mol) hydrazine hydrate and heated slowly to 180° C. There is formation of hydrazone, which starting from 160° C. is transformed with splitting off of nitrogen to UDCA. The reaction mixture is held at 180° C. for 8 hours for completing the reaction. The reaction mixture is cooled to below 100° C., and 1500 ml water is added. Then the UDCA is precipitated by acidifying with hydrochloric acid. The product is obtained at a yield of 96.2 g to 99.2 g (up to 95%-98%).

Reaction Example 6: Enzymatic Conversion of DHCA to 12-Keto-UDCA by 7β-HSDH, FHD D221G and 3α-HSDH The purpose of this example is to investigate whether a two-step enzymatic conversion of DHCA to 12-keto-UDCA with simultaneous cofactor regeneration with an FDH mutant used according to the invention is possible. As the FDH mutant D221G used accepts both NADP$^+$ and NAD$^+$ as cofactor, for the NADH-dependent 3α-HSDH it is not necessary for the reaction mixture to contain any additional cofactor regeneration system.

Examples of two partial reactions are illustrated graphically below. FDH+ designates the mutant FDH D221G.

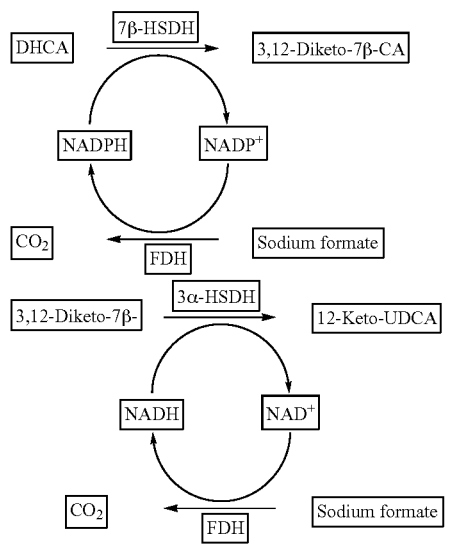

For this, the enzymes 7β-HSDH from *Collinsella aerofaciens*, 3α-HSDH from *Comamonas testosteroni* and the FDH mutant D221G derived from FDH from *Mycobacterium vaccae* were expressed separately from one another in a modified *E. coli* expression strain and were used for the reaction. The *E. coli* strain used for expression was modified so that it does not express any 7α-HSDH enzyme activity. This side activity, widely occurring in *E. coli*, can lead, in reactions of the present type (stereospecific conversion of the 7-keto group), to undesirable side reactions and therefore to contamination of the reaction product to be produced.

In the next experiment, the knock-out strain *E. coli* BL21(DE3)A7α-HSDH was used, which is described in the applicant's earlier European patent application EP 10164003.5. Reference is expressly made hereby to the disclosure of this patent application.

6.1 Plasmids Used

Plasmids for the expression of 7β-HSDH, 3α-HSDH and FHD D221G:
pET28a(+)-7β-HSDH,
pET22b(+)-3α-HSDH and
pET21a(+)-FDH-D221G.

6.2 Bacterial Strains and Culture Conditions:

The aforementioned knock-out strain *E. coli* BL21(DE3) A7α-HSDH was cultured at 37° C. in LB medium containing the necessary antibiotics. After induction with 0.5 mM IPTG on reaching $OD_{600}=0.8$, incubation was continued at 140 rpm for a period of 12 hours at 25° C.

6.3 Enzyme Overexpression and Purification

Overexpression of 7β-HSDH, 3α-HSDH and the FDH mutant D221G in *E. coli* BL21(DE3)A7α-HSDH and enzyme purification were carried out in the same conditions as described above in production example 2 for the overexpression and purification of 7β-HSDH in *E. coli* BL21 (DE3). The yields per liter of culture medium (shaken flask at $OD_{600}$~6) were as follows:
7β-HSDH: 3883 U (for DHCA and NADPH)
3α-HSDH: 6853 U (for DHCA and NADH)
FDH mutant: 47 U (for sodium formate and NAD+).

Content and purity of the proteins were determined by SDS-PAGE and densitometer scanning using Scion Image Beta 4.0.2 (Scion, USA).

6.4 Preparative-Scale Enzymatic Synthesis of 12-Keto-UDCA 800 ml of a reaction mixture containing 7β-HSDH (2.4 U×ml$^{-1}$), 3α-HSDH (2.4 U×ml$^{-1}$), FDH D221G (0.325 U×ml$^{-1}$), NADP+ (10 μM), NAD+ (10 μM), sodium formate (250 mM), DHCA (10 mM, 3.2 g) and potassium phosphate buffer (50 mM, pH 6) was stirred at 24° C. All three enzymes that were employed in this experiment were used as cell raw extracts without an additional purification step. After 12 hours the reaction was stopped by removing the enzymes by ultrafiltration using a membrane with a pore size of 10 kDa (Millipore, USA). The product in the filtrate was purified by acidifying with hydrochloric acid to pH 2 followed by paper filtration. After drying the product at 60° C. overnight, 2.9 g of the desired product was obtained.

The product was analyzed by HPLC and NMR.
Analysis Data (Partial):
$^1$H NMR (deuterated DMSO, 500 MHz) δ=3.92 (2H, m, H-3α and H-7β) and
$^1$H NMR (deuterated DMSO, 125 MHz) δ=69.38 (CH, 3-C); δ=69.09 (CH, 7-C); δ=213.86 (C, 12-C)
Yield: 90.6%
Purity: 99%

Reaction Example 7: Whole-Cell Biotransformation of DHCA to 12-Keto-UDCA by Coexpression of FDH D221G, 7β-HSDH and 3α-HSDH in the Two-Plasmid System The aim was to investigate whether a two-step whole-cell reduction of dehydrocholic acid (DHCA) to 12-keto-ursodeoxycholic acid (12-keto-UDCA) (cf. scheme according to reaction example 6, above) is possible.

For this, the knockout strain *E. coli* BL21 (DE3) hdhA$^-$ KanR+ pET21a(+) FDH 7β-HSDH pCOLA(mod) 3α-HSDH prepared above was used, in which, in addition to the 7β-HSDH and the mutant FDH D221G, a 3α-HSDH from *Comamonas testosteroni* is expressed recombinantly. As the FDH mutant used accepts both NADP+ and NAD+ as cofactor, for the NADH-dependent 3α-HSDH it was not necessary to insert any additional cofactor regeneration system into the biotransformation strain.

7.1 Strain Used:
*Escherichia coli* BL21 (DE3) hdhA$^-$ KanR+

7.2 Molecular Biology Procedures Used 7.2.1 Polymerase Chain Reaction

The polymerase chain reaction (PCR) was used for cloning the 7β-HSDH. The plasmid pET22b(+) 7β-HSDH served as template for amplification of the 7β-HSDH.

PCR reactions were carried out in 500 μL PCR tubes with 20 μL reaction volume. The reactions were carried out in a Thermocycler from the company Eppendorf. For amplification of 7β-HSDH, in each case 4 μL HF-buffer, 1 μL template DNA, 1 μL each of forward and reverse primer (10 μM), 0.4 μL of deoxynucleotide triphosphate solution (10 mM) and 0.2 μL of Phusion DNA polymerase (2 U/μL) were added. The volume of the preparation was adjusted to 20 μL with RNase-free water.

For the reaction, first a 2-min initial denaturation step was carried out at 98° C. Then 34 cycles of denaturation (30 s at 98° C.), primer hybridization (2 min at 48° C.) and elongation (2 min at 72° C.) were carried out. As a last step, final elongation of 10 min was carried out at 72° C. before stopping the polymerase chain reaction by cooling to 4° C.

7.2.2 Purification of DNA Fragments by Gel Extraction

For purification of DNA fragments, first they were separated by agarose gel electrophoresis. The corresponding bands were made visible with UV light, identified based on their size and cut out of the gel with a scalpel. Extraction was carried out with the QIAquick Gel Extraction Kit according to the manufacturer's protocol. 30-50 μL H$_2$O was used for elution of the purified DNA.

7.2.3 Restriction with Endonucleases

The restriction reactions were carried out in a total volume of 20-50 μL. For this, 10-20 U of the respective restriction enzymes was added to the DNA to be cut. In addition, the reaction buffer recommended by the manufacturer was used and optionally 0.5 μL of bovine serum albumin (BSA, 10 mg/mL) was added, based on the manufacturer's recommendation. Restriction digestion was carried out for 2 h at 37° C. Then the restricted fragments were purified either by gel extraction (vector digestion products) or using the QIAquick PCR Purification Kit (digested PCR products).

7.2.4 Purification of DNA Fragments Using the QIAquick PCR Purification Kit

In order to purify restricted PCR fragments, DNA was purified using the QIAquick PCR Purification Kit. Purification was carried out according to the manufacturer's instructions, using 30-50 μL H$_2$O for elution of the purified DNA.

7.2.5 Ligation of DNA Fragments

For cloning restricted DNA fragments into expression vectors, both DNA molecules were cut with the same restriction enzymes. By using two different enzymes, on the one hand religation of the vector can be prevented, and on the other hand the insert can be incorporated in a defined orientation. The enzyme used was T4-DNA-ligase, which catalyzes the formation of a phosphodiester bond between a free 5'-phosphate group and a free 3'-OH end of a deoxyribonucleic acid.

For cloning the expression constructs, in each case 4 μL of a gene-coding, purified DNA fragment with restricted ends was added to 12 μL of a restricted, purified vector. Then 2 μL 10× ligase buffer, 1 μL adenosine triphosphate (ATP, 1 mM) and 1 μL T4-DNA-ligase (400 U/μL) were added. The reactions continued overnight at 16° C.

7.3 Vector Constructs Used

7.3.1 pET21a(+) FDH 7β-HSDH

For this vector construct, 7β-HSDH was cloned into pET21a(+) FDH, so that the 7beta-HSDH coding gene is located downstream of the FDH. For this purpose, a stop codon had to be inserted in the FDH at the 5'-end. Compared with the original sequence (Lys-Lys-Ala-Val-stop), in this construct the C-terminal valine residue was replaced with an alanine residue and a further three amino acids were appended, resulting in the following C-terminal sequence: Lys-Lys-Ala-Ala-Gly-Asn-Ser-stop. Moreover, for increased translation, an additional ribosomal binding site was inserted in 7β-HSDH between FDH and 7beta-HSDH. The primers 7beta_fwd_EcoRI and S_7beta_rev_HindIII were used for PCR amplification of 7β-HSDH.

7beta_fwd_EcoRI (SEQ ID NO: 13):
5'-GCGAATTCG*TGAAAGGAGATATAC*ATGAACCTGAGGGAGAAG TACGG-3'

S 7beta_revHindIII (SEQ ID NO: 3):
5'-*CCC*AAGCTTCTAGTCGCGGTAGAACGA-3'

The hybridizing sequence regions (bold), restriction sites (bold underlined), ribosomal binding sites (underlined), and filling nucleotides (italics) are shown. In the primer 7beta_fwd_EcoRI, additionally a stop codon (double underlined) and a nucleotide for reading frame shift (bold) were added.

Cloning was carried out via the EcoRI and HindIII cleavage sites.

7.3.2 pCOLA(mod) 3α-HSDH

In order to be able to reduce dehydrocholic acid in two steps to 12-keto-ursodeoxycholic acid, in addition to the cofactor regeneration system FDH, the enzymes 7β-HSDH and 3α-HSDH must also be present in a cell. To make this possible, the vector construct pCOLA(mod) 3α-HSDH, a modified derivative of the pCOLA-duet vector, was prepared, which is cotransformable with pET-vectors.

For this purpose, the 3α-HSDH coding gene was cut out via the NdeI and BlpI cleavage sites from the vector pET22b (+) 3α-HSDH and, via the same cleavage sites, cloned into MCS2 of the pCOLA(mod) vector. After sequencing, it was found that at position 45 of the DNA sequence, a guanine was replaced with a cytosine, but this results in a silent mutation. However, this mutation has no effect on the amino acid sequence; therefore this is a so-called silent mutation.

Both vectors were cotransformed into the aforementioned strain, as described below. The genes are IPTG-inducible.

7.4 Heat-Shock Transformation of E. coli Cells

For this purpose, 200 μL of chemically-competent *E. coli* BL21 (DE3) hdhA$^-$ KanR$^+$ or DH5α were thawed and 1 μL DNA was added. These were first incubated on ice for 45 min. Then the cells were submitted to heat shock for 45 s at 42° C. Then 600 μL of LB medium was added to the cells and they were shaken at 37° C. and 200 rpm, so that they could develop the desired antibiotic resistance. Next the cells were centrifuged in a benchtop centrifuge at 3000 rpm for 2 min, after which 150 μL of the supernatant was discarded. The cells were resuspended in the remaining supernatant and plated out on LB-agar plates with the corresponding antibiotic. Then the plates were incubated overnight at 37° C.

In the case of cotransformation of two different plasmids, as is necessary for creating the strain that contains the plasmids pCOLA(mod) 3α-HSDH and pET21a(+) FDH 7β-HSDH, in each case 2 μL of the plasmids to be inserted was added to 50 μL of chemically-competent *E. coli* BL21 (DE3) hdhA$^-$ KanR$^+$. After transformation, the cells were added to preculture tubes with 5 mL of LB medium with the corresponding antibiotic and were incubated at 37° C. on the preculture shaker for 16-48 h at 200 rpm, until growth of bacteria in the preculture tube was detected. Next, 5 μL of the bacterial suspension was plated out on LB-agar plates with the corresponding antibiotic and was incubated overnight at 37° C.

7.5 Cultivation of the Strain in the Shaken Flask:

For expression of recombinant proteins, the corresponding *E. coli* BL21 (DE3) hdhA$^-$ KanR$^+$ comprising the two expression plasmids was incubated overnight at 37° C. and 200 rpm in 5 mL of LB medium with addition of the corresponding antibiotic. Then 200 mL of TB medium with addition of the corresponding antibiotic was inoculated with this preculture and incubated at 37° C., 250 rpm. On reaching OD600 of 0.6-0.8, expression of the recombinant protein was induced with 1 mM isopropyl-β-D-thiogalactopyranoside (IPTG) and the culture was incubated at 25° C., 160 rpm for a further 21 h.

7.6 Carrying Out Whole-Cell Biotransformation and Test Result

The reactions were carried out in suspension in 2 mL reaction volume at pH 6.0, using a cell density of OD$_{600}$=20. 25 mM or 50 mM dehydrocholic acid was selected as the substrate concentration, and the cosubstrate concentration used was 400 mM. The tests were carried out at 25° C. with exclusion of air. Samples were taken after 48 h.

In the case of the reaction mixture with 25 mM, substrate is no longer detectable, whereas for the reaction mixture with 50 mM dehydrocholic acid, a substrate peak is detectable, but its peak area is below the limit of 1 μg/mL substrate in the sample for which the HPLC method is calibrated. The same applies to the peaks of 3,12-diketo-ursodeoxycholic acid. The largest peak in the chromatograms is that of the product 12-keto-ursodeoxycholic acid.

Thus, it can be shown, surprisingly, that a two-step whole-cell reduction of dehydrocholic acid to 3-keto-ursodeoxycholic acid is possible.

Figure 7:
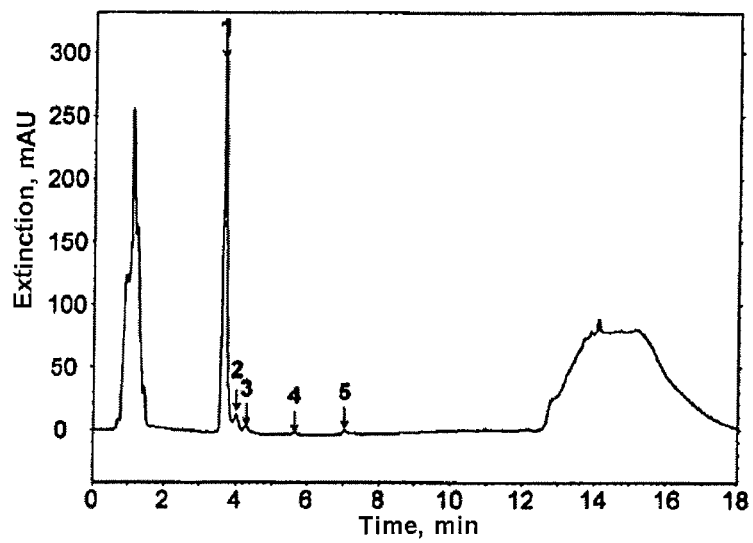
FIG. 7 shows the HPLC chromatogram of the biotransformation of DHCS with 7β-HSDH and 3α-HSDH in the whole-cell process. It shows the HPLC chromatogram of the whole-cell conversion of the strain *E. coli* BL21 (DE3) hdhA⁻ KanR⁺ pET21a(+) FDH 7β-HSDH pCOLA(mod) 3α-HSDH. The starting conditions selected were 50 mM substrate, 400 mM 15 cosubstrate, pH 6.0. Sampling was carried out after 48 h. The peaks of 12-keto-UDCA (1), an unknown by-product (2), 3,12-diketo-UDCA (3), 7,12-diketo-UDCA (4) and DHCA (5) can be seen.

The chromatograms of the HPLC measurement are shown in FIG. 7.

The HPLC analysis was carried out as follows: The chromatography column used was the reverse-phase chromatography column Hi-bar Purospher 125-4 RP-18e (5 μm) from the company Merck, Darmstadt. In this case a nonpolar phase serves as stationary phase, whereas a polar phase forms the mobile phase. The method of gradient elution was used for the HPLC analysis. An increasing proportion of acetonitrile is added to the eluent, phosphoric acid water, (pH 2.6), and the acidification of the solvent causes a uniform degree of protonation of the analytes to be investigated. After elution of all components, the chromatography column is equilibrated with the starting ratio of the two solvents. Gradient elution was carried out by first pumping a solvent mixture with a constant composition of 65% (v/v) of phosphoric acid water and 35% (v/v) of acetonitrile through the HPLC column for 3 min. From minute 3 to 7.5, the proportion of acetonitrile is increased linearly to 39% (v/v). Between minute 7.5 and 10 there is another linear increase of the proportion of acetonitrile to 40% (v/v). For elution of all sample components, the proportion of acetonitrile is increased between minute 10 and 11 also linearly to 70% (v/v) and held constantly at this value for a further two minutes. After that, the proportion of acetonitrile is reduced from minute 13 to 15 back to the initial value of 35% and the column is equilibrated with this solvent composition for 3 min. The flow is set at 1.000 mL/min for the total duration. Eluted analytes are detected by a UV-detector at a wavelength of 200 nm.

Reaction Example 8: Whole-Cell Biotransformation of DHCA to 12-Keto-UDCA by Coexpression of FDH D221G, 7β-HSDH and 3α-HSDH in the Single-Plasmid System The aim was to investigate whether a two-step whole-cell reduction of dehydrocholic acid to 12-keto-ursodeoxycholic acid in a cellular single-plasmid system is possible.
8.1 Plasmids Used:

Restriction sites are underlined; ribosomal binding sites are bold.
8.2 Production of the Vector:

The plasmid construct pET21a(+) FDH 7β-HSDH(G39A) 3α-HSDH (FIG. 8) is prepared as follows: Starting from the plasmid pET21a(+) FDH 7β-HSDH the wild-type 3α-HSDH (*C. testosteroni*; SEQ ID NO: 5, 6) was cloned in after 7β-HSDH via the HindIII and NotI cleavage sites. For amplification of 3α-HSDH, the primers 3alpha_fwd_HindIII and 3alpha_rev_NotI were used, with the plasmid pET22b(+) 3α-HSDH serving as template for this. Then the G39A mutation was inserted into 7β-HSDH by site-directed mutagenesis according to the QuikChange protocol. The mutagenesis primers 7beta_mut_G39A_fwd and 7beta_mut_G39A_rev were used.
8.3 Reaction:

The plasmid prepared was transformed into *E. coli* BL21 (DE3) hdhA⁻ KanR⁺. With the resultant strain *E. coli* BL21 (DE3) hdhA⁻ KanR⁺ pET21a(+) FDH 7β-HSDH(G39A) 3α-HSDH, whole-cell reactions were carried out under the following conditions at the 150-mL scale: cell density OD 30, 50 mM DHCA, 750 mM sodium formate, suspended in 50 mM potassium phosphate buffer (pH 6.5) as cell and substrate suspension. The reactions were carried out for 3.5 h at 25° C. The results of the HPLC analysis (for procedure see reaction example 7, above) are shown in FIG. 9.

Production Example 6: Production of Further 7β-HSDS Mutants and Characterization Thereof One possibility for generating an NADH-specific 7β-HSDH consists of modifying the available enzyme by various techniques of mutagenesis. Therefore, using site-directed mutagenesis, individual amino acids of 7β-HSDH were to be substituted with others, which cause change of the cofactor specificity of 7β-HSDH from NADPH to NADH, so that advantageously NADP can be replaced with the less expensive NAD.
6.1 Primers Altogether, the 7β-HSDH mutants G39D, G39D/R40L, G39D/R40I and G39D/R40V were produced. The G39D mutant is produced by Quickchange mutagenesis, and the other mutants are produced by the PCR method of Sanchis et al. (Sanchis J, Fernández L, Carballeira J D, Drone J, Gumulya Y, Höbenreich H, Kahakeaw D, Kille S, Lohmer R, Peyralans J J, Podteteniefff J, Prasad S, Soni P, Taglieber A, Wu S, Zilly F E, Reetz M T. Improved PCR method for the creation of saturation mutagenesis libraries in directed evolution: application to difficult-to-amplify templates. Appl Microbiol Biotechnol. 2008 November; 81(2): 387-97). A sequence comparison of the wild type and of the mutants produced is shown in FIG. 10. The following primers were used for the mutagenesis, with the bases shown in italics coding in each case for the exchanged amino acid:

| Designation | Sequence | SEQ ID NO |
|---|---|---|
| 3alpha_fwd_HindIII | 5'-CCC<u>AAGCTT</u>AAGGAGATATACATGTCCATCATCGTGATAAGCG-3' | 16 |
| 3alpha_rev_NotI | 5'-ATAAGAAT<u>GCGGCCGC</u>TCAGAACTGTGTCGG GCG-3' | 17 |
| 7beta_mut_G39A_fwd | 5'-CGTCGTCATGGTCGCCCGTCGCGAGG-3' | 9 |
| 7beta_mut_G39A_rev | 5'-CCTCGCGACGGGCGACCATGACGACG-3' | 10 |

G39D
7beta mut G39D fwd (SEQ ID NO: 41):
CGTCGTCATGGTCGACCGTCGCGAGG

7beta mut G39D rev (SEQ ID NO: 42):
CCTCGCGACGGTCGACCATGACGACG

G39D R40L
7beta mut G39D R40L fwd (SEQ ID NO: 43):
CGTCGTCATGGTCGACCTGCGCGAGG

3alphamut_AntiMid_rev (SEQ ID NO: 44):
CCGCCGCATCCATACCGCCAGTTGTTTACCC

G39D R40I
7beta mut G39D R40I fwd (SEQ ID NO: 45):
CGTCGTCATGGTCGACATTCGCGAGG

3alphamut_AntiMid_rev (SEQ ID NO: 44):
CCGCCGCATCCATACCGCCAGTTGTTTACCC

G39D R40V
7beta mut G39D R40V fwd (SEQ ID NO: 46):
CGTCGTCATGGTCGACGTTCGCGAGG

Figure 11:
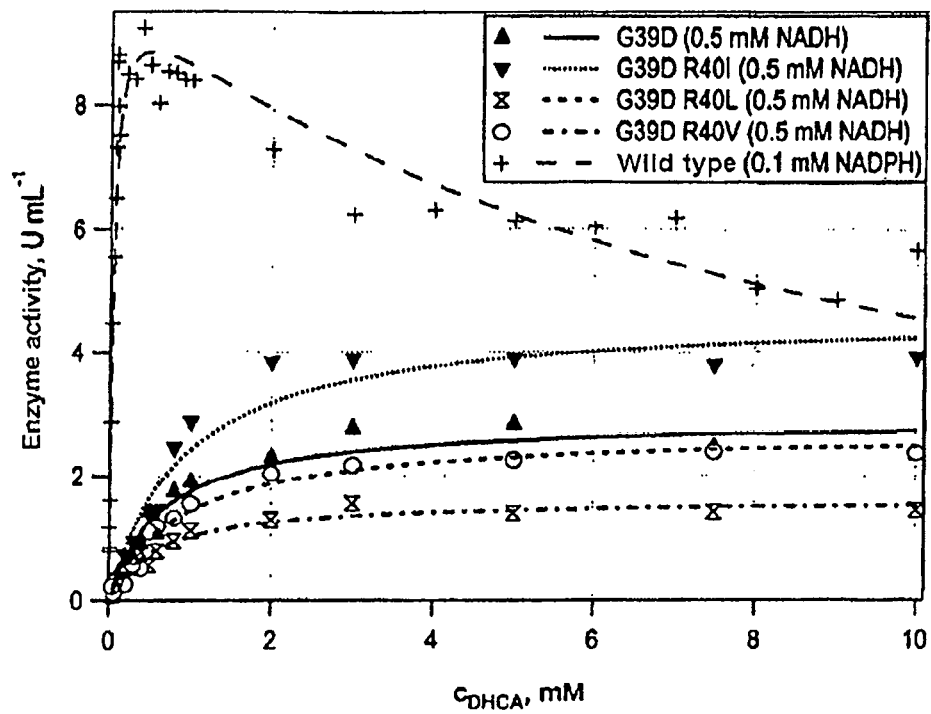
FIG. 11 shows an enzyme-kinetic investigation of 7β-HSDH and the mutants thereof. The specific enzyme activity is plotted versus different substrate concentrations used (DHCA concentration) at a constant cofactor concentration of 0.1 mM NADPH or 0.5 mM NADH.

3alphamut_AntiMid_rev (SEQ ID NO: 44):
CCGCCGCATCCATACCGCCAGTTGTTTACCC 6.2 Enzyme-Kinetic Investigation of the 7β-HSDH Mutants The mutants prepared are evaluated by means of enzyme-kinetic investigations, the results of which are shown as graphs in FIG. 11. 0.1 mM NADPH is used as cofactor for investigating the unmodified 7β-HSDH, but 0.5 mM NADH is used for investigating the 7β-HSDH mutants. The need to increase the cofactor concentration in the enzyme-kinetic investigation of the 7β-HSDH mutants is due to the increased semisaturation concentrations for the cofactor NADH in the mutants. From the plots of substrate concentration versus specific enzyme activity, the characteristic curves of Michaelis-Menten kinetics can be seen for the 7β-HSDH mutants, whereas the curve of Michaelis-Menten kinetics with substrate inhibition can be seen from the plot for the unmodified wild-type 7β-HSDH. Accordingly, the classical Michaelis-Menten model (equation 1) was used for evaluating the measurement series of the 7β-HSDH mutants and the Michaelis-Menten model with substrate inhibition was used for the measurement series of the unmodified wild-type 7β-HSDH (equation 2).

$$EA_x = v_{max} \cdot \frac{c_S}{K_m + c_S} \quad \text{Equation 1 (Michaelis-Menten equation)}$$

$EA_x$: specific enzyme activity, U mg$^{-1}$=μmol min$^{-1}$ mg$^{-1}$
$v_{max}$: maximum specific enzyme activity, U mg$^{-1}$=μmol min$^{-1}$ mg$^{-1}$
$c_s$: substrate or cofactor concentration, mol L$^{-1}$
$K_m$: semisaturation concentration, mol L$^{-1}$ $$EA_x = v_{max} \cdot \frac{c_S}{K_m + \left(1 + \frac{(c_S)}{(K_i)}\right)c_S} \quad \text{Equation 2 (Michaelis-Menten equation with substrate inhibition)}$$

$EA_x$: specific enzyme activity, U mg$^{-1}$=μmol min$^{-1}$ mg$^{-1}$
$v_{max}$: maximum specific enzyme activity, U mg$^{-1}$=μmol min$^{-1}$ mg$^{-1}$
$c_s$: substrate or cofactor concentration, mol L$^{-1}$
$K_m$: semisaturation concentration, mol L$^{-1}$
$K$: inhibition constant, mol L$^{-1}$ The following table gives enzyme-kinetic parameters of the unmodified wild-type 7β-HSDH and the mutants thereof with altered cofactor specificity. NADPH is used as cofactor for the wild type, whereas NADH is used as cofactor for the mutants.

|  | $K_m$, DHCA, μM | $K_i$, DHCA, μM | $v_{max}$, U mg-1 |
| --- | --- | --- | --- |
| Wild type | 31 ± 5 | 8600 ± 1500 | 14.6 ± 1.0 |
| G39D | 660 ± 120 | n.d. | 2.90 ± 0.16 |
| G39D R40I | 920 ± 170 | n.d. | 4.64 ± 0.27 |
| G39D R40V | 880 ± 120 | n.d. | 2.69 ± 0.12 |
| G39D R40L | 560 ± 80 | n.d. | 1.60 ± 0.07 |

Production Example 7: Production of Further 7β-HSDS Mutants and Characterization Thereof Further 7β-HSDS mutants were produced in a preparation parallel to production example 6.

7.1 Primers

The mutagenesis primers shown below were used for the site-directed mutagenesis of 7β-HSDH. The primers were selected on the basis of the 7β-HSDH gene sequence, so that they bring about the desired amino acid exchange. It was noted that the base to be mutated is localized centrally in the primer, and that the melting points of the primer pairs are located in the same region.

The following primer pairs were used for preparing the mutants:

TABLE

Primers used for the site-directed mutagenesis of 7β-HSDH

| Designation | Position | Primer | 5'→3' Sequence |
| --- | --- | --- | --- |
| G39D_for | G39D | forward | GTCGTCATGGTCGACCGTCGCGAGGAG |
| G39D_rev |  | reverse | CTCCTCGCGACGGTCGACCATGACGAC |
| G39D/RT40I_for | G39D/R40I | forward | GTCATGGTCGACATTCGCGAGGAG |
| G39D/R40I_rev |  | reverse | CTCCTCGCGAATGTCGACCATGAC |
| R40D_for | R40I | forward | GTCATGGTCGGCGATCGCGAGGAGAAG |
| R40D_rev |  | reverse | CTTCTCCTCGCGATCGCCGACCATGAC |

TABLE-continued

Primers used for the site-directed mutagenesis of 7β-HSDH

| Designation | Position | Primer | 5'→3' Sequence |
|---|---|---|---|
| R40D/R41I_for | R40D/R41I | forward | GTCATGGTCGGCGATATCGAGGAGAAGCTG |
| R40D/R41I_rev | | reverse | CAGCTTCTCCTCGATATCGCCGACCATGAC |
| DIN_for | G39D/R40I/R41N | forward | ATGGTCGACATTAACGAGGAGAAGCTG |
| DIN_rev | | reverse | CAGCTTCTCCTCGTTAATGTCGACCAT |

7.2 PCR Program

In the reaction, first there was a 2-min initial denaturation step at 98° C. This was followed by 23 cycles of denaturation (30 s at 98° C.), primer hybridization (1 min at 60-68° C.) and elongation (3.5 min at 72° C.). As the last step, a final elongation was carried out for 10 min at 72° C. before the polymerase chain reaction was stopped by cooling to 4° C.

7.3 PCR Assay

TABLE

PCR assay for the production of the different 7β-HSDH variants

| | |
|---|---|
| HF buffer (5x) | 10 µl |
| dNTP mix (10 mM) | 1.0 µl |
| Forward primer (10 pmol/µl) | 5 µl |
| Reverse primer (10 pmol/µl) | 5 µl |
| Template | 1.5 µl |
| Phusion polymerase | 0.5 µl |
| DMSO | 2.5 µl |
| ddH$_2$O | 24.5 µl |
| | 50 µl |

A pET21a vector with the 7β-HSDH (wild type) was used as template.

7.4 Procedure

For targeted exchange of amino acids in protein sequences, the DNA sequence of the corresponding gene is submitted to site-directed mutation. For this, mutually complementary primers are used, which carry the desired mutation in their sequence. N6-adenine-methylated, double-stranded plasmid DNA, which carries the gene to be mutated, serves as template. N6-adenine-methylated plasmid DNA is isolated from dam E. coli strain, for example E. coli DH5.

The polymerase chain reaction is carried out as described above. The primers are lengthened complementarily to the template, so that plasmids with the desired mutation are formed, which have a strand break. In contrast to other PCR reactions, the increase in DNA yield is in this case only linear, as newly formed DNA molecules cannot serve as template for the PCR reaction.

On completion of the PCR reaction, the PCR product was purified using a PCR-Purification-Kit (Analytik Jena) and the parental, N6-adenine-methylated DNA was digested with the restriction enzyme DpnI. This enzyme has the particular characteristic that it restricts N6-adenine-methylated DNA nonspecifically, but not the newly formed, non-methylated DNA.

Restriction was carried out by adding 1 µL DpnI to the PCR reaction mixture and incubating for 2 h or overnight at 37° C.

5 µl of this preparation were used for the transformation of 100 µl of chemically-competent DH5α cells. After plasmid isolation, successful mutation was confirmed by sequencing.

7.5 Characterization

The mutation was introduced into 7β-HSDH by site-directed mutagenesis according to the QuikChange protocol. The mutagenesis primers from the table shown in Section 7.1 were used.

Using the assays given in the "Methods" section for photometric measurement of activity, the activity of the mutated enzymes was measured in the presence of NADPH or NADH. The activities found are presented in the following table.

TABLE

Activity found for the different 7β-HSDH variants

| | Volumetric activity [U/ml] | | Specific activity [U/mg] | |
|---|---|---|---|---|
| Mutants produced | NADPH | NADH | NADPH | NADH |
| G39D | 119 | 2 | 5.1 | 0.1 |
| G39D/R40I | 0 | 21 | 0 | 0.8 |
| R40D | 0 | 3 | 0 | 0.1 |
| R40D/R41I | 0 | 3 | 0 | 0.2 |
| G39D/R40I/R41N | 0 | 6 | 0 | 0.3 |
| 7β-HSDH (WT) | 134 | 0 | 5.6 | 0 |

Figure 12:
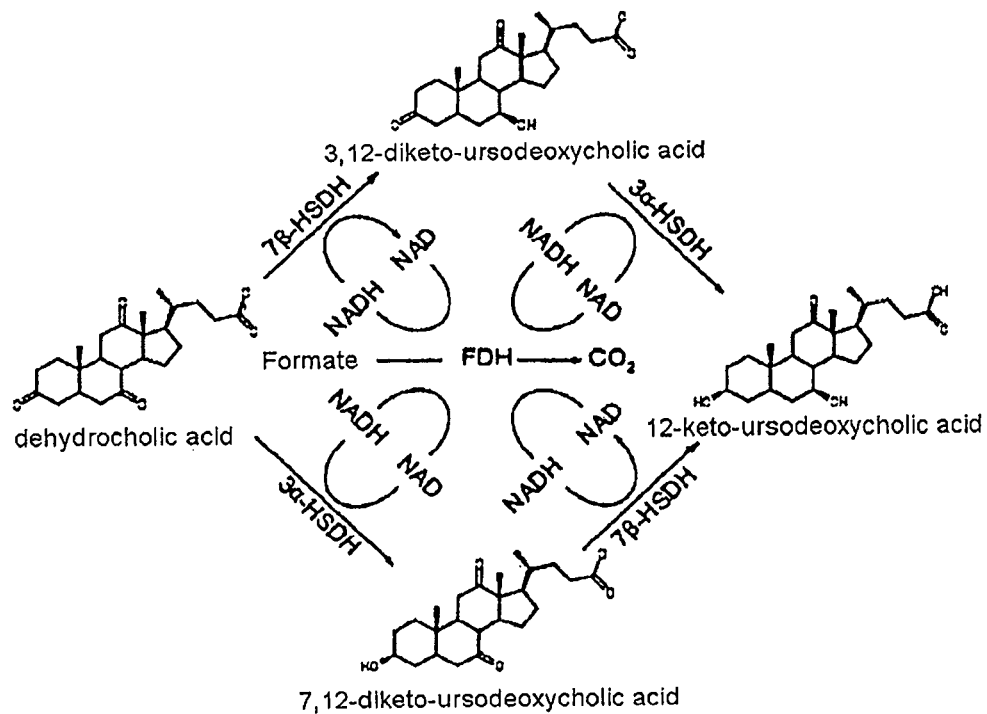
FIG. 12 shows a schematic representation of a two-step enzymatic reduction of dehydrocholic acid to 12-keto-ursodeoxycholic acid according to the invention, wherein an NADH-dependent 7β-HSDH is used and a formate dehydrogenase (FDH) is used for cofactor regeneration.

Reaction Example 9: Using NADH-Dependent 7β-HSDH in the Whole-Cell Reduction of Dehydrocholic Acid to 3,12-Diketo-UDCA The use of NADH-dependent 7β-HSDH, produced in production example 6, in the whole-cell biocatalytic conversion of DHCA to 3,12-diketo-UDCA is demonstrated below. To improve comprehension, a review of possible reaction pathways and reaction products is shown in FIG. 12.

Figure 13:
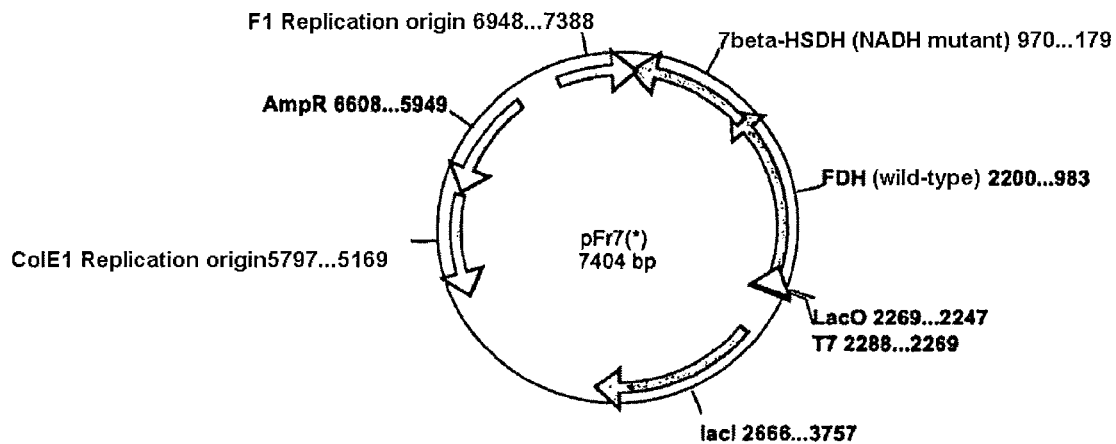
FIG. 13 shows a schematic representation of the principle of construction of the vectors pFr7(D), pFr7(DI), pFr7(DL) and pFr7(DV) that were used for the expression of various NADH-dependent mutants of 7β-HSDH.

In the present case, the 7β-HSDH mutants together with an NADH-dependent formate dehydrogenase from Mycobacterium vaccae were inserted in an expression vector. The vector into which 7β-HSDH (G39D) is inserted bears the designation pFr7(D), corresponding to SEQ ID NO:49; the vector into which 7β-HSDH (G39D R40L) is inserted bears the designation pFr7(DL), corresponding to SEQ ID NO:50; the vector into which 7β-HSDH (G39D R40I) is inserted bears the designation pFr7(DI), corresponding to SEQ ID NO:51, and the vector into which 7β-HSDH (G39D R40V) is inserted bears the designation pFr7(DV), corresponding to SEQ ID NO:52. A general plasmid map of these vectors is shown in FIG. 13.

These vectors were transformed into the strain E. coli BL49 (identical to E. coli BL21(DE3) hdhA$^-$ KanR$^+$). From these strains, firstly 5 mL overnight cultures were grown in LB medium with 100 mg L$^{-1}$ ampicillin. In each case 1 mL of these overnight cultures was transferred on the next day into 200 mL of TB medium in shaken flasks with 100 mg L$^{-1}$ ampicillin. These cultures were cultured at 37° C. and 250 rpm in the shaking incubator, until an OD of 0.6-0.8 was reached. Then induction was carried out with 1 mM isopropyl-β-D-thiogalactopyranoside (IPTG). The subsequent expression phase was carried out for 21 h at 25° C. and 160 rpm. The cells were harvested by 10-minute centrifugation at 3220 g.

Whole-cell biotransformation reactions were set up with the cells produced in this way. The concentrations of the substrate DHCA and of the product 3,12-diketo-UDCA in the reaction mixture at various time points was determined by high-performance liquid chromatography (HPLC).

Figure 14:
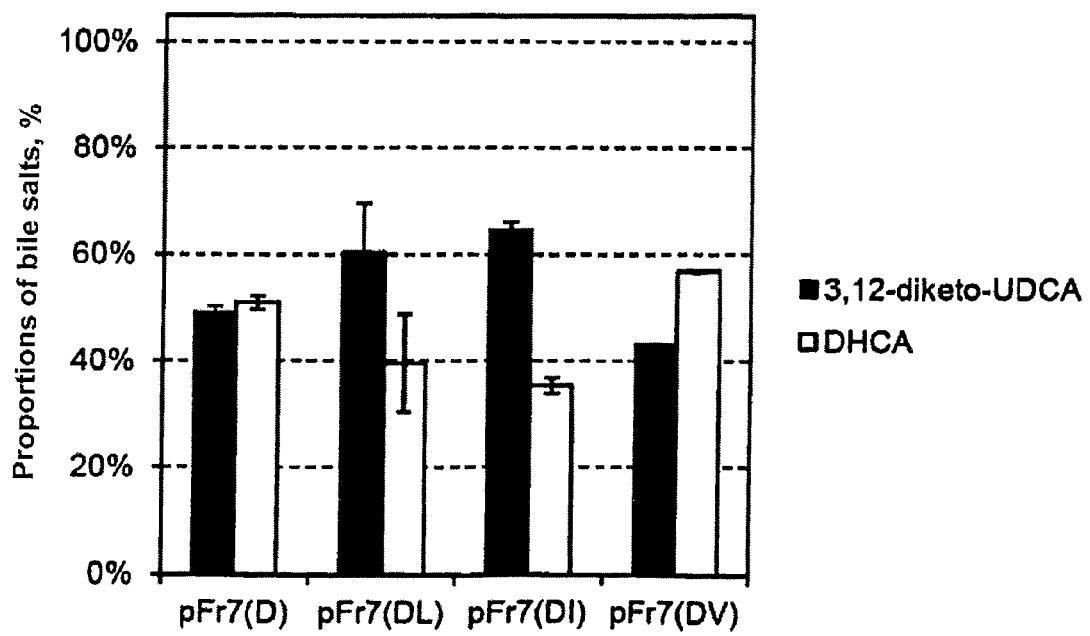
FIG. 14 shows the proportions of bile salts in biotransformation batches using NADH-dependent 7β-HSDH mutants. Results after 24 h process time and using 100 mM substrate (DHCA) are shown.

The reaction mixtures for the biotransformations contained 17.7 g $L^{-1}{}_{BTM}$ whole-cell biocatalysts, 100 mM substrate (DHCA), 500 mM sodium formate and are suspended in 50 mM potassium formate buffer (pH 6.5). The process took place at the 20 mL scale as a batch process without pH monitoring. The concentrations of product and substrate after 24 h are shown in FIG. 14. It can be seen that all mutants are suitable for the whole-cell biocatalytic conversion of DHCA to 3,12-diketo-UDCA.

Reaction Example 10: Using NADH-Dependent 7β-HSDH in the Two-Step Whole-Cell Reduction of Dehydrocholic Acid to 12-Keto-UDCA The use of NADH-dependent 7β-HSDH in the two-step whole-cell biocatalytic conversion of DHCA to 12-diketo-UDCA is to be demonstrated below. The mutants 7β-HSDH (G39D) together with an NADH-dependent formate dehydrogenase from *Mycobacterium vaccae* and an NADH-dependent 3α-HSDH from *Comamonas testosteroni* were inserted into an expression vector. The use of 7β-HSDH (G39D) is shown as an example for all NADH-dependent 7β-HSDHs. The vector bears the designation pFr3T7(D) and is shown schematically in FIG. 15.

These vectors were transformed into the strain *E. coli* BL49 (identical to *E. coli* BL21(DE3) hdhA⁻ KanR⁻); the resultant strain bears the designation *E. coli* BL49 pFr3T7 (D). This strain was cultured in the 7 L bioreactor at a working volume of 4 L in the defined minimal medium. A brief initial phase at 37° C. was followed by a substrate-limited exponential growth phase at 30° C. On reaching an optical density of 25-30, protein expression of the cells was induced by adding 0.5 mM IPTG. Expression was then carried out for 24 h at 20° C. The cells (32.0 g $L^{-1}{}_{BTM}$) were harvested by centrifugation, resuspended in potassium phosphate buffer (pH 6.5) and stored according to the standard protocol at −20° C.

Figure 16:
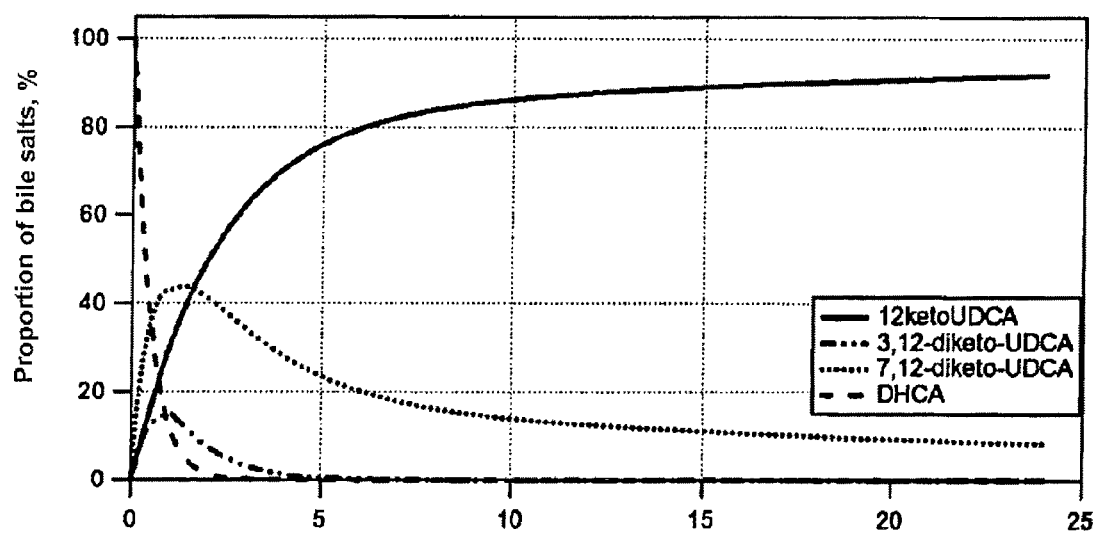
FIG. 16 shows the result of a whole-cell biotransformation with the strain *E. coli* BL49 pFr3T7(D), which comprises the NADH-dependent 7β-HSDH (G39D), an NADH-dependent 3α-HSDH and an NADH-dependent FDH. The biotransformations were carried out in the following conditions: 20 mL reaction volume, 17.7 g/l$_{BTM}$ cells, 100 mM DHCA, 500 mM ammonium formate, 26% glycerol, 50 mM MgCl$_2$, 50 mM KPi buffer (pH 6.5). During the first 5 hours the pH was adjusted manually with formic acid to the initial value at hourly intervals.

Biotransformation was set up at the 20-mL scale in the following reaction conditions: 100 mM DHCA, 17.7 g $L^{-1}{}_{BTM}$ of the stored biocatalyst, 500 mM ammonium formate, 26% glycerol, 50 mM $MgCl_2$, suspended in 50 mM KPi buffer (pH 6.5). Using manual pH adjustment, the pH was maintained during the first 5 hours of the biotransformation process at pH 6.5. The bile salt concentrations are shown as a function of time in FIG. 16. After 24 h, 92% of the product 12-keto-UDCA had formed. The conversion of DHCA to 3,12-diketo-UDCA and the conversion of 7,12-diketo-UDCA to 12-keto-UDCA show that all the reactions of 7β-HSDH shown in FIG. 12 are in fact catalyzed by 7β-HSDH (G39D).

Reaction Example 11: Two-Step Reduction of Dehydrocholic Acid in a Single-Cell System One route for the synthesis of ursodesoxycholic acid comprises the chemical oxidation of cholic acid to dehydrocholic acid with subsequent asymmetric enzymatic reductions of the 3-carbonyl group to the 3α-hydroxyl group and of the 7-carbonyl group to the 7β-hydroxyl group followed by chemical removal of the 12-carbonyl group.

For this synthesis route, the enzymes 7β-hydroxysteroid dehydrogenase (7β-HSDH) and 3α-hydroxysteroid dehydrogenase (3α-HSDH) are required for catalysis of the enzymatic reduction reactions. In the reaction, in addition cofactors (NADH or NADPH) are consumed stoichiometrically, and in an economic process these must be regenerated. Enzymatic regeneration possibilities are often preferred for this. Suitable enzymes include formate dehydrogenases (FDH), glucose dehydrogenases (GDH), glucose-6-phosphate dehydrogenases (G6PDH), alcohol dehydrogenases (ADH) or phosphite dehydrogenases (PtDH).

In contrast to the use of isolated enzymes, in whole-cell biocatalysis, with the necessary enzymes within a host organism, typically a unicellular microorganism, it is not possible to add individual enzymes in individual amounts to the reaction medium. In this case the enzyme activities must be balanced by modifying the expression level of all participating enzymes either by cultivation methods or by genetic modification of the whole-cell biocatalyst.

In the present example, vectors were used according to the invention, which contain all three genes for 7β-HSDH, 3α-HSDH and FDH. The vectors are constructed so that the expression level of the three genes in the designated host strain, especially whole-cell biocatalyst strains based on *Escherichia coli* BL21(DE3), are adapted in such a way that all three enzymes have enzyme activities that are as similar as possible.

Figure 17A:
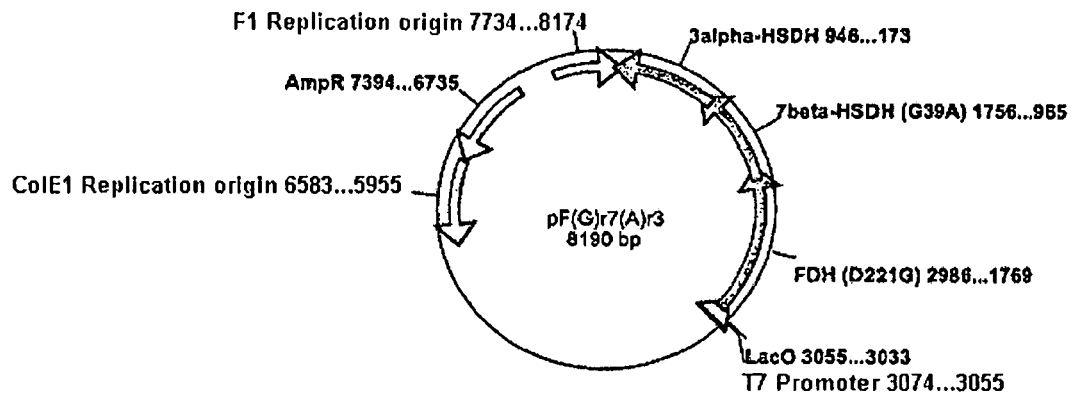
FIG. 17A shows a schematic representation of vector pF(G)r7(A)r3 which corresponds to the vector shown in FIG. 8)
Figure 18:
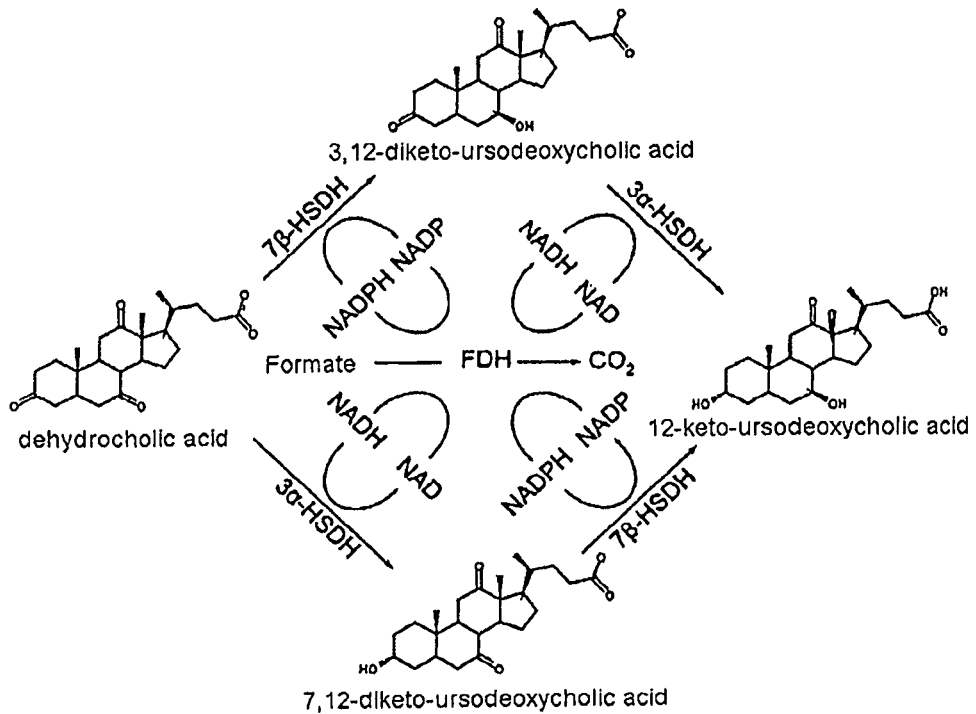
FIG. 18 shows a schematic representation of the two-step enzymatic reduction of dehydrocholic acid to 12-keto-ursodeoxycholic acid, wherein an NADPH-dependent 7β-HSDH is used and a formate dehydrogenase (FDH) mutant, which regenerates both NADPH– and NADH, is used for cofactor regeneration.

The three genes required in the whole-cell reduction of dehydrocholic acid to 12-keto-ursodeoxycholic acid are located on one and the same vector. These are genes that code for the following enzymes: an NADPH-dependent 7β-HSDH from *Collinsella aerofaciens*, an NADH-dependent 3α-HSDH from *Comamonas testosteroni*, a mutated FDH from *Mycobacterium vaccae* that is both NAD- and NADP-dependent. The expression levels of these three genes are balanced by the genetic construct, so that optimal whole-cell biocatalysis can be carried out. In the present example the 7β-HSDH mutants G39A and G39S were inserted instead of an unmodified wild-type enzyme into a vector for the whole-cell biocatalysis. The vectors bear the designations pF(G)r7(A)r3 and pF(G)r7(S)r3 and are shown in FIGS. 17a and b. FIG. 18 shows a schematic representation of the possible reaction pathways and reaction products.

These vectors according to the invention were transformed into *Escherichia coli* production strains. These strains represent the whole-cell biocatalyst. The host strain used is a modified *E. coli* BL21(DE3) with the designation *E. coli* BL49. However, the host organism is not restricted to this host strain. The *E. coli* BL49 transformed with pF(G)r7(A)r3 bears the designation *E. coli* BL49 pF(G)r7(A)r3, and the *E. coli* BL49 transformed with pF(G)r7(S)r3 bears the designation *E. coli* BL49 pF(G)r7(S)r3.

11.1 Two-Step Whole-Cell Reduction of Dehydrocholic Acid at the 20-mL Scale

The biocatalysts were compared by whole-cell biotransformation at the 20-mL scale. For this, first a 5 mL overnight culture was grown in LB medium with 100 mg L-1 ampicillin. On the next day, 1 mL of this overnight culture was transferred into 200 mL of TB medium in a shaken flask with 100 mg of L-1 ampicillin. These cultures were cultured at 37° C. and 250 rpm in the shaking incubator, until an OD of 0.6-0.8 was reached. Then induction was carried out with 1 mM isopropyl-β-D-thiogalactopyranoside (IPTG). The subsequent expression phase was carried out for 21 h at 25° C. and 160 rpm. The cells were harvested by 10-minute centrifugation at 3220 g.

Whole-cell biotransformation reactions were set up with the cells produced in this way. The amount of the product (12-keto-UDCA) formed in the reaction mixture was decisive for assessment of the cells. The concentrations of the substrate DHCA, of the intermediates 3,12-diketo-UDCA and 7,12-diketo-UDCA and of the product 12-keto-UDCA in the reaction mixture were determined by high-performance liquid chromatography (HPLC).

The reaction mixtures for the biotransformations contained 11.8 g $L^{-1}_{BTM}$ whole-cell biocatalysts, 100 mM substrate (DHCA), 500 mM sodium formate and were suspended in 50 mM potassium formate buffer (pH 6.5). The process was carried out at the 20 mL scale as a batch process without pH monitoring. The following table gives the results of the whole-cell biotransformation described above after a process time of 5 h. The two new strains *E. coli* BL49 pF(G)r7(S)r3 and *E. coli* BL49 pF(G)r7(A)r3 are compared with a reference strain *E. coli* BL49 pF(G)r7 pC3. With the reference strain *E. coli* BL49 pF(G)r7 pC3 only 5.7±1.0% of product (12-keto-UDCA) was formed, whereas with the new biocatalysts 38.4±8.2% 12-keto-UDCA was formed with the strain *E. coli* BL49 pF(G)r7(S)r3 and 47.7±2.1% 12-keto-UDCA with the strain *E. coli* BL49 pF(G)r7(A)r3. Therefore the product concentration in the reaction mixture had increased relative to the reference strain by a factor of 6.7 (*E. coli* BL49 pF(G)r7(S)r3) and by a factor of 8.4 (*E. coli* BL49 pF(G)r7(A)r3).

Accordingly, the following table shows proportions of bile salts in biotransformation batches after 5 h when using 100 mM substrate (DHCA). The batches with the two new biocatalyst strains *E. coli* BL49 pF(G)r7(A)r3 and *E. coli* BL49 pF(G)r7(S)r3 are shown in comparison with the strain *E. coli* BL49 pF(G)r7 pC3 according to the prior art:

|  | Proportions of bile salts, % | | | |
| --- | --- | --- | --- | --- |
|  | 12-keto-UDCA | 3,12-diketo-UDCA | 7,12-diketo-UDCA | DHCA |
| *E. coli* BL49 pF(G)r7 pC3 | 5.7 ± 1.0% | 9.2 ± 0.2% | 40.5 ± 1.9% | 44.6 ± 3.1% |
| *E. coli* BL49 pF(G)r7(A)r3 | 47.7 ± 2.1% | 2.4 ± 0.5% | 48.9 ± 1.6% | 1.0 ± 0.0% |
| *E. coli* BL49 pF(G)r7(S)r3 | 38.4 ± 8.2% | 2.7 ± 2.7% | 57.4 ± 4.4% | 1.5 ± 1.8% |

11.2 Two-Step Whole-Cell Reduction of Dehydrocholic Acid at the 1 L Scale

Through process control, product formation with the biocatalyst *E. coli* BL49 pF(G)r7(A)r3 was increased relative to the milliliter scale. For this, the biocatalyst was cultured in the 7 L bioreactor at a working volume of 4 L in the defined minimal medium. After a brief initial phase at 37° C., there was a substrate-limited exponential growth phase at 30° C. On reaching an optical density of 25-30, protein expression of the cells was induced by adding 0.5 mM IPTG. Expression was then carried out for 10 h at 25° C., before the cells were harvested by centrifugation and were stored at −20° C.

Figure 19:
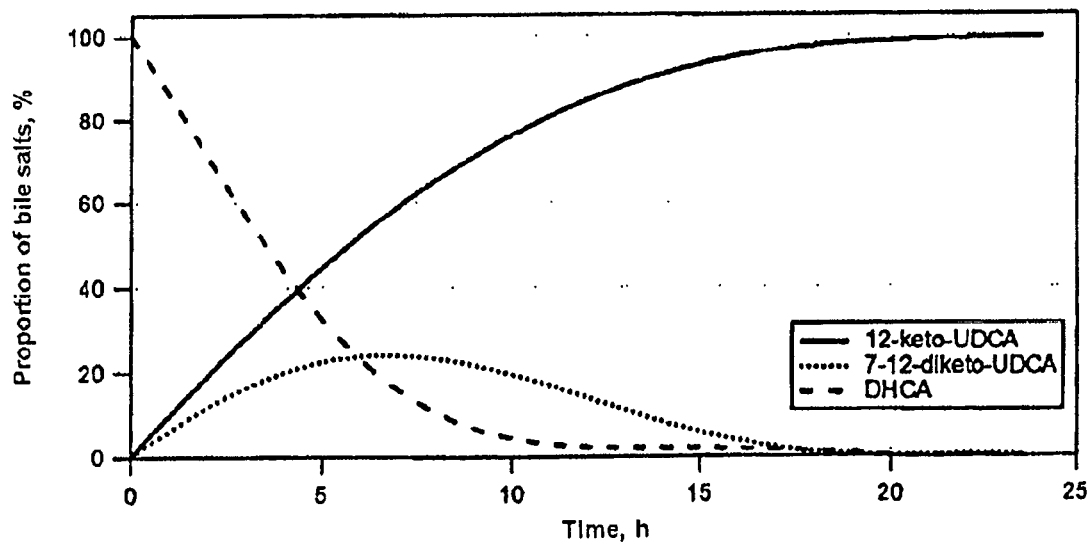
FIG. 19 shows a time-resolved variation of the biotransformation with the strain *E. coli* BL49 pF(G)r7(A)r3 at the liter scale. The batch contained 70 mM DHCA, 17.79 g/l$_{BTM}$ of the stored biocatalyst, 500 mM sodium formate, 26% (v/v) glycerol, 50 mM MgCl$_2$, in 50 mM KPi buffer (pH 6.5). Using pH adjustment, the pH was maintained at pH 6.5 throughout the biotransformation.

The biotransformation was set up in a 1 L bioreactor in the following reaction conditions: 70 mM DHCA, 17.7 g $L^{-1}_{BTM}$ of the stored biocatalyst, 500 mM sodium formate, 26% (v/v) glycerol, 50 mM MgCl$_2$, suspended in 50 mM KPi buffer (pH 6.5). Using pH adjustment, the pH was maintained at pH 6.5 throughout the biotransformation. The variation of the bile salt concentrations as a function of time is shown in FIG. 19. After 21 h, 99.4% of product (12-keto-UDCA) had formed and only 0.6% of the by-product 3,12-diketo-UDCA was detectable.

Reaction Example 12: Two-Step Reduction of Dehydrocholic Acid in a Single-Cell System Using a Glucose Dehydrogenase for Cofactor Regeneration In this example, in addition to an NADPH-dependent 7β-HSDH from *Collinsella aerofaciens* (mutant G39A) and an NADH-dependent 3α-HSDH from *Comamonas testosteroni*, a GDH from *Bacillus subtilis* that is both NAD- and NADP-dependent for the cofactor regeneration is expressed in a whole-cell biocatalyst (single-cell system) for the two-step reduction of DHCA to 12-keto-UDCA. The nucleic acid sequence and the associated amino acid sequence of this GDH are given as SEQ ID NO:47 and SEQ ID NO:48 respectively.

Figure 20:
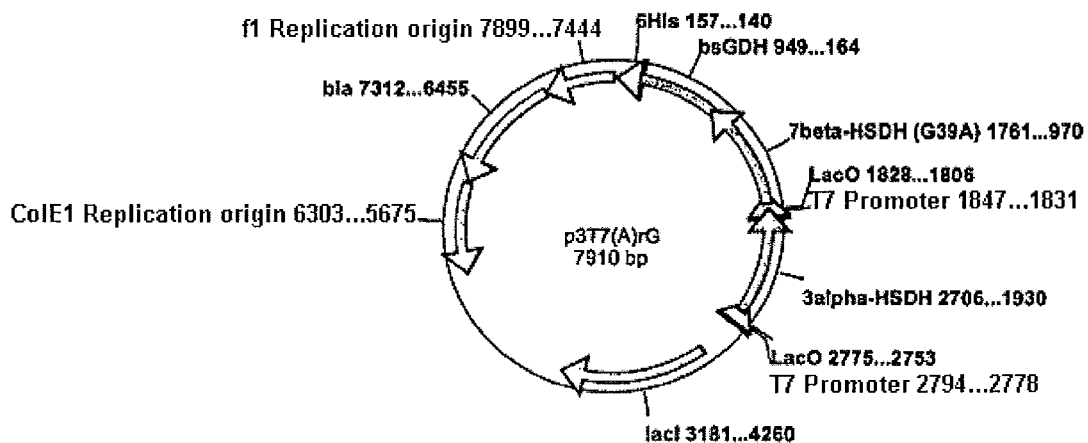
FIG. 20 shows a schematic representation of the vector p3T7(A)rG.
Figure 21:
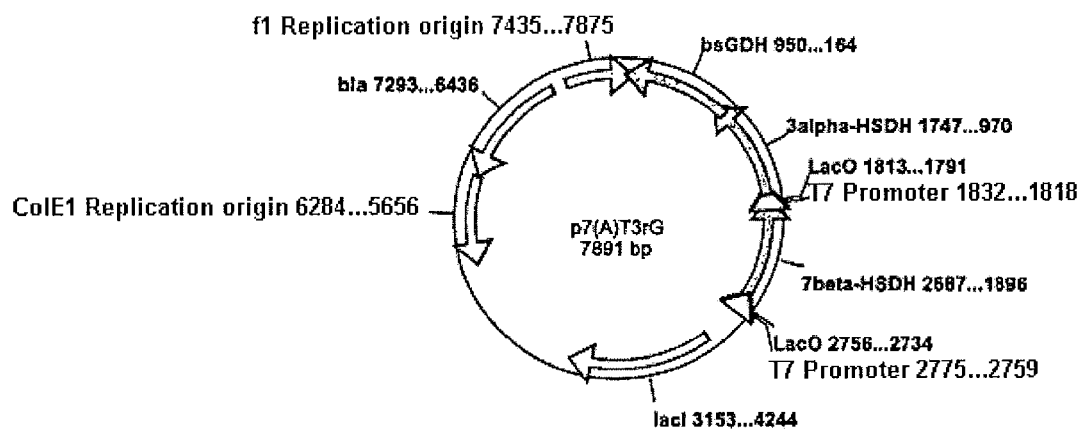
FIG. 21 shows a schematic representation of the vector p7(A)T3rG.

The vectors used for this bear the designations p3T7(A)rG and p7(A)T3rG and are shown in FIG. 20 and FIG. 21 respectively.

The vectors according to the invention were transformed into *Escherichia coli* production strains. These strains represent the whole-cell biocatalyst. The host strain used is a modified *E. coli* BL21(DE3) with the designation *E. coli* BL49 (identical to *E. coli* BL21(DE3) hdhA$^-$ KanR$^+$). However, the host organism is not restricted to this host strain. The *E. coli* BL49 transformed with p7(A)T3rG bears the designation *E. coli* BL49 p7(A)T3rG, and the *E. coli* BL49 transformed with p3T7(A)rG bears the designation *E. coli* BL49 p3T7(A)rG.

With the newly produced biocatalysts, using a total of 17.7 g/L BTM biocatalysts, 100 mM DHCA can be converted to an extent of 98% to 12-keto-UDCA.

12.1 Two-Step Whole-Cell Reduction of Dehydrocholic Acid at the 20-mL Scale

The biocatalysts were compared by whole-cell biotransformation at the 20-mL scale. Cultivation and determination of the concentration of the substrate DHCA, of the intermediates 3,12-diketo-UDCA and 7,12-diketo-UDCA and of the product 12-keto-UDCA in the reaction mixture were carried out as described in reaction example 11.1.

The reaction mixtures for the biotransformations contained 11.8 g/L BTM whole-cell biocatalysts, 100 mM substrate (DHCA), 500 mM glucose and were suspended in 50 mM potassium formate buffer (pH 7.3). The process took place at the 20 mL scale as a batch process without pH monitoring. Perforation of the biocatalysts was not necessary. The following table shows the results of the whole-cell biotransformation described above after a process time of 24 h, showing the results of the whole-cell biotransformation with the two strains E. coli BL49 p7(A)T3rG and E. coli BL49 p3T7(A)rG. With the new biocatalysts, using 11.8 g $L^{-1}_{BTM}$ biocatalyst, within 24 h 100 mM dehydrocholic acid (DHCA) can be converted to an extent of 46% (E. coli BL49 p3T7(A)rG) or 68% (E. coli BL49 p7(A)T3rG) to 12-keto-ursodeoxycholic acid (12-keto-UDCA). The following table shows proportions of bile salts in biotransformation batches after 24 h, using 100 mM substrate (DHCA) (batches with the two new biocatalyst strains E. coli BL49 p3T7(A)rG and E. coli BL49 p7(A)T3rG):

| | Proportions of bile salts, % | | | |
|---|---|---|---|---|
| | 12-keto-UDCA | 3,12-diketo-UDCA | 7,12-diketo-UDCA | DHCA |
| E. coli BL49 p3T7(A)rG | 46 ± 6% | 7 ± 1% | 7 ± 1% | 40.0 ± 2% |
| E. coli BL49 p7(A)T3rG | 68 ± 19% | 15 ± 3% | 1 ± 1% | 12 ± 10% |

12.2 Two-Step Whole-Cell Reduction of Dehydrocholic Acid with Cells of the Strain E. coli BL49 p7(A)T3rG Cultured in the Bioreactor at the 20-mL Scale The strain E. coli BL49 p7(A)T3rG was cultured in the 7 L bioreactor at a working volume of 4 L in the defined minimal medium. After a brief initial phase at 37° C. there was a substrate-limited exponential growth phase at 30° C. On reaching an optical density of 25-30, protein expression of the cells was induced by adding 0.5 mM IPTG. Expression was then carried out for 24 h at 20° C. The cells (46.7 g/L BTM) were harvested by centrifugation, resuspended in potassium phosphate buffer (pH 6.5) and stored according to the standard protocol at −20° C. At the time of harvesting, the enzyme activities were: 16.4 U/mL 7β-HSDH, 3.6 U/mL 3α-HSDH, 44.9 U/mL GDH (NADP), 18.1 U/mL GDH (NAD).

Figure 22A:
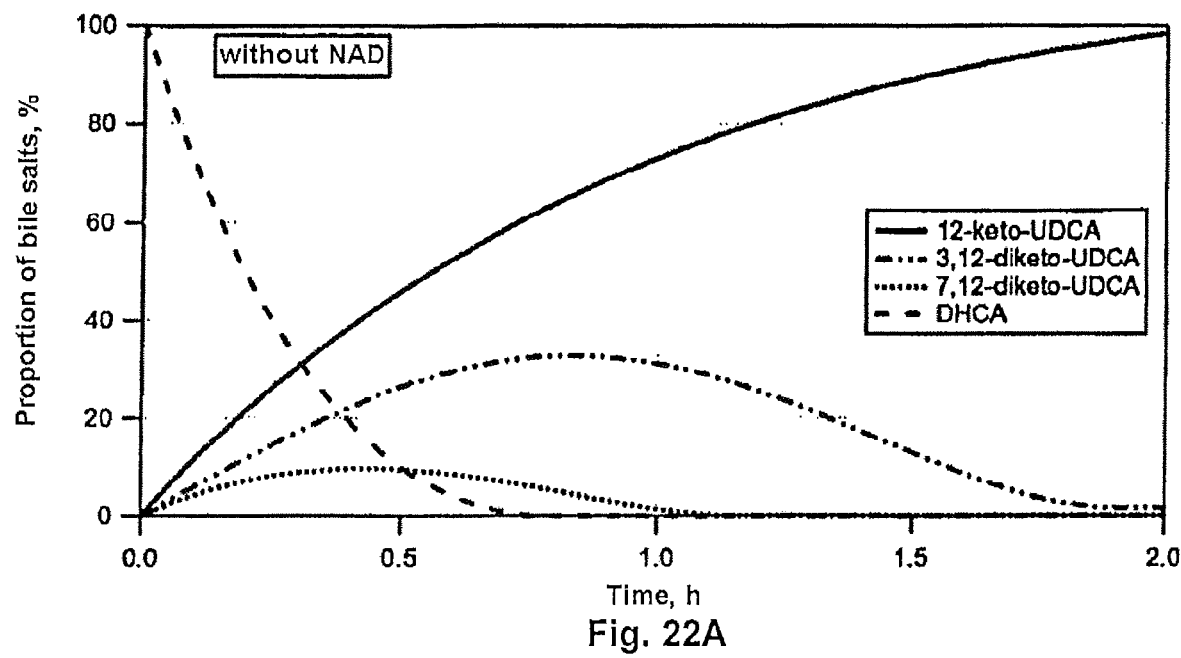
FIG. 22A and FIG. 22B show a time-resolved variation of the biotransformation with the strain *E. coli* BL49 p7(A)T3rG, which comprises a GDH for cofactor regeneration. The batch contained 100 mM DHCA, 17.7 g/l$_{BTM}$ of the stored biocatalyst, 500 mM glucose, 10 mM MgCl$_2$, in 50 mM KPi buffer (pH 7) without (FIG. 22A) and with 0.1 mM NAD (FIG. 22B). The pH was adjusted manually with potassium hydroxide solution to the initial value.
Figure 22B:
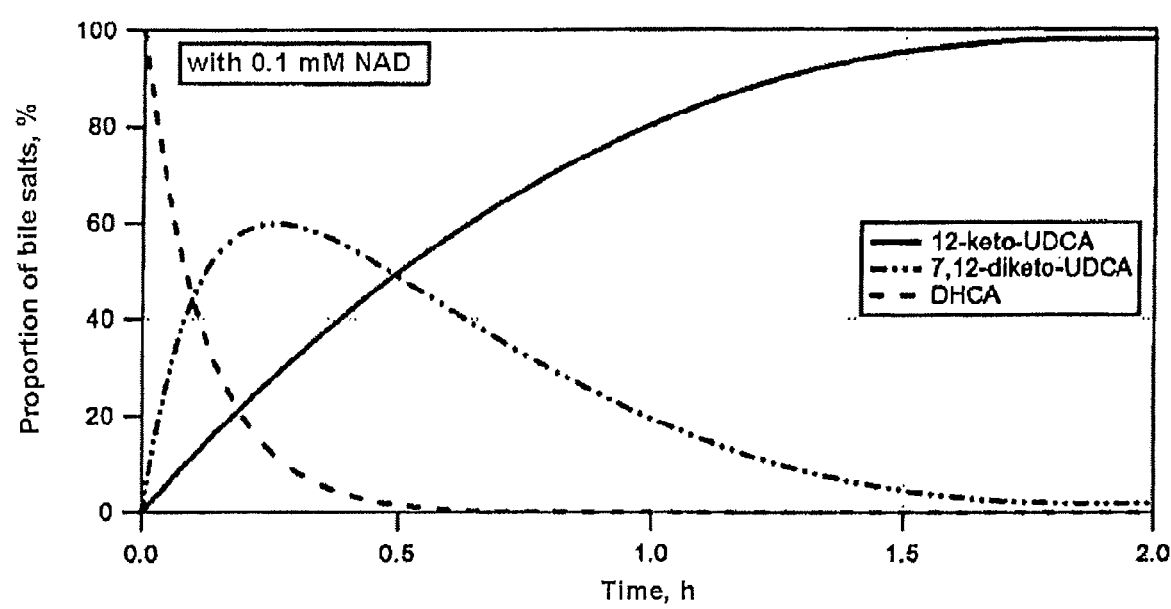

Biotransformation was set up at the 20-mL scale in the following reaction conditions: 100 mM DHCA, 17.7 g/L BTM of the stored biocatalyst, 500 mM glucose, 10 mM $MgCl_2$, suspended in 50 mM KPi buffer (pH 7). Using manual pH adjustment, the pH was maintained throughout the biotransformation at pH 7. The reactions were carried out either without cofactor addition or with addition of 0.1 mM NAD. The variation of the bile salt concentrations as a function of time is shown in FIG. 22. After 2 h, with and without addition of NAD, in each case≥98% of product (12-keto-UDCA) was formed.

Using altogether 17.7 g/L BTM biocatalysts, 100 mM DHCA were converted to an extent of 98% to 12-keto-UDCA.

Reaction Example 13: Two-Step Reduction of Dehydrocholic Acid with Parallel Use of Two Different Whole-Cell Biocatalysts In this example, two whole-cell biocatalysts were used instead of one whole-cell biocatalyst. For this purpose, an NADP-specific FDH from Mycobacterium vaccae and an NADPH-specific 7β-HSDH from Collinsella aerofaciens were expressed in one of these biocatalysts, whereas an NAD-dependent FDH from Mycobacterium vaccae and an NADH-dependent 3α-HSDH from Comamonas testosteroni were expressed in the other biocatalyst.

In the present example, concretely the vector pF(G)r7(A), which comprises genes for an NADP-specific FDH from Mycobacterium vaccae and for an NADPH-specific 7β-HSDH from Collinsella aerofaciens, and the vector pFr3, which comprises genes for an NAD-dependent FDH from Mycobacterium vaccae and for an NADH-dependent 3α-HSDH from Comamonas testosteroni, were used. The vectors pF(G)r7(A) and pFr3 are shown in FIG. 23 a and b. FIG. 24 shows a reaction scheme with possible routes and products. However, the invention is not restricted to these two stated vectors, but can comprise all conceivable vectors that comprise genes for a 7β-HSDH and a suitable cofactor regeneration enzyme in combination with vectors that comprise genes for a 3α-HSDH and a suitable cofactor regeneration enzyme.

13.1 Whole-Cell Reduction of DHCA Using Two Biocatalysts in Different Mixture Ratios The whole-cell reduction of DHCA to 12-keto-UDCA with different mixture ratios of the biocatalysts E. coli BL49 pF(G)r7(A) and E. coli BL49 pFr3 is shown in the following example. In this case, a total amount of biocatalyst of 17.7 g $L^{-1}_{BTM}$ was used in each case for three batches. However, different proportions of the two biocatalysts were used in the batches. These are 8.85 g $L^{-1}_{BTM}$ E. coli BL49 pF(G)r7(A) and 8.85 g $L^{-1}_{BTM}$ E. coli BL49 pFr3

10.33 g $L^{-1}_{BTM}$ E. coli BL49 pF(G)r7(A) and 7.38 g $L^{-1}_{BTM}$ E. coli BL49 pFr3

11.80 g $L^{-1}_{BTM}$ E. coli BL49 pF(G)r7(A) and 5.90 g $L^{-1}_{BTM}$ E. coli BL49 pFr3

Figure 25:
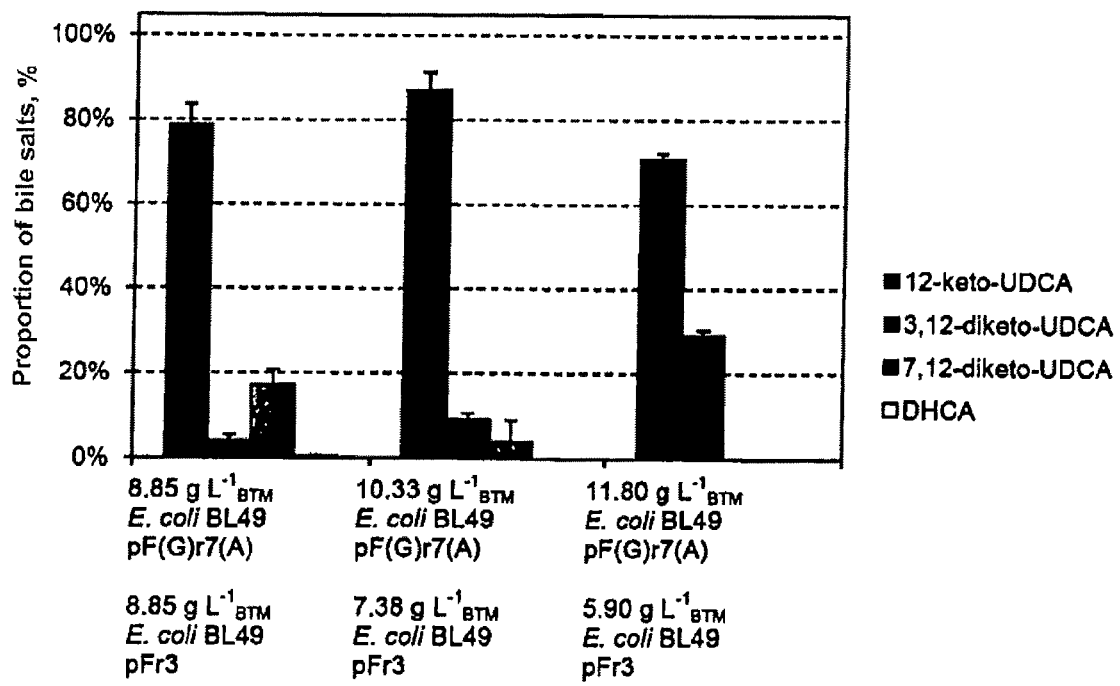
FIG. 25 shows the proportions of bile salts of biotransformation batches after 24 h when using 70 mM substrate (DHCA). The batches are shown when using different proportions of the two biocatalyst strains *E. coli* BL49 pF(G)r7(A) and *E. coli* BL49 pFr3.

These biocatalysis reactions were carried out at a working volume of 20 mL. Further constituents of the batches were: 70 mM DHCA, 500 mL sodium formate, 26% glycerol, 50 mM $MgCl_2$, suspended in 50 mL potassium phosphate buffer (pH 6.5). The reactions were carried out for 24 h. The proportions of bile salts after 24 h are shown in FIG. 25.

In the preparation with 8.85 g $L^{-1}_{BTM}$ E. coli BL49 pF(G)r7(A) and 8.85 g $L^{-1}_{BTM}$ E. coli BL49 pFr3, 79% 12-keto-UDCA, 4% 3,12-diketo-UDCA and 17% 7,12-diketo-UDCA are formed, in the preparation with 10.33 g $L^{-1}_{BTM}$ E. coli BL49 pF(G)r7(A) and 7.38 g $L^{-1}_{BTM}$ E. coli BL49 pFr3, 87% 12-keto-UDCA, 9% 3,12-diketo-UDCA and 4% 7,12-diketo-UDCA are formed and in the preparation with 11.80 g $L^{-1}_{BTM}$ E. coli BL49 pF(G)r7(A) and 5.90 g $L^{-1}_{BTM}$ E. coli BL49 pFr3, 71% 12-keto-UDCA and 29% 3,12-diketo-UDCA are formed. It can be seen from the proportions of the intermediates formed that in the case of the preparation with 8.85 g $L^{-1}_{BTM}$ E. coli BL49 pF(G)r7(A) and 8.85 g $L^{-1}_{BTM}$ E. coli BL49 pFr3 the reaction of 3α-HSDH takes place at an increased rate, as in this case a high proportion of the intermediate 7,12-diketo-UDCA is formed, whereas in the case of the preparation of 11.80 g $L^{-1}_{BTM}$ E. coli BL49 pF(G)r7(A) and 5.90 g $L^{-1}_{BTM}$ E. coli BL49 pFr3 the reaction of 7β-HSDH takes place at an increased rate and accordingly a high proportion of the intermediate 3,12-diketo-UDCA is formed. In the preparation with 10.33 g $L^{-1}_{BTM}$ E. coli BL49 pF(G)r7(A) and 7.38 g $L^{-1}_{BTM}$ E. coli BL49 pFr3, the reactions of 7β-HSDH and of 3α-HSDH are adjusted so that both occur at a roughly equal rate, as can be seen from the almost uniform formations of intermediates. As a result, the highest proportion of the product 12-keto-UDCA (87%) can be formed with this preparation.

This example shows that the rate of the individual reaction steps can be influenced by adjusting the proportions of the biocatalysts used.

13.1 Whole-Cell Reduction of DHCA Using Two Biocatalysts at the 1 L Scale

Figure 26:
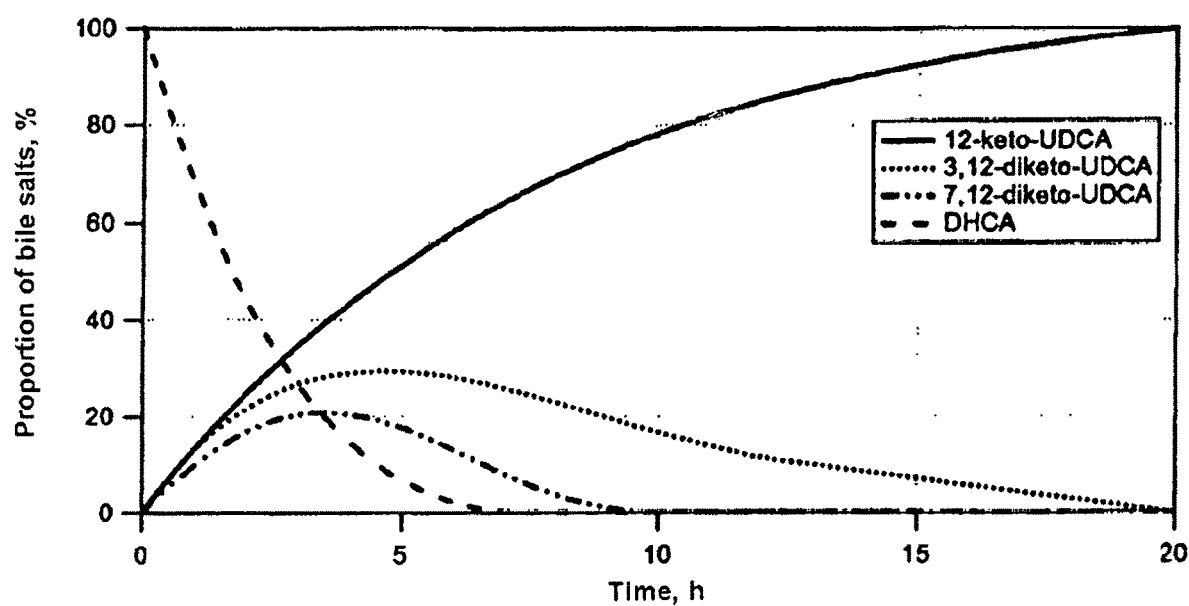
FIG. 26 shows a time-resolved variation of biotransformation with the biocatalysts *E. coli* BL49 pF(G)r7(A) and *E. coli* BL49 pFr3 liter scale. The batch contained 90 mM DHCA, 8.85 g/l$_{BTM}$ *E. coli* BL49 pF(G)r7(A) and 8.85 g/l$_{BTM}$ *E. coli* BL49 pFr3, 500 mM ammonium formate, 26% (v/v) glycerol, 50 mM MgCl$_2$, in 50 mM KPi buffer (pH 6.5). Using pH adjustment, the pH was maintained with formic acid at pH 6.5 throughout the biotransformation.

Through process control, using the biocatalysts E. coli BL49 pF(G)r7(A) and E. coli BL49 pFr3, product formation could be increased relative to the milliliter scale. The biotransformation was set up in a 1 L bioreactor in the following reaction conditions: 90 mM DHCA, with 8.85 g $L^{-1}_{BTM}$ E. coli BL49 pF(G)r7(A) and 8.85 g $L^{-1}_{BTM}$ E. coli BL49 pFr3, 500 mM ammonium formate, 26% (v/v) glycerol, 50 mM $MgCl_2$, suspended in 50 mM KPi buffer (pH 6.5). Using pH adjustment with formic acid, the pH was maintained at pH 6.5 throughout the biotransformation. The variation of the bile salt concentrations as a function of time is shown in FIG. 26. After 20 h, 99.4% product (12-keto-UDCA) had formed, and only a total of 0.6% of the intermediates 3,12-diketo-UDCA and 7,12-diketo-UDCA was detectable.

Figure 15:
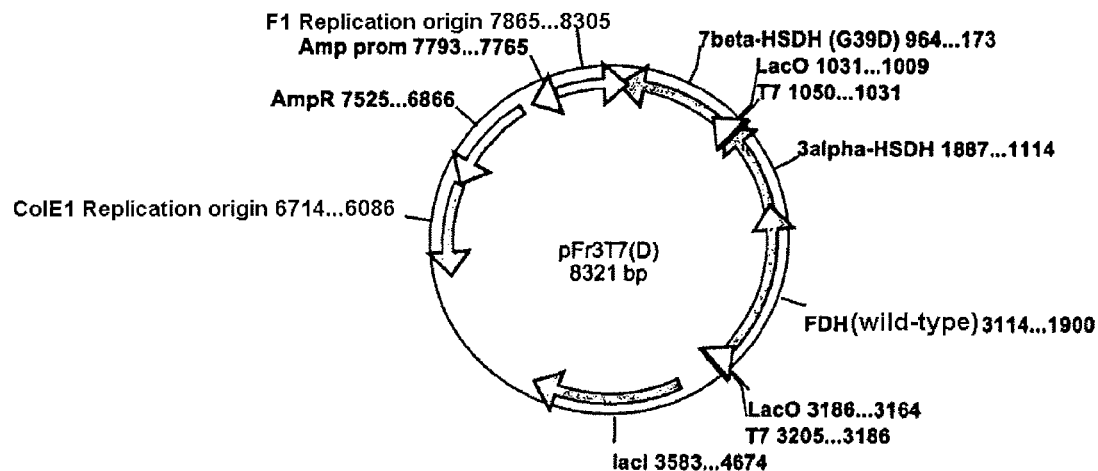
FIG. 15 shows a schematic representation of the vector pFr3T7(D).
Figure 17B:
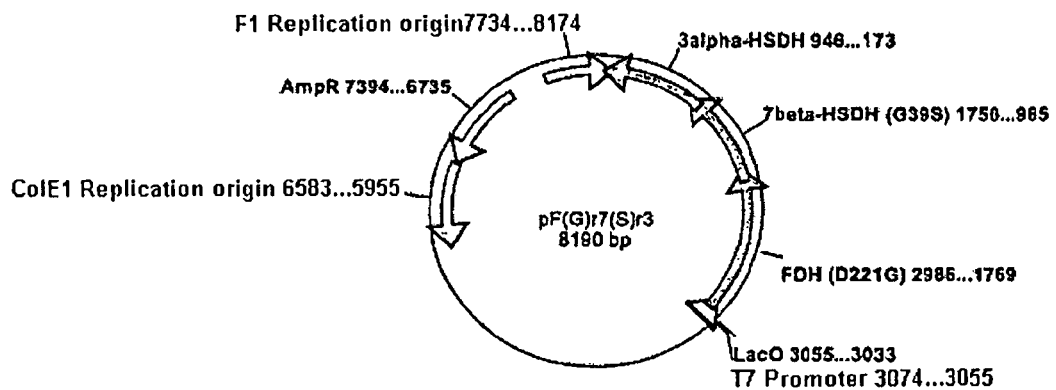
FIG. 17B shows a schematic representation of vector pF(G)r7(S)r3.
Figure 23A:
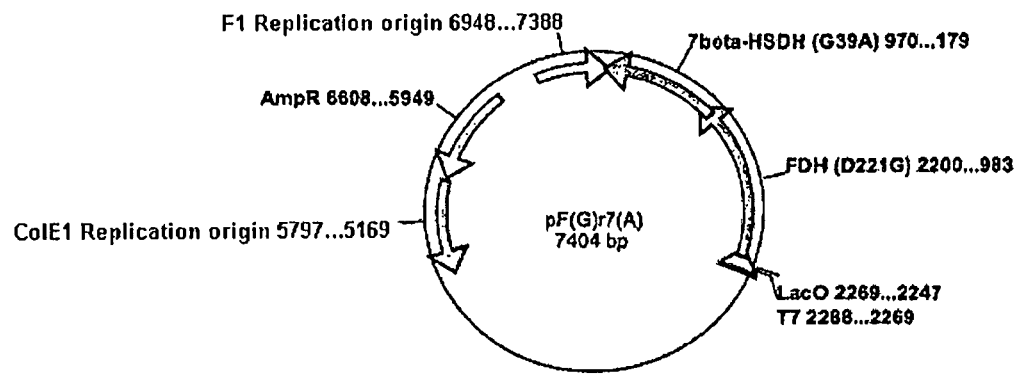
FIG. 23A shows a schematic representation of vector pF(G)r7(A) and FIG. 23B shows a schematic representation of vector pFr3.
Figure 23B:
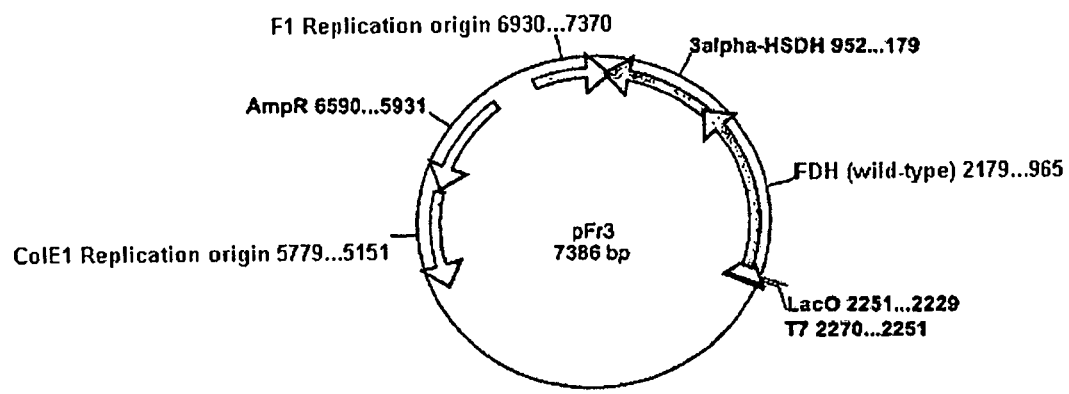
Figure 24:
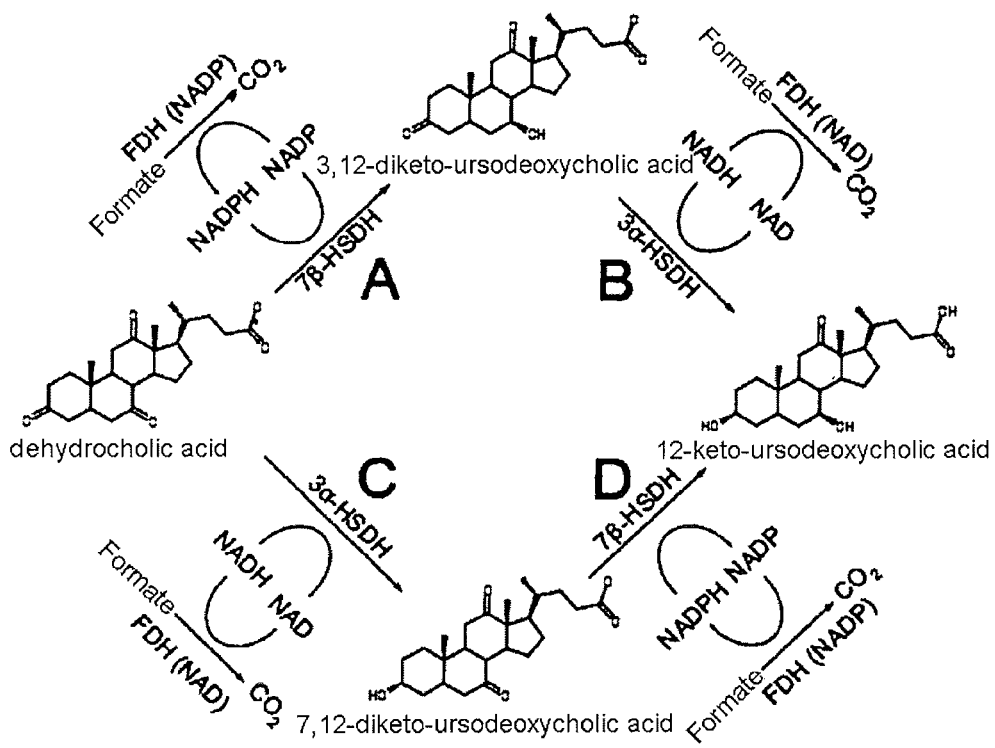
FIG. 24 shows a schematic representation of the two-step enzymatic reduction of dehydrocholic acid to 12-keto-ursodeoxycholic acid using two different whole-cell biocatalysts. Reactions A and D are catalyzed by a 7β-HSDH containing whole-cell biocatalyst, and reactions B and C are catalyzed by a 3α-HSDH containing whole-cell biocatalyst. In the course of the two-step reaction, the intermediate 3,12-diketo-ursodeoxycholic acid must pass from the 7β-HSDH containing whole-cell biocatalyst into the 3α-HSDH containing whole-cell biocatalyst, and the intermediate 7,12-diketo-ursodeoxycholic acid must pass from the 3α-HSDH containing whole-cell biocatalysts into the 7β-HSDH containing whole-cell biocatalyst.

Using the biocatalysts according to the invention, with the use of a total of 17.7 g $L^{-1}_{BTM}$ biocatalysts, 90 mM DHCA could be converted to an extent of 99.5% to 12-keto-UDCA. Assignment of SEQ ID NOs:

| SEQ ID NO: | Description | Type |
| --- | --- | --- |
| 1 | 7β-HSDH | NS |
| 2 | 7β-HSDH | AS |
| 3 | Primer S 7beta_rev_HindIII | NS |
| 4 | Primer | NS |
| 5 | 3α-HSDH (C. testosteroni) | NS |
| 6 | 3α-HSDH (C. testosteroni) | AS |
| 7 | 3α-HSDH (R. norvegicus) | NS |
| 8 | 3α-HSDH (R. norvegicus) | AS |
| 9 | Primer 7beta_mut_G39A_fwd | NS |
| 10 | Primer 7beta_mut_G39A_rev | NS |
| 11 | Primer 7beta_mut_G39S_fwd | NS |
| 12 | Primer 7beta_mut_G39S_rev | NS |
| 13 | Primer 7beta_fwd_EcoRI | NS |
| 14 | FDH D221G | NS |
| 15 | FDH D221G | AS |
| 16 | Primer 3alpha_fwd_HindIII | NS |
| 17 | Primer 3alpha_rev_NotI | NS |
| 18 | pET22a FDH D221G 7β-HSDH | NS |
| 19 | FDH D221G | AS |
| 20 | 7beta-HSDH | AS |
| 21 | pCOLA(mod) 3α-HSDH | NS |
| 22 | 3α-HSDH | AS |
| 23 | Primer fdh_for | NS |
| 24 | Primer fdh_rev | NS |
| 25 | 7α-HSDH | NS |
| 26 | 7α-HSDH | AS |
| 27 | Primer 467|468a-IBS | NS |
| 28 | Primer 467|468a-EBS1d | NS |
| 29 | Primer 467|468a-EBS2 | NS |
| 30 | Primer mt1 | NS |
| 31 | Primer Nl_fdh_R | NS |
| 32 | Primer 7alpha-ko-check_fwd | NS |
| 33 | Primer 7alpha-ko-check_rev | NS |
| 34 | FDH D221G with deletion and His-Tag | NS |
| 35 | FDH D221G with deletion and His-Tag | AS |
| 36 | FDH wild type, M. vaccae | AS |
| 37 | 7β-HSDH G39D | AS |
| 38 | 7β-HSDH G39D/R40L | AS |
| 39 | 7β-HSDH G39D/R40I | AS |
| 40 | 7β-HSDH G39D/R40V | AS |
| 41 | Primer for G39D (7beta mut G39D fwd) | NS |
| 42 | Primer for G39D (7beta mut G39D rev) | NS |
| 43 | Primer for G39D R40L (7beta mut G39D R40L fwd) | NS |
| 44 | Primer 3alphamut_AntiMid_rev | NS |
| 45 | Primer for G39D R40I (7beta mut G39D R40I fwd) | NS |
| 46 | Primer 7beta mut G39D R40V fwd | NS |
| 47 | GDH, B. subtilis | NS |
| 48 | GDH B. subtilis | AS |
| 49 | Vector pFr7(D) | NS |
| 50 | Vector pFr7(DL) | NS |
| 51 | Vector pFr7(DI) | NS |
| 52 | Vector pFr7(DV) | NS |
| 53 | PCR Primer "G39D_for" | NS |
| 54 | PCR Primer "G39D_rev" | NS |
| 55 | PCR Primer "G39D/R40I_for" | NS |
| 56 | PCR Primer "G39D/R40I_rev" | NS |
| 57 | PCR Primer "R40D_for" | NS |
| 58 | PCR Primer "R40D_rev" | NS |
| 59 | PCR Primer "R40D/R41I_for" | NS |
| 60 | PCR Primer "R40D/R41I_rev" | NS |
| 61 | PCR Primer "DIN_for" | NS |
| 62 | PCR Primer "DIN_rev" | NS |
| 63 | Plasmid pFr3T7(D), FIG. 15 | NS |
| 64 | Plasmid pF(G)r7(A)r3, FIG. 17a | NS |
| 65 | Plasmid pF(G)r7(S)r3, FIG. 17b | NS |
| 66 | Plasmid p3T7(A)rG, FIG. 20 | NS |
| 67 | Plasmid p7(A)T3rG, FIG. 21 | NS |
| 68 | Plasmid pF(G)r7(A), FIG. 23a | NS |
| 69 | Plasmid pFr3, FIG. 23b | NS |

AS = amino acid sequence
NS = nucleic acid sequence

Reference is made expressly to the disclosure of the documents mentioned herein.

The invention claimed is:

1. A 7β-HSDH mutant, which catalyzes at least the stereospecific enzymatic reduction of a 7-ketosteroid to the corresponding 7-hydroxysteroid, wherein the mutant has at least 90% sequence identity to SEQ ID NO:2 and at least one mutation in the sequence motif VMVGRRE corresponding to positions 36 to 42 of SEQ ID NO:2, wherein the mutation is selected from the group consisting of:
   a) the single mutation G39$X_1$;
   b) the single mutation R40$X_2$;
   c) the double mutation G39$X_1$ R40$X_2$
   d) the double mutation R40$X_2$ R41$X_3$;
   e) the double mutation G39$X_1$ R41$X_3$; and
   f) the triple mutation G39$X_1$ R40$X_2$ R41$X_3$; wherein each of $X_1$, $X_2$ and $X_3$ can be the same or different and stands for mutated amino acid residues.

2. The 7β-HSDH mutant of claim 1, wherein the mutant has decreased substrate inhibition for a 7-ketosteroid substrate.

* * * * *

SEQUENCE LISTING

<160> NUMBER OF SEQ ID NOS: 69

<210> SEQ ID NO 1
<211> LENGTH: 792
<212> TYPE: DNA
<213> ORGANISM: Collinsella aerofaciens
<220> FEATURE:
<221> NAME/KEY: CDS
<222> LOCATION: (1)..(789)

<400> SEQUENCE: 1

```
atg aac ctg agg gag aag tac ggt gag tgg ggc ctg atc ctg ggc gcg      48
Met Asn Leu Arg Glu Lys Tyr Gly Glu Trp Gly Leu Ile Leu Gly Ala
1               5                  10                  15 acc gag ggc gtc ggc aag gcg ttc tgc gag aag atc gcc gcc ggc ggc      96
Thr Glu Gly Val Gly Lys Ala Phe Cys Glu Lys Ile Ala Ala Gly Gly
            20                  25                  30 atg aac gtc gtc atg gtc ggc cgt cgc gag gag aag ctg aac gtg ctc     144
Met Asn Val Val Met Val Gly Arg Arg Glu Glu Lys Leu Asn Val Leu
```

```
                35                  40                  45
gca ggc gag atc cgc gag acc tac ggc gtg gag acc aag gtc gtg cgc       192
Ala Gly Glu Ile Arg Glu Thr Tyr Gly Val Glu Thr Lys Val Val Arg
 50                  55                  60 gcc gac ttt agc cag ccc ggc gct gcc gag acc gtc ttc gcc gcg acc       240
Ala Asp Phe Ser Gln Pro Gly Ala Ala Glu Thr Val Phe Ala Ala Thr
 65                  70                  75                  80 gag ggc ctg gac atg ggc ttc atg agc tac gtg gcc tgc ctg cac agc       288
Glu Gly Leu Asp Met Gly Phe Met Ser Tyr Val Ala Cys Leu His Ser
                 85                  90                  95 ttc ggt aag atc cag gac acc ccc tgg gag aag cac gag gcc atg atc       336
Phe Gly Lys Ile Gln Asp Thr Pro Trp Glu Lys His Glu Ala Met Ile
            100                 105                 110 aac gtc aac gtc gtg acc ttc ctc aag tgc ttc cac cac tac atg cgg       384
Asn Val Asn Val Val Thr Phe Leu Lys Cys Phe His His Tyr Met Arg
        115                 120                 125 atc ttt gcc gcc cag gac cgc ggc gcc gtg atc aac gtc tcg tcg atg       432
Ile Phe Ala Ala Gln Asp Arg Gly Ala Val Ile Asn Val Ser Ser Met
    130                 135                 140 acc ggc atc agc tcc agc ccc tgg aac ggc cag tac ggc gcg ggc aag       480
Thr Gly Ile Ser Ser Ser Pro Trp Asn Gly Gln Tyr Gly Ala Gly Lys
145                 150                 155                 160 gcc ttc atc ctc aag atg acc gag gcc gtg gcc tgc gag tgc gag ggc       528
Ala Phe Ile Leu Lys Met Thr Glu Ala Val Ala Cys Glu Cys Glu Gly
                165                 170                 175 acc ggc gtc gac gtc gag gtc atc acc ctc ggc acc acc cta acc ccc       576
Thr Gly Val Asp Val Glu Val Ile Thr Leu Gly Thr Thr Leu Thr Pro
            180                 185                 190 agc ctg ctg tcc aac ctc ccc ggc ggc ccg cag ggc gag gcc gtc atg       624
Ser Leu Leu Ser Asn Leu Pro Gly Gly Pro Gln Gly Glu Ala Val Met
        195                 200                 205 aag atc gcc ctc acc ccc gag gag tgc gtt gac gag gcc ttt gag aag       672
Lys Ile Ala Leu Thr Pro Glu Glu Cys Val Asp Glu Ala Phe Glu Lys
    210                 215                 220 ctg ggt aag gag ctc tcc gtc atc gcc ggc cag cgc aac aag gac tcc       720
Leu Gly Lys Glu Leu Ser Val Ile Ala Gly Gln Arg Asn Lys Asp Ser
225                 230                 235                 240 gtc cac gac tgg aag gca aac cac acc gag gac gag tac atc cgc tac       768
Val His Asp Trp Lys Ala Asn His Thr Glu Asp Glu Tyr Ile Arg Tyr
                245                 250                 255 atg ggg tcg ttc tac cgc gac tag                                       792
Met Gly Ser Phe Tyr Arg Asp
            260

<210> SEQ ID NO 2
<211> LENGTH: 263
<212> TYPE: PRT
<213> ORGANISM: Collinsella aerofaciens

<400> SEQUENCE: 2

Met Asn Leu Arg Glu Lys Tyr Gly Glu Trp Gly Leu Ile Leu Gly Ala
 1               5                  10                  15

Thr Glu Gly Val Gly Lys Ala Phe Cys Glu Lys Ile Ala Ala Gly Gly
                20                  25                  30

Met Asn Val Val Met Val Gly Arg Arg Glu Glu Lys Leu Asn Val Leu
            35                  40                  45

Ala Gly Glu Ile Arg Glu Thr Tyr Gly Val Glu Thr Lys Val Val Arg
        50                  55                  60

Ala Asp Phe Ser Gln Pro Gly Ala Ala Glu Thr Val Phe Ala Ala Thr
```

```
                65                  70                  75                  80
Glu Gly Leu Asp Met Gly Phe Met Ser Tyr Val Ala Cys Leu His Ser
                    85                  90                  95

Phe Gly Lys Ile Gln Asp Thr Pro Trp Glu Lys His Glu Ala Met Ile
                100                 105                 110

Asn Val Asn Val Val Thr Phe Leu Lys Cys Phe His His Tyr Met Arg
            115                 120                 125

Ile Phe Ala Ala Gln Asp Arg Gly Ala Val Ile Asn Val Ser Ser Met
        130                 135                 140

Thr Gly Ile Ser Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
                180                 185                 190

Ser Leu Leu Ser Asn Leu Pro Gly Gly Pro Gln Gly Glu Ala Val Met
                195                 200                 205

Lys Ile Ala Leu Thr Pro Glu Glu Cys Val Asp Glu Ala Phe Glu Lys
            210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp
                260

<210> SEQ ID NO 3
<211> LENGTH: 31
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 3
gggaattcca tatgaacctg agggagaagt a                                    31

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 4
cccaagcttc tagtcgcggt agaacga                                         27

<210> SEQ ID NO 5
<211> LENGTH: 774
<212> TYPE: DNA
<213> ORGANISM: Comamonas testosteroni
<220> FEATURE:
<221> NAME/KEY: CDS
<222> LOCATION: (1)..(771)

<400> SEQUENCE: 5 atg tcc atc atc gtg ata agc ggc tgc gcc acc ggc att ggt gcc gct     48
Met Ser Ile Ile Val Ile Ser Gly Cys Ala Thr Gly Ile Gly Ala Ala
1               5                   10                  15
```

```
acg cgc aag gtc ctg gag gcg gcc ggt cac cag atc gta ggc atc gat      96
Thr Arg Lys Val Leu Glu Ala Ala Gly His Gln Ile Val Gly Ile Asp
            20                  25                  30 ata cgc gat gcg gaa gtg att gcc gat ctc tcg acg gcc gaa ggt cga     144
Ile Arg Asp Ala Glu Val Ile Ala Asp Leu Ser Thr Ala Glu Gly Arg
        35                  40                  45 aag cag gcg att gcc gat gta ctg gcg aag tgc agc aag ggc atg gac     192
Lys Gln Ala Ile Ala Asp Val Leu Ala Lys Cys Ser Lys Gly Met Asp
    50                  55                  60 ggc ctg gtg ctg tgc gcc ggc ctg gga ccg cag acc aag gtg ctt ggc     240
Gly Leu Val Leu Cys Ala Gly Leu Gly Pro Gln Thr Lys Val Leu Gly
65                  70                  75                  80 aat gtg gtt tcg gtc aat tat ttt ggc gcg acc gag ctg atg gat gcc     288
Asn Val Val Ser Val Asn Tyr Phe Gly Ala Thr Glu Leu Met Asp Ala
                85                  90                  95 ttt ttg cca gcg ctg aaa aaa ggc cat cag ccc gca gcc gtc gtc atc     336
Phe Leu Pro Ala Leu Lys Lys Gly His Gln Pro Ala Ala Val Val Ile
            100                 105                 110 tcg tcc gtg gct tcc gcg cat ctg gct ttt gac aag aac cca ctg gcg     384
Ser Ser Val Ala Ser Ala His Leu Ala Phe Asp Lys Asn Pro Leu Ala
        115                 120                 125 ctg gca ctg gaa gcc ggc gag gaa gcc aag gcc cgc gcc att gtc gaa     432
Leu Ala Leu Glu Ala Gly Glu Glu Ala Lys Ala Arg Ala Ile Val Glu
    130                 135                 140 cat gcg gga gag cag ggc gga aat ctg gcc tat gcg ggc agc aag aat     480
His Ala Gly Glu Gln Gly Gly Asn Leu Ala Tyr Ala Gly Ser Lys Asn
145                 150                 155                 160 gct ttg acg gtg gct gtg cgc aaa cgc gcc gcc gcc tgg ggc gag gct     528
Ala Leu Thr Val Ala Val Arg Lys Arg Ala Ala Ala Trp Gly Glu Ala
                165                 170                 175 ggc gtg cgc ctg aac acc atc gcc ccc ggt gca acc gag act ccc ttg     576
Gly Val Arg Leu Asn Thr Ile Ala Pro Gly Ala Thr Glu Thr Pro Leu
            180                 185                 190 ctg cag gcg ggc ctg cag gac ccg cgc tat ggc gaa tcc att gcc aag     624
Leu Gln Ala Gly Leu Gln Asp Pro Arg Tyr Gly Glu Ser Ile Ala Lys
        195                 200                 205 ttc gtt cct ccc atg ggc cgc cgt gcc gag ccg tcc gag atg gcg tcg     672
Phe Val Pro Pro Met Gly Arg Arg Ala Glu Pro Ser Glu Met Ala Ser
    210                 215                 220 gtc atc gcc ttt ttg atg agc ccg gcc gca agc tat gtg cat ggc gcg     720
Val Ile Ala Phe Leu Met Ser Pro Ala Ala Ser Tyr Val His Gly Ala
225                 230                 235                 240 cag atc gtc att gat ggc ggc att gat gcg gtg atg cgc ccg aca cag     768
Gln Ile Val Ile Asp Gly Gly Ile Asp Ala Val Met Arg Pro Thr Gln
                245                 250                 255 ttc tga                                                             774
Phe

<210> SEQ ID NO 6
<211> LENGTH: 257
<212> TYPE: PRT
<213> ORGANISM: Comamonas testosteroni

<400> SEQUENCE: 6

Met Ser Ile Ile Val Ile Ser Gly Cys Ala Thr Gly Ile Gly Ala Ala
1               5                   10                  15

Thr Arg Lys Val Leu Glu Ala Ala Gly His Gln Ile Val Gly Ile Asp
            20                  25                  30

Ile Arg Asp Ala Glu Val Ile Ala Asp Leu Ser Thr Ala Glu Gly Arg
        35                  40                  45
```

```
Lys Gln Ala Ile Ala Asp Val Leu Ala Lys Cys Ser Lys Gly Met Asp
         50                  55                  60

Gly Leu Val Leu Cys Ala Gly Leu Gly Pro Gln Thr Lys Val Leu Gly
 65                  70                  75                  80

Asn Val Val Ser Val Asn Tyr Phe Gly Ala Thr Glu Leu Met Asp Ala
                 85                  90                  95

Phe Leu Pro Ala Leu Lys Lys Gly His Gln Pro Ala Ala Val Val Ile
            100                 105                 110

Ser Ser Val Ala Ser Ala His Leu Ala Phe Asp Lys Asn Pro Leu Ala
        115                 120                 125

Leu Ala Leu Glu Ala Gly Glu Glu Ala Lys Ala Arg Ala Ile Val Glu
130                 135                 140

His Ala Gly Glu Gln Gly Gly Asn Leu Ala Tyr Ala Gly Ser Lys Asn
145                 150                 155                 160

Ala Leu Thr Val Ala Val Arg Lys Arg Ala Ala Ala Trp Gly Glu Ala
                165                 170                 175

Gly Val Arg Leu Asn Thr Ile Ala Pro Gly Ala Thr Glu Thr Pro Leu
            180                 185                 190

Leu Gln Ala Gly Leu Gln Asp Pro Arg Tyr Gly Glu Ser Ile Ala Lys
        195                 200                 205

Phe Val Pro Pro Met Gly Arg Arg Ala Glu Pro Ser Glu Met Ala Ser
210                 215                 220

Val Ile Ala Phe Leu Met Ser Pro Ala Ala Ser Tyr Val His Gly Ala
225                 230                 235                 240

Gln Ile Val Ile Asp Gly Gly Ile Asp Ala Val Met Arg Pro Thr Gln
                245                 250                 255

Phe
```

<210> SEQ ID NO 7
<211> LENGTH: 969
<212> TYPE: DNA
<213> ORGANISM: Rattus norvegicus
<220> FEATURE:
<221> NAME/KEY: CDS
<222> LOCATION: (1)..(966)

<400> SEQUENCE: 7

```
atg gat tcc ata tct ctg cgt gta gca cta aat gat ggt aac ttc att    48
Met Asp Ser Ile Ser Leu Arg Val Ala Leu Asn Asp Gly Asn Phe Ile
1               5                   10                  15 cct gta ctg ggg ttt gga acc act gtg cct gag aag gtt gct aag gat    96
Pro Val Leu Gly Phe Gly Thr Thr Val Pro Glu Lys Val Ala Lys Asp
            20                  25                  30 gaa gtt atc aag gct act aaa ata gct ata gat aat gga ttc cgc cat   144
Glu Val Ile Lys Ala Thr Lys Ile Ala Ile Asp Asn Gly Phe Arg His
        35                  40                  45 ttt gac tct gct tat ttg tac gaa gta gaa gag gaa gtg ggc caa gcc   192
Phe Asp Ser Ala Tyr Leu Tyr Glu Val Glu Glu Glu Val Gly Gln Ala
    50                  55                  60 att aga agc aag att gaa gac ggc act gtg aag aga gaa gat ata ttc   240
Ile Arg Ser Lys Ile Glu Asp Gly Thr Val Lys Arg Glu Asp Ile Phe
65                  70                  75                  80 tat act tca aag ctt tgg agc act ttc cat aga cca gag ctg gtc cga   288
Tyr Thr Ser Lys Leu Trp Ser Thr Phe His Arg Pro Glu Leu Val Arg
                85                  90                  95 act tgc ttg gaa aag aca ctg aaa agc act caa ctg gac tat gtg gat   336
Thr Cys Leu Glu Lys Thr Leu Lys Ser Thr Gln Leu Asp Tyr Val Asp
            100                 105                 110
```

```
                    100                 105                 110
ctt tat att att cat ttc cca atg gct ttg cag cct gga gat ata ttt       384
Leu Tyr Ile Ile His Phe Pro Met Ala Leu Gln Pro Gly Asp Ile Phe
        115                 120                 125 ttc cca cga gat gag cat gga aaa cta ttg ttt gaa aca gtg gat atc       432
Phe Pro Arg Asp Glu His Gly Lys Leu Leu Phe Glu Thr Val Asp Ile
130                 135                 140 tgt gac aca tgg gag gcc atg gaa aag tgt aag gat gca gga ttg gcc       480
Cys Asp Thr Trp Glu Ala Met Glu Lys Cys Lys Asp Ala Gly Leu Ala
145                 150                 155                 160 aag tct att ggg gtg tcc aac ttt aac tgc agg cag ctg gag agg att       528
Lys Ser Ile Gly Val Ser Asn Phe Asn Cys Arg Gln Leu Glu Arg Ile
                165                 170                 175 ctg aat aag cca ggg ctc aaa tac aag cct gtg tgc aac cag gtg gaa       576
Leu Asn Lys Pro Gly Leu Lys Tyr Lys Pro Val Cys Asn Gln Val Glu
            180                 185                 190 tgt cac ctt tat ctc aac cag agc aaa atg ctg gac tat tgt aag tca       624
Cys His Leu Tyr Leu Asn Gln Ser Lys Met Leu Asp Tyr Cys Lys Ser
        195                 200                 205 aaa gac atc att ctg gtt tcc tac tgc acg ctg gga agt tca cga gac       672
Lys Asp Ile Ile Leu Val Ser Tyr Cys Thr Leu Gly Ser Ser Arg Asp
210                 215                 220 aaa aca tgg gtg gat cag aaa agt cca gtt ctc cta gat gat cca gtt       720
Lys Thr Trp Val Asp Gln Lys Ser Pro Val Leu Leu Asp Asp Pro Val
225                 230                 235                 240 ctt tgt gcc ata gca aag aag tac aag caa acc cca gcc cta gtt gcc       768
Leu Cys Ala Ile Ala Lys Lys Tyr Lys Gln Thr Pro Ala Leu Val Ala
                245                 250                 255 ctt cgc tac cag ctg cag cgt ggg gtt gtg ccc ctg atc agg agt ttc       816
Leu Arg Tyr Gln Leu Gln Arg Gly Val Val Pro Leu Ile Arg Ser Phe
            260                 265                 270 aac gcg aag cgg atc aaa gag cta aca cag gtt ttt gaa ttc cag ttg       864
Asn Ala Lys Arg Ile Lys Glu Leu Thr Gln Val Phe Glu Phe Gln Leu
        275                 280                 285 gct tca gag gac atg aaa gcc ctg gat ggc ttg aac aga aat ttc aga       912
Ala Ser Glu Asp Met Lys Ala Leu Asp Gly Leu Asn Arg Asn Phe Arg
290                 295                 300 tac aac aat gca aaa tat ttt gat gac cat ccc aat cat cca ttt act       960
Tyr Asn Asn Ala Lys Tyr Phe Asp Asp His Pro Asn His Pro Phe Thr
305                 310                 315                 320 gat gaa tag                                                           969
Asp Glu <210> SEQ ID NO 8
<211> LENGTH: 322
<212> TYPE: PRT
<213> ORGANISM: Rattus norvegicus

<400> SEQUENCE: 8

Met Asp Ser Ile Ser Leu Arg Val Ala Leu Asn Asp Gly Asn Phe Ile
1               5                   10                  15

Pro Val Leu Gly Phe Gly Thr Thr Val Pro Glu Lys Val Ala Lys Asp
            20                  25                  30

Glu Val Ile Lys Ala Thr Lys Ile Ala Ile Asp Asn Gly Phe Arg His
        35                  40                  45

Phe Asp Ser Ala Tyr Leu Tyr Glu Val Glu Glu Val Gly Gln Ala
    50                  55                  60

Ile Arg Ser Lys Ile Glu Asp Gly Thr Val Lys Arg Glu Asp Ile Phe
65                  70                  75                  80
```

-continued

```
Tyr Thr Ser Lys Leu Trp Ser Thr Phe His Arg Pro Glu Leu Val Arg
                 85                  90                  95

Thr Cys Leu Glu Lys Thr Leu Lys Ser Thr Gln Leu Asp Tyr Val Asp
            100                 105                 110

Leu Tyr Ile Ile His Phe Pro Met Ala Leu Gln Pro Gly Asp Ile Phe
        115                 120                 125

Phe Pro Arg Asp Glu His Gly Lys Leu Leu Phe Glu Thr Val Asp Ile
    130                 135                 140

Cys Asp Thr Trp Glu Ala Met Glu Lys Cys Lys Asp Ala Gly Leu Ala
145                 150                 155                 160

Lys Ser Ile Gly Val Ser Asn Phe Asn Cys Arg Gln Leu Glu Arg Ile
                165                 170                 175

Leu Asn Lys Pro Gly Leu Lys Tyr Lys Pro Val Cys Asn Gln Val Glu
            180                 185                 190

Cys His Leu Tyr Leu Asn Gln Ser Lys Met Leu Asp Tyr Cys Lys Ser
        195                 200                 205

Lys Asp Ile Ile Leu Val Ser Tyr Cys Thr Leu Gly Ser Ser Arg Asp
    210                 215                 220

Lys Thr Trp Val Asp Gln Lys Ser Pro Val Leu Leu Asp Asp Pro Val
225                 230                 235                 240

Leu Cys Ala Ile Ala Lys Lys Tyr Lys Gln Thr Pro Ala Leu Val Ala
                245                 250                 255

Leu Arg Tyr Gln Leu Gln Arg Gly Val Val Pro Leu Ile Arg Ser Phe
            260                 265                 270

Asn Ala Lys Arg Ile Lys Glu Leu Thr Gln Val Phe Glu Phe Gln Leu
        275                 280                 285

Ala Ser Glu Asp Met Lys Ala Leu Asp Gly Leu Asn Arg Asn Phe Arg
    290                 295                 300

Tyr Asn Asn Ala Lys Tyr Phe Asp Asp His Pro Asn His Pro Phe Thr
305                 310                 315                 320

Asp Glu

<210> SEQ ID NO 9
<211> LENGTH: 26
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 9
cgtcgtcatg gtcgcccgtc gcgagg                                          26

<210> SEQ ID NO 10
<211> LENGTH: 26
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 10
cctcgcgacg ggcgaccatg acgacg                                          26

<210> SEQ ID NO 11
<211> LENGTH: 26
<212> TYPE: DNA
<213> ORGANISM: Artificial Sequence
```

```
<220> FEATURE:
<223> OTHER INFORMATION: Description of Artificial Sequence: Synthetic
      PCR primer

<400> SEQUENCE: 11
cgtcgtcatg gtcagccgtc gcgagg                                            26

<210> SEQ ID NO 12
<211> LENGTH: 26
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 12
cctcgcgacg gctgaccatg acgacg                                            26

<210> SEQ ID NO 13
<211> LENGTH: 47
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 13
gcgaattcgt gaaaggagat atacatgaac ctgagggaga agtacgg                     47

<210> SEQ ID NO 14
<211> LENGTH: 1206
<212> TYPE: DNA
<213> ORGANISM: Artificial Sequence
<220> FEATURE:
<223> OTHER INFORMATION: Description of Artificial Sequence: Synthetic
      formate dehydrogenase mutant polynucleotide
<220> FEATURE:
<221> NAME/KEY: CDS
<222> LOCATION: (1)..(1203)

<400> SEQUENCE: 14 atg gca aag gtc ctg tgc gtt ctt tac gat gat ccg gtc gac ggc tac         48
Met Ala Lys Val Leu Cys Val Leu Tyr Asp Asp Pro Val Asp Gly Tyr
1               5                   10                  15 ccg aag acc tat gcc cgc gac gat ctt ccg aag atc gac cac tat ccg         96
Pro Lys Thr Tyr Ala Arg Asp Asp Leu Pro Lys Ile Asp His Tyr Pro
            20                  25                  30 ggc ggc cag atc ttg ccg acg ccg aag gcc atc gac ttc acg ccc ggg        144
Gly Gly Gln Ile Leu Pro Thr Pro Lys Ala Ile Asp Phe Thr Pro Gly
        35                  40                  45 cag ttg ctc ggc tcc gtc tcc ggc gag ctc ggc ctg cgc gaa tat ctc        192
Gln Leu Leu Gly Ser Val Ser Gly Glu Leu Gly Leu Arg Glu Tyr Leu
    50                  55                  60 gaa tcc aac ggc cac acc ctg gtc gtg acc tcc gac aag gac ggc ccc        240
Glu Ser Asn Gly His Thr Leu Val Val Thr Ser Asp Lys Asp Gly Pro
65                  70                  75                  80 gac tcg gtg ttc gag cgc gag ctg gtc gat gcg gat gtc gtc atc tcc        288
Asp Ser Val Phe Glu Arg Glu Leu Val Asp Ala Asp Val Val Ile Ser
                85                  90                  95 cag ccc ttc tgg ccg gcc tat ctg acg ccc gag cgc atc gcc aag gcc        336
Gln Pro Phe Trp Pro Ala Tyr Leu Thr Pro Glu Arg Ile Ala Lys Ala
            100                 105                 110 aag aac ctg aag ctc gcg ctc acc gcc ggc atc ggt tcc gac cac gtc        384
Lys Asn Leu Lys Leu Ala Leu Thr Ala Gly Ile Gly Ser Asp His Val
        115                 120                 125
```

```
gat ctt cag tcg gct atc gac cgc aac gtc acc gtg gcg gaa gtc acc      432
Asp Leu Gln Ser Ala Ile Asp Arg Asn Val Thr Val Ala Glu Val Thr
    130                 135                 140 tac tgc aac tcg atc agc gtc gcc gag cat gtg gtg atg atg atc ctg      480
Tyr Cys Asn Ser Ile Ser Val Ala Glu His Val Val Met Met Ile Leu
145                 150                 155                 160 tcg ctg gtg cgc aac tat ctg ccc tcg cac gaa tgg gcg cgg aag ggc      528
Ser Leu Val Arg Asn Tyr Leu Pro Ser His Glu Trp Ala Arg Lys Gly
                165                 170                 175 ggc tgg aac atc gcc gac tgc gtc tcc cac gcc tac gac ctc gag gcg      576
Gly Trp Asn Ile Ala Asp Cys Val Ser His Ala Tyr Asp Leu Glu Ala
            180                 185                 190 atg cat gtc ggc acc gtg gcc gcc ggc cgc atc ggt ctc gcg gtg ctg      624
Met His Val Gly Thr Val Ala Ala Gly Arg Ile Gly Leu Ala Val Leu
            195                 200                 205 cgc cgt ctg gcg ccg ttc gac gtg cac ctg cac tac acc ggc cgt cac      672
Arg Arg Leu Ala Pro Phe Asp Val His Leu His Tyr Thr Gly Arg His
210                 215                 220 cgc ctg ccg gaa tcg gtc gag aag gag ctc aac ctc acc tgg cac gcg      720
Arg Leu Pro Glu Ser Val Glu Lys Glu Leu Asn Leu Thr Trp His Ala
225                 230                 235                 240 acc cgc gag gac atg tat ccg gtt tgc gac gtg gtg acg ctg aac tgc      768
Thr Arg Glu Asp Met Tyr Pro Val Cys Asp Val Val Thr Leu Asn Cys
                245                 250                 255 ccg ctg cac ccc gaa acc gag cac atg atc aat gac gag acg ctg aag      816
Pro Leu His Pro Glu Thr Glu His Met Ile Asn Asp Glu Thr Leu Lys
            260                 265                 270 ctg ttc aag cgt ggc gcc tac atc gtc aac acc gcc cgc ggc aag ctg      864
Leu Phe Lys Arg Gly Ala Tyr Ile Val Asn Thr Ala Arg Gly Lys Leu
            275                 280                 285 tgc gac cgc gat gcc gtg gca cgt gcg ctc gaa tcc ggc cgg ctg gcc      912
Cys Asp Arg Asp Ala Val Ala Arg Ala Leu Glu Ser Gly Arg Leu Ala
        290                 295                 300 ggc tat gcc ggc gac gtg tgg ttc ccg cag ccg gcg ccg aag gac cac      960
Gly Tyr Ala Gly Asp Val Trp Phe Pro Gln Pro Ala Pro Lys Asp His
305                 310                 315                 320 ccc tgg cgg acg atg ccc tat aac ggc atg acc ccg cac atc tcc ggc     1008
Pro Trp Arg Thr Met Pro Tyr Asn Gly Met Thr Pro His Ile Ser Gly
                325                 330                 335 acc acg ctg acc gcg cag gcg cgt tat gcg gcg ggc acc cgc gag atc     1056
Thr Thr Leu Thr Ala Gln Ala Arg Tyr Ala Ala Gly Thr Arg Glu Ile
            340                 345                 350 ctg gag tgc ttc ttc gag ggc cgt ccg atc cgc gac gaa tac ctc atc     1104
Leu Glu Cys Phe Phe Glu Gly Arg Pro Ile Arg Asp Glu Tyr Leu Ile
            355                 360                 365 gtg cag ggc ggc gct ctt gcc ggc acc ggc gcg cat tcc tac tcg aag     1152
Val Gln Gly Gly Ala Leu Ala Gly Thr Gly Ala His Ser Tyr Ser Lys
        370                 375                 380 ggc aat gcc acc ggc ggt tcg gaa gag gcc gcc aag ttc aag aag gcg     1200
Gly Asn Ala Thr Gly Gly Ser Glu Glu Ala Ala Lys Phe Lys Lys Ala
385                 390                 395                 400 gtc tga                                                             1206
Val

<210> SEQ ID NO 15
<211> LENGTH: 401
<212> TYPE: PRT
<213> ORGANISM: Artificial Sequence
<220> FEATURE:
<223> OTHER INFORMATION: Description of Artificial Sequence: Synthetic
``` construct polypeptide

<400> SEQUENCE: 15

Met Ala Lys Val Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
            20                  25                  30

Gly Gly Gln Ile Leu Pro Thr Pro Lys Ala Ile Asp Phe Thr Pro Gly
        35                  40                  45

Gln Leu Leu Gly Ser Val Ser Gly Glu Leu Gly Leu Arg Glu Tyr Leu
    50                  55                  60

Glu Ser Asn Gly His Thr Leu Val Val Thr Ser Asp Lys Asp Gly Pro
65                  70                  75                  80

Asp Ser Val Phe Glu Arg Glu Leu Val Asp Ala Asp Val Val Ile Ser
                85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
        115                 120                 125

Asp Leu Gln Ser Ala Ile Asp Arg Asn Val Thr Val Ala Glu Val Thr
    130                 135                 140

Tyr Cys Asn Ser Ile Ser Val Ala Glu His Val Val Met Met Ile Leu
145                 150                 155                 160

Ser Leu Val Arg Asn Tyr Leu Pro Ser His Glu Trp Ala Arg Lys Gly
                165                 170                 175

Gly Trp Asn Ile Ala Asp Cys Val Ser His Ala Tyr Asp Leu Glu Ala
            180                 185                 190

Met His Val Gly Thr Val Ala Ala Gly Arg Ile Gly Leu Ala Val Leu
        195                 200                 205

Arg Arg Leu Ala Pro Phe Asp Val His Leu His Tyr Thr Gly Arg His
210                 215                 220

Arg Leu Pro Glu Ser Val Glu Lys Glu Leu Asn Leu Thr Trp His Ala
225                 230                 235                 240

Thr Arg Glu Asp Met Tyr Pro Val Cys Asp Val Val Thr Leu Asn Cys
                245                 250                 255

Pro Leu His Pro Glu Thr Glu His Met Ile Asn Asp Glu Thr Leu Lys
            260                 265                 270

Leu Phe Lys Arg Gly Ala Tyr Ile Val Asn Thr Ala Arg Gly Lys Leu
        275                 280                 285

Cys Asp Arg Asp Ala Val Ala Arg Ala Leu Glu Ser Gly Arg Leu Ala
290                 295                 300

Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

Leu Glu Cys Phe Phe Glu Gly Arg Pro Ile Arg Asp Glu Tyr Leu Ile
        355                 360                 365

Val Gln Gly Gly Ala Leu Ala Gly Thr Gly Ala His Ser Tyr Ser Lys
370                 375                 380

Gly Asn Ala Thr Gly Gly Ser Glu Glu Ala Ala Lys Phe Lys Lys Ala
385                 390                 395                 400

Val

<210> SEQ ID NO 16
<211> LENGTH: 43
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 16
cccaagctta aggagatata catgtccatc atcgtgataa gcg                          43

<210> SEQ ID NO 17
<211> LENGTH: 34
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 17
ataagaatgc ggccgctcag aactgtgtcg ggcg                                    34

<210> SEQ ID NO 18
<211> LENGTH: 7404
<212> TYPE: DNA
<213> ORGANISM: Artificial Sequence
<220> FEATURE:
<223> OTHER INFORMATION: Description of Artificial Sequence: Synthetic
      plasmid pET21a FDH D221G 7beta-HSDH polypeptide
<220> FEATURE:
<221> NAME/KEY: CDS
<222> LOCATION: (5208)..(6422)
<223> OTHER INFORMATION: FDH D221G
<220> FEATURE:
<221> NAME/KEY: CDS
<222> LOCATION: (6435)..(7226)
<223> OTHER INFORMATION: 7beta-HSDH

<400> SEQUENCE: 18
tggcgaatgg gacgcgccct gtagcggcgc attaagcgcg gcgggtgtgg tggttacgcg    60
cagcgtgacc gctacacttg ccagcgccct agcgcccgct cctttcgctt tcttcccttc   120
ctttctcgcc acgttcgccg gctttccccg tcaagctcta atcggggggc tccctttagg   180
gttccgattt agtgctttac ggcacctcga ccccaaaaaa cttgattagg gtgatggttc   240
acgtagtggg ccatcgccct gatagacggt ttttcgccct ttgacgttgg agtccacgtt   300
ctttaatagt ggactcttgt tccaaactgg aacaacactc aaccctatct cggtctattc   360
ttttgattta agggatttt tgccgatttc ggcctattgg ttaaaaaatg agctgattta    420
acaaaaattt aacgcgaatt ttaacaaaat attaacgttt acaatttcag gtggcacttt   480
tcggggaaat gtgcgcggaa cccctatttg tttatttttc taaatacatt caaatatgta   540
tccgctcatg agacaataac cctgataaat gcttcaataa tattgaaaaa ggaagagtat   600
gagtattcaa catttccgtg tcgcccttat ccctttttt gcggcatttt gccttcctgt    660
ttttgctcac ccagaaacgc tggtgaaagt aaaagatgct gaagatcagt tgggtgcacg   720
agtgggttac atcgaactgg atctcaacag cggtaagatc cttgagagtt ttcgccccga   780
agaacgtttt ccaatgatga gcacttttaa agttctgcta tgtggcgcgg tattatcccg   840
tattgacgcc gggcaagagc aactcggtcg ccgcatacac tattctcaga atgacttggt   900
tgagtactca ccagtcacag aaaagcatct tacggatggc atgacagtaa gagaattatg   960

```
cagtgctgcc ataaccatga gtgataacac tgcggccaac ttacttctga caacgatcgg    1020
aggaccgaag gagctaaccg cttttttgca caacatgggg gatcatgtaa ctcgccttga    1080
tcgttgggaa ccggagctga atgaagccat accaaacgac gagcgtgaca ccacgatgcc    1140
tgcagcaatg gcaacaacgt tgcgcaaact attaactggc gaactactta ctctagcttc    1200
ccggcaacaa ttaatagact ggatggaggc ggataaagtt gcaggaccac ttctgcgctc    1260
ggcccttccg gctggctggt ttattgctga taaatctgga gccggtgagc gtgggtctcg    1320
cggtatcatt gcagcactgg ggccagatgg taagccctcc cgtatcgtag ttatctacac    1380
gacggggagt caggcaacta tggatgaacg aaatagacag atcgctgaga taggtgcctc    1440
actgattaag cattggtaac tgtcagacca agtttactca tatatacttt agattgattt    1500
aaaacttcat ttttaattta aaaggatcta ggtgaagatc ctttttgata atctcatgac    1560
caaaatccct taacgtgagt tttcgttcca ctgagcgtca gaccccgtag aaaagatcaa    1620
aggatcttct tgagatcctt ttttctgcg cgtaatctgc tgcttgcaaa caaaaaaacc    1680
accgctacca gcggtggttt gtttgccgga tcaagagcta ccaactcttt ttccgaaggt    1740
aactggcttc agcagagcgc agataccaaa tactgtcctt ctagtgtagc cgtagttagg    1800
ccaccacttc aagaactctg tagcaccgcc tacataccte gctctgctaa tcctgttacc    1860
agtggctgct gccagtggcg ataagtcgtg tcttaccggg ttggactcaa gacgatagtt    1920
accggataag gcgcagcggt cgggctgaac ggggggttcg tgcacacagc ccagcttgga    1980
gcgaacgacc tacaccgaac tgagatacct acagcgtgag ctatgagaaa gcgccacgct    2040
tcccgaaggg agaaaggcgg acaggtatcc ggtaagcggc agggtcggaa caggagagcg    2100
cacgagggag cttccagggg gaaacgcctg gtatctttat agtcctgtcg ggtttcgcca    2160
cctctgactt gagcgtcgat ttttgtgatg ctcgtcaggg gggcggagcc tatggaaaaa    2220
cgccagcaac gcggcctttt tacggttcct ggccttttgc tggccttttg ctcacatgtt    2280
ctttcctgcg ttatccctg attctgtgga taaccgtatt accgcctttg agtgagctga    2340
taccgctcgc cgcagccgaa cgaccgagcg cagcgagtca gtgagcgagg aagcggaaga    2400
gcgcctgatg cggtattttc tccttacgca tctgtgcggt atttcacacc gcatatatgg    2460
tgcactctca gtacaatctg ctctgatgcc gcatagttaa gccagtatac actccgctat    2520
cgctacgtga ctgggtcatg gctgcgcccc gacacccgcc aacacccgct gacgcgccct    2580
gacgggcttg tctgctcccg gcatccgctt acagacaagc tgtgaccgtc tccgggagct    2640
gcatgtgtca gaggttttca ccgtcatcac cgaaacgcgc gaggcagctg cggtaaagct    2700
catcagcgtg gtcgtgaagc gattcacaga tgtctgcctg ttcatccgcg tccagctcgt    2760
tgagtttctc cagaagcgtt aatgtctggc ttctgataaa gcgggccatg ttaagggcgg    2820
ttttttcctg tttggtcact gatgcctccg tgtaaggggg atttctgttc atggggtaa    2880 tgataccgat gaaacgagag aggatgctca cgatacgggt tactgatgat gaacatgccc    2940
ggttactgga acgttgtgag ggtaaacaac tggcggtatg gatgcggcgg gaccagagaa    3000
aaatcactca gggtcaatgc cagcgcttcg ttaatacaga tgtaggtgtt ccacagggta    3060
gccagcagca tcctgcgatg cagatccgga acataatggt gcagggcgct gacttccgcg    3120
tttccagact ttacgaaaca cggaaaccga agaccattca tgttgttgct caggtcgcag    3180
acgttttgca gcagcagtcg cttcacgttc gctcgcgtat cggtgattca ttctgctaac    3240
cagtaaggca accccgccag cctagccggg tcctcaacga caggagcacg atcatgcgca    3300
cccgtggggc cgccatgccg cgataatggc ctgcttctc gccgaaacgt ttggtggcgg    3360
```

```
gaccagtgac gaaggcttga gcgagggcgt gcaagattcc gaataccgca agcgacaggc   3420
cgatcatcgt cgcgctccag cgaaagcggt cctcgccgaa aatgacccag agcgctgccg   3480
gcacctgtcc tacgagttgc atgataaaga agacagtcat aagtgcggcg acgatagtca   3540
tgccccgcgc ccaccggaag gagctgactg ggttgaaggc tctcaagggc atcggtcgag   3600
atcccggtgc ctaatgagtg agctaactta cattaattgc gttgcgctca ctgcccgctt   3660
tccagtcggg aaacctgtcg tgccagctgc attaatgaat cggccaacgc gcggggagag   3720
gcggtttgcg tattgggcgc cagggtggtt tttcttttca ccagtgagac gggcaacagc   3780
tgattgccct tcaccgcctg gccctgagag agttgcagca agcggtccac gctggtttgc   3840
cccagcaggc gaaaatcctg tttgatggtg gttaacggcg ggatataaca tgagctgtct   3900
tcggtatcgt cgtatcccac taccgagata tccgcaccaa cgcgcagccc ggactcggta   3960
atggcgcgca ttgcgcccag cgccatctga tcgttggcaa ccagcatcgc agtgggaacg   4020
atgccctcat tcagcatttg catggtttgt tgaaaaccgg acatggcact ccagtcgcct   4080
tcccgttccg ctatcggctg aatttgattg cgagtgagat atttatgcca gccagccaga   4140
cgcagacgcg ccgagacaga acttaatggg cccgctaaca gcgcgatttg ctggtgaccc   4200
aatgcgacca gatgctccac gcccagtcgc gtaccgtctt catgggagaa aataatactg   4260
ttgatgggtg tctggtcaga gacatcaaga ataacgccg gaacattagt gcaggcagct   4320
tccacagcaa tggcatcctg gtcatccagc ggatagttaa tgatcagccc actgacgcgt   4380
tgcgcgagaa gattgtgcac cgccgcttta caggcttcga cgccgcttcg ttctaccatc   4440
gacaccacca cgctggcacc cagttgatcg gcgcgagatt taatcgccgc gacaatttgc   4500
gacggcgcgt gcagggccag actggaggtg caacgccaa tcagcaacga ctgtttgccc   4560
gccagttgtt gtgccacgcg gttgggaatg taattcagct ccgccatcgc cgcttccact   4620
ttttcccgcg ttttcgcaga aacgtggctg gcctggttca ccacgcggga aacggtctga   4680
taagagacac cggcatactc tgcgacatcg tataacgtta ctggtttcac attcaccacc   4740
ctgaattgac tctcttccgg cgctatcat gccataccgc gaaaggtttt gcgccattcg   4800
atggtgtccg gatctcgac gctctccctt atgcgactcc tgcattagga agcagcccag   4860
tagtaggttg aggccgttga gcaccgccgc cgcaaggaat ggtgcatgca aggagatggc   4920
gcccaacagt cccccggcca cggggcctgc caccataccc acgccgaaac aagcgctcat   4980
gagcccgaag tggcgagccc gatcttcccc atcggtgatg tcggcgatat aggcgccagc   5040
aaccgcacct gtggcgccgg tgatgccggc cacgatgcgt ccggcgtaga ggatcgagat   5100
ctcgatcccg cgaaattaat acgactcact ataggggaat tgtgagcgga taacaattcc   5160
cctctagaaa taattttgtt taactttaag aaggagatat acatatg atg gca aag     5216
                                                    Met Ala Lys
                                                      1 gtc ctg tgc gtt ctt tac gat gat ccg gtc gac ggc tac ccg aag acc     5264
Val Leu Cys Val Leu Tyr Asp Asp Pro Val Asp Gly Tyr Pro Lys Thr
      5                  10                  15 tat gcc cgc gac gat ctt ccg aag atc gac cac tat ccg ggc ggc cag     5312
Tyr Ala Arg Asp Asp Leu Pro Lys Ile Asp His Tyr Pro Gly Gly Gln
 20                  25                  30                  35 atc ttg ccg acg ccg aag gcc atc gac ttc acg ccc ggg cag ttg ctc     5360
Ile Leu Pro Thr Pro Lys Ala Ile Asp Phe Thr Pro Gly Gln Leu Leu
                 40                  45                  50 ggc tcc gtc tcc ggc gag ctc ggc ctg cgc gaa tat ctc gaa tcc aac     5408
Gly Ser Val Ser Gly Glu Leu Gly Leu Arg Glu Tyr Leu Glu Ser Asn
```

-continued

```
                   55                  60                  65
ggc cac acc ctg gtc gtg acc tcc gac aag gac ggc ccc gac tcg gtg    5456
Gly His Thr Leu Val Val Thr Ser Asp Lys Asp Gly Pro Asp Ser Val
         70                  75                  80 ttc gag cgc gag ctg gtc gat gcg gat gtc gtc atc tcc cag ccc ttc    5504
Phe Glu Arg Glu Leu Val Asp Ala Asp Val Val Ile Ser Gln Pro Phe
 85                  90                  95 tgg ccg gcc tat ctg acg ccc gag cgc atc gcc aag gcc aag aac ctg    5552
Trp Pro Ala Tyr Leu Thr Pro Glu Arg Ile Ala Lys Ala Lys Asn Leu
100                 105                 110                 115 aag ctc gcg ctc acc gcc ggc atc ggt tcc gac cac gtc gat ctt cag    5600
Lys Leu Ala Leu Thr Ala Gly Ile Gly Ser Asp His Val Asp Leu Gln
                    120                 125                 130 tcg gct atc gac cgc aac gtc acc gtg gcg gaa gtc acc tac tgc aac    5648
Ser Ala Ile Asp Arg Asn Val Thr Val Ala Glu Val Thr Tyr Cys Asn
            135                 140                 145 tcg atc agc gtc gcc gag cat gtg gtg atg atg atc ctg tcg ctg gtg    5696
Ser Ile Ser Val Ala Glu His Val Val Met Met Ile Leu Ser Leu Val
        150                 155                 160 cgc aac tat ctg ccc tcg cac gaa tgg gcg cgg aag ggc ggc tgg aac    5744
Arg Asn Tyr Leu Pro Ser His Glu Trp Ala Arg Lys Gly Gly Trp Asn
165                 170                 175 atc gcc gac tgc gtc tcc cac gcc tac gac ctc gag gcg atg cat gtc    5792
Ile Ala Asp Cys Val Ser His Ala Tyr Asp Leu Glu Ala Met His Val
180                 185                 190                 195 ggc acc gtg gcc gcc ggc cgc atc ggt ctc gcg gtg ctg cgc cgt ctg    5840
Gly Thr Val Ala Ala Gly Arg Ile Gly Leu Ala Val Leu Arg Arg Leu
                    200                 205                 210 gcg ccg ttc gac gtg cac ctg cac tac acc ggc cgt cac cgc ctg ccg    5888
Ala Pro Phe Asp Val His Leu His Tyr Thr Gly Arg His Arg Leu Pro
            215                 220                 225 gaa tcg gtc gag aag gag ctc aac ctc acc tgg cac gcg acc cgc gag    5936
Glu Ser Val Glu Lys Glu Leu Asn Leu Thr Trp His Ala Thr Arg Glu
        230                 235                 240 gac atg tat ccg gtt tgc gac gtg gtg acg ctg aac tgc ccg ctg cac    5984
Asp Met Tyr Pro Val Cys Asp Val Val Thr Leu Asn Cys Pro Leu His
245                 250                 255 ccc gaa acc gag cac atg atc aat gac gag acg ctg aag ctg ttc aag    6032
Pro Glu Thr Glu His Met Ile Asn Asp Glu Thr Leu Lys Leu Phe Lys
260                 265                 270                 275 cgt ggc gcc tac atc gtc aac acc gcc cgc ggc aag ctg tgc gac cgc    6080
Arg Gly Ala Tyr Ile Val Asn Thr Ala Arg Gly Lys Leu Cys Asp Arg
                    280                 285                 290 gat gcc gtg gca cgt gcg ctc gaa tcc ggc cgg ctg gcc ggc tat gcc    6128
Asp Ala Val Ala Arg Ala Leu Glu Ser Gly Arg Leu Ala Gly Tyr Ala
            295                 300                 305 ggc gac gtg tgg ttc ccg cag ccg gcg ccg aag gac cac ccc tgg cgg    6176
Gly Asp Val Trp Phe Pro Gln Pro Ala Pro Lys Asp His Pro Trp Arg
        310                 315                 320 acg atg ccc tat aac ggc atg acc ccg cac atc tcc ggc acc acg ctg    6224
Thr Met Pro Tyr Asn Gly Met Thr Pro His Ile Ser Gly Thr Thr Leu
325                 330                 335 acc gcg cag gcg cgt tat gcg gcg ggc acc cgc gag atc ctg gag tgc    6272
Thr Ala Gln Ala Arg Tyr Ala Ala Gly Thr Arg Glu Ile Leu Glu Cys
340                 345                 350                 355 ttc ttc gag ggc cgt ccg atc cgc gac gaa tac ctc atc gtg cag ggc    6320
Phe Phe Glu Gly Arg Pro Ile Arg Asp Glu Tyr Leu Ile Val Gln Gly
                    360                 365                 370 ggc gct ctt gcc ggc acc ggc gcg cat tcc tac tcg aag ggc aat gcc    6368
```

```
                 Gly Ala Leu Ala Gly Thr Gly Ala His Ser Tyr Ser Lys Gly Asn Ala
                             375                 380                 385 acc ggc ggt tcg gaa gag gcc gcc aag ttc aag aag gcg gct gag aat          6416
Thr Gly Gly Ser Glu Glu Ala Ala Lys Phe Lys Lys Ala Ala Glu Asn
                390                 395                 400 tcg tga aaggagatat ac atg aac ctg agg gag aag tac ggt gag tgg ggc        6467
Ser                   Met Asn Leu Arg Glu Lys Tyr Gly Glu Trp Gly
                                  405                 410                 415 ctg atc ctg ggc gcg acc gag ggc gtc ggc aag gcg ttc tgc gag aag          6515
Leu Ile Leu Gly Ala Thr Glu Gly Val Gly Lys Ala Phe Cys Glu Lys
                420                 425                 430 atc gcc gcc ggc ggc atg aac gtc gtc atg gtc ggc cgt cgc gag gag          6563
Ile Ala Ala Gly Gly Met Asn Val Val Met Val Gly Arg Arg Glu Glu
                435                 440                 445 aag ctg aac gtg ctc gca ggc gag atc cgc gag acc tac ggc gtg gag          6611
Lys Leu Asn Val Leu Ala Gly Glu Ile Arg Glu Thr Tyr Gly Val Glu
                450                 455                 460 acc aag gtc gtg cgc gcc gac ttt agc cag ccc ggc gct gcc gag acc          6659
Thr Lys Val Val Arg Ala Asp Phe Ser Gln Pro Gly Ala Ala Glu Thr
465                 470                 475 gtc ttc gcc gcg acc gag ggc ctg gac atg ggc ttc atg agc tac gtg          6707
Val Phe Ala Ala Thr Glu Gly Leu Asp Met Gly Phe Met Ser Tyr Val
480                 485                 490                 495 gcc tgc ctg cac agc ttc ggt aag atc cag gac acc ccc tgg gag aag          6755
Ala Cys Leu His Ser Phe Gly Lys Ile Gln Asp Thr Pro Trp Glu Lys
                500                 505                 510 cac gag gcc atg atc aac gtc aac gtc gtg acc ttc ctc aag tgc ttc          6803
His Glu Ala Met Ile Asn Val Asn Val Val Thr Phe Leu Lys Cys Phe
                515                 520                 525 cac cac tac atg cgg atc ttt gcc gcc cag gac cgc ggc gcc gtg atc          6851
His His Tyr Met Arg Ile Phe Ala Ala Gln Asp Arg Gly Ala Val Ile
                530                 535                 540 aac gtc tcg tcg atg acc ggc atc agc tcc agc ccc tgg aac ggc cag          6899
Asn Val Ser Ser Met Thr Gly Ile Ser Ser Ser Pro Trp Asn Gly Gln
545                 550                 555 tac ggc gcg ggc aag gcc ttc atc ctc aag atg acc gag gcc gtg gcc          6947
Tyr Gly Ala Gly Lys Ala Phe Ile Leu Lys Met Thr Glu Ala Val Ala
560                 565                 570                 575 tgc gag tgc gag ggc acc ggc gtc gac gtc gag gtc atc acc ctc ggc          6995
Cys Glu Cys Glu Gly Thr Gly Val Asp Val Glu Val Ile Thr Leu Gly
                580                 585                 590 acc acc cta acc ccc agc ctg ctg tcc aac ctc ccc ggc ggc ccg cag          7043
Thr Thr Leu Thr Pro Ser Leu Leu Ser Asn Leu Pro Gly Gly Pro Gln
                595                 600                 605 ggc gag gcc gtc atg aag atc gcc ctc acc ccc gag gag tgc gtt gac          7091
Gly Glu Ala Val Met Lys Ile Ala Leu Thr Pro Glu Glu Cys Val Asp
                610                 615                 620 gag gcc ttt gag aag ctg ggt aag gag ctc tcc gtc atc gcc ggc cag          7139
Glu Ala Phe Glu Lys Leu Gly Lys Glu Leu Ser Val Ile Ala Gly Gln
625                 630                 635 cgc aac aag gac tcc gtc cac gac tgg aag gca aac cac acc gag gac          7187
Arg Asn Lys Asp Ser Val His Asp Trp Lys Ala Asn His Thr Glu Asp
640                 645                 650                 655 gag tac atc cgc tac atg ggg tcg ttc tac cgc gac tag aagcttgcgg          7236
Glu Tyr Ile Arg Tyr Met Gly Ser Phe Tyr Arg Asp
                660                 665 ccgcactcga gcaccaccac caccaccact gagatccggc tgctaacaaa gcccgaaagg        7296
aagctgagtt ggctgctgcc accgctgagc aataactagc ataaccccctt ggggcctcta      7356
```

-continued aacgggtctt gaggggtttt ttgctgaaag gaggaactat atccggat 7404

<210> SEQ ID NO 19
<211> LENGTH: 404
<212> TYPE: PRT
<213> ORGANISM: Artificial Sequence
<220> FEATURE:
<223> OTHER INFORMATION: Description of Artificial Sequence: Synthetic
       construct polypeptide

<400> SEQUENCE: 19

Met Ala Lys Val Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
            20                  25                  30

Gly Gly Gln Ile Leu Pro Thr Pro Lys Ala Ile Asp Phe Thr Pro Gly
        35                  40                  45

Gln Leu Leu Gly Ser Val Ser Gly Glu Leu Gly Leu Arg Glu Tyr Leu
    50                  55                  60

Glu Ser Asn Gly His Thr Leu Val Val Thr Ser Asp Lys Asp Gly Pro
65                  70                  75                  80

Asp Ser Val Phe Glu Arg Glu Leu Val Asp Ala Asp Val Ile Ser
                85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
        115                 120                 125

Asp Leu Gln Ser Ala Ile Asp Arg Asn Val Thr Val Ala Glu Val Thr
    130                 135                 140

Tyr Cys Asn Ser Ile Ser Val Ala Glu His Val Val Met Met Ile Leu
145                 150                 155                 160

Ser Leu Val Arg Asn Tyr Leu Pro Ser His Glu Trp Ala Arg Lys Gly
                165                 170                 175

Gly Trp Asn Ile Ala Asp Cys Val Ser His Ala Tyr Asp Leu Glu Ala
            180                 185                 190

Met His Val Gly Thr Val Ala Ala Gly Arg Ile Gly Leu Ala Val Leu
        195                 200                 205

Arg Arg Leu Ala Pro Phe Asp Val His Leu His Tyr Thr Gly Arg His
    210                 215                 220

Arg Leu Pro Glu Ser Val Glu Lys Glu Leu Asn Leu Thr Trp His Ala
225                 230                 235                 240

Thr Arg Glu Asp Met Tyr Pro Val Cys Asp Val Val Thr Leu Asn Cys
                245                 250                 255

Pro Leu His Pro Glu Thr Glu His Met Ile Asn Asp Glu Thr Leu Lys
            260                 265                 270

Leu Phe Lys Arg Gly Ala Tyr Ile Val Asn Thr Ala Arg Gly Lys Leu
        275                 280                 285

Cys Asp Arg Asp Ala Val Ala Arg Ala Leu Glu Ser Gly Arg Leu Ala
    290                 295                 300

Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

Leu Glu Cys Phe Phe Glu Gly Arg Pro Ile Arg Asp Glu Tyr Leu Ile
            355                 360                 365

Val Gln Gly Gly Ala Leu Ala Gly Thr Gly Ala His Ser Tyr Ser Lys
    370                 375                 380

Gly Asn Ala Thr Gly Gly Ser Glu Glu Ala Ala Lys Phe Lys Lys Ala
385                 390                 395                 400

Ala Glu Asn Ser

<210> SEQ ID NO 20
<211> LENGTH: 263
<212> TYPE: PRT
<213> ORGANISM: Artificial Sequence
<220> FEATURE:
<223> OTHER INFORMATION: Description of Artificial Sequence: Synthetic
      construct polypeptide

<400> SEQUENCE: 20

Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
                20                  25                  30

Met Asn Val Val Met Val Gly Arg Arg Glu Glu Lys Leu Asn Val Leu
            35                  40                  45

Ala Gly Glu Ile Arg Glu Thr Tyr Gly Val Gly Thr Lys Val Val Arg
    50                  55                  60

Ala Asp Phe Ser Gln Pro Gly Ala Ala Glu Thr Val Phe Ala Ala Thr
65                  70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
        115                 120                 125

Ile Phe Ala Ala Gln Asp Arg Gly Ala Val Ile Asn Val Ser Ser Met
    130                 135                 140

Thr Gly Ile Ser Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
        195                 200                 205

Lys Ile Ala Leu Thr Pro Glu Glu Cys Val Asp Glu Ala Phe Glu Lys
    210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp
            260

<210> SEQ ID NO 21
<211> LENGTH: 4302
<212> TYPE: DNA
<213> ORGANISM: Artificial Sequence
<220> FEATURE:

<223> OTHER INFORMATION: Description of Artificial Sequence: Synthetic
      plasmid pCOLA(mod) 3alpha-HSDH polynucleotide
<220> FEATURE:
<221> NAME/KEY: CDS
<222> LOCATION: (303)..(1076)
<223> OTHER INFORMATION: 3alpha-HSDH

<400> SEQUENCE: 21

```
ggggaattgt gagcggataa caattcccct gtagaaataa ttttgtttaa ctttaataag     60
gagatatacc atgggcagca gccatcacca tcatcaccac agccaggatc cgaattcgag    120
ctcggcgcgc ctgcaggtcg acaagcttgc ggccgcataa tgcttaagtc gaacagaaag    180
taatcgtatt gtacacggcc gcataatcga aattaatacg actcactata ggggaattgt    240
gagcggataa caattcccca tcttagtata ttagttaagt ataagaagga gatatacata    300 tg atg tcc atc atc gtg ata agc ggc tgc gcc acc ggc att ggt gcc       347
   Met Ser Ile Ile Val Ile Ser Gly Cys Ala Thr Gly Ile Gly Ala
   1               5                  10                 15 gct acg cgc aag gtc ctg gag gcg gcc ggt cac cag atc gta ggc atc      395
Ala Thr Arg Lys Val Leu Glu Ala Ala Gly His Gln Ile Val Gly Ile
               20                  25                  30 gat ata cgc gat gcg gaa gtg att gcc gat ctc tcg acg gcc gaa ggt      443
Asp Ile Arg Asp Ala Glu Val Ile Ala Asp Leu Ser Thr Ala Glu Gly
           35                  40                  45 cga aag cag gcg att gcc gat gta ctg gcg aag tgc agc aag ggc atg      491
Arg Lys Gln Ala Ile Ala Asp Val Leu Ala Lys Cys Ser Lys Gly Met
       50                  55                  60 gac ggc ctg gtg ctg tgc gcc ggc ctg gga ccg cag acc aag gtg ctt      539
Asp Gly Leu Val Leu Cys Ala Gly Leu Gly Pro Gln Thr Lys Val Leu
   65                  70                  75 ggc aat gtg gtt tcg gtc aat tat ttt ggc gcg acc gag ctg atg gat      587
Gly Asn Val Val Ser Val Asn Tyr Phe Gly Ala Thr Glu Leu Met Asp
80                  85                  90                  95 gcc ttt ttg cca gcg ctg aaa aaa ggc cat cag ccc gca gcc gtc gtc      635
Ala Phe Leu Pro Ala Leu Lys Lys Gly His Gln Pro Ala Ala Val Val
               100                 105                 110 atc tcg tcc gtg gct tcc gcg cat ctg gct ttt gac aag aac cca ctg      683
Ile Ser Ser Val Ala Ser Ala His Leu Ala Phe Asp Lys Asn Pro Leu
           115                 120                 125 gcg ctg gca ctg gaa gcc ggc gag gaa gcc aag gcc cgc gcc att gtc      731
Ala Leu Ala Leu Glu Ala Gly Glu Glu Ala Lys Ala Arg Ala Ile Val
       130                 135                 140 gaa cat gcg gga gag cag ggc gga aat ctg gcc tat gcg ggc agc aag      779
Glu His Ala Gly Glu Gln Gly Gly Asn Leu Ala Tyr Ala Gly Ser Lys
   145                 150                 155 aat gct ttg acg gtg gct gtg cgc aaa cgc gcc gcc gcc tgg ggc gag      827
Asn Ala Leu Thr Val Ala Val Arg Lys Arg Ala Ala Ala Trp Gly Glu
160                 165                 170                 175 gct ggc gtg cgc ctg aac acc atc gcc ccc ggt gca acc gag act ccc      875
Ala Gly Val Arg Leu Asn Thr Ile Ala Pro Gly Ala Thr Glu Thr Pro
               180                 185                 190 ttg ctg cag gcg ggc ctg cag gac ccg cgc tat ggc gaa tcc att gcc      923
Leu Leu Gln Ala Gly Leu Gln Asp Pro Arg Tyr Gly Glu Ser Ile Ala
           195                 200                 205 aag ttc gtt cct ccc atg ggc cgc cgt gcc gag ccg tcc gag atg gcg      971
Lys Phe Val Pro Pro Met Gly Arg Arg Ala Glu Pro Ser Glu Met Ala
       210                 215                 220 tcg gtc atc gcc ttt ttg atg agc ccg gcc gca agc tat gtg cat ggc     1019
Ser Val Ile Ala Phe Leu Met Ser Pro Ala Ala Ser Tyr Val His Gly
   225                 230                 235
```

```
gcg cag atc gtc att gat ggc ggc att gat gcg gtg atg cgc ccg aca      1067
Ala Gln Ile Val Ile Asp Gly Gly Ile Asp Ala Val Met Arg Pro Thr
240                 245                 250                 255 cag ttc tga gaattcgagc tccgtcgaca agcttgcggc cgcactcgag              1116
Gln Phe caccaccacc accaccactg agatccggct gctaacaaag cccgaaagga agctgagttg    1176
gctgctgcca ccgctgagca ataactagca taaccccttg gggcctctaa acgggtcttg    1236
aggggttttt tgctgaaacc tcaggcattt gagaagcaca cggtcacact gcttccggta    1296
gtcaataaac cggtaaacca gcaatagaca taagcggcta tttaacgacc ctgccctgaa    1356
ccgacgacaa gctgacgacc gggtctccgc aagtggcact tttcggggaa atgtgcgcgg    1416
aaccccctatt tgtttatttt tctaaataca ttcaaatatg tatccgctca tgaattaatt    1476
cttacgcccc gccctgccac tcatcgcagt actgttgtaa ttcattaagc attctgccga    1536
catggaagcc atcacagacg gcatgatgaa cctgaatcgc cagcggcatc agcaccttgt    1596
cgccttgcgt ataatatttg cctatggtga aacgggggc gaagaagttg tccatattgg    1656
ccacgtttaa atcaaaactg gtgaaactca cccagggatt ggctgagacg aaaaacatat    1716
tctcaataaa ccctttaggg aaataggcca ggttttcacc gtaacacgcc acatcttgcg    1776
aatatatgtg tagaaactgc cggaaatcgt cgtggtattc actccagagc gatgaaaacg    1836
tttcagtttg ctcatggaaa acggtgtaac aagggtgaac actatcccat atcaccagct    1896
caccgtcttt cattgccata cggaattccg gatgagcatt catcaggcgg gcaagaatgt    1956
gaataaaggc cggataaaac ttgtgcttat ttttctttac ggtctttaaa aaggccgtaa    2016
tatccagctg aacggtctgg ttataggtac attgagcaac tgactgaaat gcctcaaaat    2076
gttctttacg atgccattgg gatatatcaa cggtggtata tccagtgatt tttttctcca    2136
tactcttcct ttttcaatat tattgaagca tttatcaggg ttattgtctc atgagcggat    2196
acatatttga atgtatttag aaaaataaac aaataggcat gctagcgcag aaacgtccta    2256
gaagatgcca ggaggatact tagcagagag acaataaggc cggagcgaag ccgttttcc    2316
ataggctccg ccccctgac gaacatcacg aaatctgacg ctcaaatcag tggtggcgaa    2376
acccgacagg actataaaga taccaggcgt ttccccctga tggctccctc ttgcgctctc    2436
ctgttcccgt cctgcggcgt ccgtgttgtg gtggaggctt tacccaaatc accacgtccc    2496
gttccgtgta gacagttcgc tccaagctgg gctgtgtgca agaaccccc gttcagcccg    2556
actgctgcgc cttatccggt aactatcatc ttgagtccaa cccggaaaga cacgacaaaa    2616
cgccactggc agcagccatt ggtaactgag aattagtgga tttagatatc gagagtcttg    2676
aagtggtggc ctaacagagg ctacactgaa aggacagtat ttggtatctg cgctccacta    2736
aagccagtta ccaggttaag cagttcccca actgacttaa ccttcgatca aaccgcctcc    2796
ccaggcggtt ttttcgttta cagagcagga gattacgacg atcgtaaaag gatctcaaga    2856
agatccttta cggattcccg acaccatcac tctagatttc agtgcaattt atctcttcaa    2916
atgtagcacc tgaagtcagc cccatacgat ataagttgta attctcatgt tagtcatgcc    2976
ccgcgcccac cggaaggagc tgactgggtt gaaggctctc aagggcatcg gtcgagatcc    3036
cggtgcctaa tgagtgagct aacttacatt aattgcgttg cgctcactgc ccgctttcca    3096
gtcgggaaac ctgtcgtgcc agctgcatta atgaatcggc caacgcgcgg ggagaggcgg    3156
tttgcgtatt gggcgccagg gtggtttttc ttttcaccag tgagacgggc aacagctgat    3216
tgcccttcac cgcctggccc tgagagagtt gcagcaagcg gtccacgctg gtttgcccca    3276
```

-continued

```
gcaggcgaaa atcctgtttg atggtggtta acggcgggat ataacatgag ctgtcttcgg    3336
tatcgtcgta tcccactacc gagatgtccg caccaacgcg cagcccggac tcggtaatgg    3396
cgcgcattgc gcccagcgcc atctgatcgt tggcaaccag catcgcagtg ggaacgatgc    3456
cctcattcag catttgcatg gtttgttgaa aaccggacat ggcactccag tcgccttccc    3516
gttccgctat cggctgaatt tgattgcgag tgagatattt atgccagcca gccagacgca    3576
gacgcgccga gacagaactt aatgggcccg ctaacagcgc gatttgctgg tgacccaatg    3636
cgaccagatg ctccacgccc agtcgcgtac cgtcttcatg ggagaaaata atactgttga    3696
tgggtgtctg gtcagagaca tcaagaaata acgccggaac attagtgcag gcagcttcca    3756
cagcaatggc atcctggtca tccagcggat agttaatgat cagcccactg acgcgttgcg    3816
cgagaagatt gtgcaccgcc gctttacagg cttcgacgcc gcttcgttct accatcgaca    3876
ccaccacgct ggcacccagt tgatcggcgc gagatttaat cgccgcgaca atttgcgacg    3936
gcgcgtgcag ggccagactg gaggtggcaa cgccaatcag caacgactgt ttgcccgcca    3996
gttgttgtgc cacgcggttg ggaatgtaat tcagctccgc catcgccgct tccactttt    4056
cccgcgtttt cgcagaaacg tggctggcct ggttcaccac gcgggaaacg gtctgataag    4116
agacaccggc atactctgcg acatcgtata acgttactgg tttcacattc accaccctga    4176
attgactctc ttccgggcgc tatcatgcca taccgcgaaa ggttttgcgc cattcgatgg    4236
tgtccgggat ctcgacgctc tcccttatgc gactcctgca ttaggaaatt aatacgactc    4296
actata                                                               4302
```

<210> SEQ ID NO 22
<211> LENGTH: 257
<212> TYPE: PRT
<213> ORGANISM: Artificial Sequence
<220> FEATURE:
<223> OTHER INFORMATION: Description of Artificial Sequence: Synthetic construct polypeptide

<400> SEQUENCE: 22

```
Met Ser Ile Ile Val Ile Ser Gly Cys Ala Thr Gly Ile Gly Ala Ala
1               5                   10                  15

Thr Arg Lys Val Leu Glu Ala Ala Gly His Gln Ile Val Gly Ile Asp
                20                  25                  30

Ile Arg Asp Ala Glu Val Ile Ala Asp Leu Ser Thr Ala Glu Gly Arg
            35                  40                  45

Lys Gln Ala Ile Ala Asp Val Leu Ala Lys Cys Ser Lys Gly Met Asp
        50                  55                  60

Gly Leu Val Leu Cys Ala Gly Leu Gly Pro Gln Thr Lys Val Leu Gly
65                  70                  75                  80

Asn Val Val Ser Val Asn Tyr Phe Gly Ala Thr Glu Leu Met Asp Ala
                85                  90                  95

Phe Leu Pro Ala Leu Lys Lys Gly His Gln Pro Ala Ala Val Val Ile
                100                 105                 110

Ser Ser Val Ala Ser Ala His Leu Ala Phe Asp Lys Asn Pro Leu Ala
            115                 120                 125

Leu Ala Leu Glu Ala Gly Glu Glu Ala Lys Ala Arg Ala Ile Val Glu
        130                 135                 140

His Ala Gly Glu Gln Gly Gly Asn Leu Ala Tyr Ala Gly Ser Lys Asn
145                 150                 155                 160

Ala Leu Thr Val Ala Val Arg Lys Arg Ala Ala Ala Trp Gly Glu Ala
                165                 170                 175
```

-continued

```
Gly Val Arg Leu Asn Thr Ile Ala Pro Gly Ala Thr Glu Thr Pro Leu
                180                 185                 190

Leu Gln Ala Gly Leu Gln Asp Pro Arg Tyr Gly Glu Ser Ile Ala Lys
            195                 200                 205

Phe Val Pro Pro Met Gly Arg Arg Ala Glu Pro Ser Glu Met Ala Ser
    210                 215                 220

Val Ile Ala Phe Leu Met Ser Pro Ala Ala Ser Tyr Val His Gly Ala
225                 230                 235                 240

Gln Ile Val Ile Asp Gly Gly Ile Asp Ala Val Met Arg Pro Thr Gln
                245                 250                 255

Phe

<210> SEQ ID NO 23
<211> LENGTH: 29
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 23
cgatcatatg gcaaaggtcc tgtgcgttc                                      29

<210> SEQ ID NO 24
<211> LENGTH: 29
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 24
gctagaattc tcagccgcct tcttgaact                                      29

<210> SEQ ID NO 25
<211> LENGTH: 768
<212> TYPE: DNA
<213> ORGANISM: Escherichia coli
<220> FEATURE:
<221> NAME/KEY: CDS
<222> LOCATION: (1)..(765)

<400> SEQUENCE: 25 gtg ttt aat tct gac aac ctg aga ctc gac gga aaa tgc gcc atc atc      48
Val Phe Asn Ser Asp Asn Leu Arg Leu Asp Gly Lys Cys Ala Ile Ile
1               5                   10                  15 aca ggt gcg ggt gca ggt att ggt aaa gaa atc gcc att aca ttc gcg      96
Thr Gly Ala Gly Ala Gly Ile Gly Lys Glu Ile Ala Ile Thr Phe Ala
            20                  25                  30 aca gct ggc gca tct gtg gtg gtc agt gat att aac gcc gac gca gct     144
Thr Ala Gly Ala Ser Val Val Val Ser Asp Ile Asn Ala Asp Ala Ala
        35                  40                  45 aac cat gtt gta gac gaa att caa caa ctg ggt ggt cag gca ttt gcc     192
Asn His Val Val Asp Glu Ile Gln Gln Leu Gly Gly Gln Ala Phe Ala
    50                  55                  60 tgc cgt tgt gat att act tcc gaa cag gaa ctc tct gca ctg gca gac     240
Cys Arg Cys Asp Ile Thr Ser Glu Gln Glu Leu Ser Ala Leu Ala Asp
65                  70                  75                  80 ttt gct atc agt aag ctg ggt aaa gtt gat att ctg gtt aac aac gcc     288
Phe Ala Ile Ser Lys Leu Gly Lys Val Asp Ile Leu Val Asn Asn Ala
                85                  90                  95
```

```
ggt ggc ggt gga cct aaa ccg ttt gat atg cca atg gcg gat ttt cgc       336
Gly Gly Gly Gly Pro Lys Pro Phe Asp Met Pro Met Ala Asp Phe Arg
            100                 105                 110 cgt gct tat gaa ctg aat gtg ttt tct ttt ttc cat ctg tca caa ctt       384
Arg Ala Tyr Glu Leu Asn Val Phe Ser Phe Phe His Leu Ser Gln Leu
        115                 120                 125 gtt gcg cca gaa atg gaa aaa aat ggc ggt ggc gtt att ctg acc atc       432
Val Ala Pro Glu Met Glu Lys Asn Gly Gly Gly Val Ile Leu Thr Ile
    130                 135                 140 act tct atg gcg gca gaa aat aaa aat ata aac atg act tcc tat gca       480
Thr Ser Met Ala Ala Glu Asn Lys Asn Ile Asn Met Thr Ser Tyr Ala
145                 150                 155                 160 tca tct aaa gct gcg gcc agt cat ctg gtc aga aat atg gcg ttt gac       528
Ser Ser Lys Ala Ala Ala Ser His Leu Val Arg Asn Met Ala Phe Asp
                165                 170                 175 cta ggt gaa aaa aat att cgg gta aat ggc att gcg ccg ggg gca ata       576
Leu Gly Glu Lys Asn Ile Arg Val Asn Gly Ile Ala Pro Gly Ala Ile
            180                 185                 190 tta acc gat gcc ctg aaa tcc gtt att aca cca gaa att gaa caa aaa       624
Leu Thr Asp Ala Leu Lys Ser Val Ile Thr Pro Glu Ile Glu Gln Lys
        195                 200                 205 atg tta cag cac acg ccg atc aga cgt ctg ggc caa ccg caa gat att       672
Met Leu Gln His Thr Pro Ile Arg Arg Leu Gly Gln Pro Gln Asp Ile
    210                 215                 220 gct aac gca gcg ctg ttc ctt tgc tcg cct gct gcg agc tgg gta agc       720
Ala Asn Ala Ala Leu Phe Leu Cys Ser Pro Ala Ala Ser Trp Val Ser
225                 230                 235                 240 gga caa att ctc acc gtc tcc ggt ggt ggg gta cag gag ctc aat taa      768
Gly Gln Ile Leu Thr Val Ser Gly Gly Gly Val Gln Glu Leu Asn
                245                 250                 255

<210> SEQ ID NO 26
<211> LENGTH: 255
<212> TYPE: PRT
<213> ORGANISM: Escherichia coli

<400> SEQUENCE: 26

Val Phe Asn Ser Asp Asn Leu Arg Leu Asp Gly Lys Cys Ala Ile Ile
1               5                   10                  15

Thr Gly Ala Gly Ala Gly Ile Gly Lys Glu Ile Ala Ile Thr Phe Ala
            20                  25                  30

Thr Ala Gly Ala Ser Val Val Val Ser Asp Ile Asn Ala Asp Ala Ala
        35                  40                  45

Asn His Val Val Asp Glu Ile Gln Gln Leu Gly Gly Gln Ala Phe Ala
    50                  55                  60

Cys Arg Cys Asp Ile Thr Ser Glu Gln Glu Leu Ser Ala Leu Ala Asp
65                  70                  75                  80

Phe Ala Ile Ser Lys Leu Gly Lys Val Asp Ile Leu Val Asn Asn Ala
                85                  90                  95

Gly Gly Gly Gly Pro Lys Pro Phe Asp Met Pro Met Ala Asp Phe Arg
            100                 105                 110

Arg Ala Tyr Glu Leu Asn Val Phe Ser Phe Phe His Leu Ser Gln Leu
        115                 120                 125

Val Ala Pro Glu Met Glu Lys Asn Gly Gly Val Ile Leu Thr Ile
    130                 135                 140

Thr Ser Met Ala Ala Glu Asn Lys Asn Ile Asn Met Thr Ser Tyr Ala
145                 150                 155                 160

Ser Ser Lys Ala Ala Ala Ser His Leu Val Arg Asn Met Ala Phe Asp
```

165                 170                 175
Leu Gly Glu Lys Asn Ile Arg Val Asn Gly Ile Ala Pro Gly Ala Ile
            180                 185                 190

Leu Thr Asp Ala Leu Lys Ser Val Ile Thr Pro Glu Ile Glu Gln Lys
        195                 200                 205

Met Leu Gln His Thr Pro Ile Arg Arg Leu Gly Gln Pro Gln Asp Ile
    210                 215                 220

Ala Asn Ala Ala Leu Phe Leu Cys Ser Pro Ala Ala Ser Trp Val Ser
225                 230                 235                 240

Gly Gln Ile Leu Thr Val Ser Gly Gly Val Gln Glu Leu Asn
                245                 250                 255

<210> SEQ ID NO 27
<211> LENGTH: 53
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 27
aaaaaagctt ataattatcc ttataggacg tcatggtgcg cccagatagg gtg          53

<210> SEQ ID NO 28
<211> LENGTH: 60
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 28
cagattgtac aaatgtggtg ataacagata agtcgtcatg tttaacttac ctttctttgt   60

<210> SEQ ID NO 29
<211> LENGTH: 49
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 29
tgaacgcaag tttctaattt cggtttccta tcgatagagg aaagtgtct               49

<210> SEQ ID NO 30
<211> LENGTH: 29
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 30
cctgcactac accggccgtc accgcctgc                                     29

<210> SEQ ID NO 31
<211> LENGTH: 23
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 31

-continued

```
gctcgaattc tcagaccgcc ttc                                          23
```

<210> SEQ ID NO 32
<211> LENGTH: 27
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 32

```
ttaattgagc tcctgtaccc caccacc                                      27
```

<210> SEQ ID NO 33
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 33

```
gtgtttaatt ctgacaacct gagactcgac                                   30
```

<210> SEQ ID NO 34
<211> LENGTH: 1266
<212> TYPE: DNA
<213> ORGANISM: Artificial Sequence
<220> FEATURE:
<223> OTHER INFORMATION: Description of Artificial Sequence: Synthetic
      FDH D221G mutant with His-tag polynucleotide
<220> FEATURE:
<221> NAME/KEY: CDS
<222> LOCATION: (1)..(1263)

<400> SEQUENCE: 34

```
atg gca aag gtc ctg tgc gtt ctt tac gat gat ccg gtc gac ggc tac      48
Met Ala Lys Val Leu Cys Val Leu Tyr Asp Asp Pro Val Asp Gly Tyr
1               5                   10                  15 ccg aag acc tat gcc cgc gac gat ctt ccg aag atc gac cac tat ccg      96
Pro Lys Thr Tyr Ala Arg Asp Asp Leu Pro Lys Ile Asp His Tyr Pro
            20                  25                  30 ggc ggc cag atc ttg ccg acg ccg aag gcc atc gac ttc acg ccc ggg     144
Gly Gly Gln Ile Leu Pro Thr Pro Lys Ala Ile Asp Phe Thr Pro Gly
        35                  40                  45 cag ttg ctc ggc tcc gtc tcc ggc gag ctc ggc ctg cgc gaa tat ctc     192
Gln Leu Leu Gly Ser Val Ser Gly Glu Leu Gly Leu Arg Glu Tyr Leu
    50                  55                  60 gaa tcc aac ggc cac acc ctg gtc gtg acc tcc gac aag gac ggc ccc     240
Glu Ser Asn Gly His Thr Leu Val Val Thr Ser Asp Lys Asp Gly Pro
65                  70                  75                  80 gac tcg gtg ttc gag cgc gag ctg gtc gat gcg gat gtc gtc atc tcc     288
Asp Ser Val Phe Glu Arg Glu Leu Val Asp Ala Asp Val Val Ile Ser
                85                  90                  95 cag ccc ttc tgg ccg gcc tat ctg acg ccc gag cgc atc gcc aag gcc     336
Gln Pro Phe Trp Pro Ala Tyr Leu Thr Pro Glu Arg Ile Ala Lys Ala
            100                 105                 110 aag aac ctg aag ctc gcg ctc acc gcc ggc atc ggt tcc gac cac gtc     384
Lys Asn Leu Lys Leu Ala Leu Thr Ala Gly Ile Gly Ser Asp His Val
        115                 120                 125 gat ctt cag tcg gct atc gac cgc aac gtc acc gtg gcg gaa gtc acc     432
Asp Leu Gln Ser Ala Ile Asp Arg Asn Val Thr Val Ala Glu Val Thr
    130                 135                 140
```

| | | |
|---|---|---|
| tac tgc aac tcg atc agc gtc gcc gag cat gtg gtg atg atg atc ctg<br>Tyr Cys Asn Ser Ile Ser Val Ala Glu His Val Val Met Met Ile Leu<br>145     150      155     160 | | 480 |
| tcg ctg gtg cgc aac tat ctg ccc tcg cac gaa tgg gcg cgg aag ggc<br>Ser Leu Val Arg Asn Tyr Leu Pro Ser His Glu Trp Ala Arg Lys Gly<br>     165      170     175 | | 528 |
| ggc tgg aac atc gcc gac tgc gtc tcc cac gcc tac gac ctc gag gcg<br>Gly Trp Asn Ile Ala Asp Cys Val Ser His Ala Tyr Asp Leu Glu Ala<br>    180      185     190 | | 576 |
| atg cat gtc ggc acc gtg gcc gcc ggc cgc atc ggt ctc gcg gtg ctg<br>Met His Val Gly Thr Val Ala Ala Gly Arg Ile Gly Leu Ala Val Leu<br>   195      200     205 | | 624 |
| cgc cgt ctg gcg ccg ttc gac gtg cac ctg cac tac acc ggc cgt cac<br>Arg Arg Leu Ala Pro Phe Asp Val His Leu His Tyr Thr Gly Arg His<br>210      215      220 | | 672 |
| cgc ctg ccg gaa tcg gtc gag aag gag ctc aac ctc acc tgg cac gcg<br>Arg Leu Pro Glu Ser Val Glu Lys Glu Leu Asn Leu Thr Trp His Ala<br>225     230      235     240 | | 720 |
| acc cgc gag gac atg tat ccg gtt tgc gac gtg gtg acg ctg aac tgc<br>Thr Arg Glu Asp Met Tyr Pro Val Cys Asp Val Val Thr Leu Asn Cys<br>     245      250     255 | | 768 |
| ccg ctg cac ccc gaa acc gag cac atg atc aat gac gag acg ctg aag<br>Pro Leu His Pro Glu Thr Glu His Met Ile Asn Asp Glu Thr Leu Lys<br>    260      265     270 | | 816 |
| ctg ttc aag cgt ggc gcc tac atc gtc aac acc gcc cgc ggc aag ctg<br>Leu Phe Lys Arg Gly Ala Tyr Ile Val Asn Thr Ala Arg Gly Lys Leu<br>   275      280     285 | | 864 |
| tgc gac cgc gat gcc gtg gca cgt gcg ctc gaa tcc ggc cgg ctg gcc<br>Cys Asp Arg Asp Ala Val Ala Arg Ala Leu Glu Ser Gly Arg Leu Ala<br>290      295      300 | | 912 |
| ggc tat gcc ggc gac gtg tgg ttc ccg cag ccg gcg ccg aag gac cac<br>Gly Tyr Ala Gly Asp Val Trp Phe Pro Gln Pro Ala Pro Lys Asp His<br>305     310      315     320 | | 960 |
| ccc tgg cgg acg atg ccc tat aac ggc atg acc ccg cac atc tcc ggc<br>Pro Trp Arg Thr Met Pro Tyr Asn Gly Met Thr Pro His Ile Ser Gly<br>     325      330     335 | | 1008 |
| acc acg ctg acc gcg cag gcg cgt tat gcg gcg ggc acc cgc gag atc<br>Thr Thr Leu Thr Ala Gln Ala Arg Tyr Ala Ala Gly Thr Arg Glu Ile<br>    340      345     350 | | 1056 |
| ctg gag tgc ttc ttc gag ggc cgt ccg atc cgc gac gaa tac ctc atc<br>Leu Glu Cys Phe Phe Glu Gly Arg Pro Ile Arg Asp Glu Tyr Leu Ile<br>   355      360     365 | | 1104 |
| gtg cag ggc ggc gct ctt gcc ggc acc ggc gcg cat tcc tac tcg aag<br>Val Gln Gly Gly Ala Leu Ala Gly Thr Gly Ala His Ser Tyr Ser Lys<br>370      375      380 | | 1152 |
| ggc aat gcc acc ggc ggt tcg gaa gag gcc gcc aag ttc aag aag gcg<br>Gly Asn Ala Thr Gly Gly Ser Glu Glu Ala Ala Lys Phe Lys Lys Ala<br>385     390      395     400 | | 1200 |
| gct gag aat tcg agc tcc gtc gac aag ctt gcg gcc gca ctc gag cac<br>Ala Glu Asn Ser Ser Ser Val Asp Lys Leu Ala Ala Ala Leu Glu His<br>     405      410     415 | | 1248 |
| cac cac cac cac cac tga<br>His His His His His<br>   420 | | 1266 |

<210> SEQ ID NO 35
<211> LENGTH: 421
<212> TYPE: PRT
<213> ORGANISM: Artificial Sequence
<220> FEATURE:
<223> OTHER INFORMATION: Description of Artificial Sequence: Synthetic construct polypeptide

<400> SEQUENCE: 35

Met Ala Lys Val Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
            20                  25                  30

Gly Gly Gln Ile Leu Pro Thr Pro Lys Ala Ile Asp Phe Thr Pro Gly
        35                  40                  45

Gln Leu Leu Gly Ser Val Ser Gly Glu Leu Gly Leu Arg Glu Tyr Leu
    50                  55                  60

Glu Ser Asn Gly His Thr Leu Val Val Thr Ser Asp Lys Asp Gly Pro
65                  70                  75                  80

Asp Ser Val Phe Glu Arg Glu Leu Val Asp Ala Asp Val Val Ile Ser
                85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
        115                 120                 125

Asp Leu Gln Ser Ala Ile Asp Arg Asn Val Thr Val Ala Glu Val Thr
    130                 135                 140

Tyr Cys Asn Ser Ile Ser Val Ala Glu His Val Val Met Met Ile Leu
145                 150                 155                 160

Ser Leu Val Arg Asn Tyr Leu Pro Ser His Glu Trp Ala Arg Lys Gly
                165                 170                 175

Gly Trp Asn Ile Ala Asp Cys Val Ser His Ala Tyr Asp Leu Glu Ala
            180                 185                 190

Met His Val Gly Thr Val Ala Ala Gly Arg Ile Gly Leu Ala Val Leu
        195                 200                 205

Arg Arg Leu Ala Pro Phe Asp Val His Leu His Tyr Thr Gly Arg His
    210                 215                 220

Arg Leu Pro Glu Ser Val Glu Lys Glu Leu Asn Leu Thr Trp His Ala
225                 230                 235                 240

Thr Arg Glu Asp Met Tyr Pro Val Cys Asp Val Val Thr Leu Asn Cys
                245                 250                 255

Pro Leu His Pro Glu Thr Glu His Met Ile Asn Asp Glu Thr Leu Lys
            260                 265                 270

Leu Phe Lys Arg Gly Ala Tyr Ile Val Asn Thr Ala Arg Gly Lys Leu
        275                 280                 285

Cys Asp Arg Asp Ala Val Ala Arg Ala Leu Glu Ser Gly Arg Leu Ala
    290                 295                 300

Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

Leu Glu Cys Phe Phe Glu Gly Arg Pro Ile Arg Asp Glu Tyr Leu Ile
        355                 360                 365

Val Gln Gly Gly Ala Leu Ala Gly Thr Gly Ala His Ser Tyr Ser Lys
    370                 375                 380

Gly Asn Ala Thr Gly Gly Ser Glu Glu Ala Ala Lys Phe Lys Lys Ala
385                 390                 395                 400

Ala Glu Asn Ser Ser Ser Val Asp Lys Leu Ala Ala Leu Glu His
            405                 410                 415
His His His His His
            420

<210> SEQ ID NO 36
<211> LENGTH: 401
<212> TYPE: PRT
<213> ORGANISM: Mycobacterium vaccae

<400> SEQUENCE: 36

Met Ala Lys Val Leu Cys Val Leu Tyr Asp Asp Pro Val Asp Gly Tyr
1               5                   10                  15

Pro Lys Thr Tyr Ala Arg Asp Asp Leu Pro Lys Ile Asp His Tyr Pro
            20                  25                  30

Gly Gly Gln Ile Leu Pro Thr Pro Lys Ala Ile Asp Phe Thr Pro Gly
        35                  40                  45

Gln Leu Leu Gly Ser Val Ser Gly Glu Leu Gly Leu Arg Glu Tyr Leu
    50                  55                  60

Glu Ser Asn Gly His Thr Leu Val Val Thr Ser Asp Lys Asp Gly Pro
65                  70                  75                  80

Asp Ser Val Phe Glu Arg Glu Leu Val Asp Ala Asp Val Val Ile Ser
                85                  90                  95

Gln Pro Phe Trp Pro Ala Tyr Leu Thr Pro Glu Arg Ile Ala Lys Ala
            100                 105                 110

Lys Asn Leu Lys Leu Ala Leu Thr Ala Gly Ile Gly Ser Asp His Val
        115                 120                 125

Asp Leu Gln Ser Ala Ile Asp Arg Asn Val Thr Val Ala Glu Val Thr
    130                 135                 140

Tyr Cys Asn Ser Ile Ser Val Ala Glu His Val Val Met Met Ile Leu
145                 150                 155                 160

Ser Leu Val Arg Asn Tyr Leu Pro Ser His Glu Trp Ala Arg Lys Gly
                165                 170                 175

Gly Trp Asn Ile Ala Asp Cys Val Ser His Ala Tyr Asp Leu Glu Ala
            180                 185                 190

Met His Val Gly Thr Val Ala Ala Gly Arg Ile Gly Leu Ala Val Leu
        195                 200                 205

Arg Arg Leu Ala Pro Phe Asp Val His Leu His Tyr Thr Asp Arg His
    210                 215                 220

Arg Leu Pro Glu Ser Val Glu Lys Glu Leu Asn Leu Thr Trp His Ala
225                 230                 235                 240

Thr Arg Glu Asp Met Tyr Pro Val Cys Asp Val Val Thr Leu Asn Cys
                245                 250                 255

Pro Leu His Pro Glu Thr Glu His Met Ile Asn Asp Glu Thr Leu Lys
            260                 265                 270

Leu Phe Lys Arg Gly Ala Tyr Ile Val Asn Thr Ala Arg Gly Lys Leu
        275                 280                 285

Cys Asp Arg Asp Ala Val Ala Arg Ala Leu Glu Ser Gly Arg Leu Ala
    290                 295                 300

Gly Tyr Ala Gly Asp Val Trp Phe Pro Gln Pro Ala Pro Lys Asp His
305                 310                 315                 320

Pro Trp Arg Thr Met Pro Tyr Asn Gly Met Thr Pro His Ile Ser Gly
                325                 330                 335

Thr Thr Leu Thr Ala Gln Ala Arg Tyr Ala Ala Gly Thr Arg Glu Ile
            340                 345                 350

```
Leu Glu Cys Phe Phe Glu Gly Arg Pro Ile Arg Asp Glu Tyr Leu Ile
        355                 360                 365

Val Gln Gly Gly Ala Leu Ala Gly Thr Gly Ala His Ser Tyr Ser Lys
    370                 375                 380

Gly Asn Ala Thr Gly Gly Ser Glu Glu Ala Ala Lys Phe Lys Lys Ala
385                 390                 395                 400

Val

<210> SEQ ID NO 37
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide derived from Collinsella aerofaciens (G39D)

<400> SEQUENCE: 37

Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
            20                  25                  30

Met Asn Val Val Met Val Asp Arg Arg Glu Glu Lys Leu Asn Val Leu
        35                  40                  45

Ala Gly Glu Ile Arg Glu Thr Tyr Gly Val Thr Lys Val Val Arg
    50                  55                  60

Ala Asp Phe Ser Gln Pro Gly Ala Ala Glu Thr Val Phe Ala Ala Thr
65                  70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
        115                 120                 125

Ile Phe Ala Ala Gln Asp Arg Gly Ala Val Ile Asn Val Ser Ser Met
130                 135                 140

Thr Gly Ile Ser Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
        195                 200                 205

Lys Ile Ala Leu Thr Pro Glu Glu Cys Val Asp Glu Ala Phe Glu Lys
    210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp
            260

<210> SEQ ID NO 38
<211> LENGTH: 263
<212> TYPE: PRT
<213> ORGANISM: Artificial Sequence
```

<220> FEATURE:
<223> OTHER INFORMATION: Description of Artificial Sequence: Synthetic
      polypeptide derived from Collinsella aerofaciens (G39D R40L)

<400> SEQUENCE: 38

Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
            20                  25                  30

Met Asn Val Val Met Val Asp Leu Arg Glu Glu Lys Leu Asn Val Leu
        35                  40                  45

Ala Gly Glu Ile Arg Glu Thr Tyr Gly Val Glu Thr Lys Val Val Arg
    50                  55                  60

Ala Asp Phe Ser Gln Pro Gly Ala Ala Glu Thr Val Phe Ala Ala Thr
65                  70                  75                  80

Glu Gly Leu Asp Met Gly Phe Met Ser Tyr Val Ala Cys Leu His Ser
                85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
        115                 120                 125

Ile Phe Ala Ala Gln Asp Arg Gly Ala Val Ile Asn Val Ser Ser Met
130                 135                 140

Thr Gly Ile Ser Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
                165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
        195                 200                 205

Lys Ile Ala Leu Thr Pro Glu Glu Cys Val Asp Glu Ala Phe Glu Lys
    210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                245                 250                 255

Met Gly Ser Phe Tyr Arg Asp
            260

<210> SEQ ID NO 39
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide derived from Collinsella aerofaciens (G39D R40I)

<400> SEQUENCE: 39

Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
            20                  25                  30

Met Asn Val Val Met Val Asp Ile Arg Glu Glu Lys Leu Asn Val Leu
        35                  40                  45

Ala Gly Glu Ile Arg Glu Thr Tyr Gly Val Glu Thr Lys Val Val Arg
    50                  55                  60

Ala Asp Phe Ser Gln Pro Gly Ala Ala Glu Thr Val Phe Ala Thr
65                  70                  75                  80

Glu Gly Leu Asp Met Gly Phe Met Ser Tyr Val Ala Cys Leu His Ser
            85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
            115                 120                 125

Ile Phe Ala Ala Gln Asp Arg Gly Ala Val Ile Asn Val Ser Ser Met
130                 135                 140

Thr Gly Ile Ser Ser Ser Pro Trp Asn Gly Gln Tyr Gly Ala Gly Lys
145                 150                 155                 160

Ala Phe Ile Leu Lys Met Thr Glu Ala Val Ala Cys Glu Cys Glu Gly
            165                 170                 175

Thr Gly Val Asp Val Glu Val Ile Thr Leu Gly Thr Thr Leu Thr Pro
            180                 185                 190

Ser Leu Leu Ser Asn Leu Pro Gly Gly Pro Gln Gly Glu Ala Val Met
            195                 200                 205

Lys Ile Ala Leu Thr Pro Glu Glu Cys Val Asp Glu Ala Phe Glu Lys
210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
            245                 250                 255

Met Gly Ser Phe Tyr Arg Asp
            260

<210> SEQ ID NO 40
<211> LENGTH: 263
<212> TYPE: PRT
<213> ORGANISM: Artificial Sequence
<220> FEATURE:
<223> OTHER INFORMATION: Description of Artificial Sequence: Synthetic
      polypeptide derived from Collinsella aerofaciens

<400> SEQUENCE: 40

Met Asn Leu Arg Glu Lys Tyr Gly Glu Trp Gly Leu Ile Leu Gly Ala
1               5                   10                  15

Thr Glu Gly Val Gly Lys Ala Phe Cys Glu Lys Ile Ala Ala Gly Gly
            20                  25                  30

Met Asn Val Val Met Val Asp Val Arg Glu Glu Lys Leu Asn Val Leu
            35                  40                  45

Ala Gly Glu Ile Arg Glu Thr Tyr Gly Val Glu Thr Lys Val Val Arg
50                  55                  60

Ala Asp Phe Ser Gln Pro Gly Ala Ala Glu Thr Val Phe Ala Thr
65                  70                  75                  80

Glu Gly Leu Asp Met Gly Phe Met Ser Tyr Val Ala Cys Leu His Ser
            85                  90                  95

Phe Gly Lys Ile Gln Asp Thr Pro Trp Glu Lys His Glu Ala Met Ile
            100                 105                 110

Asn Val Asn Val Val Thr Phe Leu Lys Cys Phe His His Tyr Met Arg
            115                 120                 125

Ile Phe Ala Ala Gln Asp Arg Gly Ala Val Ile Asn Val Ser Ser Met
130                 135                 140

Thr Gly Ile Ser Ser Ser Pro Trp Asn Gly Gln Tyr Gly Ala Gly Lys

```
                145                 150                 155                 160
Ala Phe Ile Leu Lys Met Thr Glu Ala Val Ala Cys Glu Cys Glu Gly
                    165                 170                 175

Thr Gly Val Asp Val Glu Val Ile Thr Leu Gly Thr Thr Leu Thr Pro
                    180                 185                 190

Ser Leu Leu Ser Asn Leu Pro Gly Gly Pro Gln Gly Glu Ala Val Met
                    195                 200                 205

Lys Ile Ala Leu Thr Pro Glu Glu Cys Val Asp Glu Ala Phe Glu Lys
                    210                 215                 220

Leu Gly Lys Glu Leu Ser Val Ile Ala Gly Gln Arg Asn Lys Asp Ser
225                 230                 235                 240

Val His Asp Trp Lys Ala Asn His Thr Glu Asp Glu Tyr Ile Arg Tyr
                    245                 250                 255

Met Gly Ser Phe Tyr Arg Asp
                    260

<210> SEQ ID NO 41
<211> LENGTH: 26
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 41
cgtcgtcatg gtcgaccgtc gcgagg                                             26

<210> SEQ ID NO 42
<211> LENGTH: 26
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 42
cctcgcgacg gtcgaccatg acgacg                                             26

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 43
cgtcgtcatg gtcgacctgc gcgagg                                             26

<210> SEQ ID NO 44
<211> LENGTH: 31
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 44
ccgccgcatc cataccgcca gttgtttacc c                                       31

<210> SEQ ID NO 45
<211> LENGTH: 26
<212> TYPE: DNA
```

<213> ORGANISM: Artificial Sequence
<220> FEATURE:
<223> OTHER INFORMATION: Description of Artificial Sequence: Synthetic
      PCR primer

<400> SEQUENCE: 45
cgtcgtcatg gtcgacattc gcgagg                                          26

<210> SEQ ID NO 46
<211> LENGTH: 26
<212> TYPE: DNA
<213> ORGANISM: Artificial Sequence
<220> FEATURE:
<223> OTHER INFORMATION: Description of Artificial Sequence: Synthetic
      PCR primer

<400> SEQUENCE: 46
cgtcgtcatg gtcgacgttc gcgagg                                          26

<210> SEQ ID NO 47
<211> LENGTH: 786
<212> TYPE: DNA
<213> ORGANISM: Bacillus subtilis

<400> SEQUENCE: 47
atgtatccgg atttaaaagg aaaagtcgtc gctattacag gagctgcttc agggctcgga     60
aaggcgatgg ccattcgctt cggcaaggag caggcaaaag tggttatcaa ctattatagt    120
aataaacaag atccgaacga ggtaaaagaa gaggtcatca aggcgggcgg tgaagctgtt    180
gtcgtccaag gagatgtcac gaaagaggaa gatgtaaaaa atatcgtgca aacggcaatt    240
aaggagttcg gcacactcga tattatgatt aataatgccg gtcttgaaaa tcctgtgcca    300
tctcacgaaa tgccgctcaa ggattgggat aaagtcatcg gcacgaactt aacgggtgcc    360
tttttaggaa gccgtgaagc gattaaatat ttcgtagaaa acgatatcaa gggaaatgtc    420
attaacatgt ccagtgtgca cgaagtgatt ccttggccgt tatttgtcca ctatgcggca    480
agtaaaggcg ggataaagct gatgacagaa acattagcgt tggaatacgc gccgaagggc    540
attcgcgtca ataatattgg gccaggtgcg atcaacacgc caatcaatgc tgaaaaattc    600
gctgacccta aacagaaagc tgatgtagaa agcatgattc caatgggata tatcggcgaa    660
ccggaggaga tcgccgcagt agcagcctgg cttgcttcga aggaagccag ctacgtcaca    720
ggcatcacgt tattcgcgga cggcggtatg acacaatatc cttcattcca ggcaggccgc    780
ggttaa                                                              786

<210> SEQ ID NO 48
<211> LENGTH: 261
<212> TYPE: PRT
<213> ORGANISM: Bacillus subtilis

<400> SEQUENCE: 48

Met Tyr Pro Asp Leu Lys Gly Lys Val Val Ala Ile Thr Gly Ala Ala
1               5                   10                  15

Ser Gly Leu Gly Lys Ala Met Ala Ile Arg Phe Gly Lys Glu Gln Ala
            20                  25                  30

Lys Val Val Ile Asn Tyr Tyr Ser Asn Lys Gln Asp Pro Asn Glu Val
        35                  40                  45

Lys Glu Glu Val Ile Lys Ala Gly Gly Glu Ala Val Val Val Gln Gly
    50                  55                  60

Asp Val Thr Lys Glu Glu Asp Val Lys Asn Ile Val Gln Thr Ala Ile

```
            65                  70                  75                  80
Lys Glu Phe Gly Thr Leu Asp Ile Met Ile Asn Asn Ala Gly Leu Glu
                    85                  90                  95

Asn Pro Val Pro Ser His Glu Met Pro Leu Lys Asp Trp Asp Lys Val
                100                 105                 110

Ile Gly Thr Asn Leu Thr Gly Ala Phe Leu Gly Ser Arg Glu Ala Ile
                115                 120                 125

Lys Tyr Phe Val Glu Asn Asp Ile Lys Gly Asn Val Ile Asn Met Ser
            130                 135                 140

Ser Val His Glu Val Ile Pro Trp Pro Leu Phe Val His Tyr Ala Ala
145                 150                 155                 160

Ser Lys Gly Gly Ile Lys Leu Met Thr Glu Thr Leu Ala Leu Glu Tyr
                165                 170                 175

Ala Pro Lys Gly Ile Arg Val Asn Asn Ile Gly Pro Gly Ala Ile Asn
                180                 185                 190

Thr Pro Ile Asn Ala Glu Lys Phe Ala Asp Pro Lys Gln Lys Ala Asp
            195                 200                 205

Val Glu Ser Met Ile Pro Met Gly Tyr Ile Gly Glu Pro Glu Glu Ile
            210                 215                 220

Ala Ala Val Ala Ala Trp Leu Ala Ser Lys Glu Ala Ser Tyr Val Thr
225                 230                 235                 240

Gly Ile Thr Leu Phe Ala Asp Gly Gly Met Thr Gln Tyr Pro Ser Phe
                245                 250                 255

Gln Ala Gly Arg Gly
            260

<210> SEQ ID NO 49
<211> LENGTH: 7404
<212> TYPE: DNA
<213> ORGANISM: Artificial Sequence
<220> FEATURE:
<223> OTHER INFORMATION: Description of Artificial Sequence: Synthetic
      vector pFr7(D) polynucleotide

<400> SEQUENCE: 49
atccggatat agttcctcct ttcagcaaaa aaccccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gcaagcttct     180
agtcgcggta gaacgacccc atgtagcgga tgtactcgtc ctcggtgtgg tttgccttcc     240
agtcgtggac ggagtccttg ttgcgctggc cggcgatgac ggagagctcc ttacccagct     300
tctcaaaggc ctcgtcaacg cactcctcgg gggtgagggc gatcttcatg acggcctcgc     360
cctgcgggcc gccggggagg ttggacagca ggctgggggt tagggtggtg ccagggtga     420 tgacctcgac gtcgacgccg gtgccctcgc actcgcaggc cacggcctcg gtcatcttga     480
ggatgaaggc cttgcccgcg ccgtactggc cgttccaggg gctggagctg atgccggtca     540
tcgacgagac gttgatcacg cgccgcggt cctgggcggc aaagatccgc atgtagtggt     600
ggaagcactt gaggaaggtc acgacgttga cgttgatcat ggcctcgtgc ttctcccagg     660
gggtgtcctg gatcttaccg aagctgtgca ggcaggccac gtagctcatg aagcccatgt     720
ccaggccctc ggtcgcggcg aagacggtct cggcagcgcc gggctggcta agtcggcgc     780 gcacgacctt ggtctccacg ccgtaggtct cgcggatctc gcctgcgagc acgttcagct     840
tctcctcgcg acggtcgacc atgacgacgt catgccgcc ggcggcgatc ttctcgcaga     900
```

```
acgccttgcc gacgccctcg gtcgcgccca ggatcaggcc ccactcaccg tacttctccc    960
tcaggttcat gtatatctcc tttcacgaat tctcagccgc cttcttgaac ttggcggcct   1020
cttccgaacc gccggtggca ttgcccttcg agtaggaatg cgcgccggtg ccggcaagag   1080
cgccgccctg cacgatgagg tattcgtcgc ggatcggacg gccctcgaag aagcactcca   1140
ggatctcgcg ggtgcccgcc gcataacgcg cctgcgcggt cagcgtggtg ccggagatgt   1200
gcggggtcat gccgttatag ggcatcgtcc gccaggggtg gtccttcggc gccggctgcg   1260
ggaaccacac gtcgccggca tagccggcca gccggccgga ttcgagcgca cgtgccacgg   1320
catcgcggtc gcacagcttg ccgcgggcgg tgttgacgat gtaggcgcca cgcttgaaca   1380
gcttcagcgt ctcgtcattg atcatgtgct cggtttcggg gtgcagcggg cagttcagcg   1440
tcaccacgtc gcaaaccgga tacatgtcct cgcgggtcgc gtgccaggtg aggttgagct   1500
ccttctcgac cgattccggc aggcggtgac ggccggtgta gtgcaggtgc acgtcgaacg   1560
gcgccagacg gcgcagcacc gcgagaccga tgccggccgc ggccacggtg ccgacatgca   1620
tcgcctcgag gtcgtaggcg tgggagacgc agtcggcgat gttccagccg cccttccgcg   1680
cccattcgtg cgagggcaga tagttgcgca ccagcgacag gatcatcatc accacatgct   1740
cggcgacgct gatcgagttg cagtaggtga cttccgccac ggtgacgttg cggtcgatag   1800
ccgactgaag atcgacgtgg tcggaaccga tgccggcggt gagcgcgagc ttcaggttct   1860
tggccttggc gatgcgctcg ggcgtcagat aggccggcca aagggctgg gagatgacga   1920
catccgcatc gaccagctcg cgctcgaaca ccgagtcggg gccgtccttg tcggaggtca   1980
cgaccagggt gtgccgttg gattcgagat attcgcgcag gccgagctcg ccggagacgg   2040
agccgagcaa ctgcccgggc gtgaagtcga tggccttcgg cgtcggcaag atctggccgc   2100
ccggatagtg gtcgatcttc ggaagatcgt cgcgggcata ggtcttcggg tagccgtcga   2160
ccggatcatc gtaaagaacg cacaggacct ttgccatcat atgtatatct ccttcttaaa   2220
gttaaacaaa attatttcta gaggggaatt gttatccgct cacaattccc ctatagtgag   2280
tcgtattaat ttcgcgggat cgagatctcg atcctctacg ccggacgcat cgtggccggc   2340
atcaccggcg ccacaggtgc ggttgctggc gcctatatcg ccgacatcac cgatgggaa   2400
gatcgggctc gccacttcgg gctcatgagc gcttgtttcg gcgtgggtat ggtggcaggc   2460
cccgtggccg ggggactgtt gggcgccatc tccttgcatg caccattcct tgcggcggcg   2520
gtgctcaacg gcctcaacct actactgggc tgcttcctaa tgcaggagtc gcataaggga   2580
gagcgtcgag atcccggaca ccatcgaatg gcgcaaaacc tttcgcggta tggcatgata   2640
gcgcccggaa gagagtcaat tcagggtggt gaatgtgaaa ccagtaacgt tatacgatgt   2700
cgcagagtat gccggtgtct cttatcagac cgtttcccgc gtggtgaacc aggccagcca   2760
cgtttctgcg aaaacgcggg aaaaagtgga agcggcgatg gcggagctga attacattcc   2820
caaccgcgtg gcacaacaac tggcgggcaa acagtcgttg ctgattggcg ttgccacctc   2880
cagtctggcc ctgcacgcgc cgtcgcaaat tgtcgcggcg attaaatctc gcgccgatca   2940
actgggtgcc agcgtggtgg tgtcgatggt agaacgaagc ggcgtcgaag cctgtaaagc   3000
ggcggtgcac aatcttctcg cgcaacgcgt cagtgggctg atcattaact atccgctgga   3060
tgaccaggat gccattgctg tggaagctgc ctgcactaat gttccggcgt tatttcttga   3120
tgtctctgac cagacaccca tcaacagtat tattttctcc catgaagacg gtacgcgact   3180
gggcgtggag catctggtcg cattgggtca ccagcaaatc gcgctgttag cgggcccatt   3240
aagttctgtc tcggcgcgtc tgcgtctggc tggctggcat aaatatctca ctcgcaatca   3300
```

-continued

```
aattcagccg atagcggaac gggaaggcga ctggagtgcc atgtccggtt ttcaacaaac    3360
catgcaaatg ctgaatgagg gcatcgttcc cactgcgatg ctggttgcca acgatcagat    3420
ggcgctgggc gcaatgcgcg ccattaccga gtccgggctg cgcgttggtg cggatatctc    3480
ggtagtggga tacgacgata ccgaagacag ctcatgttat atcccgccgt taaccaccat    3540
caaacaggat tttcgcctgc tggggcaaac cagcgtggac cgcttgctgc aactctctca    3600
gggccaggcg gtgaagggca atcagctgtt gcccgtctca ctggtgaaaa gaaaaaccac    3660
cctggcgccc aatacgcaaa ccgcctctcc ccgcgcgttg gccgattcat taatgcagct    3720
ggcacgacag gtttcccgac tggaaagcgg gcagtgagcg caacgcaatt aatgtaagtt    3780
agctcactca ttaggcaccg ggatctcgac cgatgccctt gagagccttc aacccagtca    3840
gctccttccg gtgggcgcgg ggcatgacta tcgtcgccgc acttatgact gtcttcttta    3900
tcatgcaact cgtaggacag gtgccggcag cgctctgggt cattttcggc gaggaccgct    3960
ttcgctggag cgcgacgatg atcggcctgt cgcttgcgct attcggaatc ttgcacgccc    4020
tcgctcaagc cttcgtcact ggtcccgcca ccaaacgttt cggcgagaag caggccatta    4080
tcgccggcat ggcggcccca cgggtgcgca tgatcgtgct cctgtcgttg aggacccggc    4140
taggctggcg gggttgcctt actggttagc agaatgaatc accgatacgc gagcgaacgt    4200
gaagcgactc ctgctgcaaa acgtctgcga cctgagcaac aacatgaatg gtcttcggtt    4260
tccgtgtttc gtaaagtctg gaaacgcgga agtcagcgcc ctgcaccatt atgttccgga    4320
tctgcatcgc aggatgctgc tggctaccct gtggaacacc tacatctgta ttaacgaagc    4380
gctggcattg accctgagtg atttttctct ggtcccgccg catccatacc gccagttgtt    4440
taccctcaca acgttccagt aaccgggcat gttcatcatc agtaacccgt atcgtgagca    4500
tcctctctcg tttcatcggt atcattaccc ccatgaacag aaatcccccct tacacggagg    4560 catcagtgac caaacaggaa aaaaccgccc ttaacatggc ccgctttatc agaagccaga    4620
cattaacgct tctggagaaa ctcaacgagc tggacgcgga tgaacaggca gacatctgtg    4680
aatcgcttca cgaccacgct gatgagcttt accgcagctg cctcgcgcgt ttcggtgatg    4740
acggtgaaaa cctctgacac atgcagctcc cggagacggt cacagcttgt ctgtaagcgg    4800
atgccgggag cagacaagcc cgtcagggcg cgtcagcggg tgttggcggg tgtcggggcg    4860
cagccatgac ccagtcacgt agcgatagcg gagtgtatac tggcttaact atgcggcatc    4920
agagcagatt gtactgagag tgcaccatat atgcggtgtg aaataccgca cagatgcgta    4980
aggagaaaat accgcatcag gcgctcttcc gcttcctcgc tcactgactc gctgcgctcg    5040
gtcgttcggc tgcggcgagc ggtatcagct cactcaaagg cggtaatacg gttatccaca    5100
gaatcagggg ataacgcagg aaagaacatg tgagcaaaag gccagcaaaa ggccaggaac    5160
cgtaaaaagg ccgcgttgct ggcgtttttc cataggctcc gcccccctga cgagcatcac    5220
aaaaatcgac gctcaagtca gaggtggcga aacccgacag gactataaag ataccaggcg    5280
tttccccctg gaagctccct cgtgcgctct cctgttccga ccctgccgct taccggatac    5340
ctgtccgcct ttctcccttc gggaagcgtg gcgctttctc atagctcacg ctgtaggtat    5400
ctcagttcgg tgtaggtcgt tcgctccaag ctgggctgtg tgcacgaacc ccccgttcag    5460
cccgaccgct gcgccttatc cggtaactat cgtcttgagt ccaacccggt aagacacgac    5520
ttatcgccac tggcagcagc cactggtaac aggattagca gagcgaggta tgtaggcggt    5580
gctacagagt tcttgaagtg gtggcctaac tacggctaca ctagaaggac agtatttggt    5640
```

| | |
|---|---|
| atctgcgctc tgctgaagcc agttaccttc ggaaaaagag ttggtagctc ttgatccggc | 5700 |
| aaacaaacca ccgctggtag cggtggtttt tttgtttgca agcagcagat tacgcgcaga | 5760 |
| aaaaaaggat ctcaagaaga tcctttgatc ttttctacgg ggtctgacgc tcagtggaac | 5820 |
| gaaaactcac gttaagggat tttggtcatg agattatcaa aaaggatctt cacctagatc | 5880 |
| cttttaaatt aaaaatgaag ttttaaatca atctaaagta tatatgagta aacttggtct | 5940 |
| gacagttacc aatgcttaat cagtgaggca cctatctcag cgatctgtct atttcgttca | 6000 |
| tccatagttg cctgactccc cgtcgtgtag ataactacga tacgggaggg cttaccatct | 6060 |
| ggccccagtg ctgcaatgat accgcgagac ccacgctcac cggctccaga tttatcagca | 6120 |
| ataaaccagc cagccggaag ggccgagcgc agaagtggtc ctgcaacttt atccgcctcc | 6180 |
| atccagtcta ttaattgttg ccgggaagct agagtaagta gttcgccagt taatagtttg | 6240 |
| cgcaacgttg ttgccattgc tgcaggcatc gtggtgtcac gctcgtcgtt tggtatggct | 6300 |
| tcattcagct ccggttccca acgatcaagg cgagttacat gatcccccat gttgtgcaaa | 6360 |
| aaagcggtta gctccttcgg tcctccgatc gttgtcagaa gtaagttggc cgcagtgtta | 6420 |
| tcactcatgg ttatggcagc actgcataat tctcttactg tcatgccatc cgtaagatgc | 6480 |
| ttttctgtga ctggtgagta ctcaaccaag tcattctgag aatagtgtat gcggcgaccg | 6540 |
| agttgctctt gcccggcgtc aatacgggat aataccgcgc cacatagcag aactttaaaa | 6600 |
| gtgctcatca ttggaaaacg ttcttcgggg cgaaaactct caaggatctt accgctgttg | 6660 |
| agatccagtt cgatgtaacc cactcgtgca cccaactgat cttcagcatc ttttactttc | 6720 |
| accagcgttt ctgggtgagc aaaaacagga aggcaaaatg ccgcaaaaaa gggaataagg | 6780 |
| gcgacacgga aatgttgaat actcatactc ttcctttttc aatattattg aagcatttat | 6840 |
| cagggttatt gtctcatgag cggatacata tttgaatgta tttagaaaaa taaacaaata | 6900 |
| ggggttccgc gcacatttcc ccgaaaagtg ccacctgaaa ttgtaaacgt taatattttg | 6960 |
| ttaaaattcg cgttaaattt ttgttaaatc agctcatttt ttaaccaata ggccgaaatc | 7020 |
| ggcaaaatcc cttataaatc aaaagaatag accgagatag ggttgagtgt tgttccagtt | 7080 |
| tggaacaaga gtccactatt aaagaacgtg gactccaacg tcaaagggcg aaaaaccgtc | 7140 |
| tatcagggcg atggcccact acgtgaacca tcaccctaat caagttttt ggggtcgagg | 7200 |
| tgccgtaaag cactaaatcg gaaccctaaa gggagccccc gatttagagc ttgacgggga | 7260 |
| aagccggcga acgtggcgag aaaggaaggg aagaaagcga aaggagcggg cgctagggcg | 7320 |
| ctggcaagtg tagcggtcac gctgcgcgta accaccacac ccgccgcgct taatgcgccg | 7380 |
| ctacagggcg cgtcccattc gcca | 7404 |

<210> SEQ ID NO 50
<211> LENGTH: 7404
<212> TYPE: DNA
<213> ORGANISM: Artificial Sequence
<220> FEATURE:
<223> OTHER INFORMATION: Description of Artificial Sequence: Synthetic
      vector pFr7(DL) polynucleotide

<400> SEQUENCE: 50

| | |
|---|---|
| atccggatat agttcctcct ttcagcaaaa aacccctcaa gacccgttta gaggccccaa | 60 |
| ggggttatgc tagttattgc tcagcggtgg cagcagccaa ctcagcttcc tttcgggctt | 120 |
| tgttagcagc cggatctcag tggtggtggt ggtggtgctc gagtgcggcc gcaagcttct | 180 |
| agtcgcggta gaacgacccc atgtagcgga tgtactcgtc ctcggtgtgg tttgccttcc | 240 |

```
agtcgtggac ggagtccttg ttgcgctggc cggcgatgac ggagagctcc ttacccagct    300
tctcaaaggc ctcgtcaacg cactcctcgg gggtgagggc gatcttcatg acggcctcgc    360
cctgcgggcc gccggggagg ttggacagca ggctgggggt tagggtggtg ccgagggtga    420
tgacctcgac gtcgacgccg gtgccctcgc actcgcaggc cacggcctcg gtcatcttga    480
ggatgaaggc cttgcccgcg ccgtactggc cgttccaggg gctggagctg atgccggtca    540
tcgacgagac gttgatcacg gcgccgcggt cctgggcggc aaagatccgc atgtagtggt    600
ggaagcactt gaggaaggtc acgacgttga cgttgatcat ggcctcgtgc ttctcccagg    660
gggtgtcctg gatcttaccg aagctgtgca ggcaggccac gtagctcatg aagcccatgt    720
ccaggccctc ggtcgcggcg aagacggtct cggcagcgcc gggctggcta aagtcggcgc    780
gcacgacctt ggtctccacg ccgtaggtct cgcggatctc gcctgcgagc acgttcagct    840
tctcctcgcg caggtcgacc atgacgacgt tcatgccgcc ggcggcgatc ttctcgcaga    900
acgccttgcc gacgccctcg gtcgcgccca ggatcaggcc ccactcaccg tacttctccc    960
tcaggttcat gtatatctcc tttcacgaat tctcagccgc cttcttgaac ttggcggcct   1020
cttccgaacc gccggtggca ttgcccttcg agtaggaatg cgcgccggtg ccggcaagag   1080
cgccgccctg cacgatgagg tattcgtcgc ggatcggacg gccctcgaag aagcactcca   1140
ggatctcgcg ggtgcccgcc gcataacgcg cctgcgcggt cagcgtggtg ccggagatgt   1200
gcggggtcat gccgttatag ggcatcgtcc gccaggggtg gtccttcggc gccggctgcg   1260
ggaaccacac gtcgccggca tagccggcca gccggccgga ttcgagcgca cgtgccacgg   1320
catcgcggtc gcacagcttg ccgcgggcgg tgttgacgat gtaggcgcca cgcttgaaca   1380
gcttcagcgt ctcgtcattg atcatgtgct cggtttcggg gtgcagcggg cagttcagcg   1440
tcaccacgtc gcaaaccgga tacatgtcct cgcgggtcgc gtgccaggtg aggttgagct   1500
ccttctcgac cgattccggc aggcggtgac ggccggtgta gtgcaggtgc acgtcgaacg   1560
gcgccagacg gcgcagcacc gcgagaccga tgcggccggc ggccacggtg ccgacatgca   1620
tcgcctcgag gtcgtaggcg tgggagacgc agtcggcgat gttccagccg cccttccgcg   1680
cccattcgtg cgagggcaga tagttgcgca ccagcgacag gatcatcatc accacatgct   1740
cggcgacgct gatcgagttg cagtaggtga cttccgccac ggtgacgttg cggtcgatag   1800
ccgactgaag atcgacgtgg tcggaaccga tgccggcggt gagcgcgagc ttcaggttct   1860
tggccttggc gatgcgctcg ggcgtcagat aggccggcca gaagggctgg gagatgacga   1920
catccgcatc gaccagctcg cgctcgaaca ccgagtcggg gccgtccttg tcggaggtca   1980
cgaccagggt gtggccgttg gattcgagat attcgcgcag gccgagctcg ccggagacgg   2040
agccgagcaa ctgcccgggc gtgaagtcga tggccttcgg cgtcggcaag atctggccgc   2100
ccggatagtg gtcgatcttc ggaagatcgt cgcgggcata ggtcttcggg tagccgtcga   2160
ccggatcatc gtaaagaacg cacaggacct ttgccatcat atgtatatct ccttcttaaa   2220
gttaaacaaa attatttcta gagggggaatt gttatccgct cacaattccc ctatagtgag   2280
tcgtattaat ttcgcgggat cgagatctcg atcctctacg ccggacgcat cgtggccggc   2340
atcaccggcg ccacaggtgc ggttgctggc gcctatatcg ccgacatcac cgatgggaa    2400 gatcgggctc gccacttcgg gctcatgagc gcttgtttcg gcgtgggtat ggtggcaggc   2460
cccgtggccg ggggactgtt gggcgccatc tccttgcatg caccattcct tgcggcggcg   2520
gtgctcaacg gcctcaacct actactgggc tgcttcctaa tgcaggagtc gcataaggga   2580
gagcgtcgag atcccggaca ccatcgaatg gcgcaaaacc tttcgcggta tggcatgata   2640
```

```
gcgcccggaa gagagtcaat tcagggtggt gaatgtgaaa ccagtaacgt tatacgatgt    2700
cgcagagtat gccggtgtct cttatcagac cgtttcccgc gtggtgaacc aggccagcca    2760
cgtttctgcg aaaacgcggg aaaaagtgga agcggcgatg gcggagctga attacattcc    2820
caaccgcgtg gcacaacaac tggcgggcaa acagtcgttg ctgattggcg ttgccacctc    2880
cagtctggcc ctgcacgcgc cgtcgcaaat tgtcgcggcg attaaatctc gcgccgatca    2940
actgggtgcc agcgtggtgg tgtcgatggt agaacgaagc ggcgtcgaag cctgtaaagc    3000
ggcggtgcac aatcttctcg cgcaacgcgt cagtgggctg atcattaact atccgctgga    3060
tgaccaggat gccattgctg tggaagctgc ctgcactaat gttccggcgt tatttcttga    3120
tgtctctgac cagacaccca tcaacagtat tattttctcc catgaagacg gtacgcgact    3180
gggcgtggag catctggtcg cattgggtca ccagcaaatc gcgctgttag cgggcccatt    3240
aagttctgtc tcggcgcgtc tgcgtctggc tggctggcat aaatatctca ctcgcaatca    3300
aattcagccg atagcggaac gggaaggcga ctggagtgcc atgtccggtt ttcaacaaac    3360
catgcaaatg ctgaatgagg gcatcgttcc cactgcgatg ctggttgcca acgatcagat    3420
ggcgctgggc gcaatgcgcg ccattaccga gtccgggctg cgcgttggtg cggatatctc    3480
ggtagtggga tacgacgata ccgaagacag ctcatgttat atcccgccgt taaccaccat    3540
caaacaggat tttcgcctgc tggggcaaac cagcgtggac cgcttgctgc aactctctca    3600
gggccaggcg gtgaagggca atcagctgtt gcccgtctca ctggtgaaaa gaaaaaccac    3660
cctggcgccc aatacgcaaa ccgcctctcc ccgcgcgttg gccgattcat taatgcagct    3720
ggcacgacag gtttcccgac tggaaagcgg gcagtgagcg caacgcaatt aatgtaagtt    3780
agctcactca ttaggcaccg ggatctcgac cgatgccctt gagagccttc aacccagtca    3840
gctccttccg gtgggcgcgg ggcatgacta tcgtcgccgc acttatgact gtcttcttta    3900
tcatgcaact cgtaggacag gtgccggcag cgctctgggt catttttcggc gaggaccgct    3960 ttcgctggag cgcgacgatg atcggcctgt cgcttgcggt attcggaatc ttgcacgccc    4020
tcgctcaagc cttcgtcact ggtcccgcca ccaaacgttt cggcgagaag caggccatta    4080
tcgccggcat ggcggcccca cgggtgcgca tgatcgtgct cctgtcgttg aggacccggc    4140
taggctggcg gggttgcctt actggttagc agaatgaatc accgatacgc gagcgaacgt    4200
gaagcgactg ctgctgcaaa acgtctgcga cctgagcaac aacatgaatg gtcttcggtt    4260
tccgtgtttc gtaaagtctg gaaacgcgga agtcagcgcc ctgcaccatt atgttccgga    4320
tctgcatcgc aggatgctgc tggctaccct gtggaacacc tacatctgta ttaacgaagc    4380
gctggcattg accctgagtg attttttctct ggtcccgccg catccatacc gccagttgtt    4440
taccctcaca acgttccagt aaccgggcat gttcatcatc agtaacccgt atcgtgagca    4500
tcctctctcg tttcatcggt atcattaccc ccatgaacag aaatcccccct tacacggagg    4560 catcagtgac caaacaggaa aaaaccgccc ttaacatggc ccgctttatc agaagccaga    4620
cattaacgct tctggagaaa ctcaacgagc tggacgcgga tgaacaggca gacatctgtg    4680
aatcgcttca cgaccacgct gatgagcttt accgcagctg cctcgcgcgt ttcggtgatg    4740
acggtgaaaa cctctgacac atgcagctcc cggagacggt cacagcttgt ctgtaagcgg    4800
atgccgggag cagacaagcc cgtcagggcg cgtcagcggg tgttggcggg tgtcggggcg    4860
cagccatgac ccagtcacgt agcgatagcg gagtgtatac tggcttaact atgcggcatc    4920
agagcagatt gtactgagag tgcaccatat atgcggtgtg aaataccgca cagatgcgta    4980
```

```
aggagaaaat accgcatcag gcgctcttcc gcttcctcgc tcactgactc gctgcgctcg   5040
gtcgttcggc tgcggcgagc ggtatcagct cactcaaagg cggtaatacg gttatccaca   5100
gaatcagggg ataacgcagg aaagaacatg tgagcaaaag gccagcaaaa ggccaggaac   5160
cgtaaaaagg ccgcgttgct ggcgtttttc cataggctcc gcccccctga cgagcatcac   5220
aaaaatcgac gctcaagtca gaggtggcga acccgacag gactataaag ataccaggcg   5280
tttccccctg gaagctccct cgtgcgctct cctgttccga ccctgccgct taccggatac   5340
ctgtccgcct ttctcccttc gggaagcgtg gcgctttctc atagctcacg ctgtaggtat   5400
ctcagttcgg tgtaggtcgt tcgctccaag ctgggctgtg tgcacgaacc cccgttcag   5460
cccgaccgct gcgccttatc cggtaactat cgtcttgagt ccaacccggt aagacacgac   5520
ttatcgccac tggcagcagc cactggtaac aggattagca gagcgaggta tgtaggcggt   5580
gctacagagt tcttgaagtg gtggcctaac tacggctaca ctagaaggac agtatttggt   5640
atctgcgctc tgctgaagcc agttaccttc ggaaaaagag ttggtagctc ttgatccggc   5700
aaacaaacca ccgctggtag cggtggtttt tttgtttgca agcagcagat tacgcgcaga   5760
aaaaaaggat ctcaagaaga tcctttgatc ttttctacgg ggtctgacgc tcagtggaac   5820
gaaaactcac gttaagggat tttggtcatg agattatcaa aaaggatctt cacctagatc   5880
cttttaaatt aaaaatgaag ttttaaatca atctaaagta tatatgagta aacttggtct   5940
gacagttacc aatgcttaat cagtgaggca cctatctcag cgatctgtct atttcgttca   6000
tccatagttg cctgactccc cgtcgtgtag ataactacga tacgggaggg cttaccatct   6060
ggccccagtg ctgcaatgat accgcgagac ccacgctcac cggctccaga tttatcagca   6120
ataaaccagc cagccggaag ggccgagcgc agaagtggtc ctgcaacttt atccgcctcc   6180
atccagtcta ttaattgttg ccgggaagct agagtaagta gttcgccagt taatagtttg   6240
cgcaacgttg ttgccattgc tgcaggcatc gtggtgtcac gctcgtcgtt ggtatggct   6300
tcattcagct ccggttccca acgatcaagg cgagttacat gatcccccat gttgtgcaaa   6360
aaagcggtta gctccttcgg tcctccgatc gttgtcagaa gtaagttggc cgcagtgtta   6420
tcactcatgg ttatggcagc actgcataat tctcttactg tcatgccatc cgtaagatgc   6480
ttttctgtga ctggtgagta ctcaaccaag tcattctgag aatagtgtat gcggcgaccg   6540
agttgctctt gcccggcgtc aatacgggat aataccgcgc cacatagcag aactttaaaa   6600
gtgctcatca ttggaaaacg ttcttcgggg cgaaaactct caaggatctt accgctgttg   6660
agatccagtt cgatgtaacc cactcgtgca cccaactgat cttcagcatc ttttactttc   6720
accagcgttt ctgggtgagc aaaaacagga aggcaaaatg ccgcaaaaaa gggaataagg   6780
gcgacacgga aatgttgaat actcatactc ttcctttttc aatattattg aagcatttat   6840
cagggttatt gtctcatgag cggatacata tttgaatgta tttagaaaaa taaacaaata   6900
ggggttccgc gcacatttcc ccgaaaagtg ccacctgaaa ttgtaaacgt taatattttg   6960
ttaaaattcg cgttaaattt ttgttaaatc agctcatttt ttaaccaata ggccgaaatc   7020
ggcaaaatcc cttataaatc aaaagaatag accgagatag ggttgagtgt tgttccagtt   7080
tggaacaaga gtccactatt aaagaacgtg gactccaacg tcaaagggcg aaaaaccgtc   7140
tatcagggcg atggcccact acgtgaacca tcaccctaat caagttttt ggggtcgagg   7200
tgccgtaaag cactaaatcg gaaccctaaa gggagccccc gatttagagc ttgacgggga   7260
aagccggcga acgtggcgag aaaggaaggg aagaaagcga aggagcgggc gctagggcg   7320
ctggcaagtg tagcggtcac gctgcgcgta accaccacac ccgccgcgct taatgcgccg   7380
```

```
ctacagggcg cgtcccattc gcca                                         7404
```

<210> SEQ ID NO 51
<211> LENGTH: 7404
<212> TYPE: DNA
<213> ORGANISM: Artificial Sequence
<220> FEATURE:
<223> OTHER INFORMATION: Description of Artificial Sequence: Synthetic
      vector pFr7(DI) polynucleotide

<400> SEQUENCE: 51

```
atccggatat agttcctcct ttcagcaaaa aaccccctcaa gacccgttta gaggccccaa     60
ggggttatgc tagttattgc tcagcggtgg cagcagccaa ctcagcttcc tttcgggctt    120
tgttagcagc cggatctcag tggtggtggt ggtggtgctc gagtgcggcc gcaagcttct    180
agtcgcggta gaacgacccc atgtagcgga tgtactcgtc ctcggtgtgg tttgccttcc    240
agtcgtggac ggagtccttg ttgcgctggc cggcgatgac ggagagctcc ttacccagct    300
tctcaaaggc ctcgtcaacg cactcctcgg gggtgagggc gatcttcatg acggcctcgc    360
cctgcgggcc gccggggagg ttggacagca ggctgggggt tagggtggtg ccgagggtga    420
tgacctcgac gtcgacgccg gtgccctcgc actcgcaggc cacggcctcg gtcatcttga    480
ggatgaaggc cttgcccgcg ccgtactggc cgttccaggg gctggagctg atgccggtca    540
tcgacgagac gttgatcacg gcgccgcggt cctgggcggc aaagatccgc atgtagtggt    600
ggaagcactt gaggaaggtc acgacgttga cgttgatcat ggcctcgtgc ttctcccagg    660
gggtgtcctg gatcttaccg aagctgtgca ggcaggccac gtagctcatg aagcccatgt    720
ccaggccctc ggtcgcggcg aagacggtct cggcagcgcc gggctggcta aagtcggcgc    780
gcacgacctt ggtctccacg ccgtaggtct cgcggatctc gcctgcgagc acgttcagct    840
tctcctcgcg aatgtcgacc atgacgacgt tcatgccgcc ggcggcgatc ttctcgcaga    900
acgccttgcc gacgccctcg gtcgcgccca ggatcaggcc ccactcaccg tacttctccc    960
tcaggttcat gtatatctcc tttcacgaat tctcagccgc cttcttgaac ttggcggcct   1020
cttccgaacc gccggtggca ttgcccttcg agtaggaatg cgcgccggtg ccggcaagag   1080
cgccgccctg cacgatgagg tattcgtcgc ggatcggacg gccctcgaag aagcactcca   1140
ggatctcgcg ggtgcccgcc gcataacgcg cctgcgcggt cagcgtggtg ccggagatgt   1200
gcggggtcat gccgttatag ggcatcgtcc gccaggggtg gtccttcggc gccggctgcg   1260
ggaaccacac gtcgccggca tagccggcca gccggccgga ttcgagcgca cgtgccacgg   1320
catcgcggtc gcacagcttg ccgcgggcgg tgttgacgat gtaggcgcca cgcttgaaca   1380
gcttcagcgt ctcgtcattg atcatgtgct cggtttcggg gtgcagcggg cagttcagcg   1440
tcaccacgtc gcaaaccgga tacatgtcct cgcgggtcgc gtgccaggtg aggttgagct   1500
ccttctcgac cgattccggc aggcggtgac ggcggtgta gtgcaggtgc acgtcgaacg   1560
gcgccagacg gcgcagcacc gcgagaccga tgcggccggc ggccacggtg ccgacatgca   1620
tcgcctcgag gtcgtaggcg tgggagacgc agtcggcgat gttccagccg cccttccgcg   1680
cccattcgtg cgagggcaga tagttgcgca ccagcgacag gatcatcatc accacatgct   1740
cggcgacgct gatcgagttg cagtaggtga cttccgccac ggtgacgttg cggtcgatag   1800
ccgactgaag atcgacgtgg tcggaaccga tgccggcggt gagcgcgagc ttcaggttct   1860
tggccttggc gatgcgctcg ggcgtcagat aggccggcca gaagggctgg gagatgacga   1920
catccgcatc gaccagctcg cgctcgaaca ccgagtcggg gccgtccttg tcggaggtca   1980
```

```
cgaccagggt gtggccgttg gattcgagat attcgcgcag gccgagctcg ccggagacgg    2040
agccgagcaa ctgcccgggc gtgaagtcga tggccttcgg cgtcggcaag atctggccgc    2100
ccggatagtg gtcgatcttc ggaagatcgt cgcgggcata ggtcttcggg tagccgtcga    2160
ccggatcatc gtaaagaacg cacaggacct ttgccatcat atgtatatct ccttcttaaa    2220
gttaaacaaa attatttcta gaggggaatt gttatccgct cacaattccc ctatagtgag    2280
tcgtattaat ttcgcgggat cgagatctcg atcctctacg ccgacgcat cgtggccggc     2340 atcaccggcg ccacaggtgc ggttgctggc gcctatatcg ccgacatcac cgatggggaa    2400
gatcgggctc gccacttcgg gctcatgagc gcttgtttcg cgtgggtat ggtggcaggc     2460 cccgtggccg ggggactgtt gggcgccatc tccttgcatg caccattcct tgcggcggcg    2520
gtgctcaacg gcctcaacct actactgggc tgcttcctaa tgcaggagtc gcataaggga    2580
gagcgtcgag atcccggaca ccatcgaatg cgcaaaacc tttcgcggta tggcatgata     2640
gcgcccggaa gagagtcaat tcagggtggt gaatgtgaaa ccagtaacgt tatacgatgt    2700
cgcagagtat gccggtgtct cttatcagac cgtttcccgc gtggtgaacc aggccagcca    2760
cgtttctgcg aaaacgcggg aaaaagtgga agcggcgatg gcggagctga attacattcc    2820
caaccgcgtg gcacaacaac tggcgggcaa acagtcgttg ctgattggcg ttgccacctc    2880
cagtctggcc ctgcacgcgc cgtcgcaaat tgtcgcggcg attaaatctc gcgccgatca    2940
actgggtgcc agcgtggtgg tgtcgatggt agaacgaagc ggcgtcgaag cctgtaaagc    3000
ggcggtgcac aatcttctcg cgcaacgcgt cagtgggctg atcattaact atccgctgga    3060
tgaccaggat gccattgctg tggaagctgc ctgcactaat gttccggcgt tatttcttga    3120
tgtctctgac cagacaccca tcaacagtat tattttctcc catgaagacg gtacgcgact    3180
gggcgtggag catctggtcg cattgggtca ccagcaaatc gcgctgttag cgggcccatt    3240
aagttctgtc tcggcgcgtc tgcgtctggc tggctggcat aaatatctca ctcgcaatca    3300
aattcagccg atagcggaac gggaaggcga ctggagtgcc atgtccggtt ttcaacaaac    3360
catgcaaatg ctgaatgagg gcatcgttcc cactgcgatg ctggttgcca acgatcagat    3420
ggcgctgggc gcaatgcgcg ccattaccga gtccgggctg cgcgttggtg cggatatctc    3480
ggtagtggga tacgacgata ccgaagacag ctcatgttat atcccgccgt taaccaccat    3540
caaacaggat tttcgcctgc tggggcaaac cagcgtggac cgcttgctgc aactctctca    3600
gggccaggcg gtgaagggca atcagctgtt gcccgtctca ctggtgaaaa gaaaaaccac    3660
cctggcgccc aatacgcaaa ccgcctctcc ccgcgcgttg gccgattcat taatgcagct    3720
ggcacgacag gtttcccgac tggaaagcgg gcagtgagcg caacgcaatt aatgtaagtt    3780
agctcactca ttaggcaccg ggatctcgac cgatgccctt gagagccttc aacccagtca    3840
gctccttccg gtgggcgcgg ggcatgacta tcgtcgccgc acttatgact gtcttcttta    3900
tcatgcaact cgtaggacag gtgccggcag cgctctgggt cattttcggc gaggaccgct    3960
ttcgctggag cgcgacgatg atcggcctgt cgcttgcggt attcggaatc ttgcacgccc    4020
tcgctcaagc cttcgtcact ggtcccgcca ccaaacgttt cggcgagaag caggccatta    4080
tcgccggcat ggcggcccca cgggtgcgca tgatcgtgct cctgtcgttg aggacccggc    4140
taggctggcg gggttgcctt actggttagc agaatgaatc accgatacgc gagcgaacgt    4200
gaagcgactg ctgctgcaaa acgtctgcga cctgagcaac aacatgaatg gtcttcggtt    4260
tccgtgtttc gtaaagtctg gaaacgcgga agtcagcgcc ctgcaccatt atgttccgga    4320
```

```
tctgcatcgc aggatgctgc tggctaccct gtggaacacc tacatctgta ttaacgaagc    4380
gctggcattg accctgagtg atttttctct ggtcccgccg catccatacc gccagttgtt    4440
taccctcaca acgttccagt aaccgggcat gttcatcatc agtaaccgt atcgtgagca     4500
tcctctctcg tttcatcggt atcattaccc ccatgaacag aaatcccct tacacggagg     4560
catcagtgac caaacaggaa aaaccgccc ttaacatggc ccgctttatc agaagccaga     4620
cattaacgct tctggagaaa ctcaacgagc tggacgcgga tgaacaggca gacatctgtg    4680
aatcgcttca cgaccacgct gatgagcttt accgcagctg cctcgcgcgt ttcggtgatg    4740
acggtgaaaa cctctgacac atgcagctcc cggagacggt cacagcttgt ctgtaagcgg    4800
atgccgggag cagacaagcc cgtcagggcg cgtcagcggg tgttggcggg tgtcggggcg    4860
cagccatgac ccagtcacgt agcgatagcg gagtgtatac tggcttaact atgcggcatc    4920
agagcagatt gtactgagag tgcaccatat atgcggtgtg aaataccgca cagatgcgta    4980
aggagaaaat accgcatcag gcgctcttcc gcttcctcgc tcactgactc gctgcgctcg    5040
gtcgttcggc tgcggcgagc ggtatcagct cactcaaagg cggtaatacg gttatccaca    5100
gaatcagggg ataacgcagg aaagaacatg tgagcaaaag gccagcaaaa ggccaggaac    5160
cgtaaaaagg ccgcgttgct ggcgtttttc cataggctcc gccccctga cgagcatcac    5220
aaaaatcgac gctcaagtca gaggtggcga accccgacag gactataaag ataccaggcg    5280
tttccccctg gaagctccct cgtgcgctct cctgttccga ccctgccgct taccggatac    5340
ctgtccgcct ttctcccttc gggaagcgtg gcgctttctc atagctcacg ctgtaggtat    5400
ctcagttcgg tgtaggtcgt tcgctccaag ctgggctgtg tgcacgaacc ccccgttcag    5460
cccgaccgct gcgccttatc cggtaactat cgtcttgagt ccaacccggt aagacacgac    5520
ttatcgccac tggcagcagc cactggtaac aggattagca gagcgaggta tgtaggcggt    5580
gctacagagt tcttgaagtg gtggcctaac tacggctaca ctagaaggac agtatttggt    5640
atctgcgctc tgctgaagcc agttaccttc ggaaaaagag ttggtagctc ttgatccggc    5700
aaacaaacca ccgctggtag cggtggtttt tttgtttgca agcagcagat tacgcgcaga    5760
aaaaaaggat ctcaagaaga tcctttgatc ttttctacgg ggtctgacgc tcagtggaac    5820
gaaaactcac gttaagggat tttggtcatg agattatcaa aaaggatctt cacctagatc    5880
cttttaaatt aaaaatgaag ttttaaatca atctaaagta tatatgagta aacttggtct    5940
gacagttacc aatgcttaat cagtgaggca cctatctcag cgatctgtct atttcgttca    6000
tccatagttg cctgactccc cgtcgtgtag ataactacga tacgggaggg cttaccatct    6060
ggccccagtg ctgcaatgat accgcgagac ccacgctcac cggctccaga tttatcagca    6120
ataaccagc cagccggaag ggccgagcgc agaagtggtc ctgcaacttt atccgcctcc    6180
atccagtcta ttaattgttg ccgggaagct agagtaagta gttcgccagt taatagtttg    6240
cgcaacgttg ttgccattgc tgcaggcatc gtggtgtcac gctcgtcgtt tggtatggct    6300
tcattcagct ccggttccca acgatcaagg cgagttacat gatcccccat gttgtgcaaa    6360
aaagcggtta gctccttcgg tcctccgatc gttgtcagaa gtaagttggc cgcagtgtta    6420
tcactcatgg ttatggcagc actgcataat tctcttactg tcatgccatc cgtaagatgc    6480
ttttctgtga ctggtgagta ctcaaccaag tcattctgag aatagtgtat gcggcgaccg    6540
agttgctctt gcccggcgtc aatacgggat aataccgcgc cacatagcag aactttaaaa    6600
gtgctcatca ttggaaaacg ttcttcgggg cgaaaactct caaggatctt accgctgttg    6660
agatccagtt cgatgtaacc cactcgtgca cccaactgat cttcagcatc ttttactttc    6720
```

```
accagcgttt ctgggtgagc aaaaacagga aggcaaaatg ccgcaaaaaa gggaataagg      6780
gcgacacgga aatgttgaat actcatactc ttccttttc aatattattg aagcatttat      6840
cagggttatt gtctcatgag cggatacata tttgaatgta tttagaaaaa taaacaaata      6900
ggggttccgc gcacatttcc ccgaaaagtg ccacctgaaa ttgtaaacgt taatatttg      6960 ttaaaattcg cgttaaattt ttgttaaatc agctcatttt ttaaccaata ggccgaaatc      7020
ggcaaaatcc cttataaatc aaaagaatag accgagatag ggttgagtgt tgttccagtt      7080
tggaacaaga gtccactatt aaagaacgtg gactccaacg tcaaagggcg aaaaaccgtc      7140
tatcagggcg atggcccact acgtgaacca tcaccctaat caagtttttt ggggtcgagg      7200
tgccgtaaag cactaaatcg aaccctaaa gggagccccc gatttagagc ttgacgggga      7260
aagccggcga acgtggcgag aaaggaaggg aagaaagcga aaggagcggg cgctagggcg      7320
ctggcaagtg tagcggtcac gctgcgcgta accaccacac ccgccgcgct taatgcgccg      7380
ctacagggcg cgtcccattc gcca                                            7404
```

<210> SEQ ID NO 52
<211> LENGTH: 7404
<212> TYPE: DNA
<213> ORGANISM: Artificial Sequence
<220> FEATURE:
<223> OTHER INFORMATION: Description of Artificial Sequence: Synthetic
    vector pFr7(DV) polynucleotide

<400> SEQUENCE: 52

```
atccggatat agttcctcct ttcagcaaaa aaccctcaa gacccgttta gaggccccaa        60
ggggttatgc tagttattgc tcagcggtgg cagcagccaa ctcagcttcc tttcgggctt      120
tgttagcagc cggatctcag tggtggtggt ggtggtgctc gagtgcggcc gcaagcttct      180
agtcgcggta gaacgacccc atgtagcgga tgtactcgtc ctcggtgtgg tttgccttcc      240
agtcgtggac ggagtccttg ttgcgctggc cggcgatgac ggagagctcc ttacccagct      300
tctcaaaggc ctcgtcaacg cactcctcgg gggtgagggc gatcttcatg acggcctcgc      360
cctgcgggcc gccggggagg ttggacagca ggctgggggt tagggtggtg ccagggtga       420 tgacctcgac gtcgacgccg gtgccctcgc actcgcaggc cacggcctcg gtcatcttga      480
ggatgaaggc cttgcccgcg ccgtactggc cgttccaggg gctggagctg atgccggtca      540
tcgacgagac gttgatcacg gcgccgcggt cctgggcggc aaagatccgc atgtagtggt      600
ggaagcactt gaggaaggtc acgacgttga cgttgatcat ggcctcgtgc ttctcccagg      660
gggtgtcctg gatcttaccg aagctgtgca ggcaggccac gtagctcatg aagcccatgt      720
ccaggccctc ggtcgcggcg aagacggtct cggcagcgcc gggctggcta agtcggcgc       780 gcacgacctt ggtctccacg ccgtaggtct cgcggatctc gcctgcgagc acgttcagct      840
tctcctcgcg aacgtcgacc atgacgacgt tcatgccgcc ggcggcgatc ttctcgcaga      900
acgccttgcc gacgccctcg gtcgcgccca ggatcaggcc ccactcaccg tacttctccc      960
tcaggttcat gtatatctcc tttcacgaat ctcagccgc cttcttgaac ttggcggcct      1020
cttccgaacc gccggtggca ttgcccttcg agtaggaatg cgcgccggtg ccggcaagag     1080
cgccgccctg cacgatgagg tattcgtcgc ggatcggacg gccctcgaag aagcactcca     1140
ggatctcgcg ggtgcccgcc gcataacgcg cctgcgcgt cagcgtggtg ccggagatgt      1200 gcgggggtcat gccgttatag ggcatcgtcc gccagggtg gtccttcggc gccggctgcg     1260
ggaaccacac gtcgccggca tagccggcca gccggccgga ttcgagcgca cgtgccacgg     1320
```

```
catcgcggtc gcacagcttg ccgcgggcgg tgttgacgat gtaggcgcca cgcttgaaca   1380
gcttcagcgt ctcgtcattg atcatgtgct cggtttcggg gtgcagcggg cagttcagcg   1440
tcaccacgtc gcaaaccgga tacatgtcct cgcgggtcgc gtgccaggtg aggttgagct   1500
ccttctcgac cgattccggc aggcggtgac ggccggtgta gtgcaggtgc acgtcgaacg   1560
gcgccagacg gcgcagcacc gcgagaccga tgcggccggc ggccacggtg ccgacatgca   1620
tcgcctcgag gtcgtaggcg tgggagacgc agtcggcgat gttccagccg cccttccgcg   1680
cccattcgtg cgagggcaga tagttgcgca ccagcgacag gatcatcatc accacatgct   1740
cggcgacgct gatcgagttg cagtaggtga cttccgccac ggtgacgttg cggtcgatag   1800
ccgactgaag atcgacgtgg tcggaaccga tgccggcggt gagcgcgagc ttcaggttct   1860
tggccttggc gatgcgctcg ggcgtcagat aggccggcca aagggctgg gagatgacga    1920
catccgcatc gaccagctcg cgctcgaaca ccgagtcggg gccgtccttg tcggaggtca   1980
cgaccagggt gtgccgttg gattcgagat attcgcgcag gccgagctcg ccggagacgg    2040
agccgagcaa ctgcccgggc gtgaagtcga tggccttcgg cgtcggcaag atctggccgc   2100
ccggatagtg gtcgatcttc ggaagatcgt cgcgggcata ggtcttcggg tagccgtcga   2160
ccggatcatc gtaaagaacg cacaggacct ttgccatcat atgtatatct ccttcttaaa   2220
gttaaacaaa attatttcta gaggggaatt gttatccgct cacaattccc ctatagtgag   2280
tcgtattaat ttcgcgggat cgagatctcg atcctctacg ccggacgcat cgtggccggc   2340
atcaccggcg ccacaggtgc ggttgctggc gcctatatcg ccgacatcac cgatggggaa   2400
gatcgggctc gccacttcgg gctcatgagc gcttgtttcg gcgtgggtat ggtggcaggc   2460
cccgtggccg ggggactgtt gggcgccatc tccttgcatg caccattcct gcggcggcg    2520
gtgctcaacg gcctcaacct actactgggc tgcttcctaa tgcaggagtc gcataaggga   2580
gagcgtcgag atcccggaca ccatcgaatg gcgcaaaacc tttcgcggta tggcatgata   2640
gcgcccggaa gagagtcaat tcagggtggt gaatgtgaaa ccagtaacgt tatacgatgt   2700
cgcagagtat gccggtgtct cttatcagac cgtttcccgc gtggtgaacc aggccagcca   2760
cgtttctgcg aaaacgcggg aaaaagtgga agcggcgatg gcggagctga attacattcc   2820
caaccgcgtg gcacaacaac tggcgggcaa acagtcgttg ctgattggcg ttgccacctc   2880
cagtctggcc ctgcacgcgc cgtcgcaaat tgtcgcggcg attaaatctc gcgccgatca   2940
actgggtgcc agcgtggtgg tgtcgatggt agaacgaagc ggcgtcgaag cctgtaaagc   3000
ggcggtgcac aatcttctcg cgcaacgcgt cagtgggctg atcattaact atccgctgga   3060
tgaccaggat gccattgctg tggaagctgc ctgcactaat gttccggcgt tatttcttga   3120
tgtctctgac cagacaccca tcaacagtat tattttctcc catgaagacg gtacgcgact   3180
gggcgtggag catctggtcg cattgggtca ccagcaaatc gcgctgttag cgggcccatt   3240
aagttctgtc tcggcgcgtc tgcgtctggc tggctggcat aaatatctca ctcgcaatca   3300
aattcagccg atagcggaac gggaaggcga ctggagtgcc atgtccggtt ttcaacaaac   3360
catgcaaatg ctgaatgagg gcatcgttcc cactgcgatg ctggttgcca acgatcagat   3420
ggcgctgggc gcaatgcgcg ccattaccga gtccgggctg cgcgttggtg cggatatctc   3480
ggtagtggga tacgacgata ccgaagacag ctcatgttat atcccgccgt taaccaccat   3540
caaacaggat tttcgcctgc tggggcaaac cagcgtggac cgcttgctgc aactctctca   3600
gggccaggcg gtgaagggca atcagctgtt gcccgtctca ctggtgaaaa gaaaaaccac   3660
```

```
cctggcgccc aataccgcaaa ccgcctctcc ccgcgcgttg gccgattcat taatgcagct    3720
ggcacgacag gtttcccgac tggaaagcgg gcagtgagcg caacgcaatt aatgtaagtt    3780
agctcactca ttaggcaccg ggatctcgac cgatgccctt gagagccttc aacccagtca    3840
gctccttccg gtgggcgcgg ggcatgacta tcgtcgccgc acttatgact gtcttcttta    3900
tcatgcaact cgtaggacag gtgccggcag cgctctgggt cattttcggc gaggaccgct    3960
ttcgctggag cgcgacgatg atcggcctgt cgcttgcgt attcggaatc ttgcacgccc    4020
tcgctcaagc cttcgtcact ggtcccgcca ccaaacgttt cggcgagaag caggccatta    4080
tcgccggcat ggcggcccca cgggtgcgca tgatcgtgct cctgtcgttg aggacccggc    4140
taggctggcg gggttgcctt actggttagc agaatgaatc accgatacgc gagcgaacgt    4200
gaagcgactg ctgctgcaaa acgtctgcga cctgagcaac aacatgaatg gtcttcggtt    4260
tccgtgtttc gtaaagtctg gaaacgcgga agtcagcgcc ctgcaccatt atgttccgga    4320
tctgcatcgc aggatgctgc tggctaccct gtggaacacc tacatctgta ttaacgaagc    4380
gctggcattg accctgagtg attttttctct ggtcccgccg catccatacc gccagttgtt    4440
taccctcaca acgttccagt aaccgggcat gttcatcatc agtaacccgt atcgtgagca    4500
tcctctctcg tttcatcggt atcattaccc ccatgaacag aaatccccct tacacggagg    4560
catcagtgac caaacaggaa aaaccgccc ttaacatggc ccgctttatc agaagccaga    4620
cattaacgct tctggagaaa ctcaacgagc tggacgcgga tgaacaggca gacatctgtg    4680
aatcgcttca cgaccacgct gatgagcttt accgcagctg cctcgcgcgt ttcggtgatg    4740
acggtgaaaa cctctgacac atgcagctcc cggagacggt cacagcttgt ctgtaagcgg    4800
atgccgggag cagacaagcc cgtcagggcg cgtcagcggg tgttggcggg tgtcggggcg    4860
cagccatgac ccagtcacgt agcgatagcg gagtgtatac tggcttaact atgcggcatc    4920
agagcagatt gtactgagag tgcaccatat atgcggtgtg aaataccgca cagatgcgta    4980
aggagaaaat accgcatcag gcgctcttcc gcttcctcgc tcactgactc gctgcgctcg    5040
gtcgttcggc tgcggcgagc ggtatcagct cactcaaagg cggtaatacg gttatccaca    5100
gaatcagggg ataacgcagg aaagaacatg tgagcaaaag gccagcaaaa ggccaggaac    5160
cgtaaaaagg ccgcgttgct ggcgtttttc cataggctcc gcccccctga cgagcatcac    5220
aaaaatcgac gctcaagtca gaggtggcga aacccgacag gactataaag ataccaggcg    5280
tttccccctg gaagctccct cgtgcgctct cctgttccga ccctgccgct taccggatac    5340
ctgtccgcct ttctcccttc gggaagcgtg gcgctttctc atagctcacg ctgtaggtat    5400
ctcagttcgg tgtaggtcgt tcgctccaag ctgggctgtg tgcacgaacc ccccgttcag    5460
cccgaccgct gcgccttatc cggtaactat cgtcttgagt ccaacccggt aagacacgac    5520
ttatcgccac tggcagcagc cactggtaac aggattagca gagcgaggta tgtaggcggt    5580
gctacagagt tcttgaagtg gtggcctaac tacggctaca ctagaaggac agtatttggt    5640
atctgcgctc tgctgaagcc agttaccttc ggaaaaagag ttggtagctc ttgatccggc    5700
aaacaaacca ccgctggtag cggtggtttt tttgtttgca agcagcagat tacgcgcaga    5760
aaaaaaggat ctcaagaaga tcctttgatc ttttctacgg ggtctgacgc tcagtggaac    5820
gaaaactcac gttaagggat tttggtcatg agattatcaa aaaggatctt cacctagatc    5880
cttttaaatt aaaaatgaag ttttaaatca atctaaagta tatatgagta aacttggtct    5940
gacagttacc aatgcttaat cagtgaggca cctatctcag cgatctgtct atttcgttca    6000
tccatagttg cctgactccc cgtcgtgtag ataactacga tacgggaggg cttaccatct    6060
```

-continued

```
ggccccagtg ctgcaatgat accgcgagac ccacgctcac cggctccaga tttatcagca      6120
ataaaccagc cagccggaag ggccgagcgc agaagtggtc ctgcaacttt atccgcctcc      6180
atccagtcta ttaattgttg ccgggaagct agagtaagta gttcgccagt taatagtttg      6240
cgcaacgttg ttgccattgc tgcaggcatc gtggtgtcac gctcgtcgtt tggtatggct      6300
tcattcagct ccggttccca acgatcaagg cgagttacat gatcccccat gttgtgcaaa      6360
aaagcggtta gctccttcgg tcctccgatc gttgtcagaa gtaagttggc cgcagtgtta      6420
tcactcatgg ttatggcagc actgcataat tctcttactg tcatgccatc cgtaagatgc      6480
ttttctgtga ctggtgagta ctcaaccaag tcattctgag aatagtgtat gcggcgaccg      6540
agttgctctt gcccggcgtc aatacgggat aataccgcgc cacatagcag aactttaaaa      6600
gtgctcatca ttggaaaacg ttcttcgggg cgaaaactct caaggatctt accgctgttg      6660
agatccagtt cgatgtaacc cactcgtgca cccaactgat cttcagcatc ttttactttc      6720
accagcgttt ctgggtgagc aaaaacagga aggcaaaatg ccgcaaaaaa gggaataagg      6780
gcgacacgga aatgttgaat actcatactc ttccttttc aatattattg aagcatttat      6840
cagggttatt gtctcatgag cggatacata tttgaatgta tttagaaaaa taaacaaata      6900
ggggttccgc gcacatttcc ccgaaaagtg ccacctgaaa ttgtaaacgt taatattttg      6960
ttaaaattcg cgttaaattt ttgttaaatc agctcatttt ttaaccaata ggccgaaatc      7020
ggcaaaatcc cttataaatc aaaagaatag accgagatag ggttgagtgt tgttccagtt      7080
tggaacaaga gtccactatt aaagaacgtg gactccaacg tcaaagggcg aaaaaccgtc      7140
tatcagggcg atggcccact acgtgaacca tcaccctaat caagttttt ggggtcgagg      7200 tgccgtaaag cactaaatcg gaaccctaaa gggagccccc gatttagagc ttgacgggga      7260
aagccggcga acgtggcgag aaaggaaggg aagaaagcga aggagcggg cgctagggcg      7320 ctggcaagtg tagcggtcac gctgcgcgta accaccacac ccgccgcgct taatgcgccg      7380
ctacagggcg cgtcccattc gcca                                            7404
```

<210> SEQ ID NO 53
<211> LENGTH: 27
<212> TYPE: DNA
<213> ORGANISM: Artificial Sequence
<220> FEATURE:
<223> OTHER INFORMATION: Description of Artificial Sequence: Synthetic
      PCR primer "G39D for"

<400> SEQUENCE: 53
gtcgtcatgg tcgaccgtcg cgaggag                                            27

<210> SEQ ID NO 54
<211> LENGTH: 27
<212> TYPE: DNA
<213> ORGANISM: Artificial Sequence
<220> FEATURE:
<223> OTHER INFORMATION: Description of Artificial Sequence: Synthetic
      PCR primer "G39D_rev"

<400> SEQUENCE: 54
ctcctcgcga cggtcgacca tgacgac                                            27

<210> SEQ ID NO 55
<211> LENGTH: 24
<212> TYPE: DNA
<213> ORGANISM: Artificial Sequence
<220> FEATURE:

```
<223> OTHER INFORMATION: Description of Artificial Sequence: Synthetic
      PCR primer "G39D/R40I_for"

<400> SEQUENCE: 55
gtcatggtcg acattcgcga ggag                                          24

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      PCR primer "G39D/R40I_rev"

<400> SEQUENCE: 56
ctcctcgcga atgtcgacca tgac                                          24

<210> SEQ ID NO 57
<211> LENGTH: 27
<212> TYPE: DNA
<213> ORGANISM: Artificial Sequence
<220> FEATURE:
<223> OTHER INFORMATION: Description of Artificial Sequence: Synthetic
      PCR primer "R40D_for"

<400> SEQUENCE: 57
gtcatggtcg gcgatcgcga ggagaag                                       27

<210> SEQ ID NO 58
<211> LENGTH: 27
<212> TYPE: DNA
<213> ORGANISM: Artificial Sequence
<220> FEATURE:
<223> OTHER INFORMATION: Description of Artificial Sequence: Synthetic
      PCR primer "R40D_rev"

<400> SEQUENCE: 58
cttctcctcg cgatcgccga ccatgac                                       27

<210> SEQ ID NO 59
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR primer "R40D/R41I_for"

<400> SEQUENCE: 59
gtcatggtcg gcgatatcga ggagaagctg                                    30

<210> SEQ ID NO 60
<211> LENGTH: 30
<212> TYPE: DNA
<213> ORGANISM: Artificial Sequence
<220> FEATURE:
<223> OTHER INFORMATION: Description of Artificial Sequence: Synthetic
      PCR primer "R40D/R41I_rev"

<400> SEQUENCE: 60
cagcttctcc tcgatatcgc cgaccatgac                                    30

<210> SEQ ID NO 61
<211> LENGTH: 27
<212> TYPE: DNA
<213> ORGANISM: Artificial Sequence
<220> FEATURE:
<223> OTHER INFORMATION: Description of Artificial Sequence: Synthetic
```

PCR primer "DIN_for"

<400> SEQUENCE: 61
atggtcgaca ttaacgagga gaagctg                                               27

<210> SEQ ID NO 62
<211> LENGTH: 27
<212> TYPE: DNA
<213> ORGANISM: Artificial Sequence
<220> FEATURE:
<223> OTHER INFORMATION: Description of Artificial Sequence: Synthetic
      PCR primer "DIN_rev"

<400> SEQUENCE: 62
cagcttctcc tcgttaatgt cgaccat                                               27

<210> SEQ ID NO 63
<211> LENGTH: 8321
<212> TYPE: DNA
<213> ORGANISM: Artificial Sequence
<220> FEATURE:
<223> OTHER INFORMATION: Description of Artificial Sequence: Synthetic
      plasmid pFr3T7(D) polynucleotide

<400> SEQUENCE: 63
atccggatat agttcctcct ttcagcaaaa aaccccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gcctagtcgc     180
ggtagaacga ccccatgtag cggatgtact cgtcctcggt gtggtttgcc ttccagtcgt     240
ggacggagtc cttgttgcgc tggccggcga tgacggagag ctccttaccc agcttctcaa     300
aggcctcgtc aacgcactcc tcggggtga gggcgatctt catgacggcc tcgccctgcg     360
ggccgccggg gaggttggac agcaggctgg gggttagggt ggtgccgagg gtgatgacct     420
cgacgtcgac gccggtgccc tcgcactcgc aggccacggc ctcggtcatc ttgaggatga     480
aggccttgcc cgcgccgtac tggccgttcc aggggctgga gctgatgccg gtcatcgacg     540
agacgttgat cacggcgccg cggtcctggg cggcaaagat ccgcatgtag tggtggaagc     600
acttgaggaa ggtcacgacg ttgacgttga tcatggcctc gtgcttctcc caggggggtgt     660 cctggatctt accgaagctg tgcaggcagg ccacgtagct catgaagccc atgtccaggc     720
cctcggtcgc ggcgaagacg gtctcggcag cgccgggctg gctaaagtcg gcgcgcacga     780
ccttggtctc cacgccgtag gtctcgcgga tctcgcctgc gagcacgttc agcttctcct     840
cgcgacggtc gaccatgacg acgttcatgc cgccggcggc gatcttctcg cagaacgcct     900
tgccgacgcc ctcggtcgcg cccaggatca ggcccactc accgtacttc tccctcaggt     960
tcatatgtat atctccttct tatacttaac taatatacta agatggggaa ttgttatccg    1020
ctcacaattc ccctatagtg agtcgtatta atttcgatta gcggccgtg tacaatacga    1080 ttactttctg ttcgacttaa gcattataag ctttcagaac tgtgtcgggc gcatcaccgc    1140
atcaatgccg ccatcaatga cgatctgcgc gccatgcaca tagcttgcgg ccgggctcat    1200
caaaaaggcg atgaccgacg ccatctcgga cggctcggca cggcggccca tgggaggaac    1260
gaacttggca atggattcgc catagcgcgg gtcctgcagg cccgcctgca gcaagggagt    1320
ctcggttgca ccgggggcga tggtgttcag gcgcacgcca gcctcgcccc aggcggcggc    1380
gcgtttgcgc acagccaccg tcaaagcatt cttgctgccc gcataggcca gatttccgcc    1440
ctgctctccc gcatgttcga caatggcgcg ggccttggct tcctcgccgg cttccagtgc    1500

```
cagcgccagt gggttcttgt caaaagccag atgcgcggaa gccacggacg agatgacgac   1560
ggctgcgggc tgatggcctt ttttcagcgc tggcaaaaag gcatccatca gctcggtcgc   1620
gccaaaataa ttgaccgaaa ccacattgcc aagcaccttg gtctgcggtc ccaggccggc   1680
gcacagcacc aggccgtcca tgcccttgct gcacttcgcc agtacatcgg caatcgcctg   1740
ctttcgacct tcggccgtcg agagatcggc aatcacttcc gcatcgcgta tatcgatgcc   1800
tacgatctgg tgaccggccg cctccaggac cttgcgcgta gccgcaccaa tgccggtggc   1860
gcagccgctt atcacgatga tggacatgta tatctccttt cacgaattct cagccgcctt   1920
cttgaacttg gcggcctctt ccgaaccgcc ggtggcattg cccttcgagt aggaatgcgc   1980
gccggtgccg gcaagagcgc cgccctgcac gatgaggtat tcgtcgcgga tcggacggcc   2040
ctcgaagaag cactccagga tctcgcgggt gcccgccgca taacgcgcct gcgcggtcag   2100
cgtggtgccg gagatgtgcg gggtcatgcc gttatagggc atcgtccgcc aggggtggtc   2160
cttcggcgcc ggctgcggga accacacgtc gccggcatag ccggccagcc ggccggattc   2220
gagcgcacgt gccacggcat cgcggtcgca cagcttgccg cgggcggtgt tgacgatgta   2280
ggcgccacgc ttgaacagct tcagcgtctc gtcattgatc atgtgctcgg tttcggggtg   2340
cagcgggcag ttcagcgtca ccacgtcgca aaccggatac atgtcctcgc gggtcgcgtg   2400
ccaggtgagg ttgagctcct tctcgaccga ttccggcagg cggtgacggt cggtgtagtg   2460
caggtgcacg tcgaacggcg ccagacggcg cagcaccgcg agaccgatgc ggccggcggc   2520
cacggtgccg acatgcatcg cctcgaggtc gtaggcgtgg gagacgcagt cggcgatgtt   2580
ccagccgccc ttccgcgccc attcgtgcga gggcagatag ttgcgcacca gcgacaggat   2640
catcatcacc acatgctcgg cgacgctgat cgagttgcag taggtgactt ccgccacggt   2700
gacgttgcgg tcgatagccg actgaagatc gacgtggtcg gaaccgatgc cggcggtgag   2760
cgcgagcttc aggttcttgg ccttggcgat gcgctcgggc gtcagatagg ccggccagaa   2820
gggctgggag atgacgacat ccgcatcgac cagctcgcgc tcgaacaccg agtcggggcc   2880
gtccttgtcg gaggtcacga ccagggtgtg gccgttggat tcgagatatt cgcgcaggcc   2940
gagctcgccg gagacggagc cgagcaactg cccgggcgtg aagtcgatgg ccttcggcgt   3000
cggcaagatc tggccgcccg gatagtggtc gatcttcgga agatcgtcgc gggcataggt   3060
cttcgggtag ccgtcgaccg gatcatcgta aagaacgcac aggaccttttg ccatcatatg   3120 tatatctcct tcttaaagtt aaacaaaatt atttctagag gggaattgtt atccgctcac   3180
aattccccta tagtgagtcg tattaatttc gcgggatcga gatctcgatc ctctacgccg   3240
gacgcatcgt ggccggcatc accggcgcca caggtgcggt tgctggcgcc tatatcgccg   3300
acatcaccga tggggaagat cgggctcgcc acttcgggct catgagcgct tgtttcggcg   3360
tgggtatggt ggcaggcccc gtggccgggg gactgttggg cgccatctcc ttgcatgcac   3420
cattccttgc ggcggcggtg ctcaacggcc tcaacctact actgggctgc ttcctaatgc   3480
aggagtcgca taagggagag cgtcgagatc ccggacacca tcgaatggcg caaaacctttt   3540 cgcggtatgg catgatagcg cccggaagag agtcaattca gggtggtgaa tgtgaaacca   3600
gtaacgttat acgatgtcgc agagtatgcc ggtgtctctt atcagaccgt ttcccgcgtg   3660
gtgaaccagg ccagccacgt ttctgcgaaa acgcgggaaa aagtggaagc ggcgatggcg   3720
gagctgaatt acattcccaa ccgcgtggca caacaactgg cgggcaaaca gtcgttgctg   3780
attggcgttg ccacctccag tctggccctg cacgcgccgt cgcaaattgt cgcggcgatt   3840
```

| | |
|---|---|
| aaatctcgcg ccgatcaact gggtgccagc gtggtggtgt cgatggtaga acgaagcggc | 3900 |
| gtcgaagcct gtaaagcggc ggtgcacaat cttctcgcgc aacgcgtcag tgggctgatc | 3960 |
| attaactatc cgctggatga ccaggatgcc attgctgtgg aagctgcctg cactaatgtt | 4020 |
| ccggcgttat ttcttgatgt ctctgaccag acacccatca acagtattat tttctcccat | 4080 |
| gaagacggta cgcgactggg cgtggagcat ctggtcgcat tgggtcacca gcaaatcgcg | 4140 |
| ctgttagcgg gcccattaag ttctgtctcg gcgcgtctgc gtctggctgg ctggcataaa | 4200 |
| tatctcactc gcaatcaaat tcagccgata gcggaacggg aaggcgactg gagtgccatg | 4260 |
| tccggttttc aacaaaccat gcaaatgctg aatgagggca tcgttcccac tgcgatgctg | 4320 |
| gttgccaacg atcagatggc gctgggcgca atgcgcgcca ttaccgagtc cgggctgcgc | 4380 |
| gttggtgcgg atatctcggt agtgggatac gacgataccg aagacagctc atgttatatc | 4440 |
| ccgccgttaa ccaccatcaa acaggatttt cgcctgctgg ggcaaaccag cgtggaccgc | 4500 |
| ttgctgcaac tctctcaggg ccaggcggtg aagggcaatc agctgttgcc cgtctcactg | 4560 |
| gtgaaaagaa aaaccaccct ggcgcccaat acgcaaaccg cctctccccg cgcgttggcc | 4620 |
| gattcattaa tgcagctggc acgacaggtt cccgactgg aaagcgggca gtgagcgcaa | 4680 |
| cgcaattaat gtaagttagc tcactcatta ggcaccggga tctcgaccga tgcccttgag | 4740 |
| agccttcaac ccagtcagct ccttccggtg ggcgcggggc atgactatcg tcgccgcact | 4800 |
| tatgactgtc ttctttatca tgcaactcgt aggacaggtg ccggcagcgc tctgggtcat | 4860 |
| tttcggcgag gaccgctttc gctggagcgc gacgatgatc ggcctgtcgc ttgcggtatt | 4920 |
| cggaatcttg cacgccctcg ctcaagcctt cgtcactggt cccgccacca aacgtttcgg | 4980 |
| cgagaagcag gccattatcg ccggcatggc ggccccacgg gtgcgcatga tcgtgctcct | 5040 |
| gtcgttgagg acccggctag gctggcgggg ttgccttact ggttagcaga atgaatcacc | 5100 |
| gatacgcgag cgaacgtgaa gcgactgctg ctgcaaaacg tctgcgacct gagcaacaac | 5160 |
| atgaatggtc ttcggtttcc gtgtttcgta aagtctggaa acgcggaagt cagcgccctg | 5220 |
| caccattatg ttccggatct gcatcgcagg atgctgctgg ctaccctgtg gaacacctac | 5280 |
| atctgtatta cgaagcgct ggcattgacc ctgagtgatt tttctctggt cccgccgcat | 5340 |
| ccataccgcc agttgtttac cctcacaacg ttccagtaac cgggcatgtt catcatcagt | 5400 |
| aacccgtatc gtgagcatcc tctctcgttt catcggtatc attaccccca tgaacagaaa | 5460 |
| tcccccttac acggaggcat cagtgaccaa acaggaaaaa accgccctta acatggcccg | 5520 |
| ctttatcaga agccagacat taacgcttct ggagaaactc aacgagctgg acgcggatga | 5580 |
| acaggcagac atctgtgaat cgcttcacga ccacgctgat gagctttacc gcagctgcct | 5640 |
| cgcgcgtttc ggtgatgacg gtgaaaacct ctgacacatg cagctcccgg agacggtcac | 5700 |
| agcttgtctg taagcggatg ccgggagcag acaagcccgt cagggcgcgt cagcgggtgt | 5760 |
| tggcgggtgt cggggcgcag ccatgaccca gtcacgtagc gatagcggag tgtatactgg | 5820 |
| cttaactatg cggcatcaga gcagattgta ctgagagtgc accatatatg cggtgtgaaa | 5880 |
| taccgcacag atgcgtaagg agaaaatacc gcatcaggcg ctcttccgct tcctcgctca | 5940 |
| ctgactcgct gcgctcggtc gttcggctgc ggcgagcgg atcagctcac tcaaaggcgg | 6000 |
| taatacggtt atccacagaa tcaggggata acgcaggaaa gaacatgtga gcaaaaggcc | 6060 |
| agcaaaaggc caggaaccgt aaaaaggccg cgttgctggc gtttttccat aggctccgcc | 6120 |
| cccctgacga gcatcacaaa aatcgacgct caagtcagag gtggcgaaac ccgacaggac | 6180 |
| tataaagata ccaggcgttt ccccctggaa gctccctcgt gcgctctcct gttccgaccc | 6240 |

```
tgccgcttac cggatacctg tccgcctttc tcccttcggg aagcgtggcg ctttctcata    6300
gctcacgctg taggtatctc agttcggtgt aggtcgttcg ctccaagctg ggctgtgtgc    6360
acgaaccccc cgttcagccc gaccgctgcg ccttatccgg taactatcgt cttgagtcca    6420
acccggtaag acacgactta tcgccactgg cagcagccac tggtaacagg attagcagag    6480
cgaggtatgt aggcggtgct acagagttct tgaagtggtg gcctaactac ggctacacta    6540
gaaggacagt atttggtatc tgcgctctgc tgaagccagt taccttcgga aaaagagttg    6600
gtagctcttg atccggcaaa caaaccaccg ctggtagcgg tggtttttt gtttgcaagc    6660 agcagattac gcgcagaaaa aaggatctc aagaagatcc tttgatcttt tctacggggt    6720
ctgacgctca gtggaacgaa aactcacgtt aagggatttt ggtcatgaga ttatcaaaaa    6780
ggatcttcac ctagatcctt ttaaattaaa aatgaagttt taaatcaatc taagtatat     6840 atgagtaaac ttggtctgac agttaccaat gcttaatcag tgaggcacct atctcagcga    6900
tctgtctatt tcgttcatcc atagttgcct gactccccgt cgtgtagata actacgatac    6960
gggagggctt accatctggc cccagtgctg caatgatacc gcgagaccca cgctcaccgg    7020
ctccagattt atcagcaata aaccagccag ccggaagggc cgagcgcaga agtggtcctg    7080
caactttatc cgcctccatc cagtctatta attgttgccg ggaagctaga gtaagtagtt    7140
cgccagttaa tagtttgcgc aacgttgttg ccattgctgc aggcatcgtg gtgtcacgct    7200
cgtcgtttgg tatggcttca ttcagctccg gttcccaacg atcaaggcga gttacatgat    7260
cccccatgtt gtgcaaaaaa gcggttagct ccttcggtcc tccgatcgtt gtcagaagta    7320
agttggccgc agtgttatca ctcatggtta tggcagcact gcataattct cttactgtca    7380
tgccatccgt aagatgcttt tctgtgactg gtgagtactc aaccaagtca ttctgagaat    7440
agtgtatgcg gcgaccgagt tgctcttgcc cggcgtcaat acgggataat accgcgccac    7500
atagcagaac tttaaaagtg ctcatcattg gaaaacgttc ttcggggcga aaactctcaa    7560
ggatcttacc gctgttgaga tccagttcga tgtaacccac tcgtgcaccc aactgatctt    7620
cagcatcttt tactttcacc agcgtttctg ggtgagcaaa aacaggaagg caaaatgccg    7680
caaaaaaggg aataagggcg acacggaaat gttgaatact catactcttc ctttttcaat    7740
attattgaag catttatcag ggttattgtc tcatgagcgg atacatattt gaatgtattt    7800
agaaaaataa acaaataggg gttccgcgca catttccccg aaaagtgcca cctgaaattg    7860
taaacgttaa tattttgtta aaattcgcgt taaattttg ttaaatcagc tcattttta     7920 accaataggc cgaaatcggc aaaatccctt ataaatcaaa agaatagacc gagataggt    7980 tgagtgttgt tccagtttgg aacaagagtc cactattaaa gaacgtggac tccaacgtca    8040
aagggcgaaa aaccgtctat cagggcgatg gcccactacg tgaaccatca ccctaatcaa    8100
gttttttggg gtcgaggtgc cgtaaagcac taaatcggaa ccctaaaggg agcccccgat    8160
ttagagcttg acggggaaag ccggcgaacg tggcgagaaa ggaagggaag aaagcgaaag    8220
gagcgggcgc tagggcgctg gcaagtgtag cggtcacgct gcgcgtaacc accacacccg    8280
ccgcgcttaa tgcgccgcta cagggcgcgt cccattcgcc a                       8321
```

<210> SEQ ID NO 64
<211> LENGTH: 8190
<212> TYPE: DNA
<213> ORGANISM: Artificial Sequence
<220> FEATURE:
<223> OTHER INFORMATION: Description of Artificial Sequence: Synthetic
      pF(G)r7(A)r3 polynucleotide

<400> SEQUENCE: 64

```
atccggatat agttcctcct ttcagcaaaa aacccctcaa gacccgttta gaggccccaa      60
ggggttatgc tagttattgc tcagcggtgg cagcagccaa ctcagcttcc tttcgggctt     120
tgttagcagc cggatctcag tggtggtggt ggtggtgctc gagtgcggcc gctcagaact     180
gtgtcgggcg catcaccgca tcaatgccgc catcaatgac gatctgcgcg ccatgcacat     240
agcttgcggc cgggctcatc aaaaaggcga tgaccgacgc catctcggac ggctcggcac     300
ggcggcccat gggaggaacg aacttggcaa tggattcgcc atagcgcggg tcctgcaggc     360
ccgcctgcag caagggagtc tcggttcac cggggcgat ggtgttcagg cgcacgccag       420
cctcgcccca ggcggcggcg cgtttgcgca cagccaccgt caaagcattc ttgctgcccg     480
cataggccag atttccgccc tgctctcccg catgttcgac aatggcgcgg ccttggctt      540
cctcgccggc ttccagtgcc agcgccagtg ggttcttgtc aaaagccaga tgcgcggaag     600
ccacggacga gatgacgacg gctgcgggct gatggccttt tttcagcgct ggcaaaaagg     660
catccatcag ctcggtcgcg ccaaaataat tgaccgaaac cacattgcca agcaccttgg     720
tctgcggtcc caggccggcg cacagcacca ggccgtccat gcccttgctg cacttcgcca     780
gtacatcggc aatcgcctgc tttcgacctt cggccgtcga gagatcggca atcacttccg     840
catcgcgtat atcgatgcct acgatctggt gaccggccgc ctccaggacc ttgcgcgtag     900
cggcaccaat gccggtggcg cagccgctta tcacgatgat ggacatgtat atctccttaa     960
gcttctagtc gcggtagaac gacccccatgt agcggatgta ctcgtcctcg gtgtggtttg   1020
ccttccagtc gtggacggag tccttgttgc gctggccggc gatgacggag agctccttac    1080
ccagcttctc aaaggcctcg tcaacgcact cctcggggt gagggcgatc ttcatgacgg     1140
cctcgccctg cgggccgccg gggaggttgg acagcaggct gggggttagg gtggtgccga    1200
gggtgatgac ctcgacgtcg acgccggtgc cctcgcactc gcaggccacg gcctcggtca   1260
tcttgaggat gaaggccttg cccgcgccgt actggccgtt ccaggggctg gagctgatgc    1320
cggtcatcga cgagacgttg atcacggcgc gcggtcctg gcggcaaag atccgcatgt      1380
agtggtggaa gcacttgagg aaggtcacga cgttgacgtt gatcatggcc tcgtgcttct    1440
cccaggggt gtcctggatc ttaccgaagc tgtgcaggca ggccacgtag ctcatgaagc     1500
ccatgtccag gccctcggtc gcggcgaaga cggtctcggc agcgccgggc tggctaaagt    1560
cggcgcgcac gaccttggtc tccacgccgt aggtctcgcg gatctcgcct gcgagcacgt    1620
tcagcttctc ctcgcgacgg gcgaccatga cgacgttcat gccgccggcg gcgatcttct    1680
cgcagaacgc cttgccgacg ccctcggtcg cgcccaggat caggcccac tcaccgtact     1740
tctccctcag gttcatgtat atctccttc acgaattctc agccgccttc ttgaacttgg     1800
cggcctcttc cgaaccgccg gtggcattgc ccttcgagta ggaatgcgcg ccggtgccgg    1860
caagagcgcc gccctgcacg atgaggtatt cgtcgcggat cggacggccc tcgaagaagc    1920
actccaggat ctcgcgggtg cccgccgcat aacgcgcctg cgcggtcagc gtggtgccgg    1980
agatgtgcgg ggtcatgccg ttatagggca tcgtccgcca ggggtggtcc ttcggcgccg    2040
gctgcgggaa ccacacgtcg ccggcatagc cggccagccg gccggattcg agcgcacgtg    2100
ccacggcatc gcggtcgcac agcttgccgc gggcggtgtt gacgatgtag gcgccacgct    2160
tgaacagctt cagcgtctcg tcattgatca tgtgctcggt tcggggtgc agcgggcagt     2220
tcagcgtcac cacgtcgcaa accggataca tgtcctcgcg ggtcgcgtgc caggtgaggt    2280
```

```
tgagctcctt ctcgaccgat tccggcaggc ggtgacggcc ggtgtagtgc aggtgcacgt    2340
cgaacggcgc cagacggcgc agcaccgcga gaccgatgcg gccggcggcc acggtgccga    2400
catgcatcgc ctcgaggtcg taggcgtggg agacgcagtc ggcgatgttc cagccgccct    2460
tccgcgccca ttcgtgcgag ggcagatagt tgcgcaccag cgacaggatc atcatcacca    2520
catgctcggc gacgctgatc gagttgcagt aggtgacttc cgccacggtg acgttgcggt    2580
cgatagccga ctgaagatcg acgtggtcgg aaccgatgcc ggcggtgagc gcagcttca    2640 ggttcttggc cttggcgatg cgctcgggcg tcagataggc cggccagaag ggctgggaga    2700
tgacgacatc cgcatcgacc agctcgcgct cgaacaccga gtcggggccg tccttgtcgg    2760
aggtcacgac cagggtgtgg ccgttggatt cgagatattc gcgcaggccg agctcgccgg    2820
agacggagcc gagcaactgc ccgggcgtga agtcgatggc cttcggcgtc ggcaagatct    2880
ggccgcccgg atagtggtcg atcttcggaa gatcgtcgcg ggcataggtc ttcgggtagc    2940
cgtcgaccgg atcatcgtaa agaacgcaca ggacctttgc catcatatgt atatctcctt    3000
cttaaagtta aacaaaatta tttctagagg ggaattgtta tccgctcaca attccctat    3060 agtgagtcgt attaatttcg cgggatcgag atctcgatcc tctacgccgg acgcatcgtg    3120
gccggcatca ccggcgccac aggtgcggtt gctggcgcct atatcgccga catcaccgat    3180
ggggaagatc gggctcgcca cttcgggctc atgagcgctt gtttcggcgt gggtatggtg    3240
gcaggccccg tggccggggg actgttgggc gccatctcct tgcatgcacc attccttgcg    3300
gcggcggtgc tcaacggcct caacctacta ctgggctgct tcctaatgca ggagtcgcat    3360
aagggagagc gtcgagatcc cggacaccat cgaatgcgc aaaacctttc gcggtatggc    3420
atgatagcgc ccggaagaga gtcaattcag ggtggtgaat gtgaaaccag taacgttata    3480
cgatgtcgca gagtatgccg gtgtctctta tcagaccgtt tcccgcgtgg tgaaccaggc    3540
cagccacgtt tctgcgaaaa cgcgggaaaa agtggaagcg gcgatggcgg agctgaatta    3600
cattcccaac cgcgtggcac aacaactggc gggcaaacag tcgttgctga ttggcgttgc    3660
cacctccagt ctggccctgc acgcgccgtc gcaaattgtc gcggcgatta aatctcgcgc    3720
cgatcaactg ggtgccagcg tggtggtgtc gatggtagaa cgaagcggcg tcgaagcctg    3780
taaagcggcg gtgcacaatc ttctcgcgca acgcgtcagt gggctgatca ttaactatcc    3840
gctggatgac caggatgcca ttgctgtgga agctgcctgc actaatgttc cggcgttatt    3900
tcttgatgtc tctgaccaga cacccatcaa cagtattatt ttctcccatg aagacggtac    3960
gcgactgggc gtggagcatc tggtcgcatt gggtcaccag caaatcgcgc tgttagcggg    4020
cccattaagt tctgtctcgg cgcgtctgcg tctggctggc tggcataaat atctcactcg    4080
caatcaaatt cagccgatag cggaacggga aggcgactgg agtgccatgt ccggttttca    4140
acaaaccatg caaatgctga atgagggcat cgttcccact gcgatgctgg ttgccaacga    4200
tcagatggcg ctgggcgcaa tgcgcgccat taccgagtcc gggctgcgcg ttggtgcgga    4260
tatctcggta gtgggatacg acgataccga agacagctca tgttatatcc cgccgttaac    4320
caccatcaaa caggattttc gcctgctggg gcaaaccagc gtggaccgct tgctgcaact    4380
ctctcagggc caggcggtga agggcaatca gctgttgccc gtctcactgg tgaaaagaaa    4440
aaccaccctg gcgcccaata cgcaaaccgc ctctccccgc gcgttggccg attcattaat    4500
gcagctggca cgacaggttt cccgactgga aagcgggcag tgagcgcaac gcaattaatg    4560
taagttagct cactcattag gcaccgggat ctcgaccgat gcccttgaga gccttcaacc    4620
cagtcagctc cttccggtgg gcgcggggca tgactatcgt cgccgcactt atgactgtct    4680
```

```
tctttatcat gcaactcgta ggacaggtgc cggcagcgct ctgggtcatt ttcggcgagg    4740
accgctttcg ctggagcgcg acgatgatcg gcctgtcgct tgcggtattc ggaatcttgc    4800
acgccctcgc tcaagccttc gtcactggtc ccgccaccaa acgtttcggc gagaagcagg    4860
ccattatcgc cggcatggcg gccccacggg tgcgcatgat cgtgctcctg tcgttgagga    4920
cccggctagg ctggcggggt tgccttactg gttagcagaa tgaatcaccg atacgcgagc    4980
gaacgtgaag cgactgctgc tgcaaaacgt ctgcgacctg agcaacaaca tgaatggtct    5040
tcggtttccg tgtttcgtaa agtctggaaa cgcggaagtc agcgccctgc accattatgt    5100 tccgatctg catcgcagga tgctgctggc taccctgtgg aacacctaca tctgtattaa    5160
cgaagcgctg gcattgaccc tgagtgattt ttctctggtc ccgccgcatc cataccgcca    5220
gttgtttacc ctcacaacgt tccagtaacc gggcatgttc atcatcagta acccgtatcg    5280
tgagcatcct ctctcgtttc atcggtatca ttaccccat gaacagaaat ccccccttaca    5340 cggaggcatc agtgaccaaa caggaaaaaa ccgcccttaa catggcccgc tttatcagaa    5400
gccagacatt aacgcttctg gagaaactca acgagctgga cgcggatgaa caggcagaca    5460
tctgtgaatc gcttcacgac cacgctgatg agctttaccg cagctgcctc gcgcgtttcg    5520
gtgatgacgg tgaaaacctc tgacacatgc agctcccgga gacggtcaca gcttgtctgt    5580
aagcggatgc cgggagcaga caagcccgtc agggcgcgtc agcgggtgtt ggcgggtgtc    5640
ggggcgcagc catgacccag tcacgtagcg atagcggagt gtatactggc ttaactatgc    5700
ggcatcagag cagattgtac tgagagtgca ccatatatgc ggtgtgaaat accgcacaga    5760
tgcgtaagga gaaaataccg catcaggcgc tcttccgctt cctcgctcac tgactcgctg    5820
cgctcggtcg ttcggctgcg gcgagcggta tcagctcact caaaggcggt aatacggtta    5880
tccacagaat caggggataa cgcaggaaag aacatgtgag caaaaggcca gcaaaaggcc    5940
aggaaccgta aaaaggccgc gttgctggcg ttttttccata ggctccgccc ccctgacgag    6000
catcacaaaa atcgacgctc aagtcagagg tggcgaaacc cgacaggact ataaagatac    6060
caggcgtttc cccctggaag ctccctcgtg cgctctcctg ttccgaccct gccgcttacc    6120
ggatacctgt ccgcctttct cccttcggga agcgtggcgc tttctcatag ctcacgctgt    6180
aggtatctca gttcggtgta ggtcgttcgc tccaagctgg gctgtgtgca cgaaccccc    6240 gttcagcccg accgctgcgc cttatccggt aactatcgtc ttgagtccaa cccggtaaga    6300
cacgacttat cgccactggc agcagccact ggtaacagga ttagcagagc gaggtatgta    6360
ggcggtgcta cagagttctt gaagtggtgg cctaactacg gctacactag aaggacagta    6420
tttggtatct gcgctctgct gaagccagtt accttcggaa aaagagttgg tagctcttga    6480
tccggcaaac aaaccaccgc tggtagcggt ggtttttttg tttgcaagca gcagattacg    6540
cgcagaaaaa aaggatctca agaagatcct ttgatctttt ctacggggtc tgacgctcag    6600
tggaacgaaa actcacgtta agggattttg gtcatgagat tatcaaaaag gatcttcacc    6660
tagatccttt taaattaaaa atgaagtttt aaatcaatct aaagtatata tgagtaaact    6720
tggtctgaca gttaccaatg cttaatcagt gaggcaccta tctcagcgat ctgtctattt    6780
cgttcatcca tagttgcctg actccccgtc gtgtagataa ctacgatacg ggagggctta    6840
ccatctggcc ccagtgctgc aatgataccg cgagacccac gctcaccggc tccagattta    6900
tcagcaataa accagccagc cggaagggcc gagcgcagaa gtggtcctgc aactttatcc    6960
gcctccatcc agtctattaa ttgttgccgg gaagctagag taagtagttc gccagttaat    7020
```

| | |
|---|---|
| agtttgcgca acgttgttgc cattgctgca ggcatcgtgg tgtcacgctc gtcgtttggt | 7080 |
| atggcttcat tcagctccgg ttcccaacga tcaaggcgag ttacatgatc ccccatgttg | 7140 |
| tgcaaaaaag cggttagctc cttcggtcct ccgatcgttg tcagaagtaa gttggccgca | 7200 |
| gtgttatcac tcatggttat ggcagcactg cataattctc ttactgtcat gccatccgta | 7260 |
| agatgctttt ctgtgactgg tgagtactca accaagtcat tctgagaata gtgtatgcgg | 7320 |
| cgaccgagtt gctcttgccc ggcgtcaata cgggataata ccgcgccaca tagcagaact | 7380 |
| ttaaaagtgc tcatcattgg aaaacgttct tcggggcgaa aactctcaag gatcttaccg | 7440 |
| ctgttgagat ccagttcgat gtaacccact cgtgcaccca actgatcttc agcatctttt | 7500 |
| actttcacca gcgtttctgg gtgagcaaaa acaggaaggc aaaatgccgc aaaaaaggga | 7560 |
| ataagggcga cacggaaatg ttgaatactc atactcttcc ttttcaata ttattgaagc | 7620 |
| atttatcagg gttattgtct catgagcgga tacatatttg aatgtattta gaaaaataaa | 7680 |
| caaatagggg ttccgcgcac atttccccga aaagtgccac ctgaaattgt aaacgttaat | 7740 |
| attttgttaa aattcgcgtt aaattttgt taaatcagct catttttaa ccaataggcc | 7800 |
| gaaatcggca aaatccctta taaatcaaaa gaatagaccg agataggt gagtgttgtt | 7860 |
| ccagtttgga acaagagtcc actattaaag aacgtggact ccaacgtcaa agggcgaaaa | 7920 |
| accgtctatc agggcgatgg cccactacgt gaaccatcac cctaatcaag tttttttgggg | 7980 |
| tcgaggtgcc gtaaagcact aaatcggaac cctaaaggga gcccccgatt tagagcttga | 8040 |
| cggggaaagc cggcgaacgt ggcgagaaag gaagggaaga aagcgaaagg agcgggcgct | 8100 |
| agggcgctgg caagtgtagc ggtcacgctg cgcgtaacca ccacacccgc cgcgcttaat | 8160 |
| gcgccgctac agggcgcgtc ccattcgcca | 8190 |

<210> SEQ ID NO 65
<211> LENGTH: 8190
<212> TYPE: DNA
<213> ORGANISM: Artificial Sequence
<220> FEATURE:
<223> OTHER INFORMATION: Description of Artificial Sequence: Synthetic
    pF(G)r7(S)r3 polynucleotide

<400> SEQUENCE: 65

| | |
|---|---|
| atccggatat agttcctcct ttcagcaaaa aaccccctcaa gacccgttta gaggccccaa | 60 |
| ggggttatgc tagttattgc tcagcggtgg cagcagccaa ctcagcttcc tttcgggctt | 120 |
| tgttagcagc cggatctcag tggtggtggt ggtggtgctc gagtgcggcc gctcagaact | 180 |
| gtgtcgggcg catcaccgca tcaatgccgc catcaatgac gatctgcgcg ccatgcacat | 240 |
| agcttgcggc cgggctcatc aaaaaggcga tgaccgacgc catctcggac ggctcggcac | 300 |
| ggcggcccat gggaggaacg aacttggcaa tggattcgcc atagcgcggg tcctgcaggc | 360 |
| ccgcctgcag caagggagtc tcggttgcac cggggggcgat ggtgttcagg cgcacgccag | 420 |
| cctcgcccca ggcggcggcg cgtttgcgca cagccaccgt caaagcattc ttgctgcccg | 480 |
| cataggccag atttccgccc tgctctcccg catgttcgac aatggcgcgg gccttggctt | 540 |
| cctcgccggc ttccagtgcc agcgccagtg ggttcttgtc aaaagccaga tgcgcggaag | 600 |
| ccacggacga gatgacgacg gctgcgggct gatggccttt tttcagcgct ggcaaaaagg | 660 |
| catccatcag ctcggtcgcg ccaaaataat tgaccgaaac cacattgcca agcaccttgg | 720 |
| tctgcggtcc caggccggcg cacagcacca ggccgtccat gcccttgctg cacttcgcca | 780 |
| gtacatcggc aatcgcctgc tttcgacctt cggccgtcga gagatcggca atcacttccg | 840 |

```
catcgcgtat atcgatgcct acgatctggt gaccggccgc ctccaggacc ttgcgcgtag    900
cggcaccaat gccggtggcg cagccgctta tcacgatgat ggacatgtat atctccttaa    960
gcttctagtc gcggtagaac gaccccatgt agcggatgta ctcgtcctcg gtgtggtttg   1020
ccttccagtc gtggacggag tccttgttgc gctggccggc gatgacggag agctccttac   1080
ccagcttctc aaaggcctcg tcaacgcact cctcgggggt gagggcgatc ttcatgacgg   1140
cctcgccctg cgggccgccg gggaggttgg acagcaggct gggggttagg gtggtgccga   1200
gggtgatgac ctcgacgtcg acgccggtgc cctcgcactc gcaggccacg gcctcggtca   1260
tcttgaggat gaaggccttg cccgcgccgt actggccgtt ccaggggctg gagctgatgc   1320
cggtcatcga cgagacgttg atcacggcgc cgcggtcctg ggcggcaaag atccgcatgt   1380
agtggtggaa gcacttgagg aaggtcacga cgttgacgtt gatcatggcc tcgtgcttct   1440
cccagggggt gtcctggatc ttaccgaagc tgtgcaggca ggccacgtag ctcatgaagc   1500
ccatgtccag gccctcggtc gcggcgaaga cggtctcggc agcgccgggc tggctaaagt   1560
cggcgcgcac gaccttggtc tccacgccgt aggtctcgcg gatctcgcct gcgagcacgt   1620
tcagcttctc ctcgcgacgg ctgaccatga cgacgttcat gccgccggcg gcgatcttct   1680
cgcagaacgc cttgccgacg ccctcggtcg cgcccaggat caggcccac tcaccgtact   1740
tctccctcag gttcatgtat atctcctttc acgaattctc agccgccttc ttgaacttgg   1800
cggcctcttc cgaaccgccg gtggcattgc ccttcgagta ggaatgcgcg ccggtgccgg   1860
caagagcgcc gccctgcacg atgaggtatt cgtcgcggat cggacggccc tcgaagaagc   1920
actccaggat ctcgcgggtg cccgccgcat aacgcgcctg cgcggtcagc gtggtgccgg   1980
agatgtgcgg ggtcatgccg ttatagggca tcgtccgcca ggggtggtcc ttcggcgccg   2040
gctgcgggaa ccacacgtcg ccggcatagc cggccagccg gccggattcg agcgcacgtg   2100
ccacggcatc gcggtcgcac agcttgccgc gggcggtgtt gacgatgtag cgccacgct   2160
tgaacagctt cagcgtctcg tcattgatca tgtgctcggt ttcggggtgc agcgggcagt   2220
tcagcgtcac cacgtcgcaa accggataca tgtcctcgcg ggtcgcgtgc caggtgaggt   2280
tgagctcctt ctcgaccgat tccggcaggc ggtgacggcc ggtgtagtgc aggtgcacgt   2340
cgaacggcgc cagacggcgc agcaccgcga gaccgatgcg gccggcggcc acggtgccga   2400
catgcatcgc ctcgaggtcg taggcgtggg agacgcagtc ggcgatgttc cagccgccct   2460
tccgcgccca ttcgtgcgag ggcagatagt tgcgcaccag cgacaggatc atcatcacca   2520
catgctcggc gacgctgatc gagttgcagt aggtgacttc cgccacgtg acgttgcggt    2580
cgatagccga ctgaagatcg acgtggtcgg aaccgatgcc ggcggtgagc gcgagcttca   2640
ggttcttggc cttggcgatg cgctcggcg tcagataggc cggccagaag ggctgggaga   2700
tgacgacatc cgcatcgacc agctcgcgct cgaacaccga gtcggggccg tccttgtcgg   2760
aggtcacgac cagggtgtgg ccgttggatt cgagatattc gcgcaggccg agctcgccgg   2820
agacggagcc gagcaactgc ccgggcgtga agtcgatggc cttcggcgtc ggcaagatct   2880
ggccgcccgg atagtggtcg atcttcggaa gatcgtcgcg ggcataggtc ttcgggtagc   2940
cgtcgaccga atcatcgtaa agaacgcaca ggacctttgc catcatatgt atatctcctt   3000
cttaaagtta aacaaaatta tttctagagg ggaattgtta tccgctcaca attccctat   3060
agtgagtcgt attaatttcg cgggatcgag atctcgatcc tctacgccgg acgcatcgtg   3120
gccggcatca ccgcgccac aggtgcggtt gctggcgcct atatcgccga catcaccgat   3180
ggggaagatc gggctcgcca cttcgggctc atgagcgctt gtttcggcgt gggtatggtg   3240
```

```
gcaggccccg tggccggggg actgttgggc gccatctcct tgcatgcacc attccttgcg    3300
gcggcggtgc tcaacggcct caacctacta ctgggctgct tcctaatgca ggagtcgcat    3360
aagggagagc gtcgagatcc cggacaccat cgaatggcgc aaaacctttc gcggtatggc    3420
atgatagcgc ccgaagagag gtcaattcag ggtggtgaat gtgaaaccag taacgttata    3480
cgatgtcgca gagtatgccg gtgtctctta tcagaccgtt tcccgcgtgg tgaaccaggc    3540
cagccacgtt tctgcgaaaa cgcgggaaaa agtggaagcg gcgatggcgg agctgaatta    3600
cattcccaac cgcgtggcac aacaactggc gggcaaacag tcgttgctga ttggcgttgc    3660
cacctccagt ctggccctgc acgcgccgtc gcaaattgtc gcggcgatta atctcgcgc     3720
cgatcaactg ggtgccagcg tggtggtgtc gatggtagaa cgaagcggcg tcgaagcctg    3780
taaagcggcg gtgcacaatc ttctcgcgca acgcgtcagt gggctgatca ttaactatcc    3840
gctggatgac caggatgcca ttgctgtgga agctgcctgc actaatgttc cggcgttatt    3900
tcttgatgtc tctgaccaga cacccatcaa cagtattatt ttctcccatg aagacggtac    3960
gcgactgggc gtggagcatc tggtcgcatt gggtcaccag caaatcgcgc tgttagcggg    4020
cccattaagt tctgtctcgg cgcgtctgcg tctggctggc tggcataaat atctcactcg    4080
caatcaaatt cagccgatag cggaacggga aggcgactgg agtgccatgt ccggttttca    4140
acaaaccatg caaatgctga atgagggcat cgttcccact gcgatgctgg ttgccaacga    4200
tcagatggcg ctgggcgcaa tgcgcgccat taccgagtcc gggctgcgcg ttggtgcgga    4260
tatctcggta gtgggatacg acgataccga agacagctca tgttatatcc gccgttaac    4320
caccatcaaa caggattttc gcctgctggg gcaaaccagc gtggaccgct tgctgcaact    4380
ctctcagggc caggcggtga agggcaatca gctgttgccc gtctcactgg tgaaaagaaa    4440
aaccaccctg gcgcccaata cgcaaaccgc ctctccccgc gcgttggccg attcattaat    4500
gcagctggca cgacaggttt cccgactgga aagcgggcag tgagcgcaac gcaattaatg    4560
taagttagct cactcattag gcaccgggat ctcgaccgat gcccttgaga gccttcaacc    4620
cagtcagctc cttccggtgg gcgcggggca tgactatcgt cgccgcactt atgactgtct    4680
tctttatcat gcaactcgta ggacaggtgc cggcagcgct ctgggtcatt ttcggcgagg    4740
accgctttcg ctggagcgcg acgatgatcg gcctgtcgct tgcggtattc ggaatcttgc    4800
acgccctcgc tcaagccttc gtcactggtc ccgccaccaa acgtttcggc gagaagcagg    4860
ccattatcgc cggcatggcg ccccacgggt gcgcatgat cgtgctcctg tcgttgagga    4920
cccggctagg ctggcggggt tgccttactg gttagcagaa tgaatcaccg atacgcgagc    4980
gaacgtgaag cgactgctgc tgcaaaacgt ctgcgacctg agcaacaaca tgaatggtct    5040
tcggtttccg tgtttcgtaa agtctggaaa cgcggaagtc agcgccctgc accattatgt    5100
tccggatctg catcgcagga tgctgctggc taccctgtgg aacacctaca tctgtattaa    5160
cgaagcgctg gcattgaccc tgagtgattt ttctctggtc ccgccgcatc cataccgcca    5220
gttgtttacc ctcacaacgt tccagtaacc gggcatgttc atcatcagta cccgtatcg    5280
tgagcatcct ctctcgtttc atcggtatca ttacccccat gaacagaaat cccccttaca    5340
cggaggcatc agtgaccaaa caggaaaaaa ccgcccttaa catggcccgc tttatcagaa    5400
gccagacatt aacgcttctg gagaaactca acgagctgga cgcggatgaa caggcagaca    5460
tctgtgaatc gcttcacgac cacgctgatg agctttaccg cagctgcctc gcgcgtttcg    5520
gtgatgacgg tgaaaacctc tgacacatgc agctcccgga gacggtcaca gcttgtctgt    5580
```

```
aagcggatgc cgggagcaga caagcccgtc agggcgcgtc agcgggtgtt ggcgggtgtc    5640
ggggcgcagc catgacccag tcacgtagcg atagcggagt gtatactggc ttaactatgc    5700
ggcatcagag cagattgtac tgagagtgca ccatatatgc ggtgtgaaat accgcacaga    5760
tgcgtaagga gaaataccg catcaggcgc tcttccgctt cctcgctcac tgactcgctg     5820
cgctcggtcg ttcggctgcg gcgagcggta tcagctcact caaaggcggt aatacggtta    5880
tccacagaat caggggataa cgcaggaaag aacatgtgag caaaaggcca gcaaaaggcc    5940
aggaaccgta aaaaggccgc gttgctggcg ttttttccata ggctccgccc ccctgacgag    6000
catcacaaaa atcgacgctc aagtcagagg tggcgaaacc cgacaggact ataaagatac    6060
caggcgtttc cccctggaag ctccctcgtg cgctctcctg ttccgacccet gccgcttacc    6120
ggataccgtgt ccgcctttct cccttcggga agcgtggcgc tttctcatag ctcacgctgt    6180
aggtatctca gttcggtgta ggtcgttcgc tccaagctgg gctgtgtgca cgaaccccce    6240
gttcagcccg accgctgcgc cttatccggt aactatcgtc ttgagtccaa cccggtaaga    6300
cacgacttat cgccactggc agcagccact ggtaacagga ttagcagagc gaggtatgta    6360
ggcggtgcta cagagttctt gaagtggtgg cctaactacg gctacactag aaggacagta    6420
tttggtatct gcgctctgct gaagccagtt accttcggaa aaagagttgg tagctcttga    6480
tccggcaaac aaaccaccgc tggtagcggt ggtttttttg tttgcaagca gcagattacg    6540
cgcagaaaaa aaggatctca agaagatcct ttgatctttt ctacggggtc tgacgctcag    6600
tggaacgaaa actcacgtta agggattttg gtcatgagat tatcaaaaag gatcttcacc    6660
tagatccttt taaattaaaa atgaagtttt aaatcaatct aaagtatata tgagtaaact    6720
tggtctgaca gttaccaatg cttaatcagt gaggcaccta tctcagcgat ctgtctattt    6780
cgttcatcca tagttgcctg actccccgtc gtgtagataa ctacgatacg ggagggctta    6840
ccatctggcc ccagtgctgc aatgataccg cgagacccac gctcaccggc tccagattta    6900
tcagcaataa accagccagc cggaagggcc gagcgcagaa gtggtcctgc aactttatcc    6960
gcctccatcc agtctattaa ttgttgccgg gaagctagag taagtagttc gccagttaat    7020
agtttgcgca acgttgttgc cattgctgca ggcatcgtgg tgtcacgctc gtcgtttggt    7080
atggcttcat tcagctccgg ttcccaacga tcaaggcgag ttacatgatc ccccatgttg    7140
tgcaaaaaag cggttagctc cttcggtcct ccgatcgttg tcagaagtaa gttggccgca    7200
gtgttatcac tcatggttat ggcagcactg cataattctc ttactgtcat gccatccgta    7260
agatgctttt ctgtgactgg tgagtactca accaagtcat tctgagaata gtgtatgcgg    7320
cgaccgagtt gctcttgccc ggcgtcaata cgggataata ccgcgccaca tagcagaact    7380
ttaaaagtgc tcatcattgg aaaacgttct cggggcgaa aactctcaag gatcttaccg    7440
ctgttgagat ccagttcgat gtaacccact cgtgcaccca actgatcttc agcatctttt    7500
actttcacca gcgtttctgg gtgagcaaaa acaggaaggc aaaatgccgc aaaaaaggga    7560
ataagggcga cacggaaatg ttgaatactc atactcttcc ttttcaata ttattgaagc     7620
atttatcagg gttattgtct catgagcgga tacatatttg aatgtattta gaaaaataaa    7680
caaataggg ttccgcgcac atttccccga aagtgccac ctgaaattgt aaacgttaat     7740
attttgttaa aattcgcgtt aaattttgt taaatcagct catttttaa ccaataggcc      7800
gaaatcggca aaatccctta taatcaaaa gaatagaccg agatagggt gagtgttgtt     7860
ccagtttgga acaagagtcc actattaaag aacgtggact ccaacgtcaa agggcgaaaa    7920
accgtctatc agggcgatgg cccactacgt gaaccatcac cctaatcaag ttttttgggg    7980
```

```
tcgaggtgcc gtaaagcact aaatcggaac cctaaaggga gcccccgatt tagagcttga    8040
cggggaaagc cggcgaacgt ggcgagaaag gaagggaaga aagcgaaagg agcgggcgct    8100
agggcgctgg caagtgtagc ggtcacgctg cgcgtaacca ccacacccgc cgcgcttaat    8160
gcgccgctac agggcgcgtc ccattcgcca                                     8190
```

<210> SEQ ID NO 66
<211> LENGTH: 7910
<212> TYPE: DNA
<213> ORGANISM: Artificial Sequence
<220> FEATURE:
<223> OTHER INFORMATION: Description of Artificial Sequence: Synthetic
      p3T7(A)rG polynucleotide

<400> SEQUENCE: 66

```
atccggatat agttcctcct ttcagcaaaa aaccccctcaa gacccgttta gaggccccaa   60
ggggttatgc tagttattgc tcagcggtgg cagcagccaa ctcagcttcc tttcgggctt   120
tgttagcagc cggatctcag tggtggtggt ggtggtgctc gagttaaccg cggcctgcct   180
ggaatgaagg atattgtgtc ataccgccgt ccgcgaataa cgtgatgcct gtgacgtagc   240
tggcttcctt cgaagcaagc caggctgcta ctgcggcgat ctcctccggt cgccgatat   300 atcccattgg aatcatgctt tctacatcag cttctctgttt agggtcagcg aattttcag   360 cattgattgg cgtgttgatc gcacctggcc caatattatt gacgcgaatg cccttcggcg   420
cgtattccaa cgctaatgtt tctgtcatca gctttatccc gcctttactt gccgcatagt   480
ggacaaataa cggccaagga atcacttcgt gcacactgga catgttaatg acatttccct   540
tgatatcgtt ttctacgaaa tatttaatcg cttcacggct tcctaaaaag gcacccgtta   600
agttcgtgcc gatgacttta tcccaatcct tgagcggcat ttcgtgagat ggcacaggat   660
tttcaagacc ggcattatta atcataatat cgagtgtgcc gaactcctta attgccgttt   720
gcacgatatt tttacatct tcctctttcg tgacatctcc ttggacgaca acagcttcac   780
cgcccgcctt gatgacctct tcttttacct cgttcggatc ttgtttatta ctataatagt   840
tgataaccac ttttgcctgc tccttgccga agcgaatggc catcgccttt ccgagccctg   900
aagcagctcc tgtaatagcg acgactttc ctttttaaatc cggatacatg tatatctcct   960
tgcggccgcc tagtcgcggt agaacgaccc catgtagcgg atgtactcgt cctcggtgtg  1020
gtttgccttc cagtcgtgga cggagtcctt gttgcgctgg ccggcgatga cggagagctc  1080
cttacccagc ttctcaaagg cctcgtcaac gcactcctcg ggggtgaggg cgatcttcat  1140
gacggcctcg ccctgcgggc cgccggggag gttggacagc aggctggggg ttagggtggt  1200
gccgagggtg atgacctcga cgtcgacgcc ggtgccctcg cactcgcagg ccacggcctc  1260
ggtcatcttg aggatgaagg ccttgcccgc gccgtactgg ccgttccagg ggctggagct  1320
gatgccggtc atcgacgaga cgttgatcac ggcgccgcgg tcctgggcgg caaagatccg  1380
catgtagtgg tggaagcact tgaggaaggt cacgacgttg acgttgatca tggcctcgtg  1440
cttctcccag ggggtgtcct ggatcttacc gaagctgtgc aggcaggcca cgtagctcat  1500
gaagcccatg tccaggccct cggtcgcggg gaagacggtc tcggcagcgc cgggctggct  1560
aaagtcggcg cgcacgacct tggtctccac gccgtaggtc tcgcggatct cgcctgcgag  1620
cacgttcagc ttctcctcgc gacgggcgac catgacgacg ttcatgccgc cggcggcgat  1680
cttctcgcag aacgccttgc cgacgccctc ggtcgcgccc aggatcaggc cccactcacc  1740
gtacttctcc ctcaggttca tatgtatatc tccttcttat acttaactaa tatactaaga  1800
```

```
tggggaattg ttatccgctc acaattcccc tatagtgagt cgtattaatt tcgattatgc   1860
ggccgtgtac aatacgatta ctttctgttc gacttaagca ttataagctt gtcgacggag   1920
ctcgaattct cagaactgtg tcgggcgcat caccgcatca atgccgccat caatgacgat   1980
ctgcgcgcca tgcacatagc ttgcggccgg gctcatcaaa aaggcgatga ccgacgccat   2040
ctcggacggc tcggcacggc ggcccatggg aggaacgaac ttggcaatgg attcgccata   2100
gcgcgggtcc tgcaggcccg cctgcagcaa gggagtctcg gttgcaccgg gggcgatggt   2160
gttcaggcgc acgccagcct cgcccaggc ggcggcgcgt ttgcgcacag ccaccgtcaa    2220
agcattcttg ctgcccgcat aggccagatt tccgccctgc tctcccgcat gttcgacaat   2280
ggcgcgggcc ttggcttcct cgccggcttc cagtgccagc gccagtgggt tcttgtcaaa   2340
agccagatgc gcggaagcca cggacgagat gacgacggct gcgggctgat ggccttttt    2400
cagcgctggc aaaaaggcat ccatcagctc ggtcgcgcca aataattga ccgaaaccac    2460
attgccaagc accttggtct gcggtcccag gccggcgcac agcaccaggc cgtccatgcc   2520
cttgctgcac ttcgccagta catcggcaat cgcctgcttt cgaccttcgg ccgtcgagag   2580
atcggcaatc acttccgcat cgcgtatatc gatgcctacg atctggtgac cggccgcctc   2640
caggaccttg cgcgtagccg caccaatgcc ggtggcgcag ccgcttatca cgatgatgga   2700
catcatatgt atatctcctt cttaaagtta aacaaaatta tttctagagg ggaattgtta   2760
tccgctcaca attcccctat agtgagtcgt attaatttcg cgggatcgag atctcgatcc   2820
tctacgccgg acgcatcgtg gccggcatca ccggcgccac aggtgcggtt gctggcgcct   2880
atatcgccga catcaccgat ggggaagatc gggctcgcca cttcgggctc atgagcgctt   2940
gtttcggcgt gggtatggtg gcaggccccg tggccggggg actgttgggc gccatctcct   3000
tgcatgcacc attccttgcg gcggcggtgc tcaacggcct caacctacta ctgggctgct   3060
tcctaatgca ggagtcgcat aagggagagc gtcgagatcc ggacaccat cgaatggcgc    3120
aaaaccttc gcggtatggc atgatagcgc ccggaagaga gtcaattcag ggtggtgaat    3180
gtgaaaccag taacgttata cgatgtcgca gagtatgccg gtgtctctta tcagaccgtt   3240
tcccgcgtgg tgaaccaggc cagccacgtt tctgcgaaaa cgcgggaaaa agtggaagcg   3300
gcgatggcgg agctgaatta cattcccaac cgcgtggcac aacaactggc gggcaaacag   3360
tcgttgctga ttggcgttgc cacctccagt ctggccctgc acgcgccgtc gcaaattgtc   3420
gcggcgatta atctcgcgc cgatcaactg ggtgccagcg tggtggtgtc gatggtagaa    3480
cgaagcggcg tcgaagcctg taaagcggcg gtgcacaatc ttctcgcgca acgcgtcagt   3540
gggctgatca ttaactatcc gctggatgac caggatgcca ttgctgtgga agctgcctgc   3600
actaatgttc cggcgttatt tcttgatgtc tctgaccaga cacccatcaa cagtattatt   3660
ttctcccatg aagacggtac gcgactgggc gtggagcatc tggtcgcatt gggtcaccag   3720
caaatcgcgc tgttagcggg cccattaagt tctgtctcgg cgcgtctgcg tctggctggc   3780
tggcataaat atctcactcg caatcaaatt cagccgatag cggaacggga aggcgactgg   3840
agtgccatgt ccggttttca acaaaccatg caaatgctga atgagggcat cgttcccact   3900
gcgatgctgg ttgccaacga tcagatggcg ctgggcgcaa tgcgcgccat taccgagtcc   3960
gggctgcgcg ttggtgcgga tatctcggta gtgggatacg acgataccga agacagctca   4020
tgttatatcc cgccgttaac caccatcaaa caggattttc gcctgctggg gcaaaccagc   4080
gtggaccgct tgctgcaact ctctcagggc caggcggtga agggcaatca gctgttgccc   4140
```

```
gtctcactgg tgaaaagaaa aaccaccctg gcgcccaata cgcaaaccgc ctctccccgc    4200
gcgttggccg attcattaat gcagctggca cgacaggttt cccgactgga aagcgggcag    4260
tgagcgcaac gcaattaatg taagttagct cactcattag gcaccgggat ctcgaccgat    4320
gcccttgaga gccttcaacc cagtcagctc cttccggtgg gcgcggggca tgactatcgt    4380
cgccgcactt atgactgtct tctttatcat gcaactcgta ggacaggtgc cggcagcgct    4440
ctgggtcatt ttcggcgagg accgctttcg ctggagcgcg acgatgatcg gcctgtcgct    4500
tgcggtattc ggaatcttgc acgccctcgc tcaagccttc gtcactggtc ccgccaccaa    4560
acgtttcggc gagaagcagg ccattatcgc cggcatggcg ccccacggg tgcgcatgat     4620
cgtgctcctg tcgttgagga cccggctagg ctggcggggt tgccttactg gttagcagaa    4680
tgaatcaccg atacgcgagc gaacgtgaag cgactgctgc tgcaaaacgt ctgcgacctg    4740
agcaacaaca tgaatggtct tcggtttccg tgtttcgtaa agtctggaaa cgcggaagtc    4800
agcgccctgc accattatgt tccggatctg catcgcagga tgctgctggc taccctgtgg    4860
aacacctaca tctgtattaa cgaagcgctg gcattgaccc tgagtgattt ttctctggtc    4920
ccgccgcatc cataccgcca gttgtttacc ctcacaacgt tccagtaacc gggcatgttc    4980
atcatcagta acccgtatcg tgagcatcct ctctcgtttc atcggtatca ttaccccccat   5040
gaacagaaat cccccttaca cggaggcatc agtgaccaaa caggaaaaaa ccgcccttaa    5100
catggcccgc tttatcagaa gccagacatt aacgcttctg gagaaactca acgagctgga    5160
cgcggatgaa caggcagaca tctgtgaatc gcttcacgac cacgctgatg agctttaccg    5220
cagctgcctc gcgcgtttcg gtgatgacgg tgaaaacctc tgacacatgc agctcccgga    5280
gacggtcaca gcttgtctgt aagcggatgc cgggagcaga caagcccgtc agggcgcgtc    5340
agcgggtgtt ggcgggtgtc ggggcgcagc catgacccag tcacgtagcg atagcggagt    5400
gtatactggc ttaactatgc ggcatcagag cagattgtac tgagagtgca ccatatatgc    5460
ggtgtgaaat accgcacaga tgcgtaagga gaaaataccg catcaggcgc tcttccgctt    5520
cctcgctcac tgactcgctg cgctcggtcg ttcggctgcg gcgagcggta tcagctcact    5580
caaaggcggt aatacggtta tccacagaat caggggataa cgcaggaaag aacatgtgag    5640
caaaaggcca gcaaaaggcc aggaaccgta aaaaggccgc gttgctggcg ttttttccata    5700
ggctccgccc ccctgacgag catcacaaaa atcgacgctc aagtcagagg tggcgaaacc    5760
cgacaggact ataaagatac caggcgtttc ccctggaag ctccctcgtg cgctctcctg     5820
ttccgaccct gccgcttacc ggatacctgt ccgcctttct cccttcggga agcgtggcgc    5880
tttctcatag ctcacgctgt aggtatctca gttcggtgta ggtcgttcgc tccaagctgg    5940
gctgtgtgca cgaaccccc gttcagcccg accgctgcgc cttatccggt aactatcgtc    6000
ttgagtccaa cccggtaaga cacgacttat cgccactggc agcagccact ggtaacagga    6060
ttagcagagc gaggtatgta ggcggtgcta cagagttctt gaagtggtgg cctaactacg    6120
gctacactag aaggacagta tttggtatct gcgctctgct gaagccagtt accttcggaa    6180
aaagagttgg tagctcttga tccggcaaac aaaccaccgc tggtagcggt ggtttttttg    6240
tttgcaagca gcagattacg cgcagaaaaa aaggatctca agaagatcct tgatctttt    6300
ctacggggtc tgacgctcag tggaacgaaa actcacgtta agggattttg gtcatgagat    6360
tatcaaaaag gatcttcacc tagatccttt taaattaaaa atgaagtttt aaatcaatct    6420
aaagtatata tgagtaaact tggtctgaca gttaccaatg cttaatcagt gaggcaccta    6480
tctcagcgat ctgtctattt cgttcatcca tagttgcctg actccccgtc gtgtagataa    6540
```

```
ctacgatacg ggagggctta ccatctggcc ccagtgctgc aatgataccg cgagacccac    6600
gctcaccggc tccagattta tcagcaataa accagccagc cggaagggcc gagcgcagaa    6660
gtggtcctgc aactttatcc gcctccatcc agtctattaa ttgttgccgg gaagctagag    6720
taagtagttc gccagttaat agtttgcgca acgttgttgc cattgctgca ggcatcgtgg    6780
tgtcacgctc gtcgtttggt atggcttcat tcagctccgg ttcccaacga tcaaggcgag    6840
ttacatgatc ccccatgttg tgcaaaaaag cggttagctc cttcggtcct ccgatcgttg    6900
tcagaagtaa gttggccgca gtgttatcac tcatggttat ggcagcactg cataattctc    6960
ttactgtcat gccatccgta agatgctttt ctgtgactgg tgagtactca accaagtcat    7020
tctgagaata gtgtatgcgg cgaccgagtt gctcttgccc ggcgtcaata cgggataata    7080
ccgcgccaca tagcagaact ttaaaagtgc tcatcattgg aaaacgttct cggggcgaa     7140 aactctcaag gatcttaccg ctgttgagat ccagttcgat gtaacccact cgtgcaccca    7200
actgatcttc agcatctttt actttcacca gcgtttctgg gtgagcaaaa acaggaaggc    7260
aaaatgccgc aaaaaaggga ataagggcga cacggaaatg ttgaatactc atactcttcc    7320
tttttcaata ttattgaagc atttatcagg gttattgtct catgagcgga tacatatttg    7380
aatgtattta gaaaaataaa caaatagggg ttccgcgcac atttccccga aaagtgccac    7440
ctgaaattgt aaacgttaat attttgttaa aattcgcgtt aaattttgt taaatcagct    7500 catttttta ccaataggcc gaaatcggca aaatccctta taaatcaaaa gaatagaccg    7560
agatagggtt gagtgttgtt ccagtttgga acaagagtcc actattaaag aacgtggact    7620
ccaacgtcaa agggcgaaaa accgtctatc agggcgatgg cccactacgt gaaccatcac    7680
cctaatcaag ttttttgggg tcgaggtgcc gtaaagcact aaatcggaac cctaaaggga    7740
gcccccgatt tagagcttga cggggaaagc cggcgaacgt ggcgagaaag gaagggaaga    7800
aagcgaaagg agcgggcgct agggcgctgg caagtgtagc ggtcacgctg cgcgtaacca    7860
ccacacccgc cgcgcttaat gcgccgctac agggcgcgtc ccattcgcca             7910
```

<210> SEQ ID NO 67
<211> LENGTH: 7891
<212> TYPE: DNA
<213> ORGANISM: Artificial Sequence
<220> FEATURE:
<223> OTHER INFORMATION: Description of Artificial Sequence: Synthetic
      p7(A)T3rG polynucleotide

<400> SEQUENCE: 67

```
atccggatat agttcctcct ttcagcaaaa aaccccctcaa gacccgttta gaggccccaa    60
ggggttatgc tagttattgc tcagcggtgg cagcagccaa ctcagcttcc tttcgggctt    120
tgttagcagc cggatctcag tggtggtggt ggtggtgctc gagttaaccg cggcctgcct    180
ggaatgaagg atattgtgtc ataccgccgt ccgcgaataa cgtgatgcct gtgacgtagc    240
tggcttcctt cgaagcaagc caggctgcta ctgcggcgat ctcctccggt tcgccgatat    300
atcccattgg aatcatgctt tctacatcag cttttctgttt agggtcagcg aatttttcag    360
cattgattgg cgtgttgatc gcacctggcc caatattatt gacgcgaatg cccttcggcg    420
cgtattccaa cgctaatgtt tctgtcatca gctttatccc gcctttactt gccgcatagt    480
ggacaaataa cggccaagga atcacttcgt gcacactgga catgttaatg acatttccct    540
tgatatcgtt ttctacgaaa tatttaatcg cttcacggct tcctaaaaag gcacccgtta    600
agttcgtgcc gatgacttta tcccaatcct tgagcggcat ttcgtgagat ggcacaggat    660
```

| | | | | | |
|---|---|---|---|---|---|
| tttcaagacc | ggcattatta | atcataatat | cgagtgtgcc | gaactcctta | attgccgttt | 720
| gcacgatatt | ttttacatct | tcctctttcg | tgacatctcc | ttggacgaca | acagcttcac | 780
| cgcccgcctt | gatgacctct | tcttttacct | cgttcggatc | ttgtttatta | ctataatagt | 840
| tgataaccac | ttttgcctgc | tccttgccga | agcgaatggc | catcgccttt | ccgagccctg | 900
| aagcagctcc | tgtaatagcg | acgactttc | cttttaaatc | cggatacatg | tatatctcct | 960
| tgcggccgct | cagaactgtg | tcgggcgcat | caccgcatca | atgccgccat | caatgacgat | 1020
| ctgcgcgcca | tgcacatagc | ttgcggccgg | gctcatcaaa | aaggcgatga | ccgacgccat | 1080
| ctcggacggc | tcggcacggc | ggcccatggg | aggaacgaac | ttggcaatgg | attcgccata | 1140
| gcgcgggtcc | tgcaggcccg | cctgcagcaa | gggagtctcg | gttgcaccgg | gggcgatggt | 1200
| gttcaggcgc | acgccagcct | cgccccaggc | ggcggcgcgt | ttgcgcacag | ccaccgtcaa | 1260
| agcattcttg | ctgcccgcat | aggccagatt | tccgccctgc | tctcccgcat | gttcgacaat | 1320
| ggcgcgggcc | ttggcttcct | cgccggcttc | cagtgccagc | gccagtgggt | tcttgtcaaa | 1380
| agccagatgc | gcggaagcca | cggacgagat | gacgacggct | gcgggctgat | ggccttttt | 1440
| cagcgctggc | aaaaaggcat | ccatcagctc | ggtcgcgcca | aaataattga | ccgaaaccac | 1500
| attgccaagc | accttggtct | gcggtcccag | gccggcgcac | agcaccaggc | cgtccatgcc | 1560
| cttgctgcac | ttcgccagta | catcggcaat | cgcctgcttt | cgaccttcgg | ccgtcgagag | 1620
| atcggcaatc | acttccgcat | cgcgtatatc | gatgcctacg | atctggtgac | cggccgcctc | 1680
| caggaccttg | cgcgtagcgg | caccaatgcc | ggtggcgcag | ccgcttatca | cgatgatgga | 1740
| catcatatgt | atatctcctt | cttatactta | actaatatac | taagatgggg | aattgttatc | 1800
| cgctcacaat | tccctatag | tgagtcgtat | taatttcgat | tatgcggccg | tgtacaatac | 1860
| gattactttc | tgttcgactt | aagcattata | agcttctagt | cgcggtagaa | cgaccccatg | 1920
| tagcggatgt | actcgtcctc | ggtgtggttt | gccttccagt | cgtggacgga | gtccttgttg | 1980
| cgctggccgg | cgatgacgga | gagctcctta | cccagcttct | caaaggcctc | gtcaacgcac | 2040
| tcctcggggg | tgagggcgat | cttcatgacg | gcctcgccct | gcgggccgcc | ggggaggttg | 2100
| gacagcaggc | tgggggttag | ggtggtgccg | agggtgatga | cctcgacgtc | gacgccggtg | 2160
| ccctcgcact | cgcaggccac | ggcctcggtc | atcttgagga | tgaaggcctt | gcccgcgccg | 2220
| tactggccgt | tccaggggct | ggagctgatg | ccggtcatcg | acgagacgtt | gatcacggcg | 2280
| ccgcggtcct | gggcggcaaa | gatccgcatg | tagtggtgga | agcacttgag | gaaggtcacg | 2340
| acgttgacgt | tgatcatggc | ctcgtgcttc | tcccaggggg | tgtcctggat | cttaccgaag | 2400
| ctgtgcaggc | aggccacgta | gctcatgaag | cccatgtcca | ggccctcggt | cgcggcgaag | 2460
| acggtctcgg | cagcgccggg | ctggctaaag | tcggcgcgca | cgaccttggt | ctccacgccg | 2520
| taggtctcgc | ggatctcgcc | tgcgagcacg | ttcagcttct | cctcgcgacg | ggcgaccatg | 2580
| acgacgttca | tgccgccggc | ggcgatcttc | tcgcagaacg | ccttgccgac | gccctcggtc | 2640
| gcgcccagga | tcaggcccca | ctcaccgtac | ttctccctca | ggttcatatg | tatatctcct | 2700
| tcttaaagtt | aaacaaaatt | atttctagag | gggaattgtt | atccgctcac | aattccccta | 2760
| tagtgagtcg | tattaatttc | gcgggatcga | gatctcgatc | ctctacgccg | gacgcatcgt | 2820
| ggccggcatc | accggcgcca | caggtgcggt | tgctggcgcc | tatatcgccg | acatcaccga | 2880
| tggggaagat | cgggctcgcc | acttcgggct | catgagcgct | tgtttcggcg | tgggtatggt | 2940
| ggcaggcccc | gtggccgggg | gactgttggg | cgccatctcc | ttgcatgcac | cattccttgc | 3000

```
ggcggcggtg ctcaacggcc tcaacctact actgggctgc ttcctaatgc aggagtcgca    3060
taagggagag cgtcgagatc ccggacacca tcgaatggcg caaaaccttt cgcggtatgg    3120
catgatagcg cccggaagag agtcaattca gggtggtgaa tgtgaaacca gtaacgttat    3180
acgatgtcgc agagtatgcc ggtgtctctt atcagaccgt ttcccgcgtg gtgaaccagg    3240
ccagccacgt ttctgcgaaa acgcgggaaa aagtggaagc ggcgatggcg gagctgaatt    3300
acattcccaa ccgcgtggca caacaactgg cgggcaaaca gtcgttgctg attggcgttg    3360
ccacctccag tctggccctg cacgcgccgt cgcaaattgt cgcggcgatt aaatctcgcg    3420
ccgatcaact gggtgccagc gtggtggtgt cgatggtaga acgaagcggc gtcgaagcct    3480
gtaaagcggc ggtgcacaat cttctcgcgc aacgcgtcag tgggctgatc attaactatc    3540
cgctggatga ccaggatgcc attgctgtgg aagctgcctg cactaatgtt ccggcgttat    3600
ttcttgatgt ctctgaccag acacccatca acagtattat tttctcccat gaagacggta    3660
cgcgactggg cgtggagcat ctggtcgcat tgggtcacca gcaaatcgcg ctgttagcgg    3720
gcccattaag ttctgtctcg gcgcgtctgc gtctggctgg ctggcataaa tatctcactc    3780
gcaatcaaat tcagccgata gcggaacggg aaggcgactg gagtgccatg tccggtttc    3840 aacaaaccat gcaaatgctg aatgagggca tcgttcccac tgcgatgctg gttgccaacg    3900
atcagatggc gctgggcgca atgcgcgcca ttaccgagtc cgggctgcgc gttggtgcgg    3960
atatctcggt agtgggatac gacgataccg aagacagctc atgttatatc cgccgttaa    4020 ccaccatcaa acaggatttt cgcctgctgg ggcaaaccag cgtggaccgc ttgctgcaac    4080
tctctcaggg ccaggcggtg aagggcaatc agctgttgcc cgtctcactg gtgaaaagaa    4140
aaaccaccct ggcgcccaat acgcaaaccg cctctccccg cgcgttggcc gattcattaa    4200
tgcagctggc acgacaggtt tcccgactgg aaagcgggca gtgagcgcaa cgcaattaat    4260
gtaagttagc tcactcatta ggcaccggga tctcgaccga tgcccttgag agccttcaac    4320
ccagtcagct ccttccggtg ggcgcggggc atgactatcg tcgccgcact tatgactgtc    4380
ttctttatca tgcaactcgt aggacaggtg ccggcagcgc tctgggtcat tttcggcgag    4440
gaccgctttc gctggagcgc gacgatgatc ggcctgtcgc ttgcggtatt cggaatcttg    4500
cacgccctcg ctcaagcctt cgtcactggt cccgccacca aacgtttcgg cgagaagcag    4560
gccattatcg ccggcatggc ggccccacgg gtgcgcatga tcgtgctcct gtcgttgagg    4620
acccggctag gctggcgggg ttgccttact ggttagcaga atgaatcacc gatacgcgag    4680
cgaacgtgaa gcgactgctg ctgcaaaacg tctgcgacct gagcaacaac atgaatggtc    4740
ttcggtttcc gtgtttcgta aagtctggaa acgcggaagt cagcgccctg caccattatg    4800
ttccggatct gcatcgcagg atgctgctgg ctaccctgtg gaacacctac atctgtatta    4860
acgaagcgct ggcattgacc ctgagtgatt tttctctggt cccgccgcat ccataccgcc    4920
agttgtttac cctcacaacg ttccagtaac cgggcatgtt catcatcagt aacccgtatc    4980
gtgagcatcc tctctcgttt catcggtatc attaccccca tgaacagaaa tcccccttac    5040
acggaggcat cagtgaccaa acaggaaaaa accgccctta acatggcccg ctttatcaga    5100
agccagacat taacgcttct ggagaaactc aacgagctgg acgcggatga acaggcagac    5160
atctgtgaat cgcttcacga ccacgctgat gagctttacc gcagctgcct cgcgcgtttc    5220
ggtgatgacg gtgaaaacct ctgacacatg cagctcccgg agacggtcac agcttgtctg    5280
taagcggatg ccgggagcag acaagcccgt caggcgcgt cagcgggtgt tggcgggtgt    5340
cggggcgcag ccatgaccca gtcacgtagc gatagcggag tgtatactgg cttaactatg    5400
```

-continued

```
cggcatcaga gcagattgta ctgagagtgc accatatatg cggtgtgaaa taccgcacag    5460
atgcgtaagg agaaaatacc gcatcaggcg ctcttccgct tcctcgctca ctgactcgct    5520
gcgctcggtc gttcggctgc ggcgagcggt atcagctcac tcaaaggcgg taatacggtt    5580
atccacagaa tcaggggata acgcaggaaa gaacatgtga gcaaaaggcc agcaaaaggc    5640
caggaaccgt aaaaaggccg cgttgctggc gtttttccat aggctccgcc cccctgacga    5700
gcatcacaaa aatcgacgct caagtcagag gtggcgaaac ccgacaggac tataaagata    5760
ccaggcgttt ccccctggaa gctccctcgt gcgctctcct gttccgaccc tgccgcttac    5820
cggatacctg tccgcctttc tcccttcggg aagcgtggcg ctttctcata gctcacgctg    5880
taggtatctc agttcggtgt aggtcgttcg ctccaagctg ggctgtgtgc acgaaccccc    5940
cgttcagccc gaccgctgcg ccttatccgg taactatcgt cttgagtcca acccggtaag    6000
acacgactta tcgccactgg cagcagccac tggtaacagg attagcagag cgaggtatgt    6060
aggcggtgct acagagttct tgaagtggtg gcctaactac ggctacacta aggacagt     6120 atttggtatc tgcgctctgc tgaagccagt taccttcgga aaaagagttg gtagctcttg    6180
atccggcaaa caaaccaccg ctggtagcgg tggttttttt gtttgcaagc agcagattac    6240
gcgcagaaaa aaaggatctc aagaagatcc tttgatcttt tctacggggt ctgacgctca    6300
gtggaacgaa aactcacgtt aagggatttt ggtcatgaga ttatcaaaaa ggatcttcac    6360
ctagatcctt ttaaattaaa aatgaagttt taaatcaatc taaagtatat atgagtaaac    6420
ttggtctgac agttaccaat gcttaatcag tgaggcacct atctcagcga tctgtctatt    6480
tcgttcatcc atagttgcct gactccccgt cgtgtagata actacgatac gggagggctt    6540
accatctggc cccagtgctg caatgatacc gcgagaccca cgctcaccgg ctccagattt    6600
atcagcaata aaccagccag ccggaagggc cgagcgcaga agtggtcctg caactttatc    6660
cgcctccatc cagtctatta attgttgccg ggaagctaga gtaagtagtt cgccagttaa    6720
tagtttgcgc aacgttgttg ccattgctgc aggcatcgtg gtgtcacgct cgtcgtttgg    6780
tatggcttca ttcagctccg gttcccaacg atcaaggcga gttacatgat cccccatgtt    6840
gtgcaaaaaa gcggttagct ccttcggtcc tccgatcgtt gtcagaagta agttggccgc    6900
agtgttatca ctcatggtta tggcagcact gcataattct cttactgtca tgccatccgt    6960
aagatgcttt tctgtgactg gtgagtactc aaccaagtca ttctgagaat agtgtatgcg    7020
gcgaccgagt tgctcttgcc cggcgtcaat acgggataat accgcgccac atagcagaac    7080
tttaaaagtg ctcatcattg gaaaacgttc ttcgggcga aaactctcaa ggatcttacc    7140
gctgttgaga tccagttcga tgtaacccac tcgtgcaccc aactgatctt cagcatcttt    7200
tactttcacc agcgtttctg ggtgagcaaa aacaggaagg caaaatgccg caaaaaaggg    7260
aataagggcg acacggaaat gttgaatact catactcttc ctttttcaat attattgaag    7320
catttatcag ggttattgtc tcatgagcgg atacatattt gaatgtattt agaaaaataa    7380
acaaataggg gttccgcgca catttccccg aaaagtgcca cctgaaattg taaacgttaa    7440
tattttgtta aaattcgcgt taaatttttg ttaaatcagc tcattttta accaataggc     7500 cgaaatcggc aaaatccctt ataaatcaaa agaatagacc gagatagggt tgagtgttgt    7560
tccagtttgg aacaagagtc cactattaaa gaacgtggac tccaacgtca aagggcgaaa    7620
aaccgtctat cagggcgatg gcccactacg tgaaccatca ccctaatcaa gttttttggg    7680
gtcgaggtgc cgtaaagcac taaatcggaa ccctaaaggg agcccccgat ttagagcttg    7740
```

-continued

```
acggggaaag ccggcgaacg tggcgagaaa ggaagggaag aaagcgaaag gagcgggcgc      7800
tagggcgctg gcaagtgtag cggtcacgct gcgcgtaacc accacacccg ccgcgcttaa      7860
tgcgccgcta cagggcgcgt cccattcgcc a                                     7891

<210> SEQ ID NO 68
<211> LENGTH: 7404
<212> TYPE: DNA
<213> ORGANISM: Artificial Sequence
<220> FEATURE:
<223> OTHER INFORMATION: Description of Artificial Sequence: Synthetic
      pF(G)r7(A) polynucleotide

<400> SEQUENCE: 68
atccggatat agttcctcct ttcagcaaaa aacccctcaa gacccgttta gaggccccaa        60
ggggttatgc tagttattgc tcagcggtgg cagcagccaa ctcagcttcc tttcgggctt       120
tgttagcagc cggatctcag tggtggtggt ggtggtgctc gagtgcggcc gcaagcttct       180
agtcgcggta gaacgacccc atgtagcgga tgtactcgtc ctcggtgtgg tttgccttcc       240
agtcgtggac ggagtccttg ttgcgctggc cggcgatgac ggagagctcc ttacccagct       300
tctcaaaggc ctcgtcaacg cactcctcgg gggtgagggc gatcttcatg acggcctcgc       360
cctgcgggcc gccggggagg ttggacagca ggctgggggt tagggtggtg ccgagggtga       420
tgacctcgac gtcgacgccg gtgccctcgc actcgcaggc cacggcctcg gtcatcttga       480
ggatgaaggc cttgcccgcg ccgtactggc cgttccaggg gctggagctg atgccggtca       540
tcgacgagac gttgatcacg gcgccgcggt cctgggcggc aaagatccgc atgtagtggt       600
ggaagcactt gaggaaggtc acgacgttga cgttgatcat ggcctcgtgc ttctcccagg       660
gggtgtcctg gatcttaccg aagctgtgca ggcaggccac gtagctcatg aagcccatgt       720
ccaggccctc ggtcgcggcg aagacggtct cggcagcgcc gggctggcta agtcggcgc        780 gcacgacctt ggtctccacg ccgtaggtct cgcggatctc gcctgcgagc acgttcagct       840
tctcctcgcg acgggcgacc atgacgacgt tcatgccgcc ggcggcgatc ttctcgcaga       900
acgccttgcc gacgccctcg gtcgcgccca ggatcaggcc ccactcaccg tacttctccc       960
tcaggttcat gtatatctcc tttcacgaat tctcagccgc cttcttgaac ttggcggcct      1020
cttccgaacc gccggtggca ttgcccttcg agtaggaatg cgcgccggtg ccggcaagag      1080
cgccgccctg cacgatgagg tattcgtcgc ggatcggacg gccctcgaag aagcactcca      1140
ggatctcgcg ggtgcccgcc gcataacgcg cctgcgcggt cagcgtggtg ccggagatgt      1200
gcggggtcat gccgttatag ggcatcgtcc gccaggggtg gtccttcggc gccggctgcg      1260
ggaaccacac gtcgccggca tagccggcca gccggccgga ttcgagcgca cgtgccacgg      1320
catcgcggtc gcacagcttg ccgcgggcgg tgttgacgat gtaggcgcca cgcttgaaca      1380
gcttcagcgt ctcgtcattg atcatgtgct cggtttcggg gtgcagcggg cagttcagcg      1440
tcaccacgtc gcaaaccgga tacatgtcct cgcgggtcgc gtgccaggtg aggttgagct      1500
ccttctcgac cgattccggc aggcggtgac ggccggtgta gtgcaggtgc acgtcgaacg      1560
gcgccagacg gcgcagcacc gcgagaccga tgcggccggc ggccacggtg ccgacatgca      1620
tcgcctcgag gtcgtaggcg tgggagacgc agtcggcgat gttccagccg cccttccgcg      1680
cccattcgtg cgagggcaga tagttgcgca ccagcgacag gatcatcatc accacatgct      1740
cggcgacgct gatcgagttg cagtaggtga cttccgccac ggtgacgttg cggtcgatag      1800
ccgactgaag atcgacgtgg tcggaaccga tgccggcggt gagcgcgagc ttcaggttct      1860
```

```
tggccttggc gatgcgctcg ggcgtcagat aggccggcca aagggctgg gagatgacga    1920
catccgcatc gaccagctcg cgctcgaaca ccgagtcggg gccgtccttg tcggaggtca    1980
cgaccagggt gtggccgttg gattcgagat attcgcgcag gccgagctcg ccggagacgg    2040
agccgagcaa ctgcccgggc gtgaagtcga tggccttcgg cgtcggcaag atctggccgc    2100
ccggatagtg gtcgatcttc ggaagatcgt cgcgggcata ggtcttcggg tagccgtcga    2160
ccggatcatc gtaaagaacg cacaggacct ttgccatcat atgtatatct ccttcttaaa    2220
gttaaacaaa attatttcta gagggggaatt gttatccgct cacaattccc ctatagtgag    2280
tcgtattaat ttcgcgggat cgagatctcg atcctctacg ccggacgcat cgtggccggc    2340
atcaccggcg ccacaggtgc ggttgctggc gcctatatcg ccgacatcac cgatgggaa    2400
gatcgggctc gccacttcgg gctcatgagc gcttgtttcg gcgtgggtat ggtggcaggc    2460
cccgtggccg ggggactgtt gggcgccatc tccttgcatg caccattcct tgcggcggcg    2520
gtgctcaacg gcctcaacct actactgggc tgcttcctaa tgcaggagtc gcataaggga    2580
gagcgtcgag atcccggaca ccatcgaatg gcgcaaaacc tttcgcggta tggcatgata    2640
gcgcccggaa gagagtcaat tcagggtggt gaatgtgaaa ccagtaacgt tatacgatgt    2700
cgcagagtat gccggtgtct cttatcagac cgtttcccgc gtggtgaacc aggccagcca    2760
cgtttctgcg aaaacgcggg aaaaagtgga agcggcgatg cggagctga attacattcc    2820
caaccgcgtg gcacaacaac tggcgggcaa acagtcgttg ctgattggcg ttgccacctc    2880
cagtctggcc ctgcacgcgc cgtcgcaaat tgtcgcggcg attaaatctc gcgccgatca    2940
actgggtgcc agcgtggtgg tgtcgatggt agaacgaagc ggcgtcgaag cctgtaaagc    3000
ggcggtgcac aatcttctcg cgcaacgcgt cagtgggctg atcattaact atccgctgga    3060
tgaccaggat gccattgctg tggaagctgc ctgcactaat gttccggcgt tatttcttga    3120
tgtctctgac cagacaccca tcaacagtat tattttctcc catgaagacg gtacgcgact    3180
gggcgtggag catctggtcg cattgggtca ccagcaaatc gcgctgttag cgggcccatt    3240
aagttctgtc tcggcgcgtc tgcgtctggc tggctggcat aaatatctca ctcgcaatca    3300
aattcagccg atagcggaac gggaaggcga ctggagtgcc atgtccggtt ttcaacaaac    3360
catgcaaatg ctgaatgagg gcatcgttcc cactgcgatg ctggttgcca acgatcagat    3420
ggcgctgggc gcaatgcgcg ccattaccga gtccgggctg cgcgttggtg cggatatctc    3480
ggtagtggga tacgacgata ccgaagacag ctcatgttat atcccgccgt taaccaccat    3540
caaacaggat tttcgcctgc tggggcaaac cagcgtggac cgcttgctgc aactctctca    3600
gggccaggcg gtgaagggca atcagctgtt gcccgtctca ctggtgaaaa gaaaaaccac    3660
cctggcgccc aatacgcaaa ccgcctctcc ccgcgcgttg gccgattcat taatgcagct    3720
ggcacgacag gtttcccgac tggaaagcgg gcagtgagcg caacgcaatt aatgtaagtt    3780
agctcactca ttaggcaccg ggatctcgac cgatgccctt gagagccttc aacccagtca    3840
gctccttccg gtgggcgcgg ggcatgacta tcgtcgccgc acttatgact gtcttcttta    3900
tcatgcaact cgtaggacag gtgccggcag cgctctgggt catttcggc gaggaccgct    3960
ttcgctggag cgcgacgatg atcggcctgt cgcttgcggt attcggaatc ttgcacgccc    4020
tcgctcaagc cttcgtcact ggtcccgcca ccaaacgttt cggcgagaag caggccatta    4080
tcgccggcat ggcggcccca cgggtgcgca tgatcgtgct cctgtcgttg aggacccggc    4140
taggctgcgg gggttgcctt actggttagc agaatgaatc accgatacgc gagcgaacgt    4200
gaagcgactg ctgctgcaaa acgtctgcga cctgagcaac aacatgaatg gtcttcggtt    4260
```

```
tccgtgtttc gtaaagtctg gaaacgcgga agtcagcgcc ctgcaccatt atgttccgga    4320
tctgcatcgc aggatgctgc tggctaccct gtggaacacc tacatctgta ttaacgaagc    4380
gctggcattg accctgagtg attttttctct ggtcccgccg catccatacc gccagttgtt    4440
taccctcaca acgttccagt aaccgggcat gttcatcatc agtaacccgt atcgtgagca    4500
tcctctctcg tttcatcggt atcattaccc ccatgaacag aaatcccct tacacggagg     4560 catcagtgac caaacaggaa aaaaccgccc ttaacatggc ccgctttatc agaagccaga    4620
cattaacgct tctggagaaa ctcaacgagc tggacgcgga tgaacaggca gacatctgtg    4680
aatcgcttca cgaccacgct gatgagcttt accgcagctg cctcgcgcgt ttcggtgatg    4740
acggtgaaaa cctctgacac atgcagctcc cggagacggt cacagcttgt ctgtaagcgg    4800
atgccgggag cagacaagcc cgtcagggcg cgtcagcggg tgttggcggg tgtcggggcg    4860
cagccatgac ccagtcacgt agcgatagcg gagtgtatac tggcttaact atgcggcatc    4920
agagcagatt gtactgagag tgcaccatat atgcggtgtg aaataccgca cagatgcgta    4980
aggagaaaat accgcatcag gcgctcttcc gcttcctcgc tcactgactc gctgcgctcg    5040
gtcgttcggc tgcggcgagc ggtatcagct cactcaaagg cggtaatacg gttatccaca    5100
gaatcagggg ataacgcagg aaagaacatg tgagcaaaag gccagcaaaa ggccaggaac    5160
cgtaaaaagg ccgcgttgct ggcgtttttc cataggctcc gcccccctga cgagcatcac    5220
aaaaatcgac gctcaagtca gaggtggcga aacccgacag gactataaag ataccaggcg    5280
tttccccctg gaagctccct cgtgcgctct cctgttccga ccctgccgct taccggatac    5340
ctgtccgcct ttctcccttc gggaagcgtg gcgctttctc atagctcacg ctgtaggtat    5400
ctcagttcgg tgtaggtcgt tcgctccaag ctgggctgtg tgcacgaacc ccccgttcag    5460
cccgaccgct gcgccttatc cggtaactat cgtcttgagt ccaacccggt aagacacgac    5520
ttatcgccac tggcagcagc cactggtaac aggattagca gagcgaggta tgtaggcggt    5580
gctacagagt tcttgaagtg gtggcctaac tacggctaca ctagaaggac agtatttggt    5640
atctgcgctc tgctgaagcc agttaccttc ggaaaaagag ttggtagctc ttgatccggc    5700
aaacaaacca ccgctggtag cggtggtttt tttgtttgca agcagcagat tacgcgcaga    5760
aaaaaaggat ctcaagaaga tcctttgatc ttttctacgg ggtctgacgc tcagtggaac    5820
gaaaactcac gttaagggat tttggtcatg agattatcaa aaaggatctt cacctagatc    5880
cttttaaatt aaaaatgaag ttttaaatca atctaaagta tatatgagta aacttggtct    5940
gacagttacc aatgcttaat cagtgaggca cctatctcag cgatctgtct atttcgttca    6000
tccatagttg cctgactccc cgtcgtgtag ataactacga tacgggaggg cttaccatct    6060
ggccccagtg ctgcaatgat accgcgagac ccacgctcac cggctccaga tttatcagca    6120
ataaaccagc cagccggaag ggccgagcgc agaagtggtc ctgcaacttt atccgcctcc    6180
atccagtcta ttaattgttg ccgggaagct agagtaagta gttcgccagt taatagtttg    6240
cgcaacgttg ttgccattgc tgcaggcatc gtggtgtcac gctcgtcgtt tggtatggct    6300
tcattcagct ccggttccca acgatcaagg cgagttacat gatcccccat gttgtgcaaa    6360
aaagcggtta gctccttcgg tcctccgatc gttgtcagaa gtaagttggc cgcagtgtta    6420
tcactcatgg ttatggcagc actgcataat tctcttactg tcatgccatc cgtaagatgc    6480
ttttctgtga ctggtgagta ctcaaccaag tcattctgag aatagtgtat gcggcgaccg    6540
agttgctctt gcccggcgtc aatacgggat aataccgcgc cacatagcag aactttaaaa    6600
```

```
gtgctcatca ttggaaaacg ttcttcgggg cgaaaactct caaggatctt accgctgttg    6660
agatccagtt cgatgtaacc cactcgtgca cccaactgat cttcagcatc ttttactttc    6720
accagcgttt ctgggtgagc aaaaacagga aggcaaaatg ccgcaaaaaa gggaataagg    6780
gcgacacgga aatgttgaat actcatactc ttccttttc aatattattg aagcatttat    6840
cagggttatt gtctcatgag cggatacata tttgaatgta tttagaaaaa taaacaaata    6900
ggggttccgc gcacatttcc ccgaaaagtg ccacctgaaa ttgtaaacgt taatattttg    6960
ttaaaattcg cgttaaattt ttgttaaatc agctcatttt ttaaccaata ggccgaaatc    7020
ggcaaaatcc cttataaatc aaaagaatag accgagatag ggttgagtgt tgttccagtt    7080
tggaacaaga gtccactatt aaagaacgtg gactccaacg tcaaagggcg aaaaaccgtc    7140
tatcagggcg atggcccact acgtgaacca tcaccctaat caagtttttt ggggtcgagg    7200
tgccgtaaag cactaaatcg aaccctaaa gggagccccc gatttagagc ttgacgggga    7260
aagccggcga acgtggcgag aaaggaaggg aagaaagcga aaggagcggg cgctagggcg    7320
ctggcaagtg tagcggtcac gctgcgcgta accaccacac ccgccgcgct taatgcgccg    7380
ctacagggcg cgtcccattc gcca                                           7404
```

<210> SEQ ID NO 69
<211> LENGTH: 7386
<212> TYPE: DNA
<213> ORGANISM: Artificial Sequence
<220> FEATURE:
<223> OTHER INFORMATION: Description of Artificial Sequence: Synthetic
     pFr3 polynucleotide

<400> SEQUENCE: 69

```
atccggatat agttcctcct ttcagcaaaa aaccccctcaa gacccgttta gaggccccaa    60
ggggttatgc tagttattgc tcagcggtgg cagcagccaa ctcagcttcc tttcgggctt    120
tgttagcagc cggatctcag tggtggtggt ggtggtgctc gagtgcggcc gcaagctttc    180
agaactgtgt cgggcgcatc accgcatcaa tgccgccatc aatgacgatc tgcgcgccat    240
gcacatagct tgcggccggg ctcatcaaaa aggcgatgac cgacgccatc tcggacggct    300
cggcacggcg gcccatggga ggaacgaact tggcaatgga ttcgccatag cgcgggtcct    360
gcaggcccgc ctgcagcaag ggagtctcgg ttgcaccggg ggcgatggtg ttcaggcgca    420
cgccagcctc gccccaggcg gcggcgcgtt tgcgcacagc caccgtcaaa gcattcttgc    480
tgcccgcata ggccagattt ccgccctgct ctcccgcatg ttcgacaatg gcgcgggcct    540
tggcttcctc gccggcttcc agtgccacgc ccagtgggtt cttgtcaaaa gccagatgcg    600
cggaagccac ggacgagatg acgacggctg cgggctgatg gccttttttc agcgctggca    660
aaaaggcatc catcagctcg gtcgcgccaa aataattgac cgaaaccaca ttgccaagca    720
ccttggtctg cggtcccagg ccggcgcaca gcaccaggcc gtccatgccc ttgctgcact    780
tcgccagtac atcggcaatc gcctgctttc gaccttcggc cgtcgagaga tcggcaatca    840
cttccgcatc gcgtatatcg atgcctacga tctggtgacc ggccgcctcc aggaccttgc    900
gcgtagccgc accaatgccg gtggcgcagc cgcttatcac gatgatggac atgtatatct    960
cctttcacga attctcagcc gccttcttga acttggcggc ctcttccgaa ccgccggtgg    1020
cattgccctt cgagtaggaa tgcgcgccgg tgccggcaag agccgccgcc tgcacgatga    1080
ggtattcgtc gcggatcgga cggccctcga agaagcactc caggatctcg cgggtgcccg    1140
ccgcataacg cgcctgcgcg gtcagcgtgg tgccggagat gtgcggggtc atgccgttat    1200
```

```
agggcatcgt ccgccagggg tggtccttcg gcgccggctg cgggaaccac acgtcgccgg   1260
catagccggc cagccggccg gattcgagcg cacgtgccac ggcatcgcgg tcgcacagct   1320
tgccgcgggc ggtgttgacg atgtaggcgc cacgcttgaa cagcttcagc gtctcgtcat   1380
tgatcatgtg ctcggtttcg gggtgcagcg ggcagttcag cgtcaccacg tcgcaaaccg   1440
gatacatgtc ctcgcgggtc gcgtgccagg tgaggttgag ctccttctcg accgattccg   1500
gcaggcggtg acggtcggtg tagtgcaggt gcacgtcgaa cggcgccaga cggcgcagca   1560
ccgcgagacc gatgcggccg gcggccacgg tgccgacatg catcgcctcg aggtcgtagg   1620
cgtgggagac gcagtcggcg atgttccagc cgcccttccg cgcccattcg tgcgagggca   1680
gatagttgcg caccagcgac aggatcatca tcaccacatg ctcggcgacg ctgatcgagt   1740
tgcagtaggt gacttccgcc acggtgacgt tgccgtcgat agccgactga agatcgacgt   1800
ggtcggaacc gatgccggcg gtgagcgcga gcttcaggtt cttggccttg gcgatgcgct   1860
cgggcgtcag ataggccggc cagaagggct gggagatgac gacatccgca tcgaccagct   1920
cgcgctcgaa caccgagtcg gggccgtcct tgtcggaggt cacgaccagg gtgtggccgt   1980
tggattcgag atattcgcgc aggccgagct cgccggagac ggagccgagc aactgcccgg   2040
gcgtgaagtc gatggccttc ggcgtcggca agatctggcc gcccggatag tggtcgatct   2100
tcggaagatc gtcgcgggca taggtcttcg ggtagccgtc gaccggatca tcgtaaagaa   2160
cgcacaggac ctttgccatc atatgtatat ctccttctta aagttaaaca aaattatttc   2220
tagaggggaa ttgttatccg ctcacaattc ccctatagtg agtcgtatta atttcgcggg   2280
atcgagatct cgatcctcta cgccggacgc atcgtggccg gcatcaccgg cgccacaggt   2340
gcggttgctg gcgcctatat cgccgacatc accgatgggg aagatcgggc tcgccacttc   2400
gggctcatga gcgcttgttt cggcgtgggt atggtgcag gccccgtggc cggggggactg   2460 ttgggcgcca tctccttgca tgcaccattc cttgcggcgg cggtgctcaa cggcctcaac   2520
ctactactgg gctgcttcct aatgcaggag tcgcataagg gagagcgtcg agatcccgga   2580
caccatcgaa tggcgcaaaa cctttcgcgg tatggcatga tagcgcccgg aagagagtca   2640
attcagggtg tgaatgtga aaccagtaac gttatacgat gtcgcagagt atgccggtgt   2700
ctcttatcag accgtttccc gcgtggtgaa ccaggccagc cacgtttctg cgaaaacgcg   2760
ggaaaaagtg gaagcggcga tggcggagct gaattacatt cccaaccgcg tggcacaaca   2820
actggcgggc aaacagtcgt tgctgattgg cgttgccacc tccagtctgg ccctgcacgc   2880
gccgtcgcaa attgtcgcgg cgattaaatc tcgcgccgat caactgggtg ccagcgtggt   2940
ggtgtcgatg gtagaacgaa gcggcgtcga agcctgtaaa gcggcggtgc acaatcttct   3000
cgcgcaacgc gtcagtgggc tgatcattaa ctatccgctg gatgaccagg atgccattgc   3060
tgtggaagct gcctgcacta atgttccggc gttatttctt gatgtctctg accagacacc   3120
catcaacagt attattttct cccatgaaga cggtacgcga ctgggcgtgg agcatctggt   3180
cgcattgggt caccagcaaa tcgcgctgtt agcgggccca ttaagttctg tctcggcgcg   3240
tctgcgtctg gctggctggc ataaatatct cactcgcaat caaattcagc cgatagcgga   3300
acgggaaggc gactggagtg ccatgtccgg ttttcaacaa accatgcaaa tgctgaatga   3360
gggcatcgtt cccactgcga tgctggttgc caacgatcag atggcgctgg gcgcaatgcg   3420
cgccattacc gagtccgggc tgcgcgttgg tgcggatatc tcggtagtgg atacgacga   3480 taccgaagac agctcatgtt atatcccgcc gttaaccacc atcaaacagg attttcgcct   3540
gctggggcaa accagcgtgg accgcttgct gcaactctct cagggccagg cggtgaaggg   3600
```

```
caatcagctg ttgcccgtct cactggtgaa agaaaaaacc accctggcgc ccaatacgca   3660
aaccgcctct ccccgcgcgt tggccgattc attaatgcag ctggcacgac aggtttcccg   3720
actggaaagc gggcagtgag cgcaacgcaa ttaatgtaag ttagctcact cattaggcac   3780
cgggatctcg accgatgccc ttgagagcct tcaacccagt cagctccttc cggtgggcgc   3840
ggggcatgac tatcgtcgcc gcacttatga ctgtcttctt tatcatgcaa ctcgtaggac   3900
aggtgccggc agcgctctgg gtcatttttcg gcgaggaccg cttttcgctgg agcgcgacga   3960 tgatcggcct gtcgcttgcg gtattcggaa tcttgcacgc cctcgctcaa gccttcgtca   4020
ctggtcccgc caccaaacgt ttcggcgaga agcaggccat tatcgccggc atggcggccc   4080
cacgggtgcg catgatcgtg ctcctgtcgt tgaggacccg gctaggctgg cggggttgcc   4140
ttactggtta gcagaatgaa tcaccgatac gcgagcgaac gtgaagcgac tgctgctgca   4200
aaacgtctgc gacctgagca acaacatgaa tggtcttcgg tttccgtgtt tcgtaaagtc   4260
tggaaacgcg gaagtcagcg ccctgcacca ttatgttccg gatctgcatc gcaggatgct   4320
gctggctacc ctgtggaaca cctacatctg tattaacgaa gcgctggcat tgaccctgag   4380 tgattttttct ctggtcccgc cgcatccata ccgccagttg tttaccctca caacgttcca   4440
gtaaccgggc atgttcatca tcagtaaccc gtatcgtgag catcctctct cgtttcatcg   4500
gtatcattac cccatgaac agaaatcccc cttacacgga ggcatcagtg accaaacagg   4560
aaaaaaccgc ccttaacatg gcccgcttta tcagaagcca gacattaacg cttctggaga   4620
aactcaacga gctggacgcg gatgaacagg cagacatctg tgaatcgctt cacgaccacg   4680
ctgatgagct ttaccgcagc tgcctcgcgc gttccggtga tgacggtgaa aacctctgac   4740
acatgcagct cccggagacg gtcacagctt gtctgtaagc ggatgccggg agcagacaag   4800
cccgtcaggg cgcgtcagcg ggtgttggcg ggtgtcgggg cgcagccatg acccagtcac   4860
gtagcgatag cggagtgtat actggcttaa ctatgcggca tcagagcaga ttgtactgag   4920
agtgcaccat atatgcggtg tgaaataccg cacagatgcg taaggagaaa ataccgcatc   4980
aggcgctctt ccgcttcctc gctcactgac tcgctgcgct cggtcgttcg gctgcgcga   5040 gcggtatcag ctcactcaaa ggcggtaata cggttatcca cagaatcagg ggataacgca   5100
ggaaagaaca tgtgagcaaa aggccagcaa aaggccagga accgtaaaaa ggccgcgttg   5160
ctggcgtttt tccataggct ccgcccccct gacgagcatc acaaaaatcg acgctcaagt   5220
cagaggtggc gaaacccgac aggactataa agataccagg cgtttccccc tggaagctcc   5280
ctcgtgcgct ctcctgttcc gaccctgccg cttaccggat acctgtccgc ctttctccct   5340
tcgggaagcg tggcgctttc tcatagctca cgctgtaggt atctcagttc ggtgtaggtc   5400
gttcgctcca agctgggctg tgtgcacgaa ccccccgttc agcccgaccg ctgcgcctta   5460
tccggtaact atcgtcttga gtccaacccg gtaagacacg acttatcgcc actggcagca   5520
gccactggta acaggattag cagagcgagg tatgtaggcg gtgctacaga gttcttgaag   5580
tggtggccta actacggcta cactagaagg acagtatttg gtatctgcgc tctgctgaag   5640
ccagttacct tcggaaaaag agttggtagc tcttgatccg gcaaacaaac caccgctggt   5700
agcggtggtt ttttttgtttg caagcagcag attacgcgca gaaaaaaagg atctcaagaa   5760
gatcctttga tcttttctac ggggtctgac gctcagtgga acgaaaactc acgttaaggg   5820
attttggtca tgagattatc aaaaaggatc ttcacctaga tccttttaaa ttaaaaatga   5880
agttttaaat caatctaaag tatatatgag taaacttggt ctgacagtta ccaatgctta   5940
```

-continued

```
atcagtgagg cacctatctc agcgatctgt ctatttcgtt catccatagt tgcctgactc    6000
cccgtcgtgt agataactac gatacgggag ggcttaccat ctggcccag tgctgcaatg     6060 ataccgcgag acccacgctc accggctcca gatttatcag caataaacca gccagccgga    6120
agggccgagc gcagaagtgg tcctgcaact ttatccgcct ccatccagtc tattaattgt    6180
tgccgggaag ctagagtaag tagttcgcca gttaatagtt tgcgcaacgt tgttgccatt    6240
gctgcaggca tcgtggtgtc acgctcgtcg tttggtatgg cttcattcag ctccggttcc    6300
caacgatcaa ggcgagttac atgatccccc atgttgtgca aaaagcggt tagctccttc     6360 ggtcctccga tcgttgtcag aagtaagttg gccgcagtgt tatcactcat ggttatggca    6420
gcactgcata attctcttac tgtcatgcca tccgtaagat gcttttctgt gactggtgag    6480
tactcaacca agtcattctg agaatagtgt atgcggcgac cgagttgctc ttgcccggcg    6540
tcaatacggg ataataccgc gccacatagc agaactttaa aagtgctcat cattggaaaa    6600
cgttcttcgg ggcgaaaact ctcaaggatc ttaccgctgt tgagatccag ttcgatgtaa    6660
cccactcgtg cacccaactg atcttcagca tcttttactt tcaccagcgt ttctgggtga    6720
gcaaaaacag gaaggcaaaa tgccgcaaaa aagggaataa gggcgacacg gaaatgttga    6780
atactcatac tcttccttt tcaatattat tgaagcattt atcagggtta ttgtctcatg      6840
agcggataca tatttgaatg tatttagaaa aataaacaaa taggggttcc gcgcacattt     6900
ccccgaaaag tgccacctga aattgtaaac gttaatattt tgttaaaatt cgcgttaaat    6960
ttttgttaaa tcagctcatt ttttaaccaa taggccgaaa tcggcaaaat cccttataaa    7020
tcaaaagaat agaccgagat agggttgagt gttgttccag tttggaacaa gagtccacta    7080
ttaaagaacg tggactccaa cgtcaaaggg cgaaaaaccg tctatcaggg cgatggccca    7140
ctacgtgaac catcacccta atcaagtttt tggggtcga ggtgccgtaa agcactaaat      7200
cggaacccta aagggagccc ccgatttaga gcttgacggg gaaagccggc gaacgtggcg    7260
agaaaggaag ggaagaaagc gaaggagcg ggcgctaggg cgctggcaag tgtagcggtc     7320
acgctgcgcg taaccaccac acccgccgcg cttaatgcgc cgctacaggg cgcgtcccat    7380
tcgcca                                                              7386
```